US010600969B2

(12) United States Patent
Mun et al.

(10) Patent No.: US 10,600,969 B2
(45) Date of Patent: *Mar. 24, 2020

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si, Chungcheongnam-do (KR)

(72) Inventors: Soung Yun Mun, Yongin-si (KR); Bum Sung Lee, Cheonan-si (KR); Jung Cheol Park, Suwon-si (KR); Hee Sun Ji, Cheonan-si (KR); Sun-Hee Lee, Hwaseong-si (KR); Jae-Taek Kwon, Jeonju-si (KR)

(73) Assignee: DUK SAN NEOLUX CO., LTD., Cheonan-si, Chungcheon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/312,444

(22) PCT Filed: Apr. 9, 2015

(86) PCT No.: PCT/KR2015/003560
§ 371 (c)(1),
(2) Date: Nov. 18, 2016

(87) PCT Pub. No.: WO2015/178585
PCT Pub. Date: Nov. 26, 2015

(65) Prior Publication Data
US 2017/0092869 A1    Mar. 30, 2017

(30) Foreign Application Priority Data

May 22, 2014   (KR) ........................ 10-2014-0061622
Dec. 2, 2014   (KR) ........................ 10-2014-0170768

(51) Int. Cl.
| | | |
|---|---|---|
| H01L 51/00 | (2006.01) |
| C07D 333/76 | (2006.01) |
| C07D 307/91 | (2006.01) |
| C07D 471/04 | (2006.01) |
| C07D 221/18 | (2006.01) |
| C07C 211/54 | (2006.01) |
| C07C 211/58 | (2006.01) |
| C07C 211/61 | (2006.01) |
| C07C 217/92 | (2006.01) |
| C07D 401/04 | (2006.01) |
| C07D 405/14 | (2006.01) |
| C07D 307/77 | (2006.01) |
| C07D 311/78 | (2006.01) |
| C07D 335/04 | (2006.01) |
| C07D 409/12 | (2006.01) |
| C07D 413/14 | (2006.01) |
| H01L 51/50 | (2006.01) |

(52) U.S. Cl.
CPC ........ *H01L 51/0061* (2013.01); *C07C 211/54* (2013.01); *C07C 211/58* (2013.01); *C07C 211/61* (2013.01); *C07C 217/92* (2013.01); *C07D 221/18* (2013.01); *C07D 307/77* (2013.01); *C07D 307/91* (2013.01); *C07D 311/78* (2013.01); *C07D 333/76* (2013.01); *C07D 335/04* (2013.01); *C07D 401/04* (2013.01); *C07D 405/14* (2013.01); *C07D 409/12* (2013.01); *C07D 413/14* (2013.01); *C07D 471/04* (2013.01); *H01L 51/006* (2013.01); *C07C 2603/18* (2017.05); *C07C 2603/42* (2017.05); *H01L 51/0003* (2013.01); *H01L 51/0005* (2013.01); *H01L 51/0052* (2013.01); *H01L 51/0054* (2013.01); *H01L 51/0056* (2013.01); *H01L 51/0058* (2013.01); *H01L 51/0072* (2013.01); *H01L 51/0073* (2013.01); *H01L 51/0074* (2013.01); *H01L 51/5056* (2013.01); *Y02E 10/549* (2013.01)

(58) Field of Classification Search
CPC .. C07D 409/12; C07D 413/14; C07D 311/78; C07C 333/76; C07C 211/54; C07C 217/92; C07C 2103/42; H01L 51/0003; H01L 51/0005; H01L 51/0052; H01L 51/0054; H01L 51/0056; H01L 51/0058; H01L 51/0061; H01L 51/0073; H01L 51/0074; H01L 51/5056
See application file for complete search history.

(56) References Cited

U.S. PATENT DOCUMENTS

| | | | | |
|---|---|---|---|---|
| 2011/0037381 A1* | 2/2011 | Rostovtsev | ............ | C09K 11/06 313/504 |
| 2012/0248426 A1* | 10/2012 | Kato | .................... | C07D 209/86 257/40 |

(Continued)

FOREIGN PATENT DOCUMENTS

| | | |
|---|---|---|
| CN | 102596907 A | 7/2012 |
| CN | 102834483 A | 12/2012 |

(Continued)

OTHER PUBLICATIONS

Machine translation of WO 2013/081410, published on Jun. 6, 2013 (Year: 2013).*

(Continued)

*Primary Examiner* — Anca Eoff
(74) *Attorney, Agent, or Firm* — Vorys, Sater, Seymour & Pease LLP; Mih Suhn Koh

(57) ABSTRACT

Provided are a compound of Formula 1 and an organic electric element including a first electrode, a second electrode, and an organic material layer between the first electrode and the second electrode and comprising the compound, the element showing improved luminous efficiency, stability, and life span.

12 Claims, 1 Drawing Sheet

(56) References Cited

U.S. PATENT DOCUMENTS

| | | | | |
|---|---|---|---|---|
| 2014/0361266 A1* | 12/2014 | Jung | ................... | H01L 51/0094 257/40 |
| 2014/0375627 A1* | 12/2014 | Kim | ..................... | G09G 3/3677 345/214 |
| 2015/0243891 A1* | 8/2015 | Kato | ................... | C07D 333/76 257/40 |
| 2016/0240790 A1* | 8/2016 | Jang | ................... | H01L 51/0061 |
| 2017/0141311 A1* | 5/2017 | Lee | ...................... | C07D 401/10 |
| 2017/0162813 A1* | 6/2017 | Lee | ...................... | C07C 211/54 |
| 2017/0288148 A1* | 10/2017 | Park | ..................... | H01L 51/0061 |
| 2017/0317289 A1* | 11/2017 | Lee | ........................ | C09K 11/06 |

FOREIGN PATENT DOCUMENTS

| | | | |
|---|---|---|---|
| CN | 103805164 A | | 5/2014 |
| CN | 103805165 A | | 5/2014 |
| JP | 2010-222261 | * | 10/2010 |
| JP | 2010222268 A | | 10/2010 |
| KR | 20090058063 A | | 6/2009 |
| KR | 10-2011-0100763 A | | 9/2011 |
| KR | 20110104765 A | | 9/2011 |
| KR | 10-2013-0060953 A | | 6/2013 |
| KR | 20130129756 A | | 11/2013 |
| WO | WO 2013/081410 | * | 6/2013 |
| WO | 2014/034795 A1 | | 3/2014 |
| WO | WO 2014/034795 | * | 3/2014 |

OTHER PUBLICATIONS

Machine translation JP 2010-222268, published on Oct. 7, 2010 (Year: 2010).*
Machine translation of JP 2010-222261, published on Oct. 7, 2010 (Year: 2010).*
The International Search Report for PCT Application No. PCT/KR2015/003560, dated Jul. 15, 2015, three pages; with English translation, two pages.
Korean Notice of Allowance for Korean Application No. 10-2014-0061622, dated Apr. 1, 2015, five pages.
Korean Office Action for Korean Application No. 10-2014-0061622, dated Oct. 2, 2014, five pages.
Korean Office Action for corresponding KR 10-2014-0170768 dated Feb. 15, 2019, eight pages.
Chinese Office Action for corresponding CN 201580027057.3 dated Feb. 27, 2019, six pages.
Chinese Office Action for corresponding Chinese Patent Application No. 201580027057.3, dated Sep. 23, 2019, 9 pages.

* cited by examiner

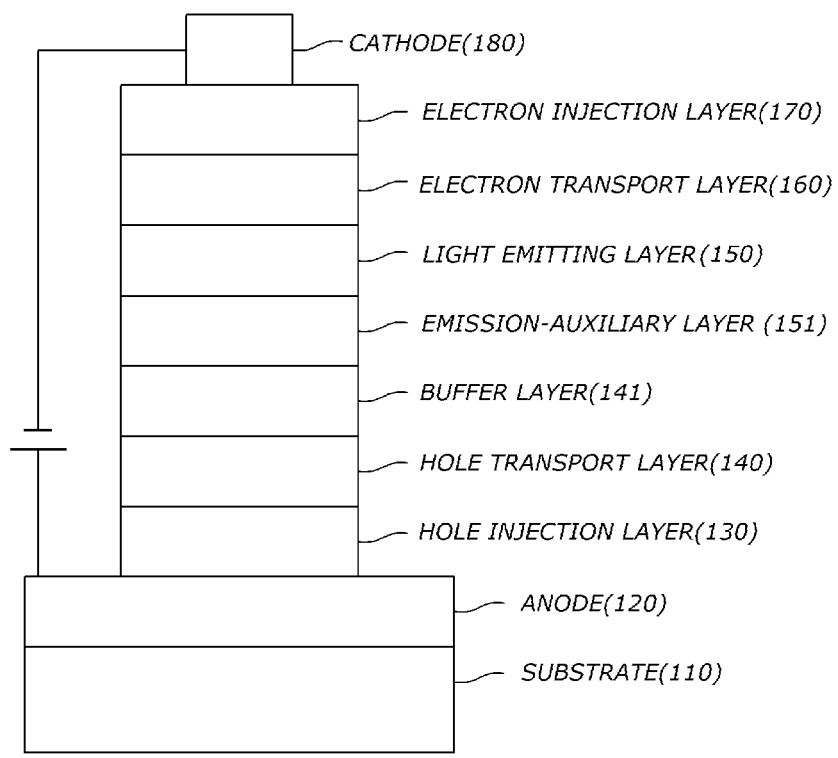

COMPOUND FOR ORGANIC ELECTRONIC ELEMENT, ORGANIC ELECTRONIC ELEMENT USING THE SAME, AND AN ELECTRONIC DEVICE THEREOF

CROSS-REFERENCE TO RELATED APPLICATION

This patent application claims benefit under 35 U.S.C. 119, 120, 121, or 365, and is a National Stage entry from International Application No. PCT/KR2015/003560, filed Apr. 9, 2014, which claims priority to Korean Patent Application No. 10-2014-0061622 filed on May 22, 2014 and Korean Patent Application No. 10-2014-0170768 filed on Dec. 2, 2014, the contents of which are hereby incorporated by reference for all purposes as if fully set forth herein.

BACKGROUND

Technical Field

The present invention relates to compounds for organic electric elements, organic electric elements comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer may have a multilayered structure including multiple layers made of different materials in order to improve the efficiency and stability of an organic electric element, and for example, may include a hole injection layer, a hole transport layer, a light emitting layer, an electron transport layer, an electron injection layer and the like.

A material used as an organic material layer in an organic electric element may be classified into a light emitting material and a charge transport material, for example, a hole injection material, a hole transport material, an electron transport material, an electron injection material and the like according to its function.

Currently, the power consumption is required more and more as size of display becomes larger and larger in the portable display market. Therefore, the power consumption is a very important factor in the portable display with a limited power source of the battery, and efficiency and life span issue also must be solved.

Efficiency, life span, driving voltage and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

Material with high hole mobility is developed as an existing hole transport layer material in order to lower the driving voltage and material with high packing density and HOMO value similar to (not quite different from) that of an light emitting layer was developed in order to enhance a hole transport. However, materials with high hole mobility have tendency to lower the efficiency.

This causes a charge unbalance in the light emitting layer since a hole mobility is higher than an electron mobility in the general organic electric element, resulting in low luminous efficiency and lifespan.

When material with relatively low packing density is used to lower the hole mobility thereby regulating the charge balance of the light emitting layer, the driving voltage increases due to the low packing density and thus Joule's heat rises thereby decreasing lifespan of an organic electric element. Therefore, there are strong needs to develop material with high packing density and still high hole trapping capacity.

SUMMARY

In order to solve one or more of the above-mentioned problems occurring in the prior art, an aspect of the present invention is to provide a compound which allows an organic electric element to improve in luminous efficiency, stability and lifespan, an organic electric element containing the same, and an electronic device including the organic electric element.

In accordance with an aspect of the present invention, the compound represented by the following Formula is provided.

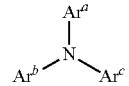

In another aspect of the present invention, organic electric elements containing the compound represented by the formula above and electronic devices including the organic electric element are provided.

By employing the compound of the present invention, the organic electric element according to one or more embodiments of the present invention can have improved luminous efficiency, thermal stability and lifespan.

BRIEF DESCRIPTION OF THE DRAWINGS

The FIGURE illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component. In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine (F), chlorine (Cl), bromine (Br), iodine (I) and so on.

Unless otherwise stated, the term "alkyl" or "alkyl group" as used herein has a single bond of 1 to 60 carbon atoms, and means aliphatic functional radicals including a linear alkyl group, a branched chain alkyl group, a cyclo alkyl group (alicyclic), or an alkyl group substituted with a cyclo alkyl.

Unless otherwise stated, the term "halo alkyl" or "halogen alkyl" as used herein includes an alkyl group substituted with a halogen.

Unless otherwise stated, the term "heteroalkyl" as used herein means alkyl substituted one or more carbon atoms with heteroatom.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cyclo alkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

The term "alkenoxyl group", "alkenoxy group", "alkenyloxyl group" or "alkenyloxy group" as used herein means an oxygen radical attached to an alkyl group, but not limited to, and has 2 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "aryl group" or "arylene group" as used herein has, but not limited to, 6 to 60 carbon atoms. Herein, the aryl group or arylene group means a monocyclic or polycyclic aromatic group, and may also be formed in conjunction with an adjacent group. Examples of "aryl group" or "arylene group" may include a phenyl group, a biphenyl group, a fluorene group, a spirofluorene group and so on.

The prefix "aryl" or "ar" means a radical substituted with an aryl group. For example, an arylalkyl may be an alkyl substituted with an aryl, and an arylalenyl may be an alkenyl substituted with aryl, and a radical substituted with an aryl has a number of carbon atoms as defined herein.

Also, when prefixes are named subsequently, it means that substituents are listed in the order described first. For example, an aryl alkoxy means an alkoxy substituted with an aryl, an alkoxyl carbonyl means a carbonyl substituted with an alkoxyl, and an aryl carbonyl alkenyl also means an alkenyl substitutes with an aryl carbonyl, wherein the aryl carbonyl may be a carbonyl substituted with an aryl.

Unless otherwise stated, the term "heteroalkyl" as used herein means alkyl containing one or more heteroatoms. Unless otherwise stated, the "hetero aryl group" or "hetero arylene group" as used herein means, but not limited to, a ring containing one or more hetero atoms, and having 2 to 60 carbon atoms. They include at least one monocyclic or polycyclic ring, and may be linked together to form a fused ring.

Unless otherwise stated, the term "heterocyclic group" as used herein means, but not limited to, a ring containing one or more hetero atoms, and having 2 to 60 carbon atoms. They include at least one monocyclic or polycyclic ring, and hetero aliphatic or hetero aromatic ring, and may be linked together to form a fused ring.

Unless otherwise stated, the term "heteroatom" as used herein represents N, O, S, P or Si and the like.

Also, the term "heterocyclic group" may include $SO_2$ instead of carbon consisting of cycle. For example, "heterocyclic group" includes compound below.

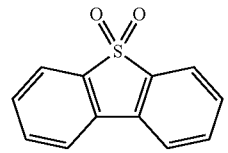 [SMILES: O=S1(=O)c2ccccc2-c2ccccc21]

Unless otherwise stated, the term "aliphatic" as used herein means aliphatic hydrocarbon, having 1 to 60 carbon atoms. The term "aliphatic ring" means aliphatic hydrocarbon ring, having 1 to 60 carbon.

Unless otherwise stated, the term "ring" as used herein means aliphatic ring having 3 to 60 carbon or aromatic ring having 6 to 60 carbon, or heterocyclic ring having 2 to 60 carbon or a fused ring formed by combinations thereof, includes saturated or unsaturated ring.

The other hetero cyclic compounds or hetero radicals may include, but not limited to, at least one hetero atom, except to the described hetero cyclic compound above.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group containing at least one heteroatom selected from the group consisting of O, N, S, Si and P.

Otherwise specified, the Formulas used in the present invention are as defined in the index definition of the substituent of the following Formula.

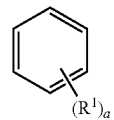

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$s may be the same and different each other, and are linked to the benzene ring as follows. when a is an integer of 4 to 6, the substituents $R^1$s are linked to carbon atom of the benzene ring in a similar manner to that. Meanwhile, hydrogen atoms linked to carbon constituting the benzene ring may not be represented as usual.

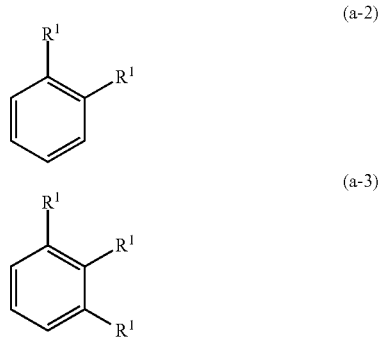

The FIGURE illustrates an organic electric element according to an embodiment of the present invention.

Referring to the FIGURE, an organic electric element 100 according to an embodiment of the present invention includes a first electrode 120 formed on a substrate 110, a second electrode 180, and an organic material layer between the first electrode 110 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, any layer(s) of the organic material layer other than the light emitting layer 150 and a hole transport layer 140 may not be formed. The organic material layer may further include a hole blocking layer, an electron blocking layer, an emission-auxiliary layer 151, a buffer layer 141 and so on, and the electron transport layer 160 and the like may serve as the hole blocking layer.

Although not shown, the organic electric element according to an embodiment of the present invention may further include at least one protective layer or one capping layer formed on at least one of the sides the first and second electrodes, which is a side opposite to the organic material layer.

The inventive compound employed in the organic material layer may be used as materials of a hole injection layer 130, a hole transport layer 140, an electron transport layer 160, an electron injection layer 170, a light emitting layer 150, an emission-auxiliary layer 151 or a capping layer and so on. For example, the inventive compound may be used as materials of at least one layer of the hole transport layer 140, the hole injection layer 130, the light emitting layer 150 and an emission-auxiliary layer 151.

It is necessary to study selection of core and a combination of sub-substituent attached to the core since a band gap, electrical properties, interfacial properties and the like may depend on the type and bonding position of a substituent even in the same core. Specially, both long life span and high efficiency can be achieved when an optimal combination of energy levels and T1 values, inherent material properties (mobility, interfacial properties, etc.) and the like among the respective layers included in the organic material layer is given.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon.

Further, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer instead of deposition. Since the organic material layer according to the present invention may be formed in various ways, the scope of protection of the present invention is not limited by a method of forming the organic material layer.

According to used materials, the organic electric element according to an embodiment of the present invention may be of a top emission type, a bottom emission type, or a dual emission type.

A WOLED (White Organic Light Emitting Device) readily allows for the formation of ultra-high definition images, and is of excellent processability as well as enjoying the advantage of being produced using conventional color filter technologies for LCDs. In this regard, various structures for WOLEDs, used as back light units, have been, in the most part, suggested and patented. Representative among the structures are a parallel side-by-side arrangement of R (Red), G (Green), B (Blue) light-emitting units, a vertical stack arrangement of RGB light-emitting units, and a CCM (color conversion material) structure in which electroluminescence from a blue (B) organic light emitting layer, and photoluminescence from an inorganic luminescent using the electroluminescence are combined. The present invention is applicable to these WOLEDs.

Further, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device, which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-tomultipoint (PMP), a remote controller, a navigation unit, a game player, various kinds of TVs, and various kinds of computers.

Hereinafter, compound according to an aspect of the present invention will be described.

The compound according to an aspect of the present invention is represented by the following Formula 1.

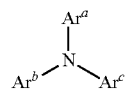

[Formula 1]

In Formula 1 above, $Ar^a$ may be represented by Formula 2 below, $Ar^b$ may be represented by Formula 3 below, and $Ar^c$ is selected from the group consisting of a $C_6$-$C_{60}$ aryl group; a fluorenyl group; a $C_2$-$C_{60}$ heterocyclic group; and a $C_1$-$C_{60}$ alkyl group. Herein, heterocyclic group may contain at least one heteroatom selected from the group consisting of O, N, S, Si, and P.

Preferably, $Ar^c$ may be a $C_6$-$C_{24}$ aryl group, a fluorenyl group, or a $C_2$-$C_{24}$ heterocyclic group, more preferably, $Ar^c$ may be a $C_6$-$C_{12}$ aryl group, a fluorenyl group, or a $C_2$-$C_{12}$ heterocyclic group. For example, $Ar^c$ may be phenyl, biphenyl, naphthyl, substituted or unsubstituted fluorenyl, dibenzothiophene, dibenzofuran, or carbazolyl.

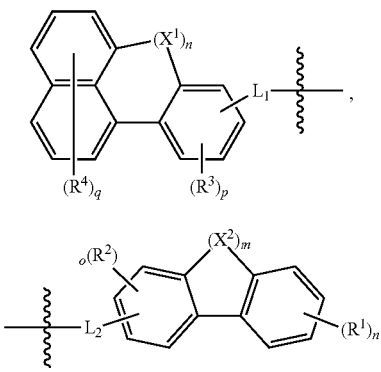

[Formula 2]

[Formula 3]

In Formula 2 and 3 above, m and n are each independently an integer of 0 or 1. For example, both m and n may be an integer of 0 or 1, n may be an integer of 0 or 1 when m is an integer of 0, or m may be an integer of 0 or 1 when n is an integer of 0. Preferably, n is also an integer of 1 when m is an integer of 1. For example, it is preferable that a ring comprising $X^1$ is also formed when a ring comprising $X^2$ is formed.

In Formula 2 and 3 above, $X^1$ and $X^2$ may be each independently any one of N(R'), O, S and C(R') (R"), wherein R' and R" are each independently selected from the group consisting of a $C_6$-$C_{60}$ aryl group; a fluorenyl group; a $C_2$-$C_{60}$ heterocyclic group containing at least one heteroatom selected from the group consisting of O, N, S, Si, and P; and a $C_1$-$C_{60}$ alkyl group.

Preferably, R' and R" may be a $C_6$-$C_{24}$ aryl group, a fluorenyl group, a $C_4$-$C_{24}$ heterocyclic group, or $C_1$-$C_{20}$ alkyl group, more preferably, R' and R" may be a $C_6$-$C_{14}$ aryl group, a fluorenyl group, a $C_2$-$C_{12}$ heterocyclic group, or $C_1$-$C_{10}$ alkyl group. For example, R' and R" may be each independently a phenyl, biphenyl, naphthyl, dibenzothiophene, 9,9-dimethylfluorene, quinazolyl, pyrimidyl, phenyl substituted with deuterium, phenyl substituted with ethenyl, phenanthrenyl, naphthyl substituted with phenyl, methyl, spirofluorenyl group and so on.

In Formula 2 and 3 above, $L_1$ and $L_2$ may be each independently selected from the group consisting of a single bond; a $C_6$-$C_{60}$ arylene group; a fluorenylene group; a $C_2$-$C_{60}$ heterocyclic group containing at least one heteroatom selected from the group consisting of O, N, S, Si, and P; and fused ring formed by a $C_3$-$C_{60}$ aliphatic ring and a $C_6$-$C_{60}$ aromatic ring. Preferably, $L_1$ and $L_2$ may be single bond, a $C_6$-$C_{24}$ arylene group, a fluorenylene group, or a $C_2$-$C_{24}$ heterocyclic group, more preferably, $L_1$ and $L_2$ may be single bond, a $C_6$-$C_{12}$ arylene group, a fluorenylene group, or a $C_2$-$C_{12}$ heterocyclic group. For example, $L_1$ and $L_2$ may be each independently phenylene, biphenylene, 9,9-dimethylfluorene, phenylene substituted with a phenyl or dibenzothiophene.

In Formula 2 and 3 above, l may be an integer of 0 to 4, o and p may be each an integer of 0 to 3, and q may be an integer of 0 to 6.

$R^1$ to $R^4$ may be each independently selected from the group consisting of deuterium; tritium; halogen; a $C_6$-$C_{60}$ aryl group; a fluorenyl group; a $C_2$-$C_{60}$ heterocyclic group containing at least one heteroatom selected from the group consisting of O, N, S, Si, and P; a $C_1$-$C_{60}$ alkyl group; a $C_2$-$C_{20}$ alkenyl group; a $C_2$-$C_{20}$ alkynyl group; $C_3$-$C_{60}$ cycloalkyl group; $C_1$-$C_{30}$ alkoxy group; a $C_6$-$C_{30}$ aryloxy group; and -$L_3$-N($R^5$) ($R^6$).

Preferably, $R^1$ to $R^4$ may be deuterium, a $C_6$-$C_{24}$ aryl group, a fluorenyl group, a $C_2$-$C_{24}$ heterocyclic group, a $C_1$-$C_{20}$ alkyl group, a $C_2$-$C_{20}$ alkenyl group, a $C_2$-$C_{20}$ alkynyl group, or -$L_3$-N($R^5$) ($R^6$), more preferably, $R^1$ to $R^4$ may be deuterium, a $C_2$-$C_6$ alkenyl group, or —N($R^5$) ($R^6$). For example, $R^1$ to $R^4$ may be each independently deuterium, ethenyl or —N($R^5$) ($R^6$).

Further, any adjacent groups of $R^1$s to $R^4$s may be linked together to form at least one ring, wherein the group(s) of $R^1$ to $R^4$ not forming a ring may be the same as defined in the above. For example, adjacent R's may be linked together to form a ring when both l and o are an integer of 2, but adjacent $R^2$s may be each independently an aryl group or a heterocyclic group even if $R^2$s are adjacent group.

Where l is 2 or more, plural R's are same or different each other, and some of the adjacent groups may be linked together to form a ring, and the other groups not forming a ring may be selected from the substituent group defined above. The same applies to plural $R^2$s to $R^4$s where o, p or q is 2 or more.

Meanwhile, the ring formed between the adjacent groups may be a $C_3$-$C_{60}$ aliphatic ring, a $C_6$-$C_{60}$ aromatic ring, a $C_2$-$C_{60}$ heterocyclic ring containing at least one heteroatom selected from the group consisting of O, N, S, Si, and P, or a fused ring formed by combination thereof, and it may be a monocyclic or polycyclic ring, and/or a saturated or unsaturated ring.

$L_3$ may be selected from the group consisting of a single bond; a $C_6$-$C_{60}$ arylene group; a fluorenylene group; a $C_2$-$C_{60}$ heterocyclic group containing at least one heteroatom selected from the group consisting of O, N, S, Si, and P; and fused ring formed by a $C_3$-$C_{60}$ aliphatic ring and a $C_6$-$C_{60}$ aromatic ring.

Preferably, $L_3$ may be a single bond, a $C_6$-$C_{24}$ arylene group, or a $C_2$-$C_{24}$ heterocyclic group, more preferably, $L_3$ may be a single bond, a $C_6$-$C_{12}$ arylene group. For example, $L_3$ may be a single bond or phenylene.

$R^5$ and $R^6$ may be each independently selected from the group consisting of a $C_6$-$C_{60}$ aryl group; a fluorenyl group; a $C_2$-$C_{60}$ heterocyclic group containing at least one heteroatom selected from the group consisting of O, N, S, Si, and P; and a $C_1$-$C_{60}$ alkyl group. Preferably, $R^5$ and $R^6$ may be a $C_6$-$C_{24}$ aryl group, a fluorenyl group or a $C_2$-$C_{24}$ heterocyclic group, and more Preferably, $R^5$ and $R^6$ may be a $C_6$-$C_{18}$ aryl group or a $C_5$-$C_{20}$ heterocyclic group. For example, $R^5$ and $R^6$ may be a phenyl, biphenyl, naphthyl, phenyl substituted with naphthyl, benzoanthracenyl substituted with methyl, pyridyl, dibenzothiophene, benzoxanthenyl or benzothioxanthenyl.

Further, $R^5$ and $R^6$, $L_3$ (except for single bond) and $R^5$, or $L_3$ (except for single bond) and $R^6$ may be linked together to form heterocyclic compound comprising N with N attached to $L_3$, $R^5$ and $R^6$.

Each of the above aryl group, fluorenyl group, heterocyclic group, fused ring group, alkyl group, alkenyl group, alkynyl group, cycloalkyl group, alkoxy group, aryloxy group, arylene group and fluorenylene group may be substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si, and P; a $C_3$-$C_{20}$ cycloalkyl group; a $C_7$-$C_{20}$ arylalkyl group; a $C_8$-$C_{20}$ arylalkenyl group; and -$L_3$-N($R^5$) ($R^6$).

According to one embodiment of the present invention, the compound represented by Formula 2 may be represented by one of Formulas below.

[Formula 4]

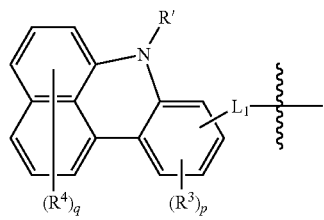

[Formula 5]

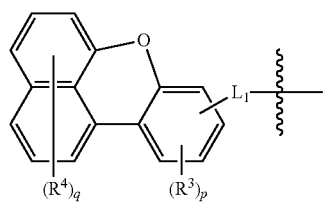

[Formula 6]

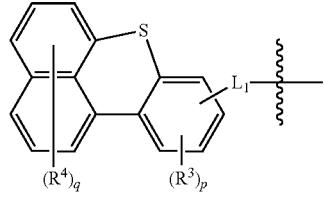

[Formula 7]

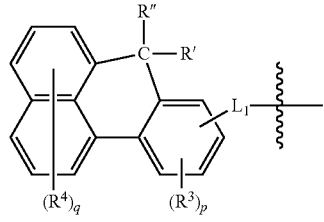

In the Formula 4 to Formula 7 above, R', R'', $R^3$, $R^4$, $L^1$, p and q are the same as defined in Formula 2 above.

According to one embodiment of the present invention, the compound represented by Formula 3 may be represented by one of Formulas below.

[Formula 8]

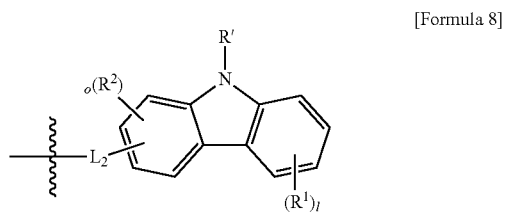

[Formula 9]

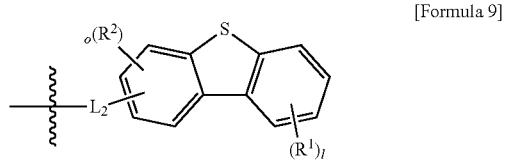

[Formula 10]

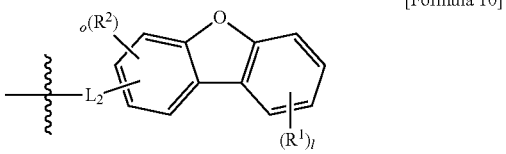

[Formula 11]

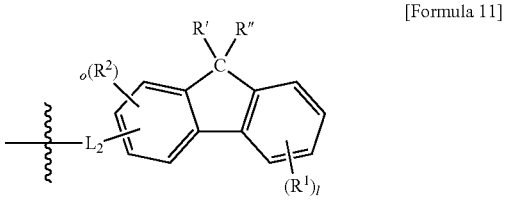

In the Formula 8 to Formula 11 above, R', R'', $R^1$, $R^2$, $L^2$, l and o are the same as defined in Formula 3 above.

Further, in the Formula 2 to Formula 11 above, at least one of $R^1$ to $R^4$ may comprise deuterium.

For more specific examples, the compound represented by Formula 1 may be any one of the following compounds.

P1-1

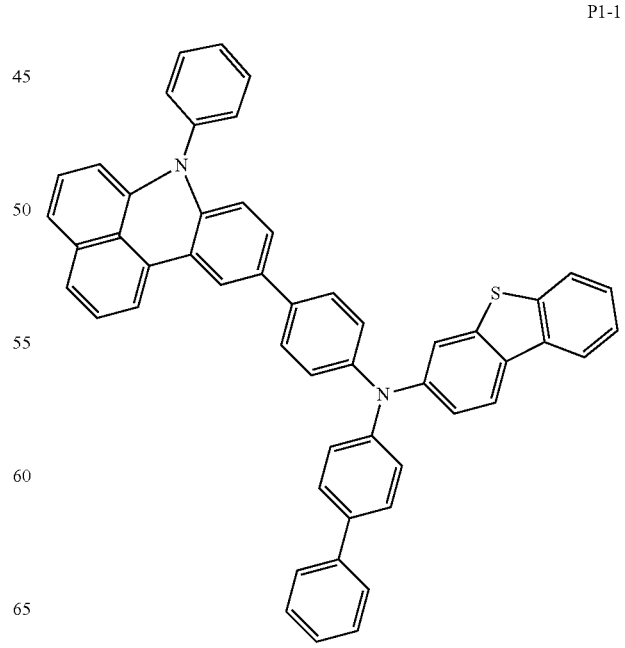

P1-2
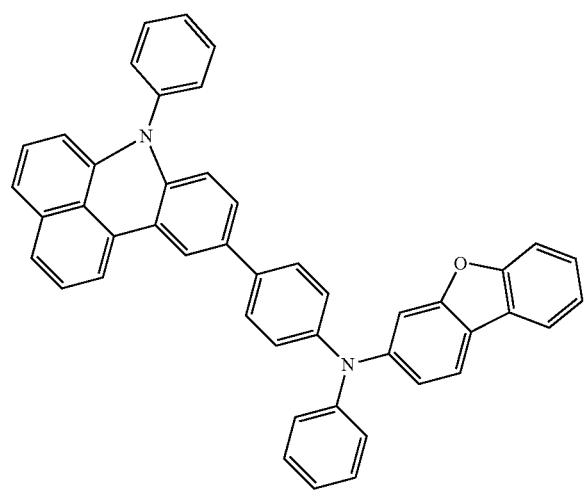
P1-3
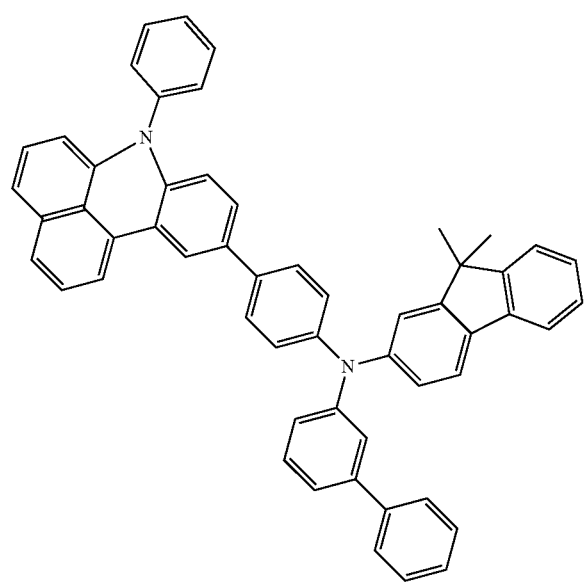
P1-4
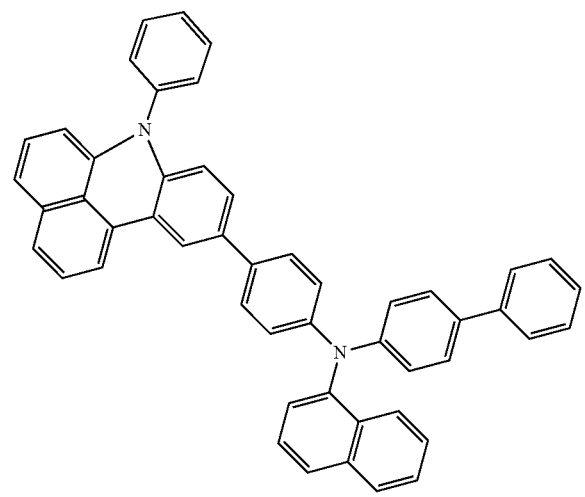
P1-5
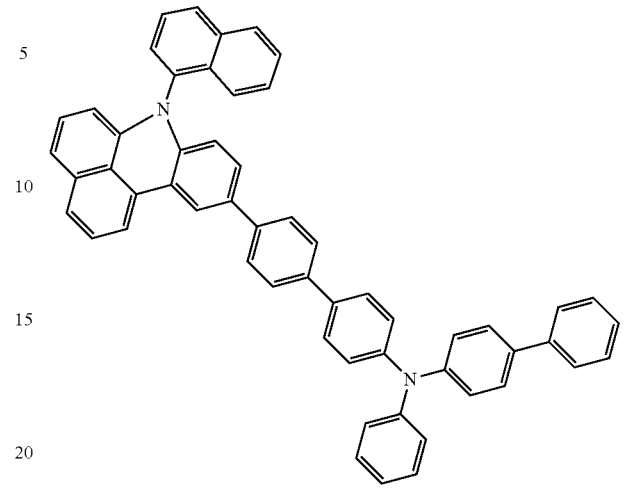
P1-6
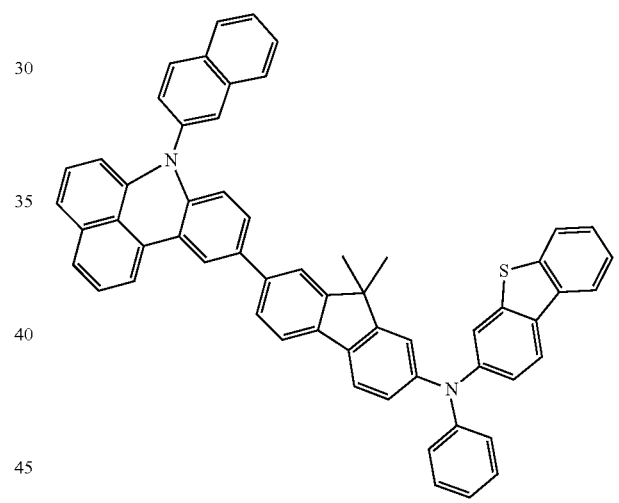
P1-7
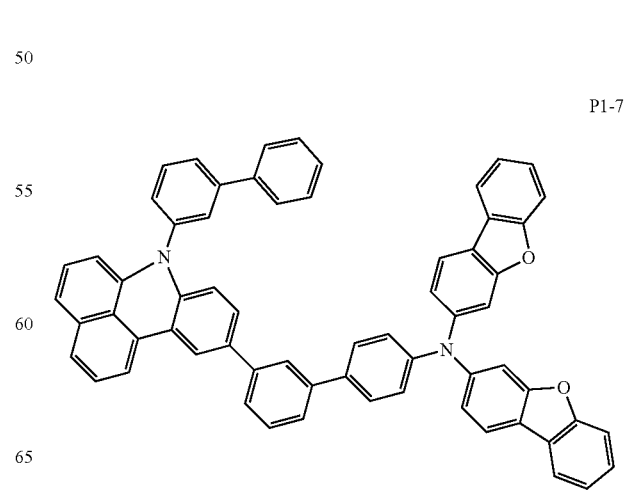

P1-8
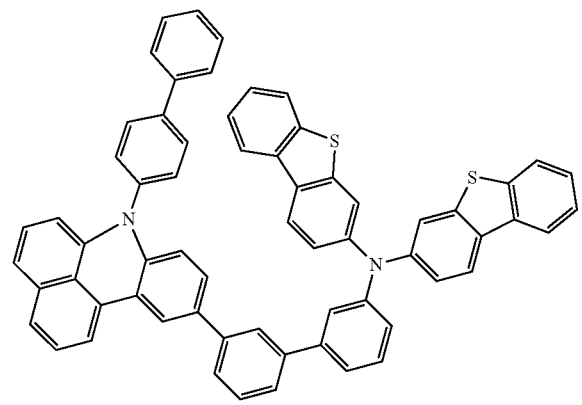
P1-9
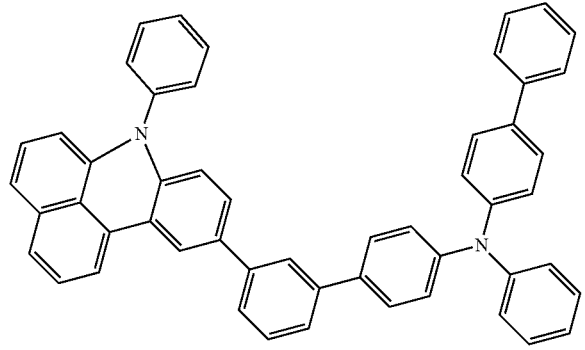
P1-10
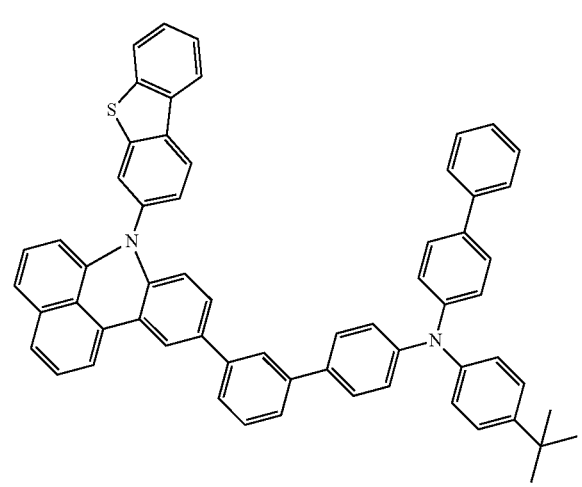
P1-11
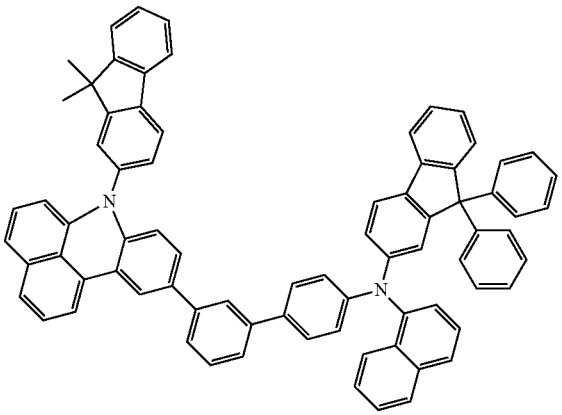
P1-12
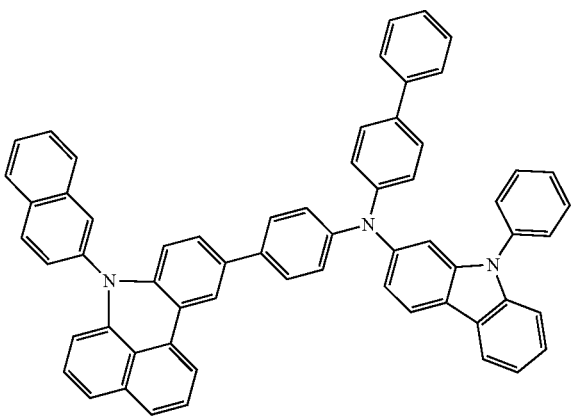
P1-13

P1-14
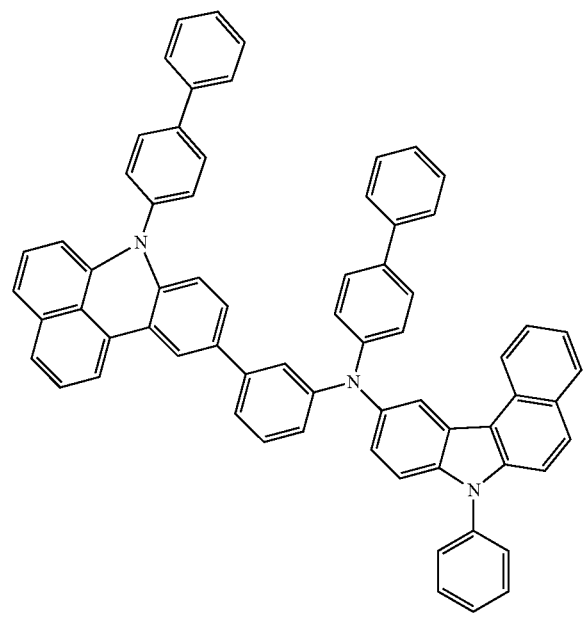
P1-16
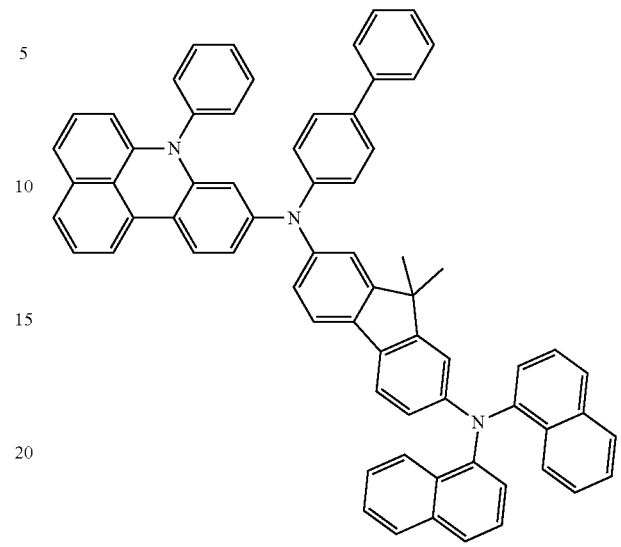
P1-17
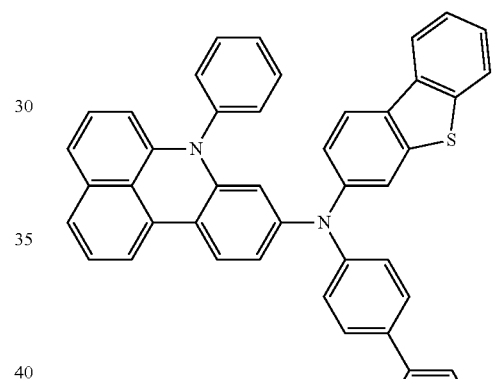
P1-15
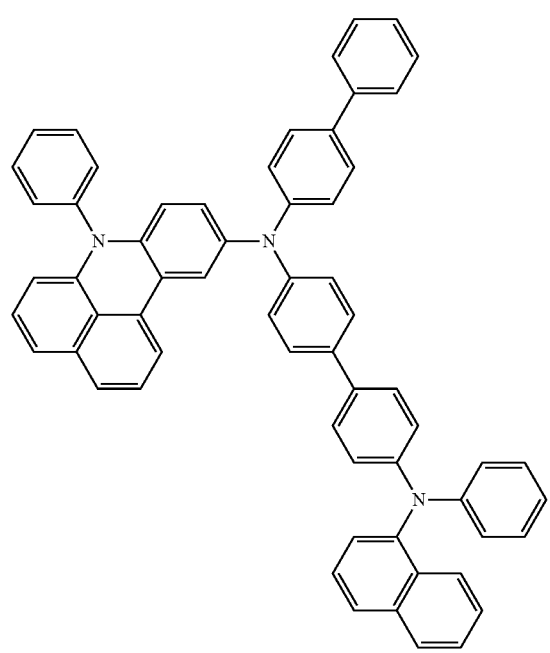
P1-18
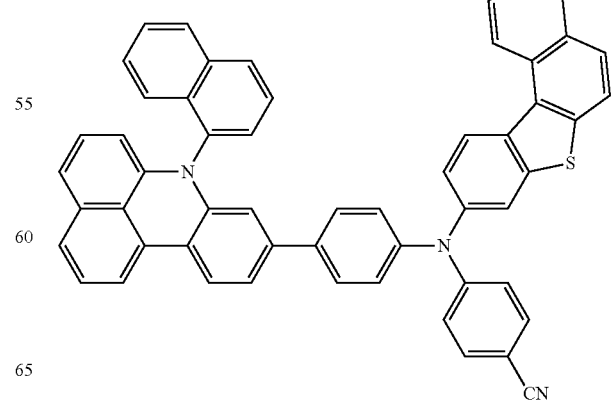

P1-19
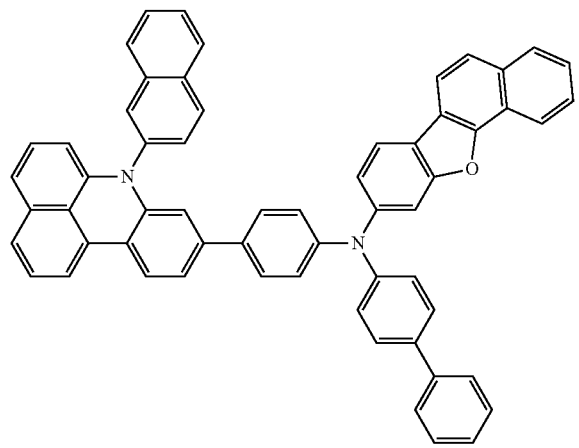
P1-20
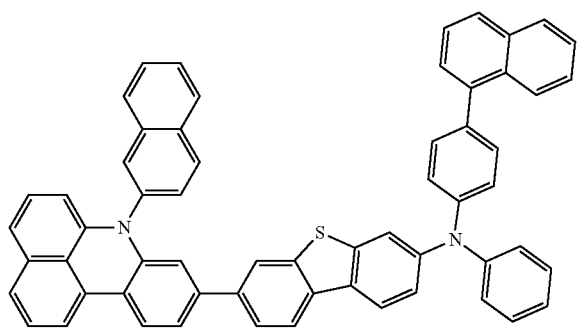
P1-21
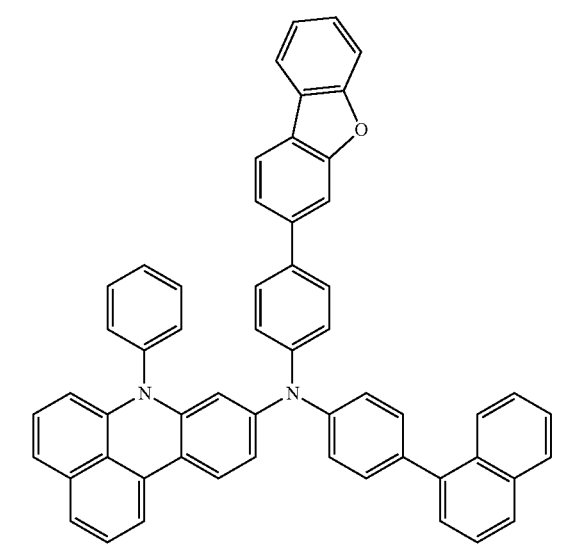
P1-22
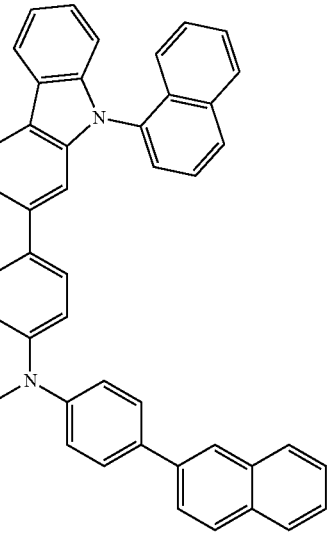
P1-23
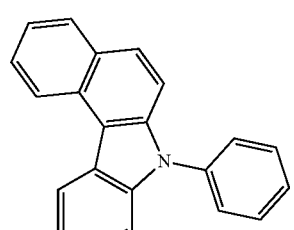
P1-24
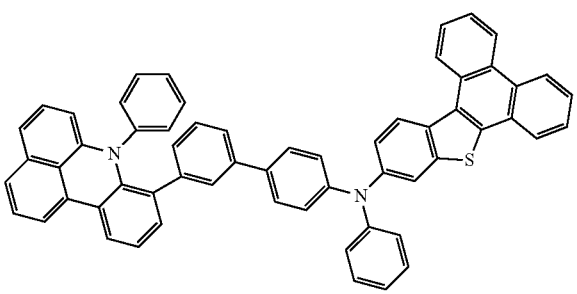

P1-25
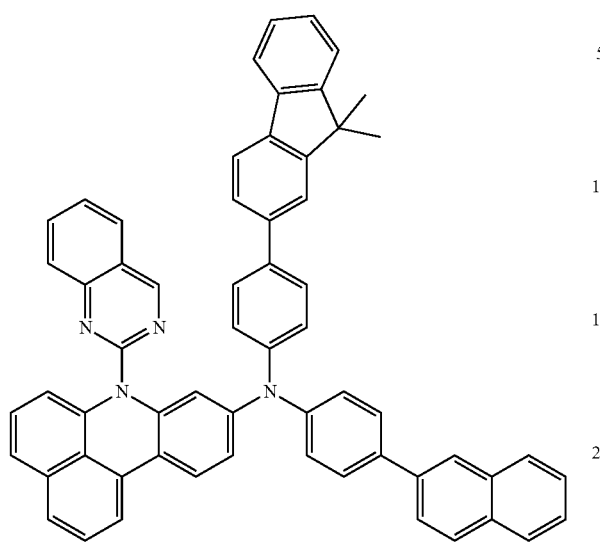
P1-26
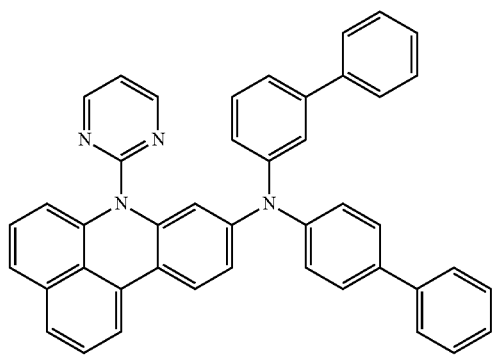
P1-27
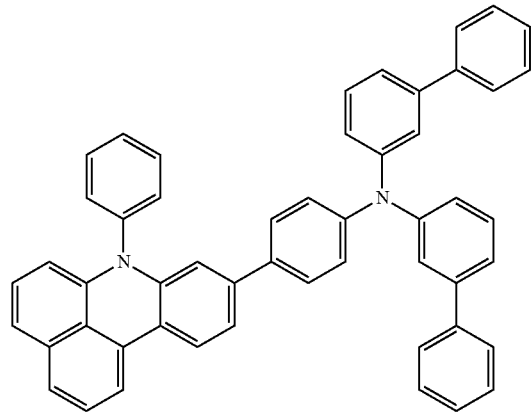
P1-28
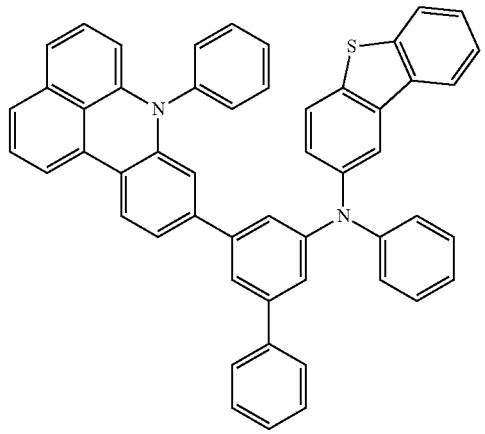
P1-29
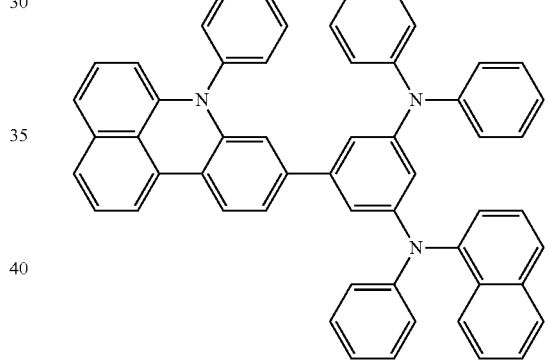
P1-30
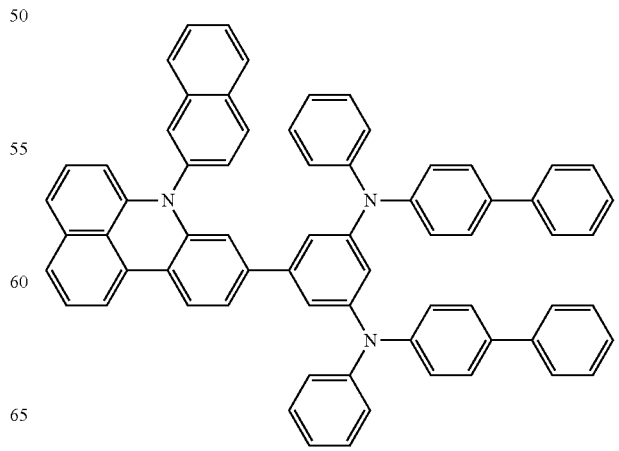

P1-31
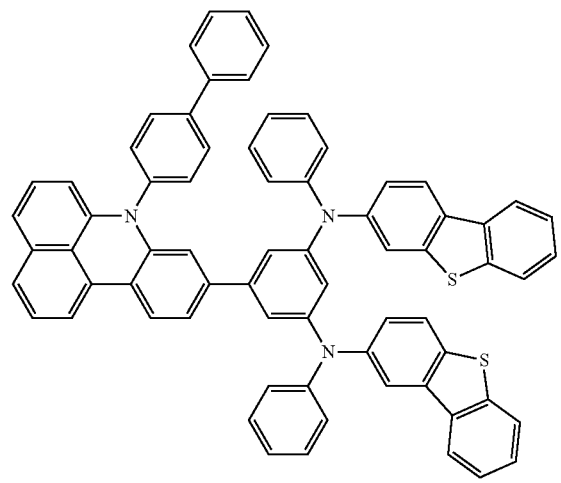
P1-32
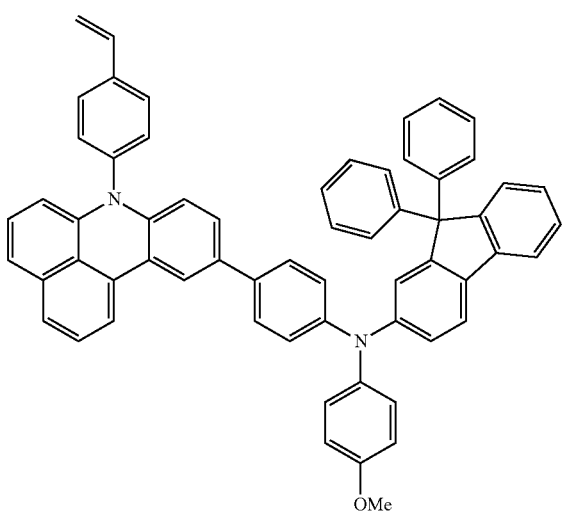
P1-33
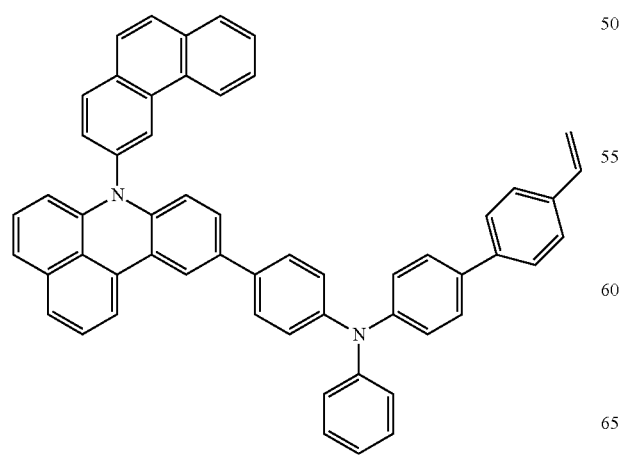
P1-34
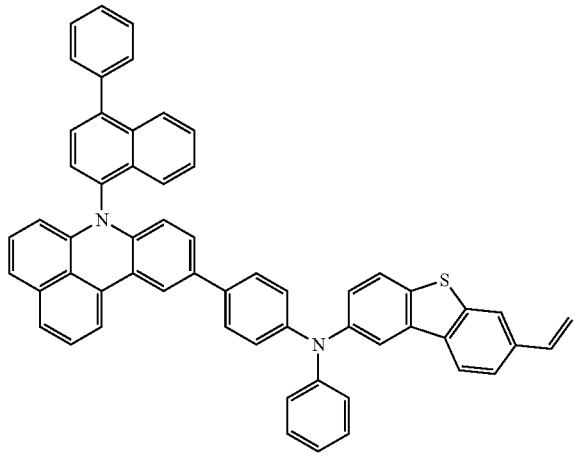
P1-35
P1-36
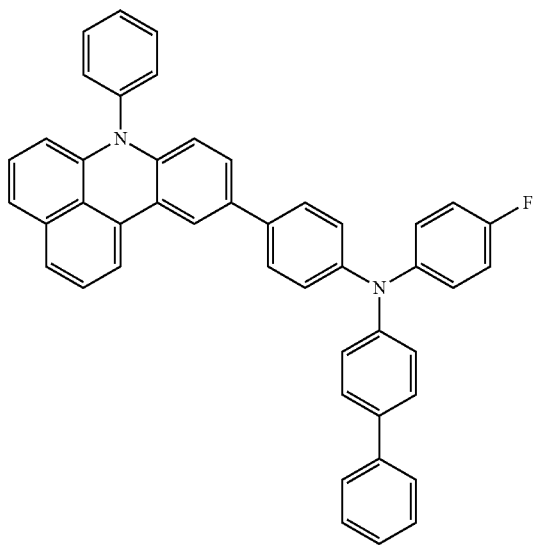

P1-37
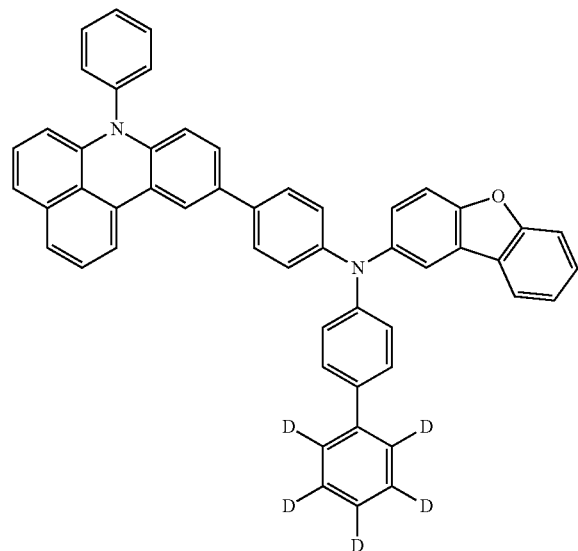
P1-38
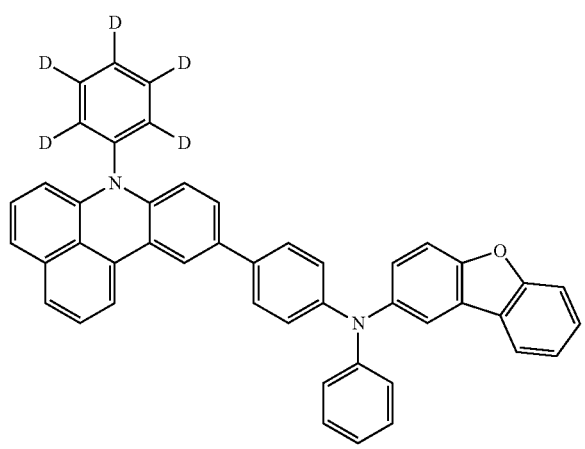
P1-39
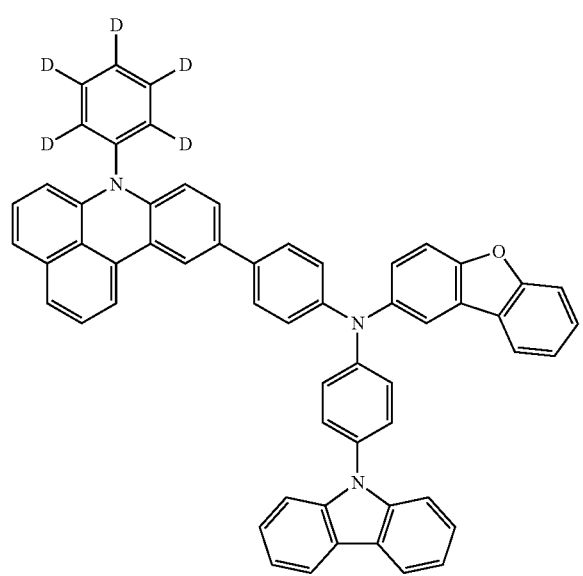
P1-40
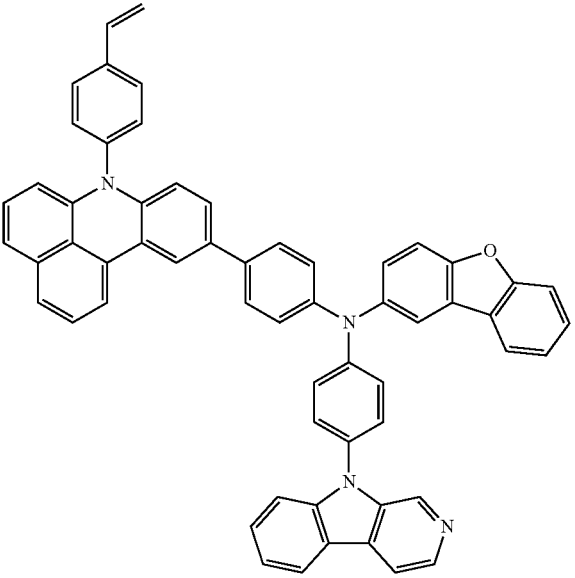
P2-1
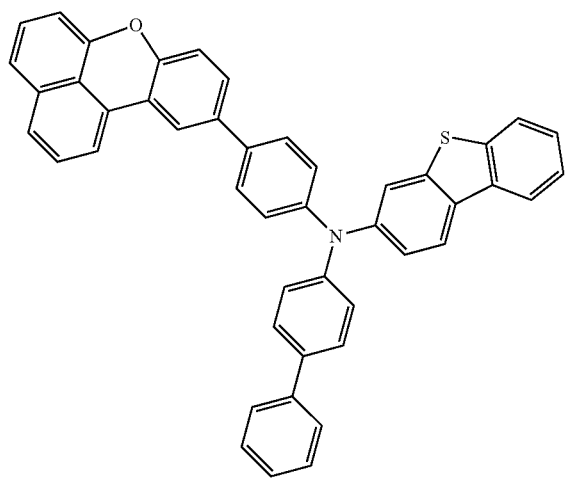
P2-2
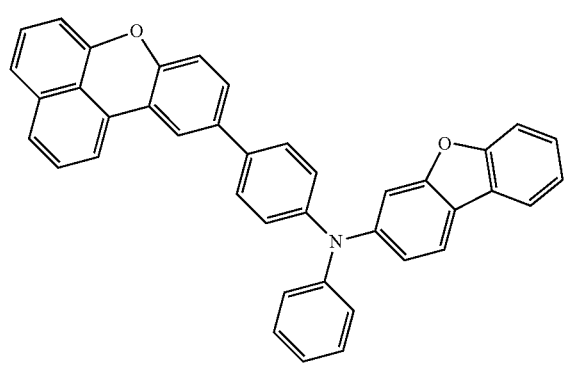

P2-3
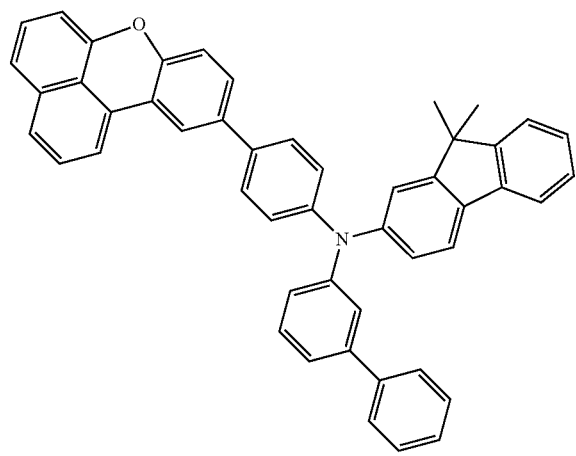
P2-4
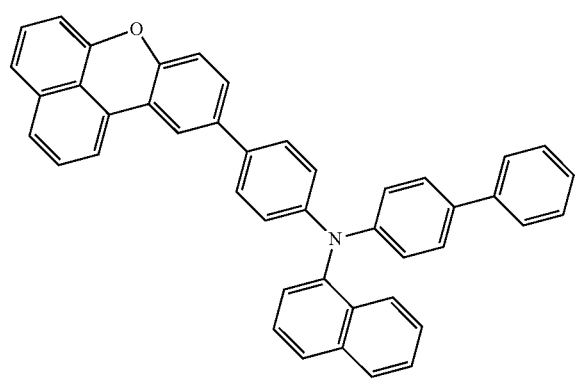
P2-5
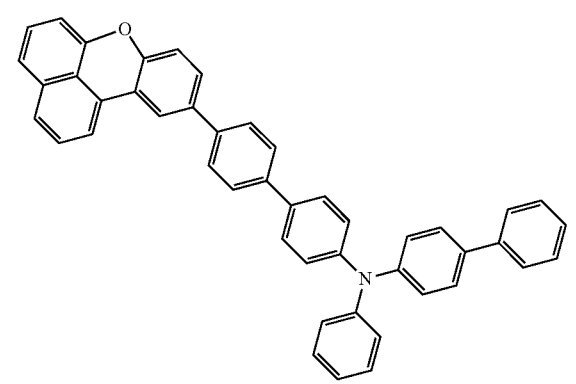
P2-6
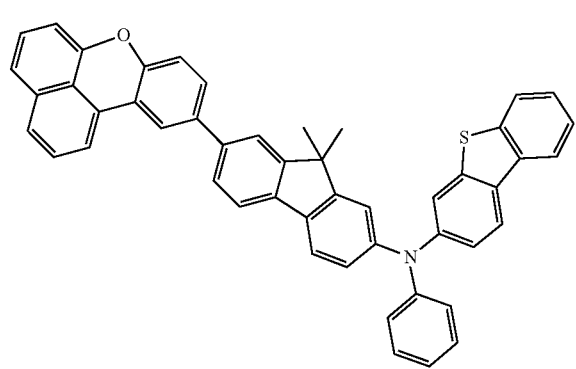
P2-7
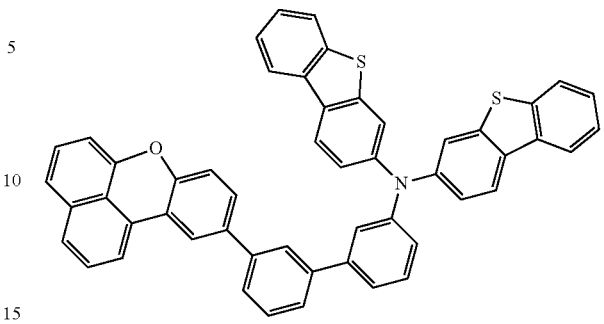
P2-8
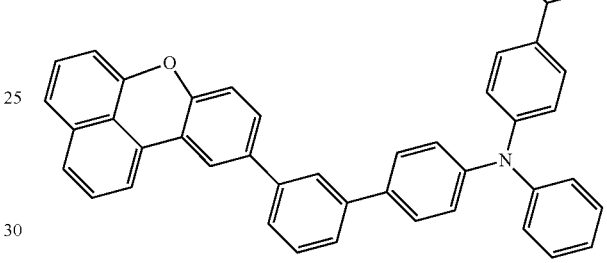
P2-9
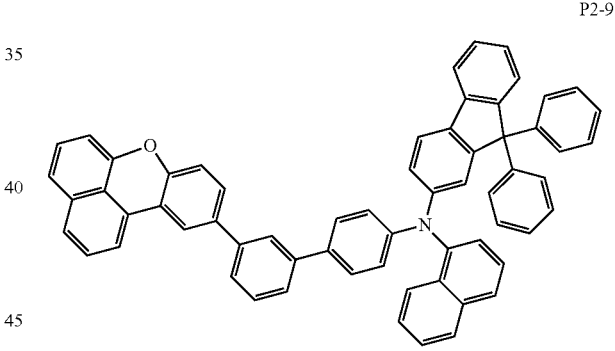
P2-10
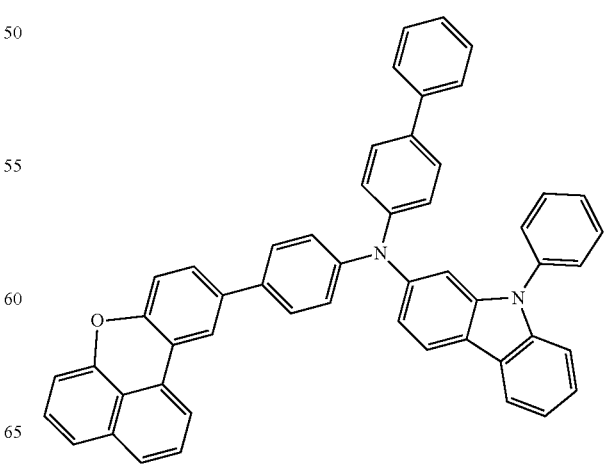

-continued
P2-11
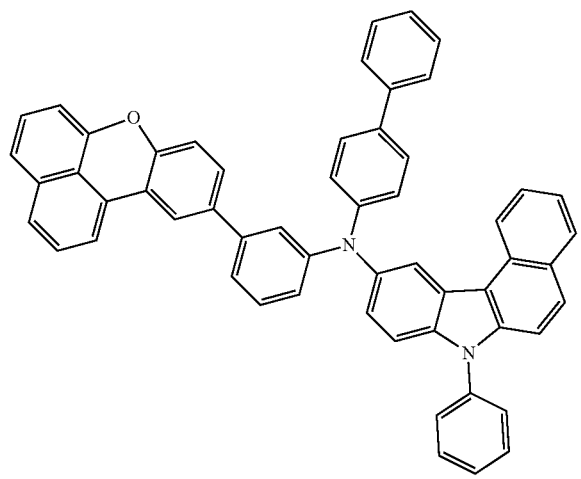
P2-12
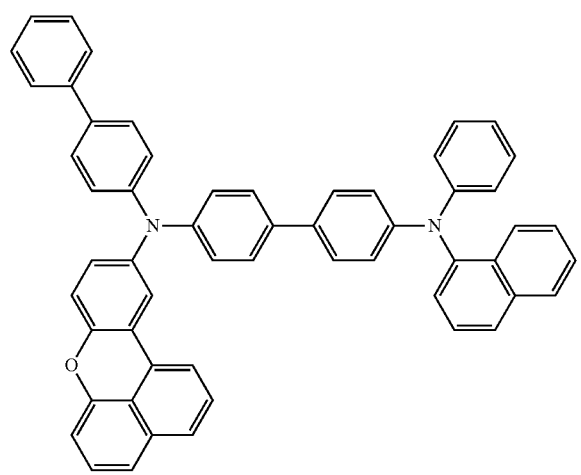
P2-13
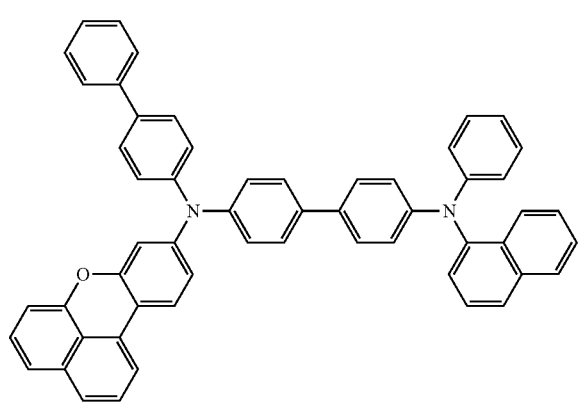
-continued
P2-14
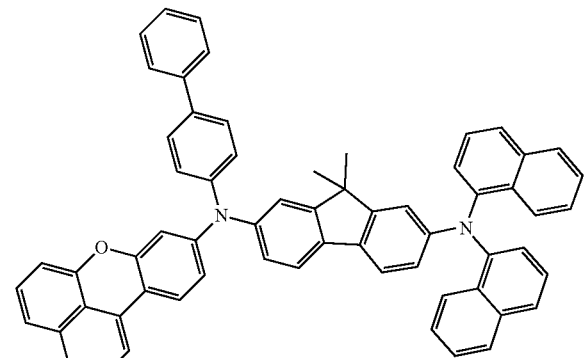
P2-15
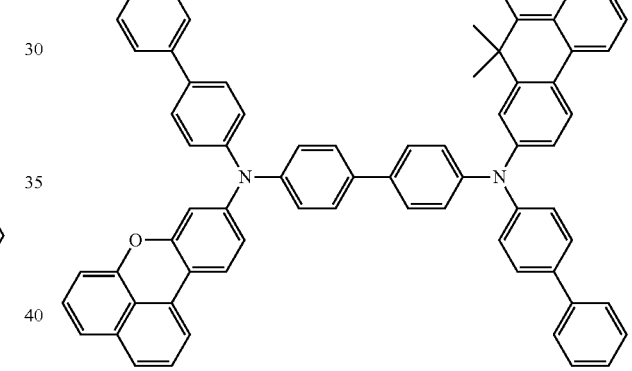
P2-16

-continued
P2-17
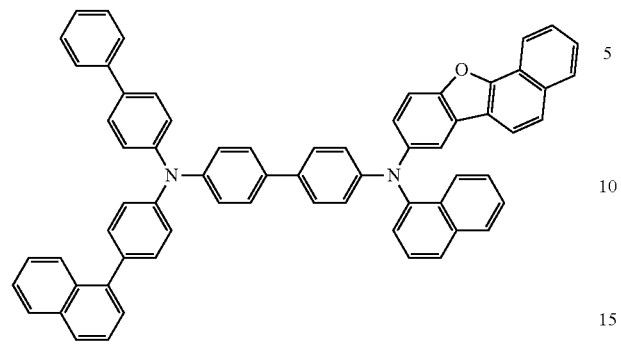
P2-18
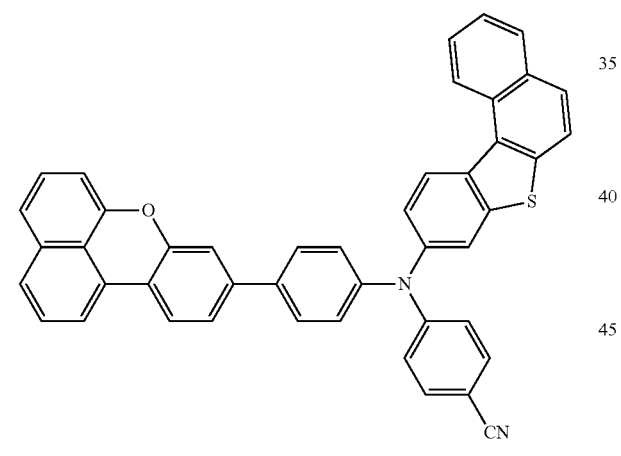
P2-19
P2-20
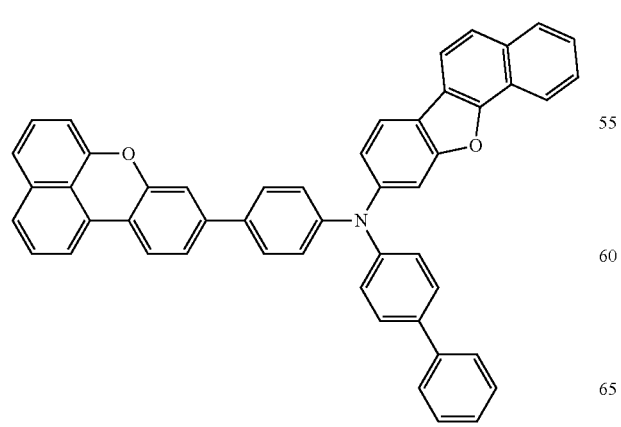
-continued
P2-21
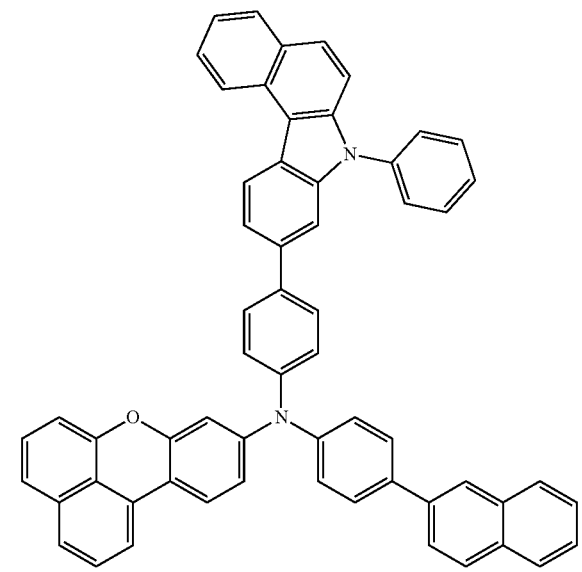
P2-22
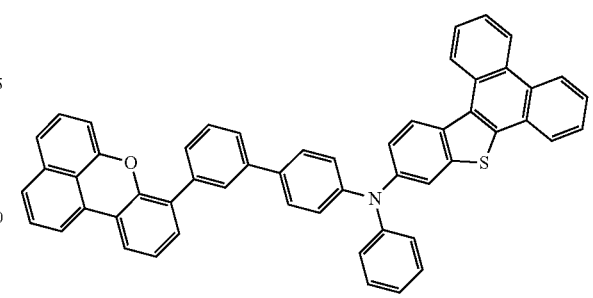
P2-23
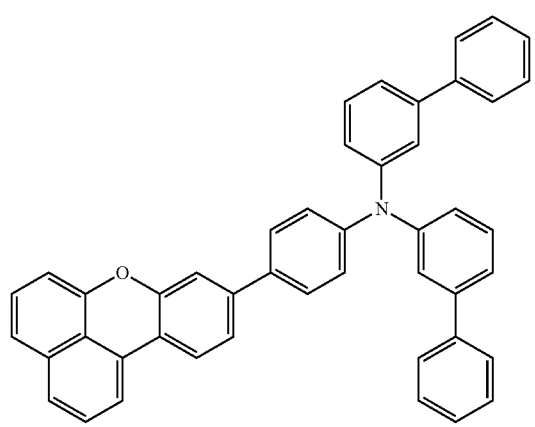

P2-24
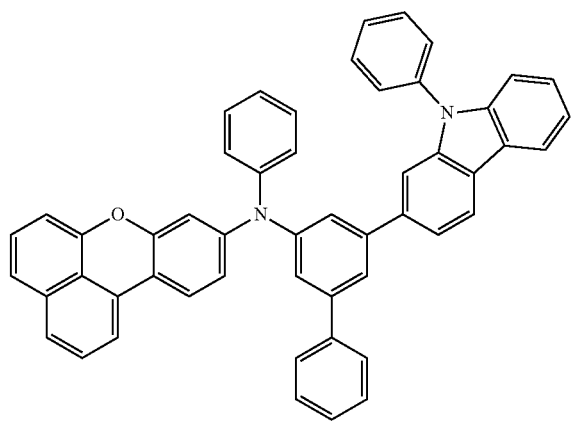
P2-25
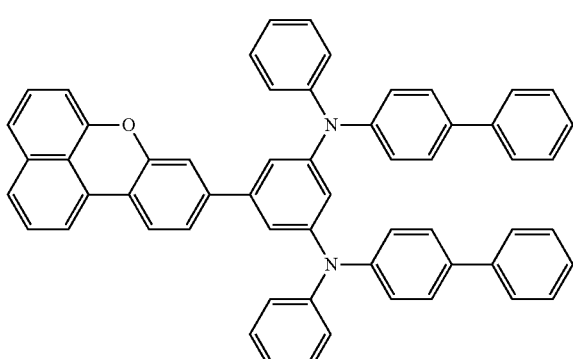
P2-26
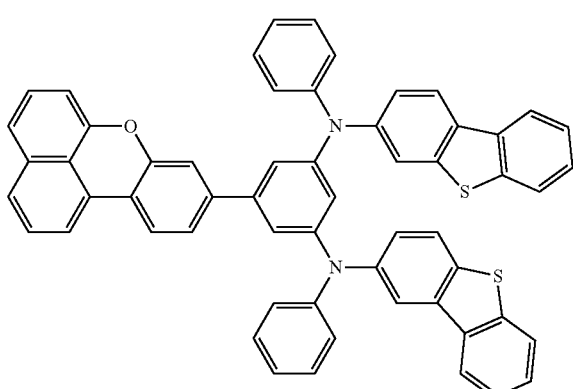
P2-27
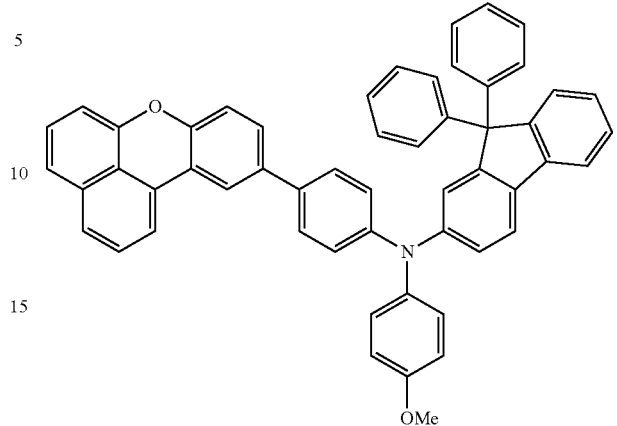
P2-28
P2-29
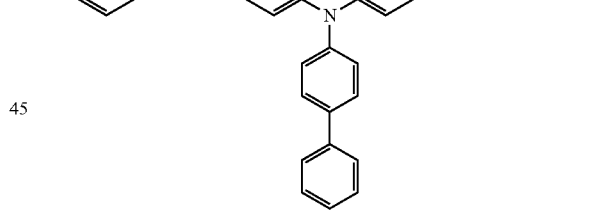
P2-30
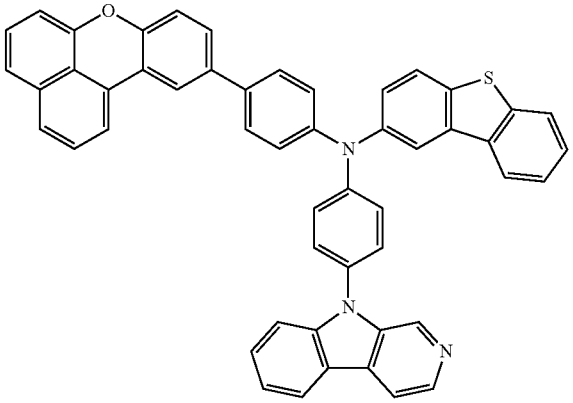

-continued
P3-1
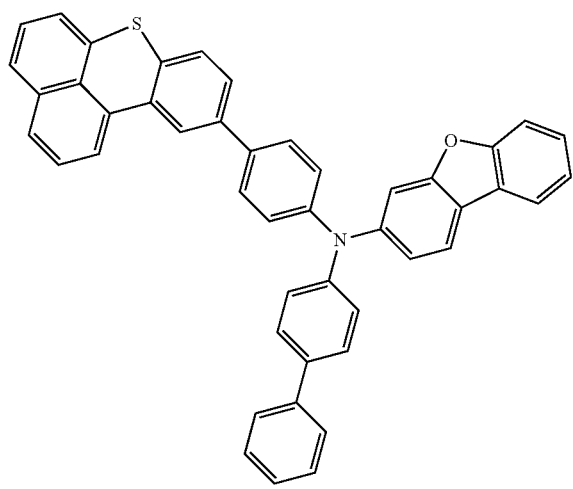
P3-2
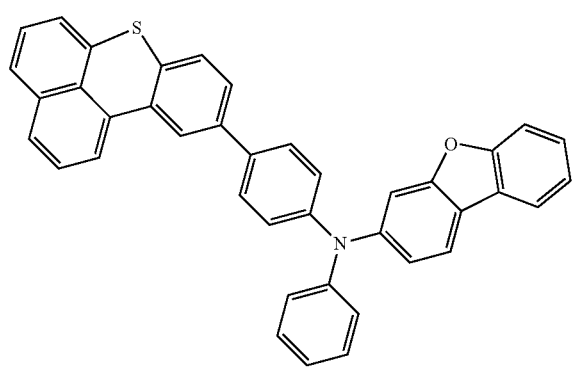
P3-3
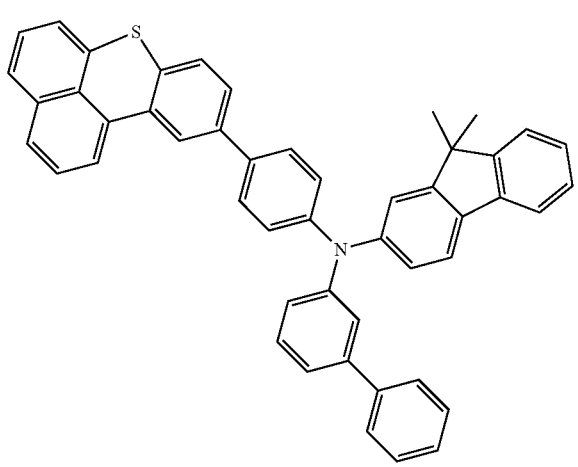
-continued
P3-4
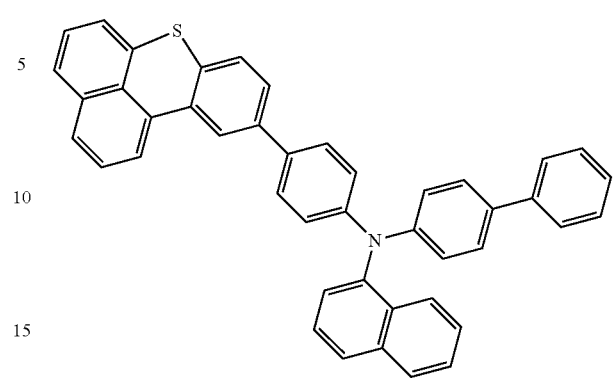
P3-5
P3-6
P3-7
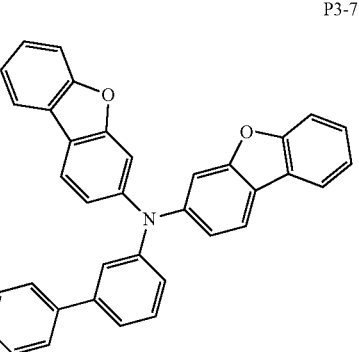

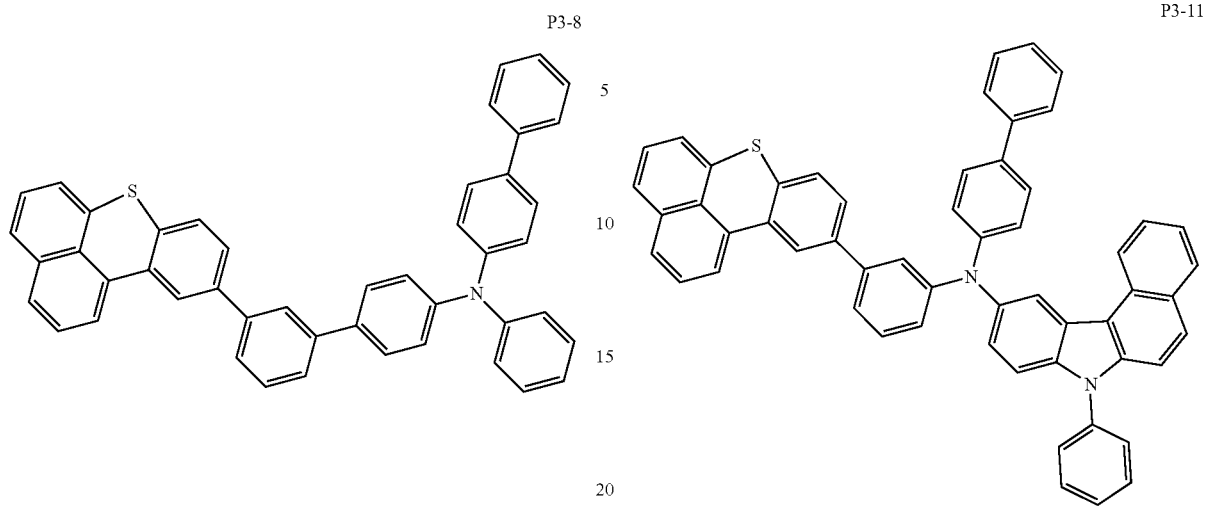
P3-8
P3-11
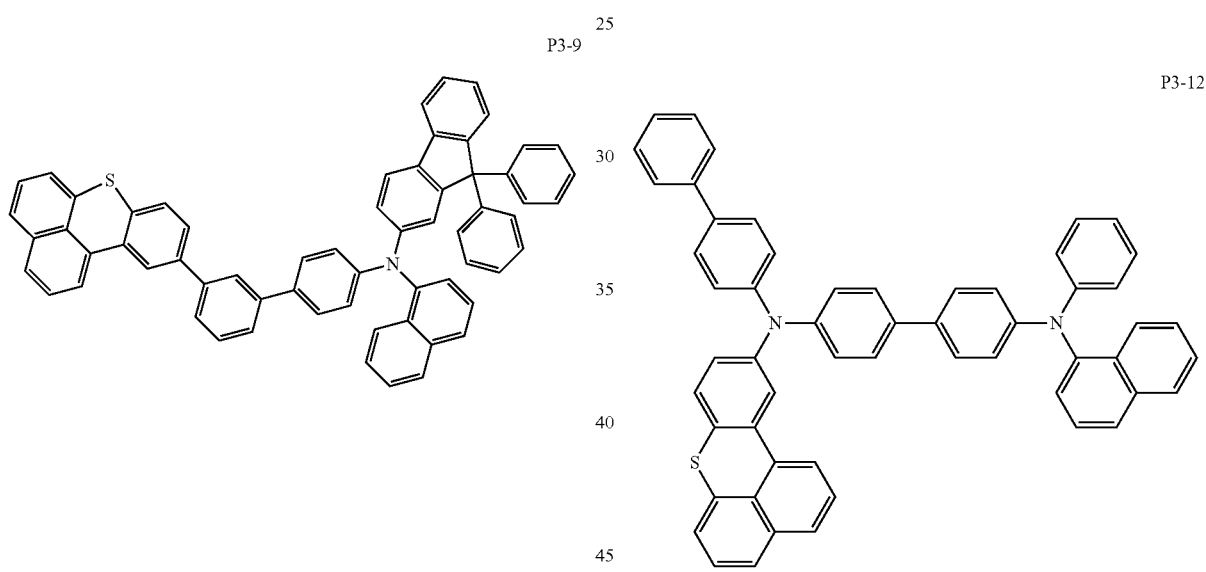
P3-9
P3-12
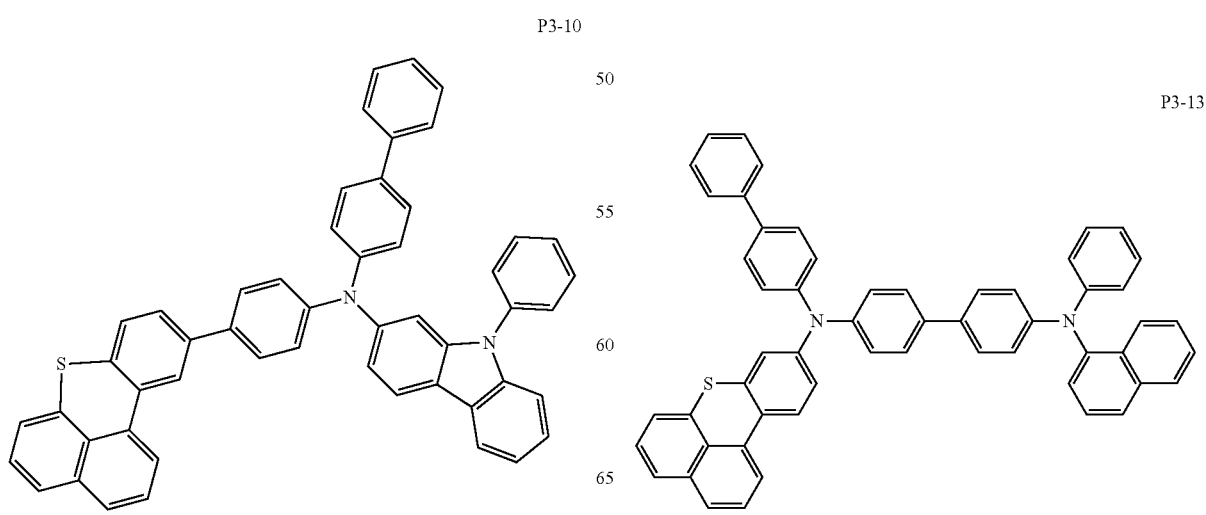
P3-10
P3-13

-continued
P3-14
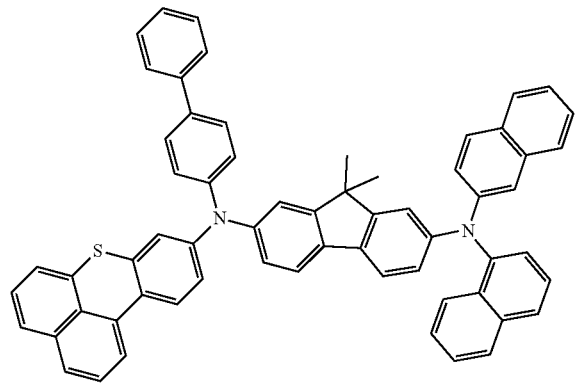
P3-18
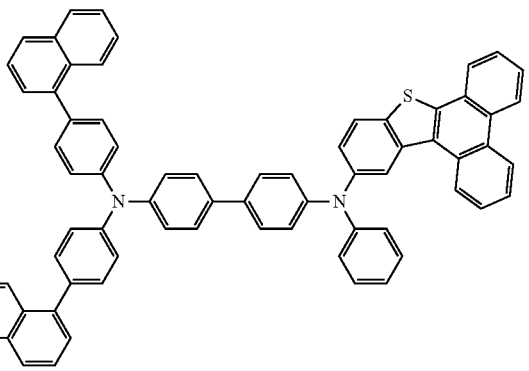
P3-15
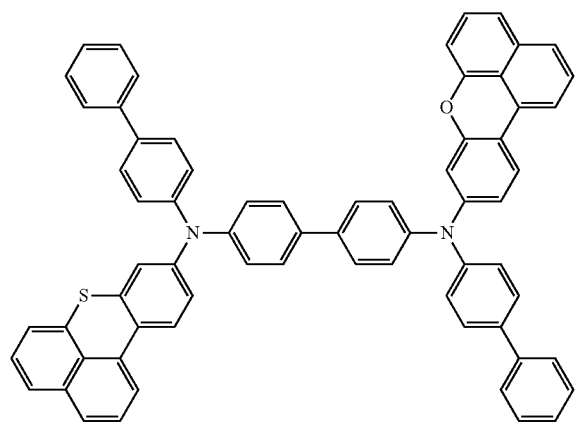
P3-19
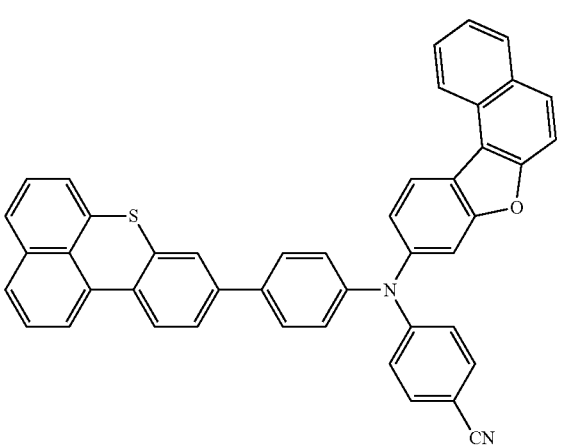
P3-16
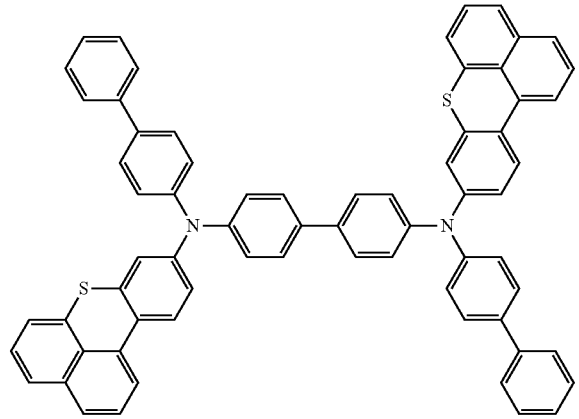
P3-17
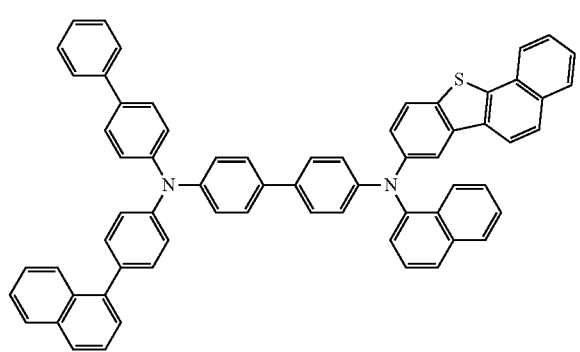
P3-20
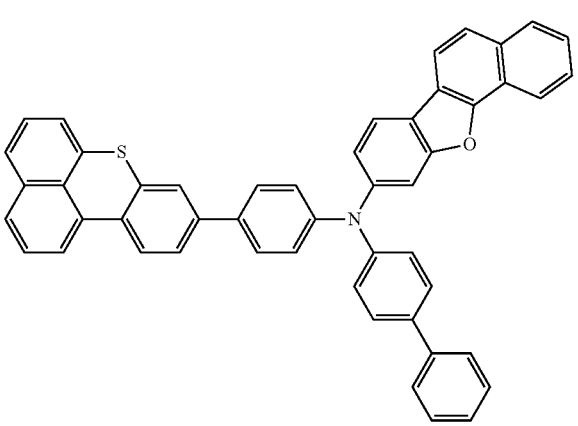

P3-21
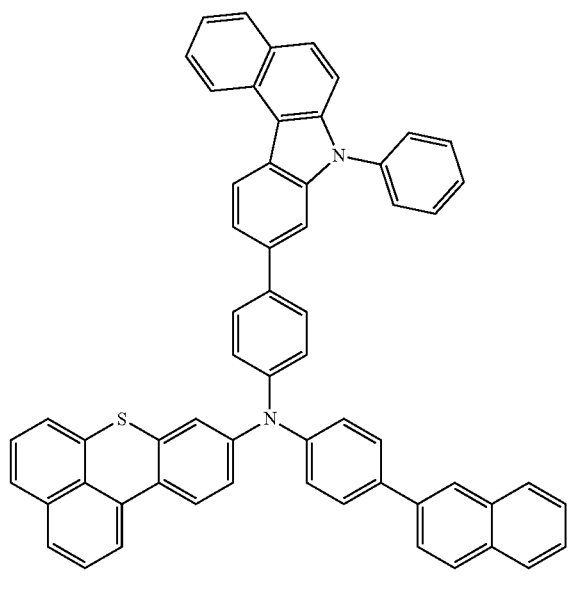
P3-24
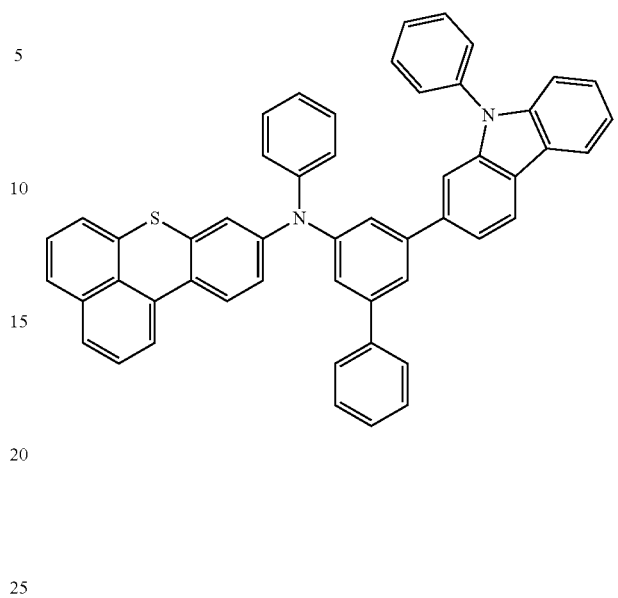
P3-22
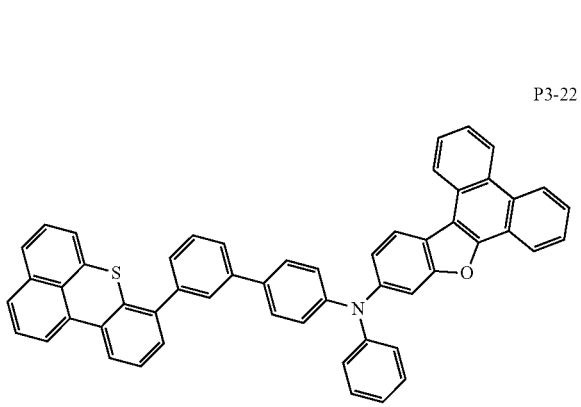
P3-25
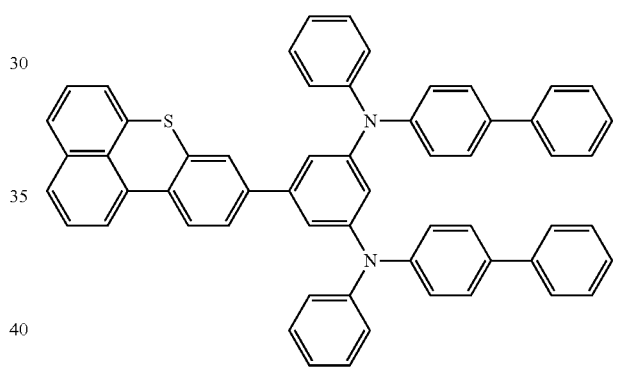
P3-23
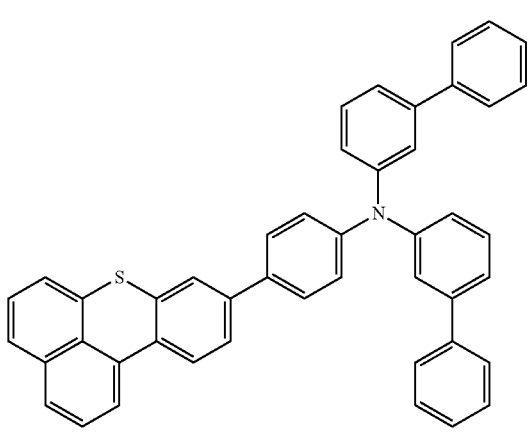
P3-26
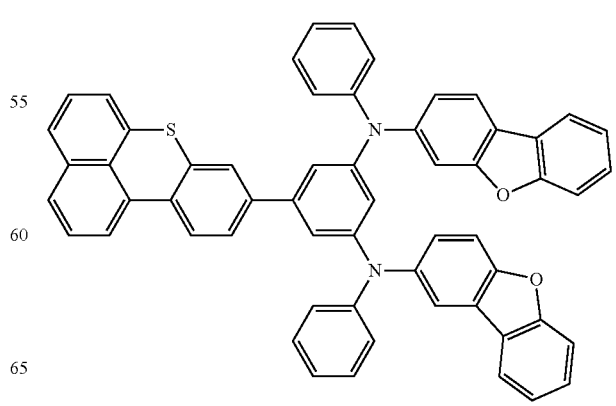

P3-27
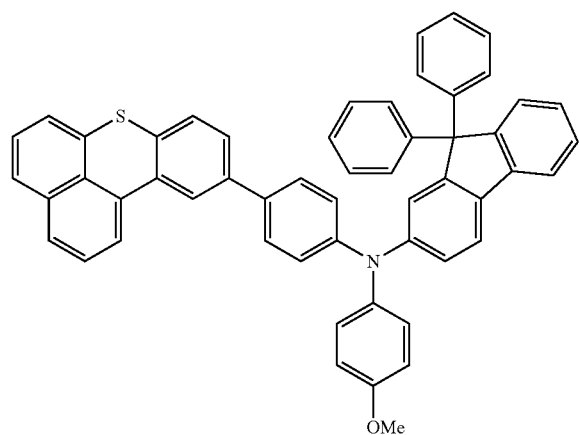
P4-1
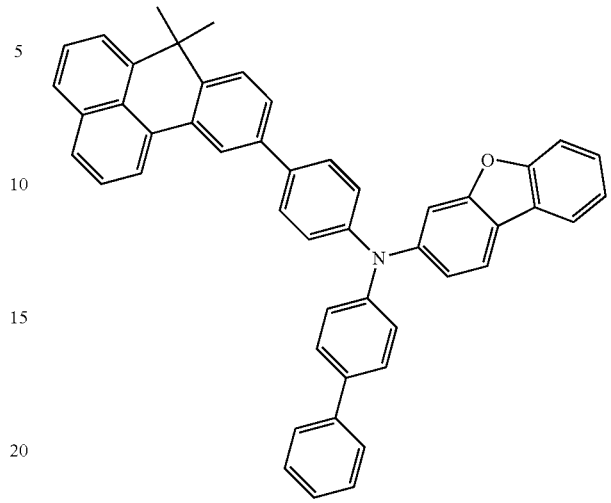
P3-28
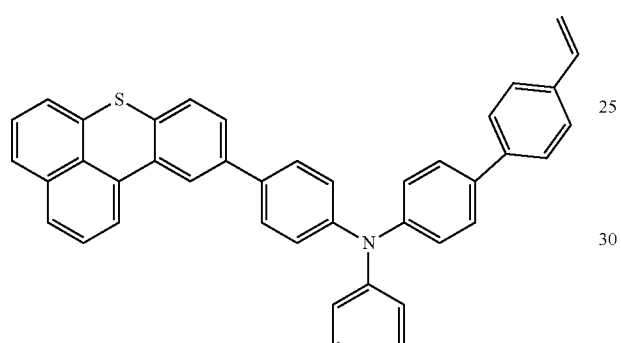
P4-2
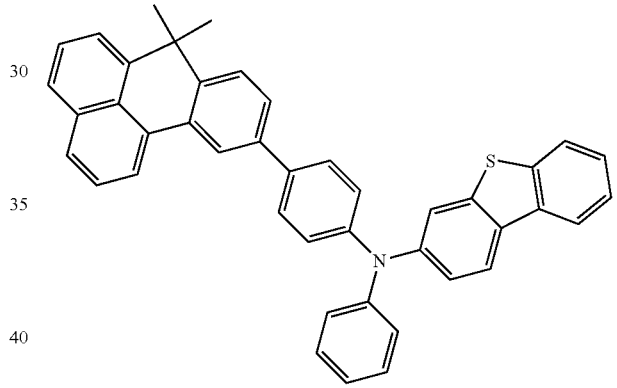
P3-29
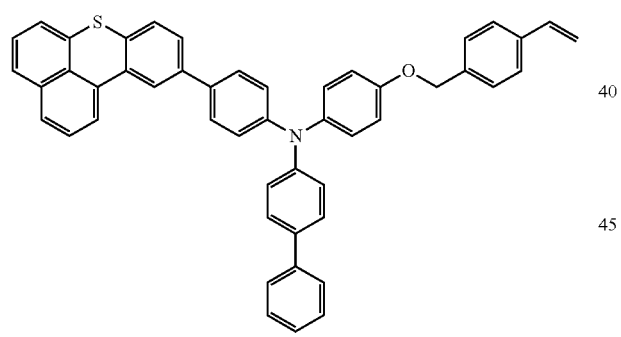
P3-30
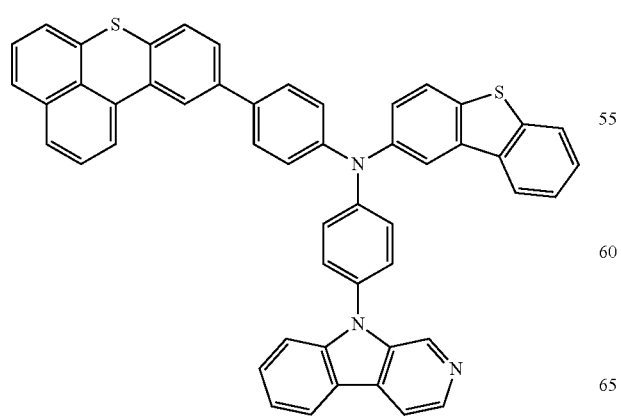
P4-3
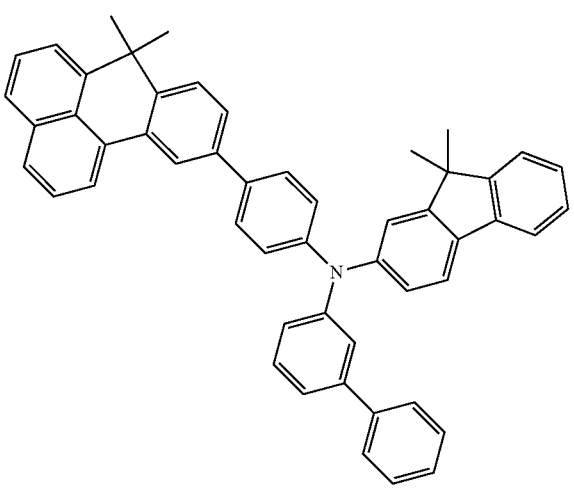

P4-4
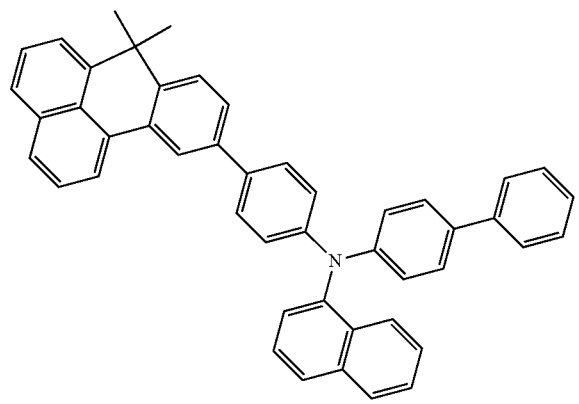
P4-5
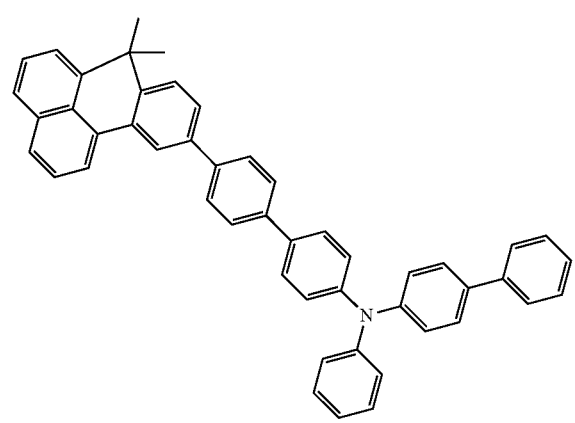
P4-6
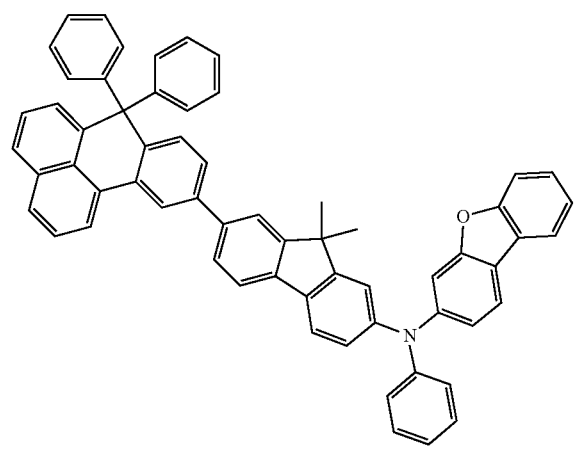
P4-7
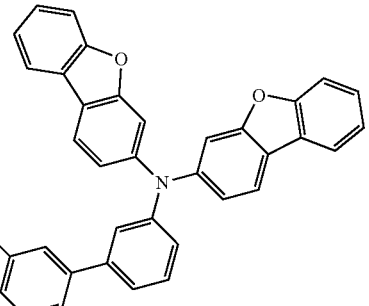
P4-8
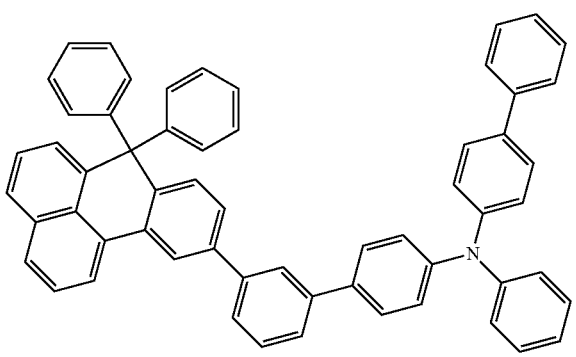
P4-9
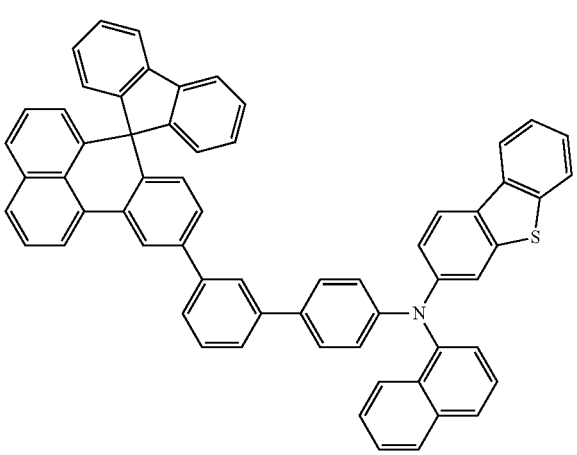

P4-10
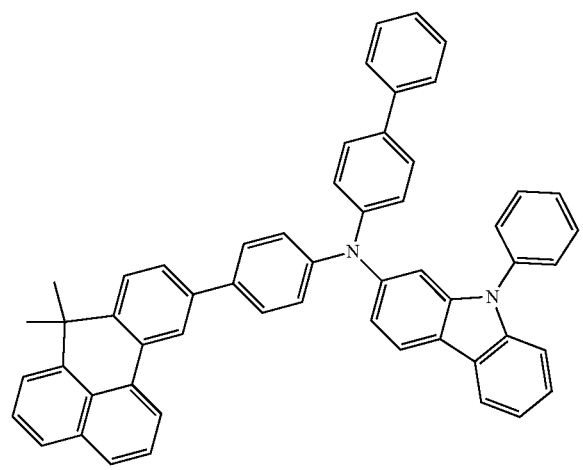
P4-11
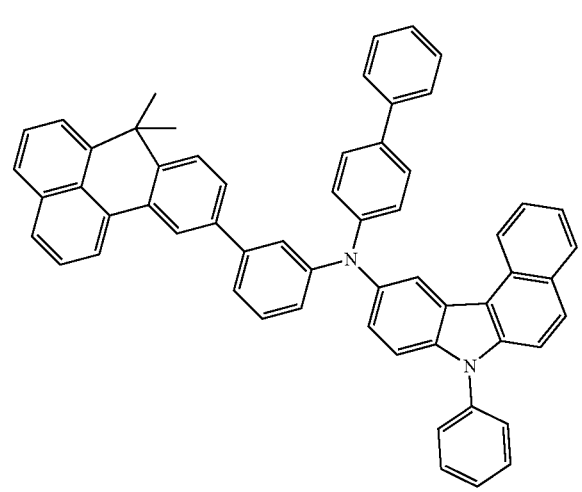
P4-12
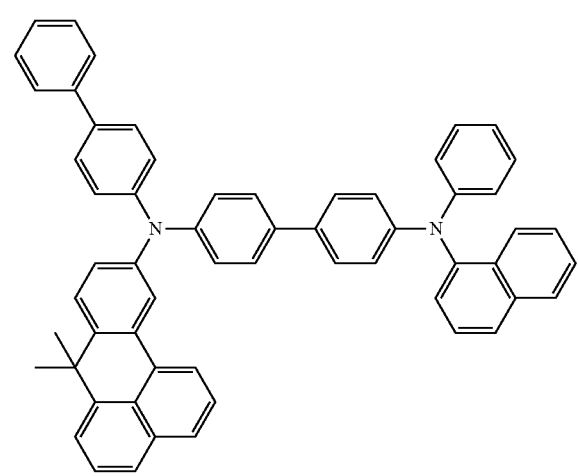
P4-13
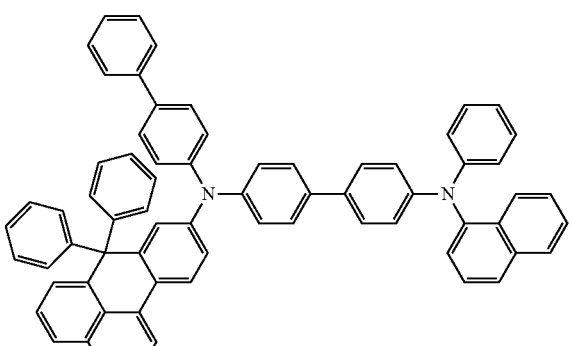
P4-14
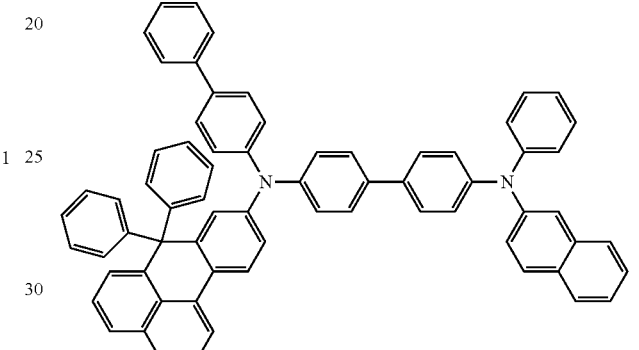
P4-15
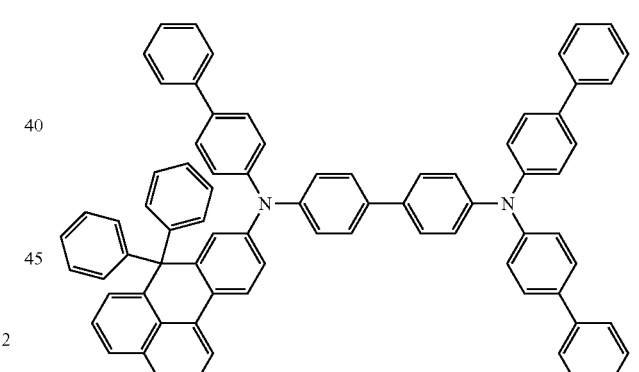
P4-16
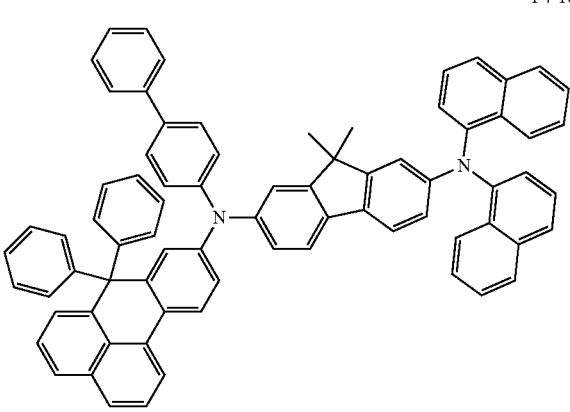

P4-17
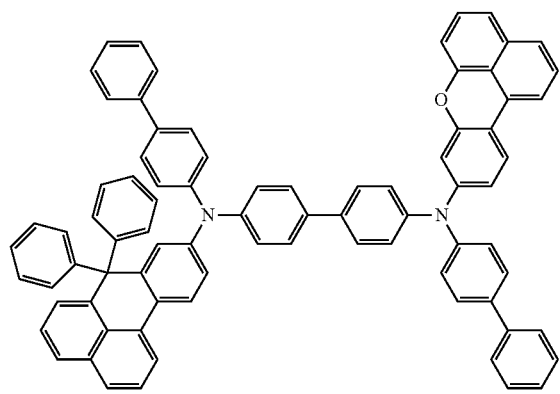
P4-18
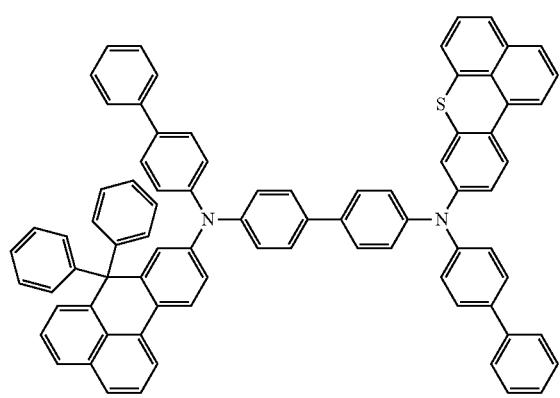
P4-19
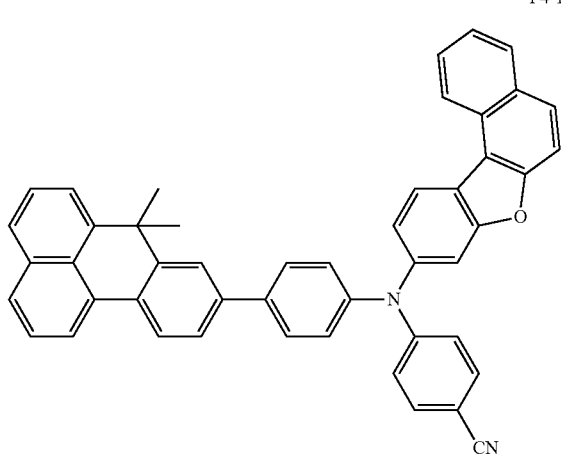
P4-20
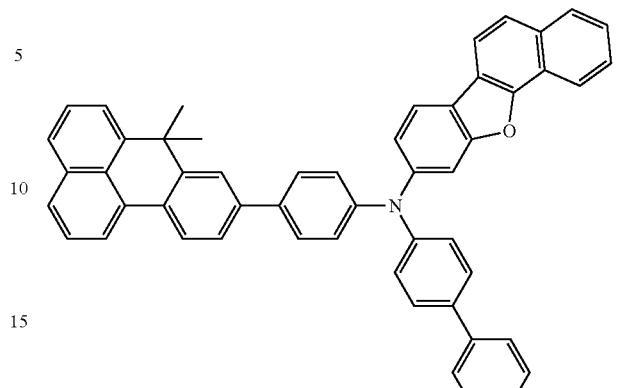
P4-21
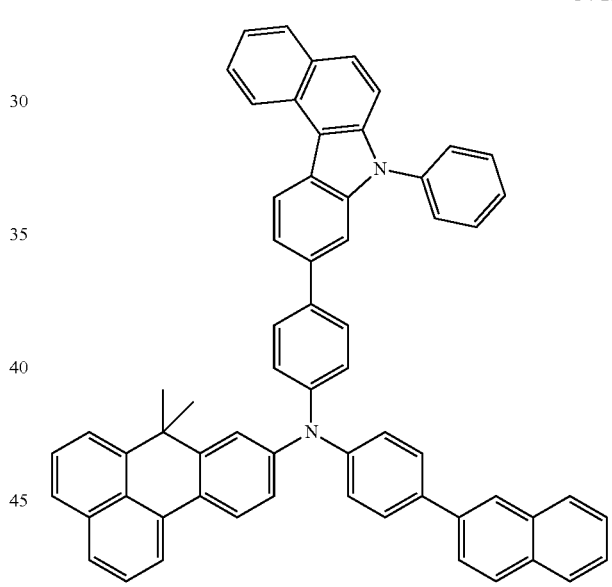
P4-22
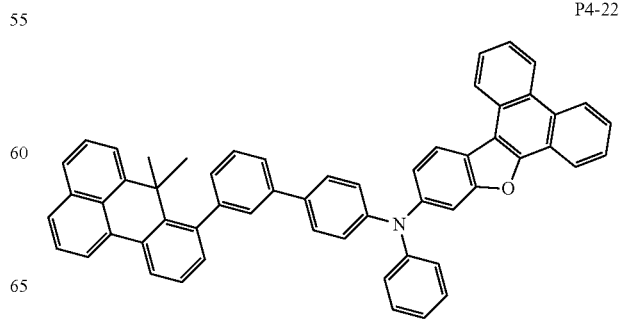

P4-23
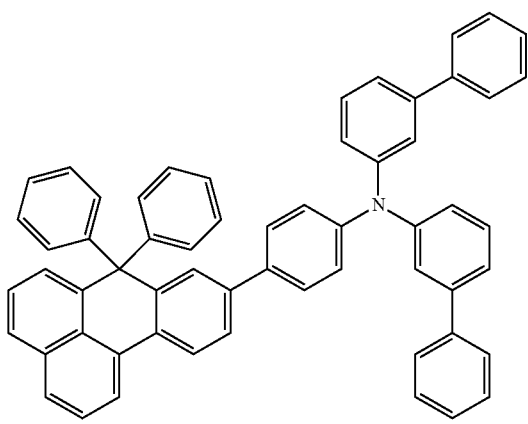
P4-26
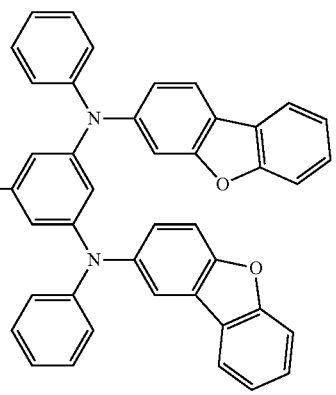
P4-24
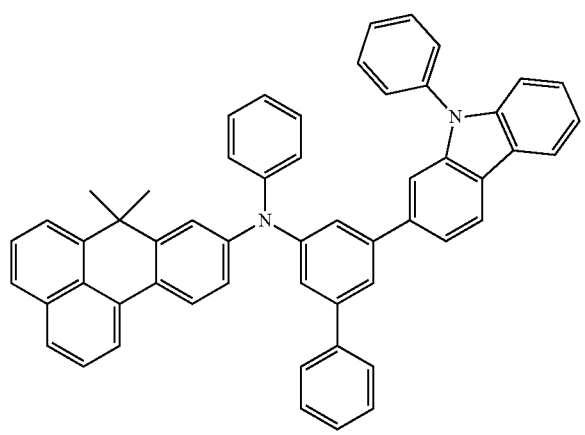
P4-27
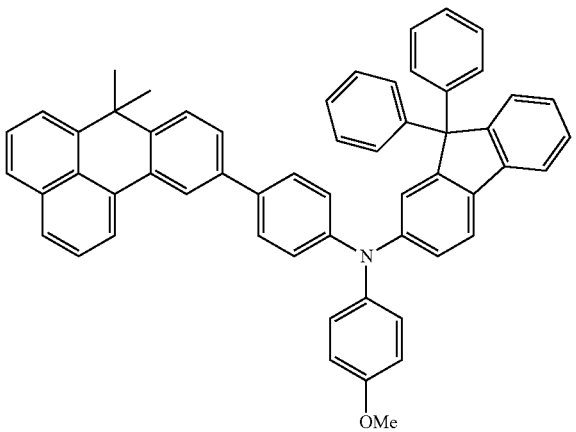
P4-25
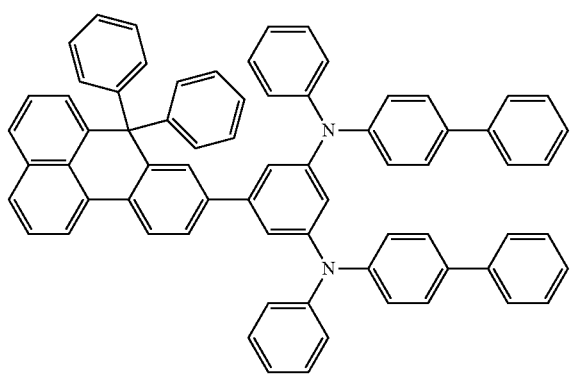
P4-28
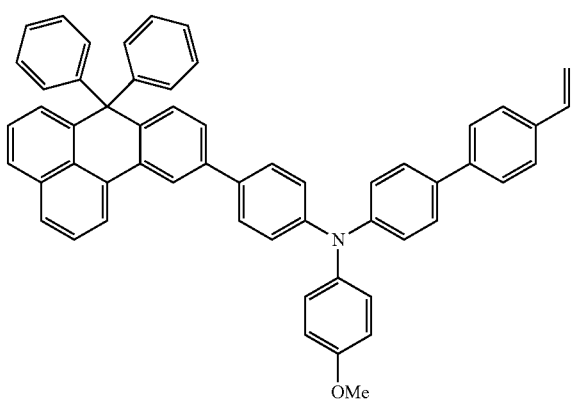

-continued

P4-29

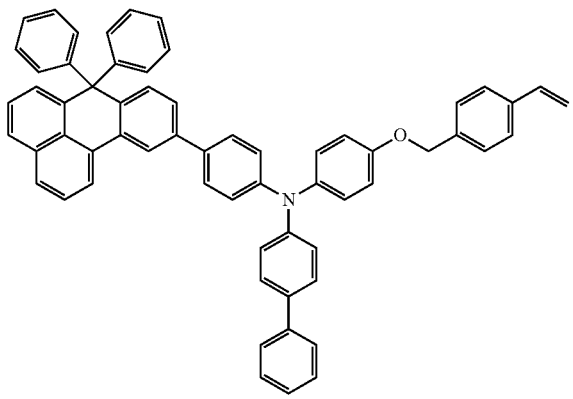

P4-30

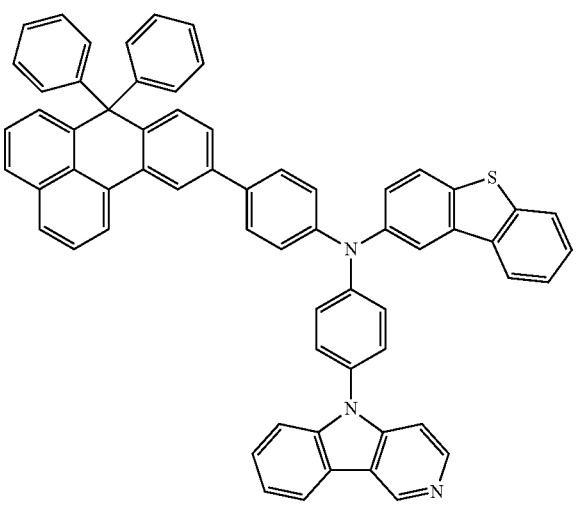

In another aspect of the present invention, a compound for an organic electric element represented by the above Formula 1 is provided.

In another aspect of the present invention, an organic electric element comprising the compound represented by the above Formula 1 is provided.

The organic electric element may comprise a first electrode, a second electrode, and an organic material layer disposed therebetween. The organic material layer may comprise the compound represented by Formula 1. The compound represented Formula 1 may be contained in at least one layer of a hole injection layer, a hole transport layer, an emission-auxiliary layer, or a light emitting layer of the organic material layer. Specially, the organic electric element comprising the organic material layer comprising at least one of the compounds represented by individual Formulas P1-1 to P1-40, P2-1 to P2-30, P3-1 to P3-30 and P4-1 to P4-30 is provided.

In another aspect of the present invention, the present invention provides an organic electric element further including at least a layer to improve luminous efficiency which is formed on at least one of the sides the first and second electrodes, which is opposite to the organic material layer.

Meanwhile, the compounds comprised in an organic material layer may be the same kind, or a mixture comprising two or more different kinds of compounds represented by Formula 1. For example, a hole transport layer of an organic material layer may comprise two different compounds such as the compound P1-1 and P1-2 or three different compounds such as the compound P1-1, P1-2 and P1-3.

Hereinafter, Synthesis Examples of the inventive compound represented by Formula 1 according to one embodiment of the present invention and Preparation Examples of an organic electric element will be described in detail by way of example. However, the following examples are only for illustrative purposes and are not intended to limit the scope of the present invention.

SYNTHESIS EXAMPLE

The final products of the present invention represented by Formula 1 can be synthesized by reaction of Sub 1 and Sub 2 as illustrated in, but not limited to, the following Reaction Scheme 1 or reaction of Sub 3 and Sub 4 as illustrated in, but not limited to, the following Reaction Scheme 2.

<Reaction Scheme 1>

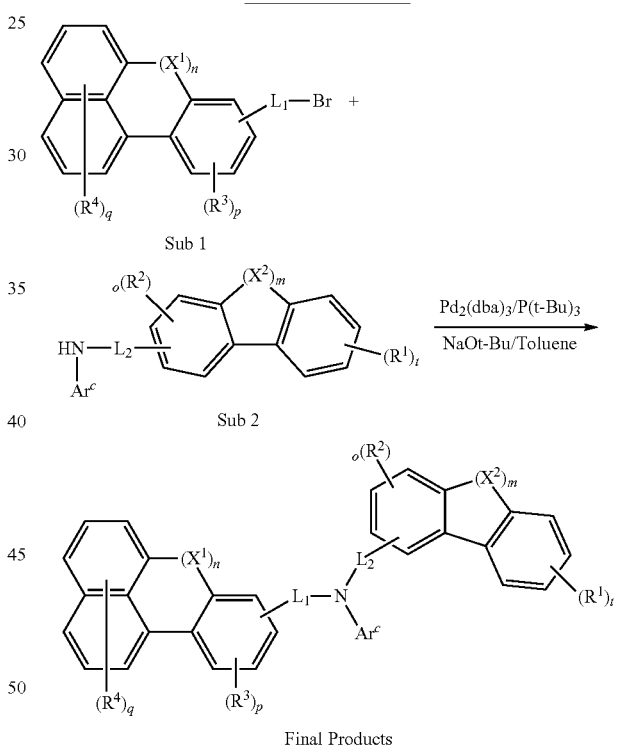

<Reaction Scheme 2>

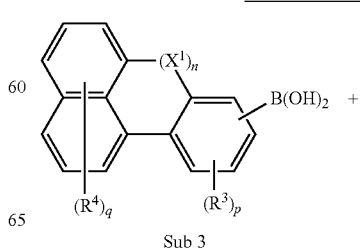

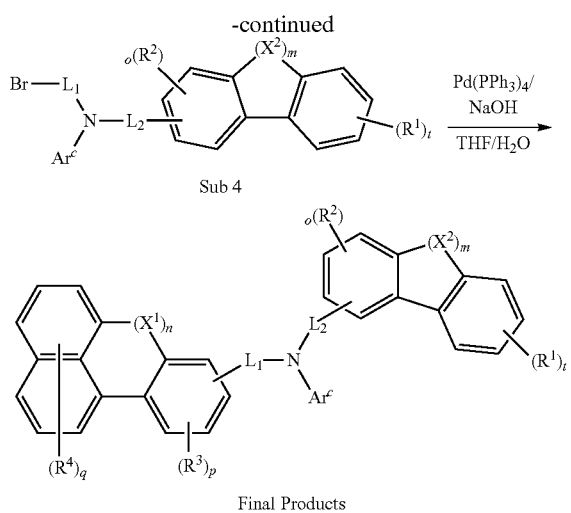

Sub 4

Final Products

I. Synthesis Example of a Starting Material
1. Synthesis of S-1 and S-3

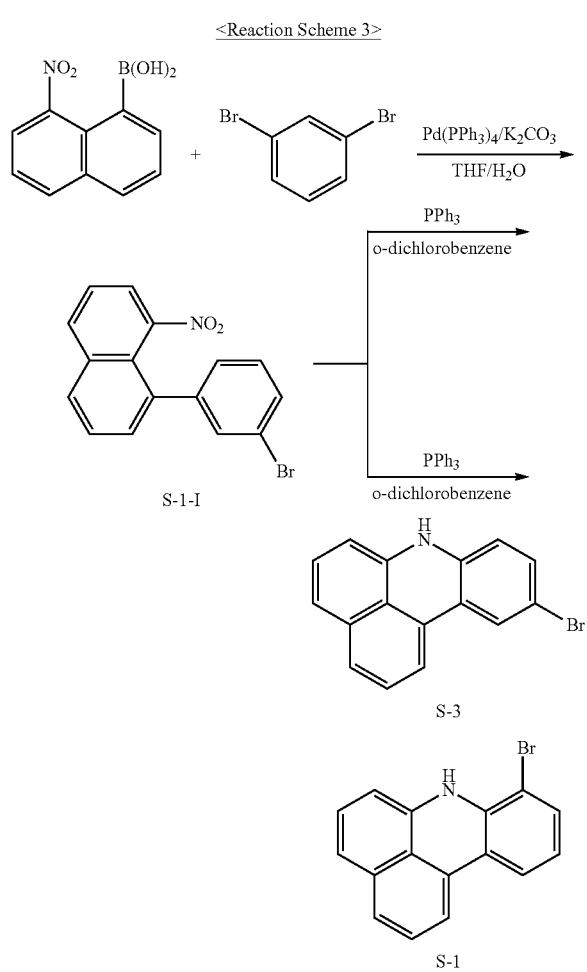

(1) Synthesis of S-1-I (8-nitronaphthalen-1-yl)boronic acid (30 g, 138.3 mmol), 1,3-dibromobenzene (35.9 g, 152.1 mmol), Pd(PPh3)4 (7.99 g, 6.91 mmol) and K$_2$CO$_3$ (57.3 g, 414.8 mmol) were loaded into a round bottom flask and then the mixture was dissolved in anhydrous THF (608 mL) and water (304 mL), followed by refluxing for 24 hours. After the completion of the reaction, a reaction product was cooled to room temperature. After that, the product was extracted with CH$_2$Cl$_2$ and washed with water. After that, a trace amount of water in the product was removed with MgSO$_4$. And then, the product was filtered under reduced pressure and concentrated. The concentrated resultant was separated by silica gel column chromatography and recrystallization, whereby compound S-1-I was obtained in the amount of 34.5 g in 76% yield.

(2) Synthesis of S-1 and S-3

Compound S-1-I (34.5 g, 105.1 mmol) and PPh$_3$ (68.94 g, 263 mmol) was dissolved in o-dichlorobenzene, followed by refluxing for 24 hours. After the completion of the reaction, solvent in product was removed by distillation under reduced pressure. And then, the concentrated resultant was separated by silica gel column chromatography, and was then recrystallized, whereby compounds of S-1 (11.8 g, 38%) and S-3 (14.3 g, 46%) were obtained.

2. Synthesis of S-2

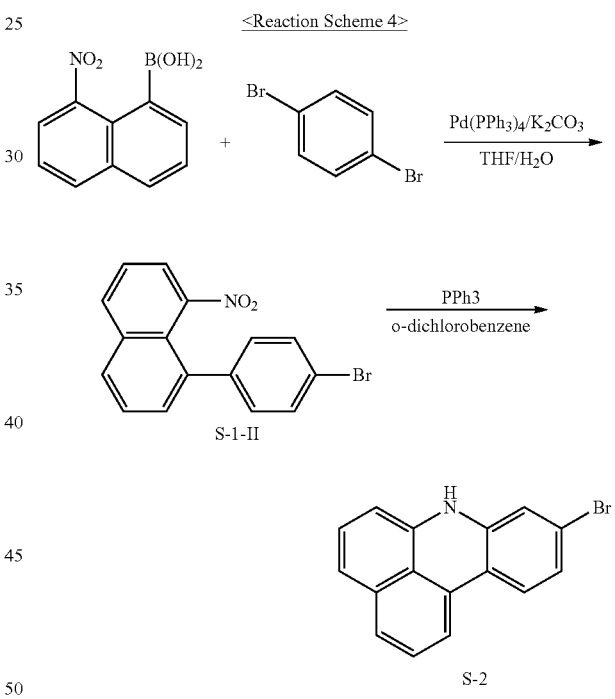

(1) Synthesis of S-1-II

Compound S-1-II was obtained in the amount of 35.4 g (78%) where (8-nitronaphthalen-1-yl)boronic acid (30 g, 138.3 mmol), 1,4-dibromobenzene (35.9 g, 152.1 mmol), Pd(PPh$_3$)$_4$ (7.99 g, 6.91 mmol) and K$_2$CO$_3$ (57.3 g, 414.8 mmol), THF (608 mL) and water (304 mL) were used in the same manner as described above for the synthesis of compound Sub S-1-I.

(2) Synthesis of S-2

Compound S-2 was obtained in the amount of 25.2 g (79%) where S-1-II (35.4 g, 107.9 mmol), PPh$_3$ (70.74 g, 269.7 mmol) and o-dichlorobenzene 442 mL were used in the same manner as described above for the synthesis of compound Sub S-1.

3. Synthesis of S-4 and S-6

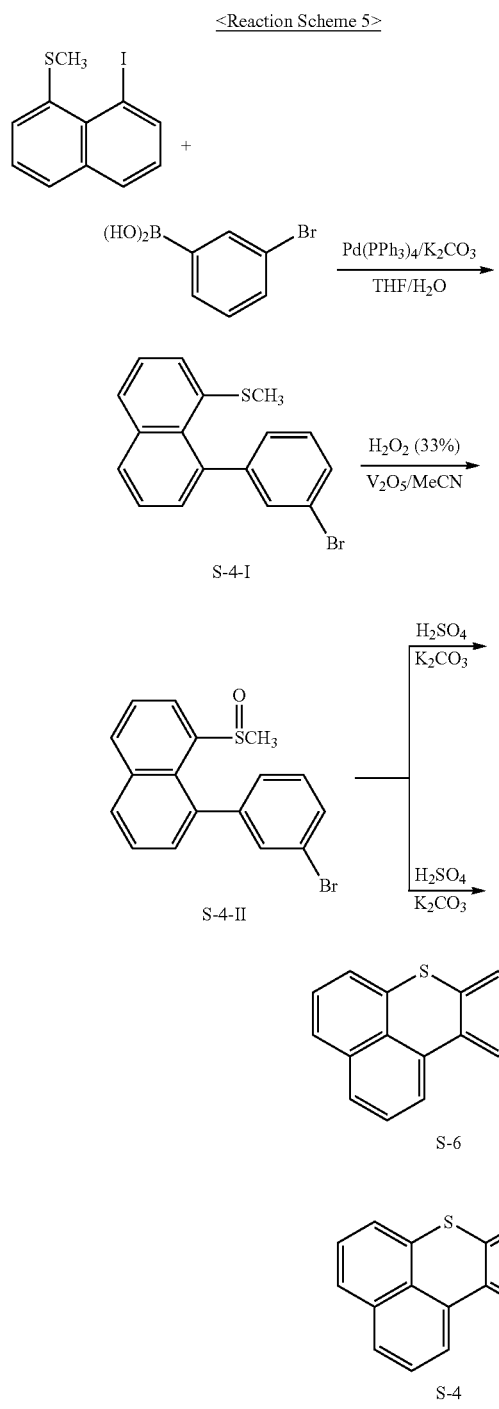

<Reaction Scheme 5>

(1) Synthesis of S-4-I

Compound S-4-I was obtained in the amount of 49.2 g (75%) where (3-bromophenyl)boronic acid (40 g, 199.2 mmol), (8-iodonaphthalen-1-yl) (methyl)sulfane (89.7 g, 298.8 mmol), Pd(PPh$_3$)$_4$ (11.5 g, 9.96 mmol), K$_2$CO$_3$ (82.6 g, 597.5 mmol), THF (876 mL) and water (438 mL) was loaded into a round bottom flask and then was used in the same manner as described above for the synthesis of compound Sub S-1-I.

(2) Synthesis of S-4-II

Compound S-4-I (49.2 g, 149.4 mmol) and V$_2$O$_5$ (2.7 g, 14.9 mmol) in a round bottom flask were dissolved in acetonitrile solution 750 mL under nitrogen atmosphere, and then were cooled to 0° C. in ice bath, followed by H$_2$O$_2$ (aq.) (20.9 mL, 224 mmol, 33%) was subsequently added and stirred at 10° C. for 1 hour. Upon the completion of the reaction, a reaction product was diluted by adding water 1 L. And then, the product was extracted with ethyl acetate 1.5 L after being heated slowly to room temperature. After that, water in the extracted organic layer was removed with MgSO$_4$. Then, the product was filtered under reduced pressure and concentrated, whereby a final product was obtained in the amount of 43.8 g in 85% yield.

(3) Synthesis of S-4 and S-6

H$_2$SO$_4$ (132 mL) was loaded into a round bottom flask and cooled to 0~5° C. After that, S-4-II (43.8 g, 126.9 mmol) was slowly added dropwise, followed by stirring at 25° C. for 2 hours. Upon the completion of the reaction, cold water 1270 mL was added slowly into the round bottom flask, followed by adding K$_2$CO$_3$ (aq.) in order to lower pH of a reaction product below 8. And then, a reaction product was extracted with ethyl acetate, and water in the extracted organic layer was removed with anhydrous MgSO$_4$. Then, the extracted product was filtered under reduced pressure and concentrated. The concentrated product was separated by silica gel column chromatography, and was then recrystallized, whereby compounds S-4 (13.11 g, 35%) and S-6 (16.11, 43%) were each obtained.

4. Synthesis of S-5

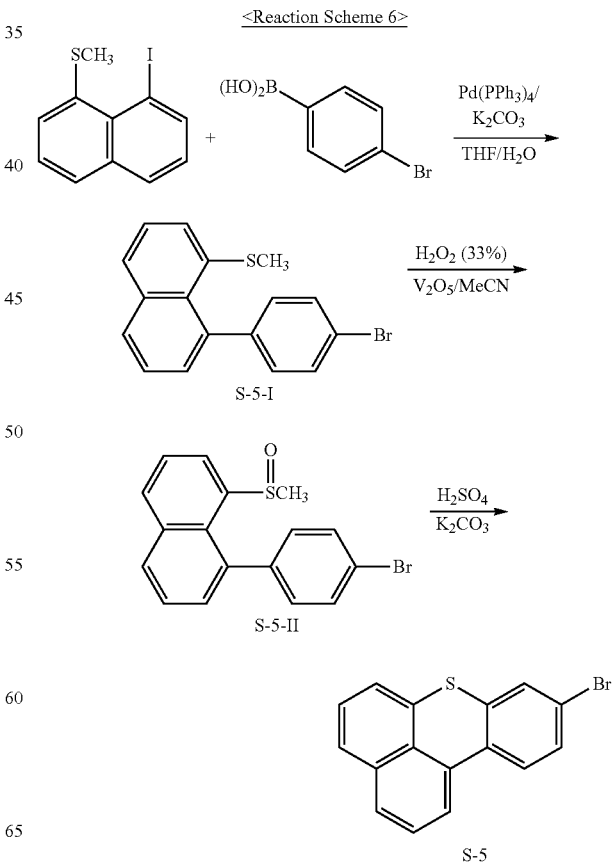

<Reaction Scheme 6>

(1) Synthesis of S-5-I

Compound S-5-I was obtained in the amount of 50.5 g (77%) where (4-bromophenyl)boronic acid (40 g, 199.2 mmol), (8-iodonaphthalen-1-yl) (methyl)sulfane (89.7 g, 298.8 mmol), Pd(PPh$_3$)$_4$ (11.5 g, 9.96 mmol), K$_2$CO$_3$ (82.6 g, 597.5 mmol), THF (876 mL) and water (438 mL) in a round bottom flask were used in the same manner as described above for the synthesis of compound Sub S-1-I.

(2) Synthesis of S-5-II

Compound S-5-II was obtained in the amount of 41.8 g (79%) where S-5-I (50.5 g, 153.4 mmol), V$_2$O$_5$ (2.8 g, 15.3 mmol), acetonitrile 770 mL, H$_2$O$_2$ (21.5 g, 230 mml) were used in the same manner as described above for the synthesis of compound Sub S-4-II.

(3) Synthesis of S-5

Compound S-5 was obtained in the amount of 27.7 g, (73%) where S-5-II (41.8 g, 121.1 mmol) and H$_2$SO$_4$ (126 mL) were used in the same manner as described above for the synthesis of compound Sub S-4.

5. Synthesis of S-8

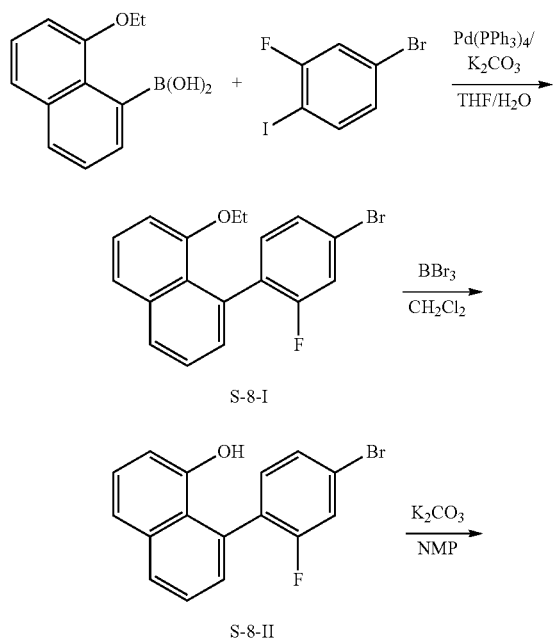

S-8-I

S-8-II

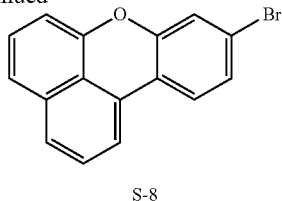

S-8

(1) Synthesis of S-8-I

Compound S-8-I was obtained in the amount of 27.6 g (69%) where (8-ethoxynaphthalen-1-yl)boronic acid (25 g, 115.7 mmol), 4-bromo-2-fluoro-1-iodobenzene (43.5 g, 144.6 mmol), P$_d$(PPh$_3$)$_4$ (6.69 g, 5.8 mmol), K$_2$CO$_3$ (48 g, 347.2 mmol), THF 510 mL and water 255 mL in a round bottom flask were used in the same manner as described above for the synthesis of compound Sub S-1-I.

(2) Synthesis of S-8-☐

Compound S-8-1 (27.6 g, 79.9 mmol) and anhydrous CH$_2$Cl$_2$ 229 mL were loaded into a round bottom flask, followed by cooling to 0☐. After that, BBr$_3$ (25.1 g, 100 mmol) was added, followed by stirring for 24 hours after being heated slowly to room temperature. Upon the completion of the reaction, the reaction product was cooled to −78° C. and methanol 300 mL was slowly added dropwise to inactivate the product. After that, the product was inactivated by adding enough water, and then the product was heated to room temperature. Then, the product was extracted with CH$_2$Cl$_2$ and a trace amount of water in an organic layer was dried with MgSO$_4$. The extracted product was filtered under reduced pressure and concentrated. The concentrated product was separated by silica gel column chromatography, and was then recrystallized, whereby a compound S-8-☐ was obtained in the amount of 24.8 g (97%).

(3) Synthesis of S-8

Compound S-8-☐ (24.8 g, 78.2 mmol), anhydrous N-methyl-2-pyridinone (337 mL) and K$_2$CO$_3$ (21.6 g, 156.4 mmol) were loaded into a round bottom flask, followed by stirring at 200☐ for 3 hours. After the completion of the reaction, the product was cooled to room temperature, followed by adding toluene 2 L and stirring for 10 minutes. After that, the product was extracted with water, followed by removing water in the product with anhydrous MgSO$_4$. The extracted product was filtered under reduced pressure and concentrated. The concentrated resultant was separated by silica gel column chromatography, and was then recrystallized, whereby a compound S-8 was obtained in the amount of 16 g (69%).

6. Synthesis of S-10 and S-12

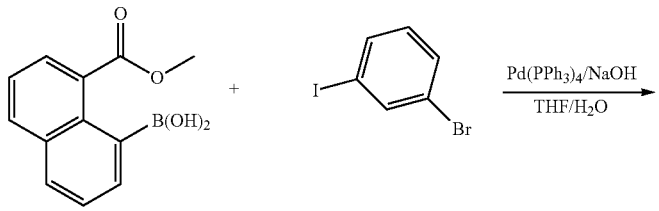

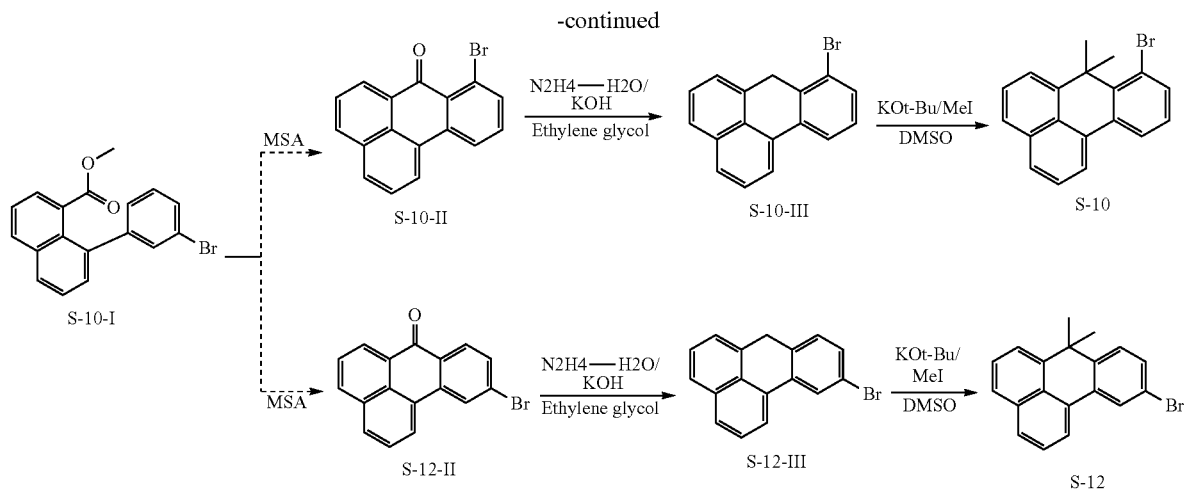

(1) Synthesis of S-10-I

Compound S-10-1 was obtained in the amount of 50.4 g (76%) where the starting material 1-bromo-3-iodobenzene (55 g, 194.4 mmol), (8-(methoxycarbonyl)naphthalen-1-yl) boronic acid (53.7 g, 233.3 mmol), Pd(PPh$_3$)$_4$ (11.2 g, 9.72 mmol), K$_2$CO$_3$ (80.6 g, 583.2 mmol), THF 856 mL and water 428 mL were used in the same manner as described above for the synthesis of compound Sub S-1-I.

(2) Synthesis of S-10-II and S-12-II

Compound S-10-I (50.4 g, 147.7 mmol) in a round bottom flask was dissolved in methanesulfonic acid 479.4 mL, followed by stirring at 50° C.~60° C. Upon the completion of the reaction, a reaction product was cooled to 0° C., followed by adding water. After that, a precipitated solid product was filtered and washed with a little water. Then, the product was dissolved in CH$_2$Cl$_2$ again, dried with MgSO$_4$ and concentrated. The concentrated resultant was separated by silica gel column chromatography, and was then recrystallized, whereby a compound S-10-II and S-12-II were each obtained in the amount of (16 g, 35%) and (21.5 g, 47%).

(3) Synthesis of S-10-III

S-10-II (16 g, 51.75 mmol) in a round bottom flask was dissolved in ethylene glycol 320 mL, followed by adding hydrazine monohydrate (77.7 g, 1552.5 mmol) and KOH (7.3 g, 129.4 mmol) and stirring at 185° C. Upon the completion of the reaction, a reaction product was cooled to 0° C., followed by adding water. After that, a precipitated solid product was filtered and washed with a little water. Then, the product was dissolved in CH$_2$Cl$_2$ again, dried with MgSO$_4$ and concentrated. The concentrated resultant was separated by silica gel column chromatography, and was then recrystallized, whereby a compound S-10-III was obtained in the amount of 14.5 g (95%).

(4) Synthesis of S-12-III

Compound S-12-III was obtained in the amount of 19 g (97%) where S-12-II (21.5 g) was used in the same manner as described above for the synthesis of compound Sub S-10-III.

(5) Synthesis of S-10

Compound S-10-III (14.5 g, 49.12 mmol) and KOt-Bu (16.5 g, 147.36 mmol) in a round bottom flask was dissolved in DMF 320 mL, followed by stirring at 0□ for 5 hours and heating to room temperature. And then, iodomethane (20.9 g, 147.36 mmol) was added to the mixture. After the completion of the reaction, the reaction product was extracted with CH$_2$Cl$_2$ and water. The extracted organic layer was dried with MgSO$_4$ and concentrated. The concentrated product was separated by silica gel column chromatography, and was then recrystallized, whereby a compound S-10 was obtained in the amount of 14.4 g (91%).

(6) Synthesis of S-12

Compound S-12 was obtained in the amount of 18.7 g (90%) where S-12-III (19 g, 64.4 mmol) was used in the same manner as described above for the synthesis of compound Sub S-10.

7. Synthesis of S-15

<Reaction Scheme 9>

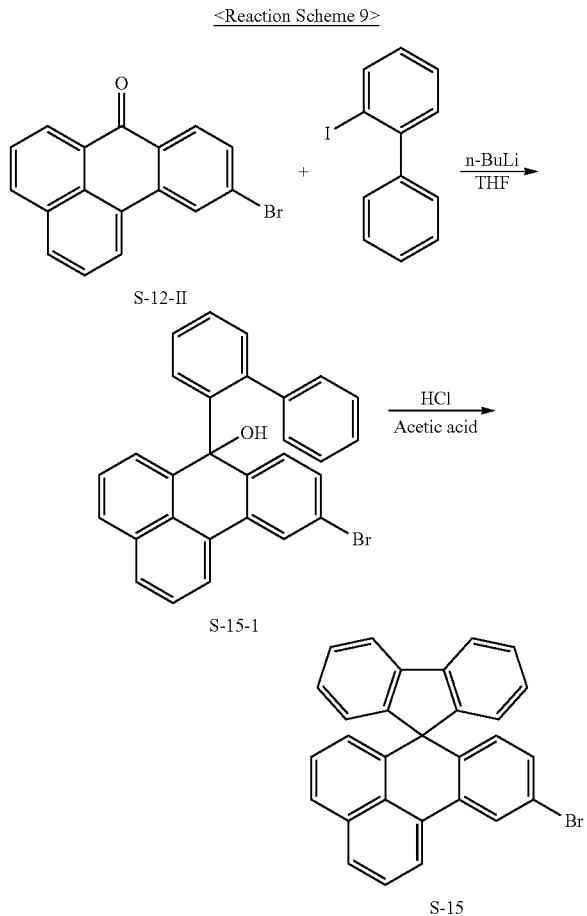

(1) Synthesis of S-15-1

2-iodo-1,1'-biphenyl (19.5 g, 69.54 mmol) in a round bottom flask was dissolved in anhydrous THF 230 mL, followed by cooling to −78□ and slowly adding dropwise n-BuLi 30.5 mL in 2.5M hexane. After 30 minutes, S-12-II (21.5 g, 69.54 mmol) dissolved in anhydrous THF 100 mL was added dropwise into the round bottom flask, followed by stirring at room temperature. Upon the reaction was terminated by adding water, a reaction product was extracted with $CH_2Cl_2$. After that, the extracted organic layer was dried with $MgSO_4$ and concentrated. The concentrated product was separated by silica gel column chromatography, and was then recrystallized, whereby a compound S-15-1 was obtained in the amount of 24.5 g (76%).

(2) Synthesis of S-15

S-15-1 (24.5 g, 52.87 mmol), acetic acid 190 mL and HCl 5.4 mL in sequence were loaded into a round bottom flask, followed by refluxing and stirring. Upon completion of the reaction, a reaction product was cooled to room temperature, and then water 270 mL was added to the product thereby a solid product was obtained. The solid product was filtered, and then was washed with water. After that, the obtained solid product was dissolved in $CH_2Cl_2$, followed by extracting with water and $CH_2Cl_2$. The extracted organic layer was dried with $MgSO_4$ and concentrated. The concentrated product was separated by silica gel column chromatography, and was then recrystallized, whereby product S-15 was obtained in the amount of 18.4 g (78%).

Examples of starting compounds include, but are not limited to, the following compounds, and FD-MS (Field Desorption-Mass Spectrometry) data of the compounds are given in Table 1 below.

S-1

S-2

S-3

S-4

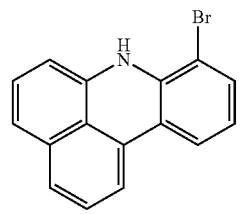

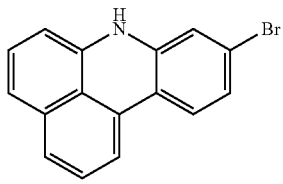

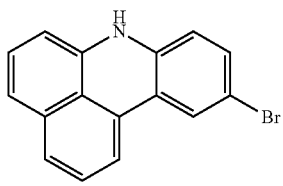

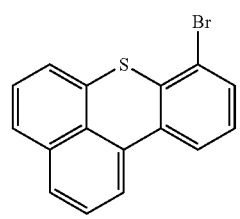

-continued

S-5

S-6

S-7

S-8

S-9

S-10

S-11

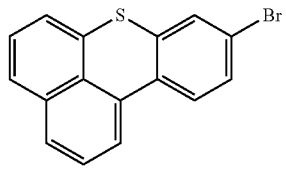

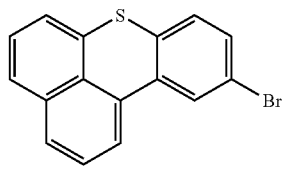

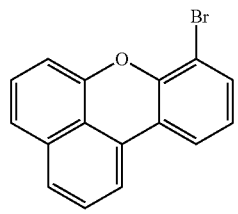

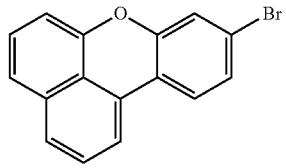

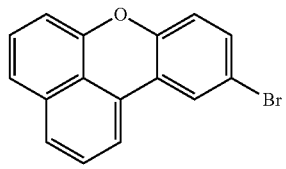

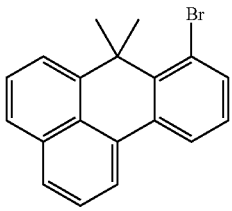

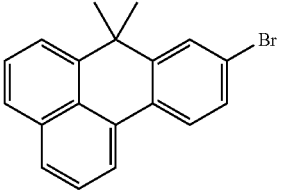

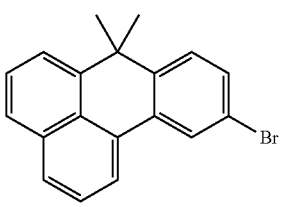 S-12
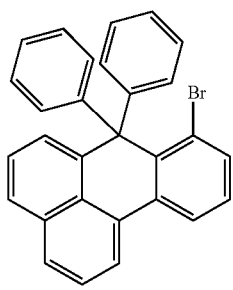 S-13
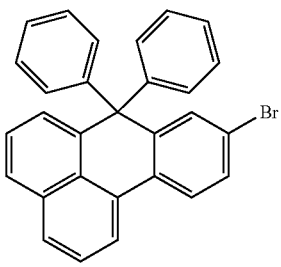 S-14
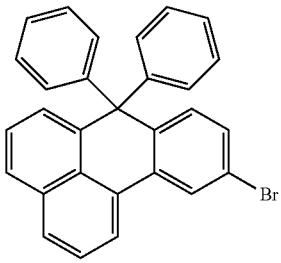 S-15
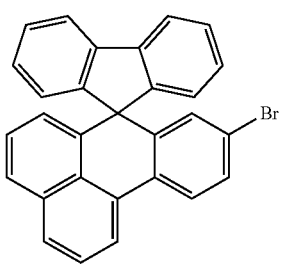 S-16
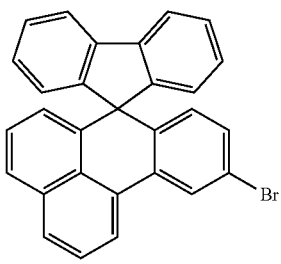 S-17
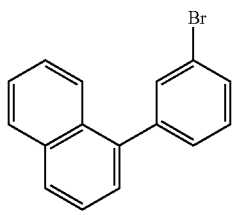 S-18
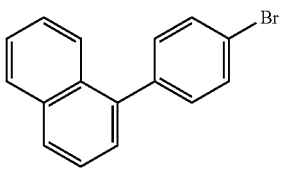 S-19
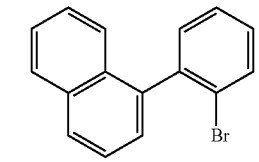 S-20
TABLE 1
| Compound | FD-MS | Compound | FD-MS |
|---|---|---|---|
| S-1 | m/z = 295.00($C_{16}H_{10}BrN$ = 296.16) | S-2 | m/z = 295.00($C_{16}H_{10}BrN$ = 296.16) |
| S-3 | m/z = 295.00($C_{16}H_{10}BrN$ = 296.16) | S-4 | m/z = 311.96($C_{16}H_9BrS$ = 313.21) |
| S-5 | m/z = 311.96($C_{16}H_9BrS$ = 313.21) | S-6 | m/z = 311.96($C_{16}H_9BrS$ = 313.21) |
| S-7 | m/z = 295.98($C_{16}H_9BrO$ = 297.15) | S-8 | m/z = 295.98($C_{16}H_9BrO$ = 295.15) |
| S-9 | m/z = 295.98($C_{16}H_9BrO$ = 297.15) | S-10 | m/z = 322.04($C_{16}H_{19}Br$ = 323.23) |
| S-11 | m/z = 322.04($C_{16}H_{19}Br$ = 323.23) | S-12 | m/z = 322.04($C_{16}H_{19}Br$ = 323.23) |
| S-13 | m/z = 446.07($C_{29}H_{19}Br$ = 447.37) | S-14 | m/z = 466.07($C_{29}H_{19}Br$ = 447.37) |
| S-15 | m/z = 446.07($C_{29}H_{19}Br$ = 447.37) | S-16 | m/z = 444.05($C_{29}H_{17}Br$ = 445.35) |
| S-17 | m/z = 444.05($C_{29}H_{17}Br$ = 445.35) | S-18 | m/z = 282.00($C_{16}H_{11}Br$ = 283.16) |
| S-19 | m/z = 282.00($C_{16}H_{11}Br$ = 283.16) | S-20 | m/z = 282.00($C_{16}H_{11}Br$ = 283.16) |

II. Synthesis Example of Sub 1
1. Synthesis of Sub 1-1

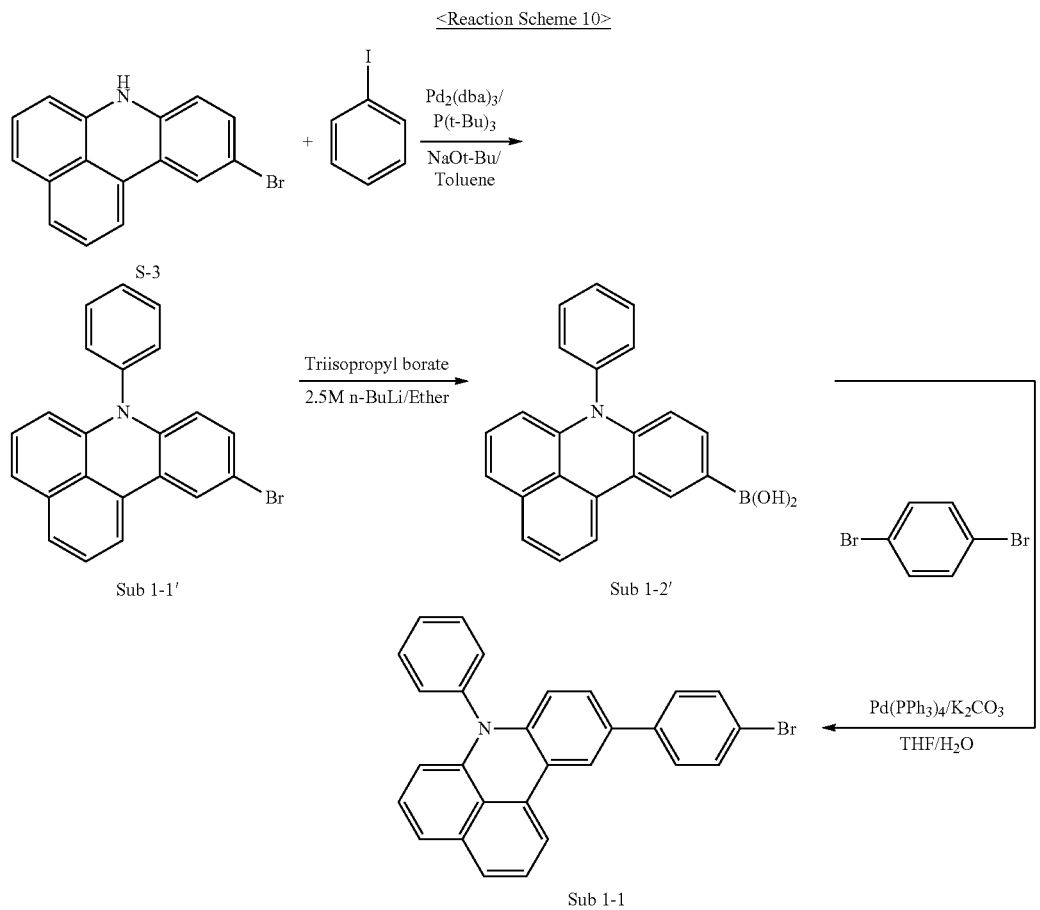

(1) Synthesis of Sub 1-1'

Compound S-3 (40 g, 135.1 mmol), iodobenzene (30.3 g, 148.6 mmol), Pd$_2$(dba)$_3$ (6.2 g, 6.75 mmol), P(t-Bu)$_3$ (2.732 g, 13.5 mmol), NaOt-Bu (38.96 g, 405.2 mmol) and toluene 1420 mL were loaded into a round bottom flask, and then the reaction proceeded at 100° C. After the completion of the reaction, the reaction product was extracted with ether and water. The extracted organic layer was dried with MgSO$_4$ and concentrated. The concentrated product was separated by silica gel column chromatography, and was then recrystallized, whereby compound Sub 1-1' was obtained in the amount of 39.2 g (78%).

(2) Synthesis of Sub 1-2'

Compound Sub 1-1' (39.2 g, 105.3 mmol) was loaded into a round bottom flask and dissolved in anhydrous ether 370 mL, followed by cooling to −78° C. After that, n-BuLi (2.5M in hexane) (46.33 mL, 115.8 mmol) was added dropwise in the round bottom flask, followed by stirring for 30 minutes. And then, after the reactant was cooled to −78° C., and triisopropyl borate (36.4 mL, 158 mmol) was added dropwise to a reactant. After that, the reactant was heated to room temperature and stirred. Then, water was added in order to dilute the reactant and 2N HCl was added, followed by stirring. After the completion of the reaction, the reaction product was extracted with ethyl acetate and water. The extracted organic layer was dried with MgSO$_4$ and concentrated. The concentrated product was separated by silica gel column chromatography, and was then recrystallized, whereby compound Sub 1-2' was obtained in the amount of 24.1 g (68%).

(3) Synthesis of Sub 1-1

Compound Sub 1-2' (24.1 g 71.5 mmol), 1,4-dibromobenzene (25.3 g, 107.2 mmol), Pd(PPh$_3$)$_4$ (4.13 g, 3.57 mmol), K$_2$CO$_3$ (29.6 g, 214.4 mmol), THF 314 mL and water 157 mL were loaded into a round bottom flask, and then the mixture was stirred and refluxed. After the completion of the reaction, the reaction product was extracted with ether and water. The extracted organic layer was dried with MgSO$_4$ and concentrated. The concentrated product was separated by silica gel column chromatography, and was then recrystallized, whereby compound Sub 1-1 was obtained in the amount of 23.4 g (73%).

2. Synthesis of Sub 1-7

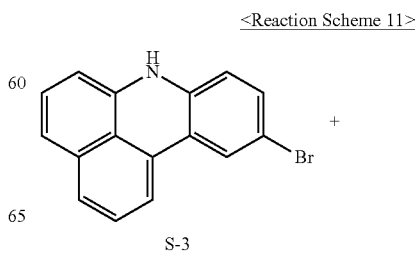

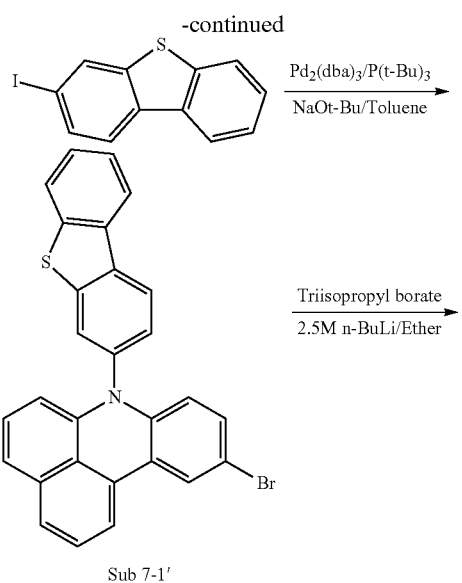

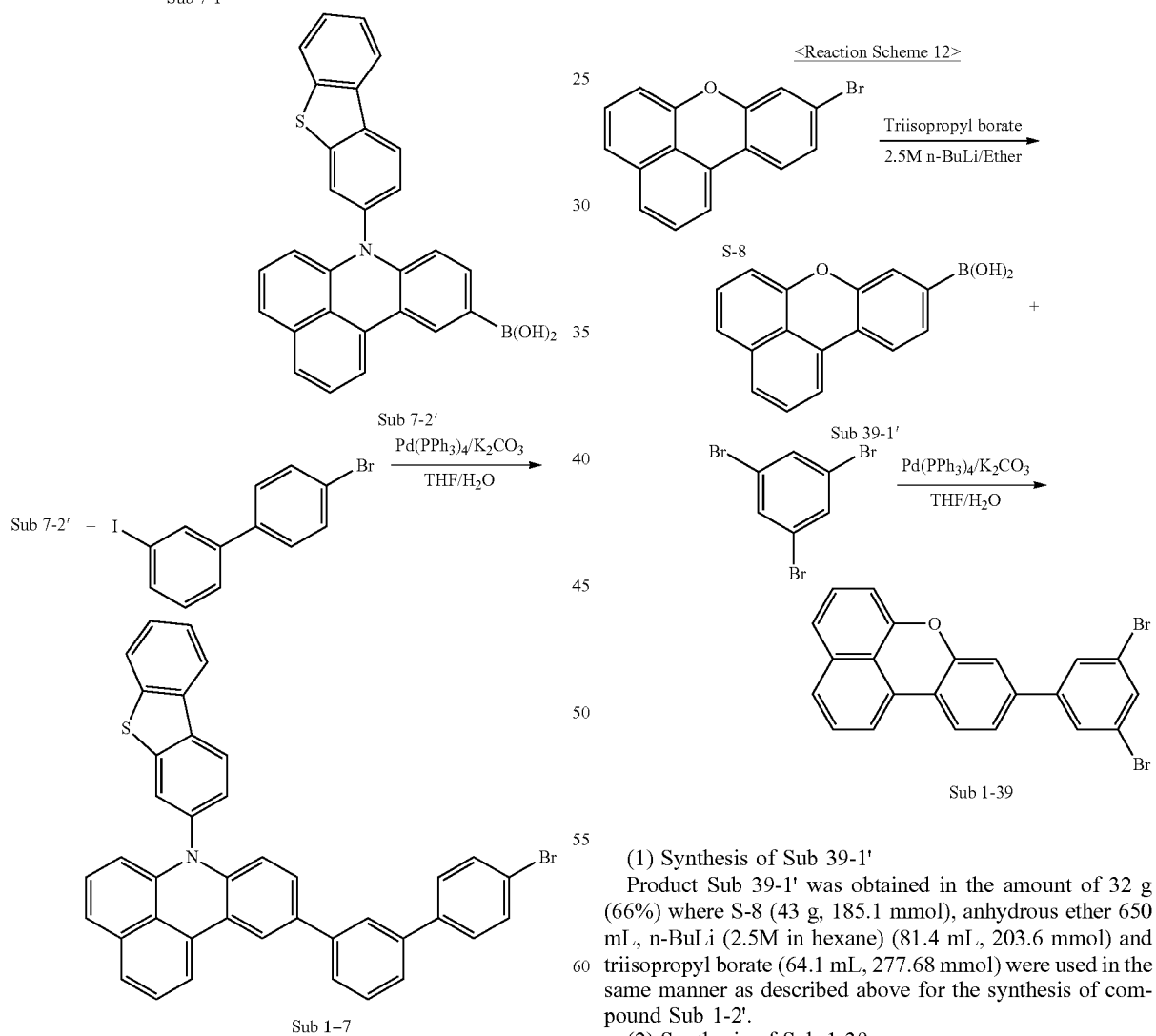

thiophene (40.3 g, 130 mmol), Pd₂(dba)₃ (5.41 g, 5.9 mmol), P(t-Bu)₃ (2.4 g, 11.8 mmol), NaOt-Bu (34.1 g, 354.5 mmol) and toluene 1240 mL were used in the same manner as described above for the synthesis of compound Sub 1-1' above.

(2) Synthesis of Sub 7-2'

Product Sub 7-2' was obtained in the amount of 27.5 g (69%) where Sub 7-1' (43 g, 89.9 mmol), anhydrous ether 315 mL, n-BuLi (2.5M in hexane) (39.5 mL, 98.9 mmol) and triisopropyl borate (31.1 mL, 134.8 mmol) were used in the same manner as described above for the synthesis of compound Sub 1-2'.

(3) Synthesis of Sub 1-7

Product Sub 1-7 was obtained in the amount of 28.9 g (74%) where Sub 7-2' (27.5 g 62.0 mmol), 4'-bromo-3-iodo-1,1'-biphenyl (33.4 g, 93.0 mmol), Pd(PPh₃)₄ (3.59 g, 3.1 mmol), K₂CO₃ (25.7 g, 186 mmol), THF 272 mL and water 136 mL were used in the same manner as described above for the synthesis of compound Sub 1-1.

3. Synthesis of Sub 1-39

(1) Synthesis of Sub 39-1'

Product Sub 39-1' was obtained in the amount of 32 g (66%) where S-8 (43 g, 185.1 mmol), anhydrous ether 650 mL, n-BuLi (2.5M in hexane) (81.4 mL, 203.6 mmol) and triisopropyl borate (64.1 mL, 277.68 mmol) were used in the same manner as described above for the synthesis of compound Sub 1-2'.

(2) Synthesis of Sub 1-39

Product Sub 1-39 was obtained in the amount of 42 g (76%) where Sub 39-1' (32 g, 122.1 mmol), 1,3,5-tribromobenzene (57.7 g, 183.2 mmol), Pd(PPh₃)₄ (7.06 g, 6.1 mmol), K₂CO₃ (50.6 g, 366.3 mmol), THF 536 mL and water 268 mL were used in the same manner as described above for the synthesis of compound Sub 1-1.

4. Synthesis of Sub 1-42

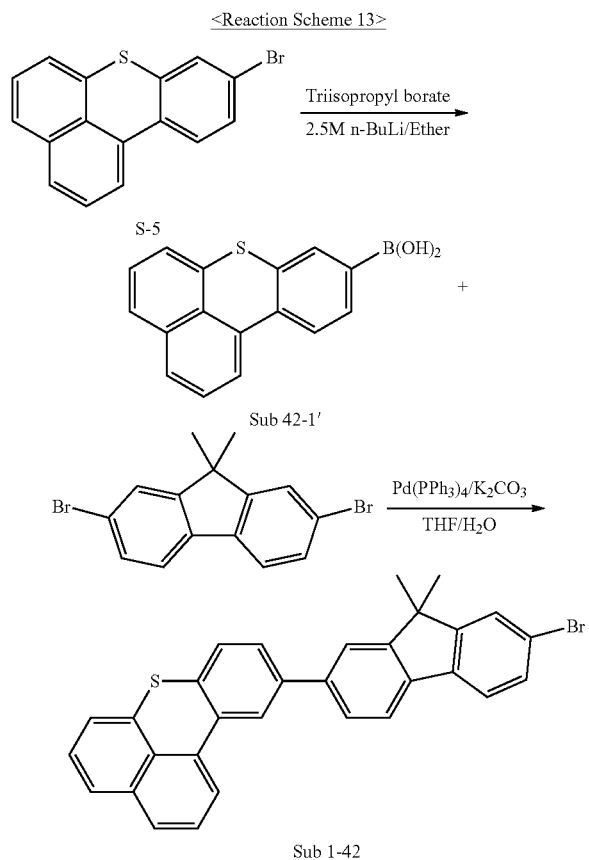

(1) Synthesis of Sub 42-1'

Product Sub 42-1' was obtained in the amount of 28 g (64%) where S-5 (50 g, 159.6 mmol), anhydrous ether 558 mL, n-BuLi (2.5M in hexane) (70.2 mL, 175.6 mmol) and triisopropyl borate (55.3 mL, 239.5 mmol) were used in the same manner as described above for the synthesis of compound Sub 1-2'.

(2) Synthesis of Sub 1-42

Product Sub 1-42 was obtained in the amount of 36.6 g (72%) where Sub 42-1' (28 g, 100.7 mmol), 2,7-dibromo-9,9-dimethyl-9H-fluorene (53.2 g, 151 mmol), Pd(PPh$_3$)$_4$ (5.82 g, 5.03 mmol), K$_2$CO$_3$ (41.7 g, 302 mmol), THF 442 mL and water 221 mL were used in the same manner as described above for the synthesis of compound Sub 5. Synthesis of Sub 1-52

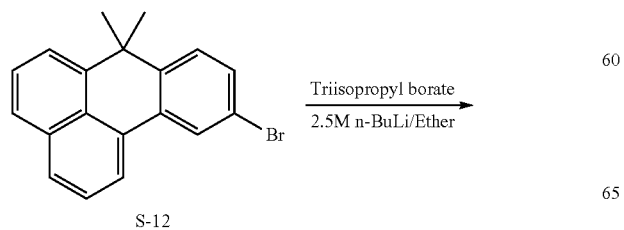

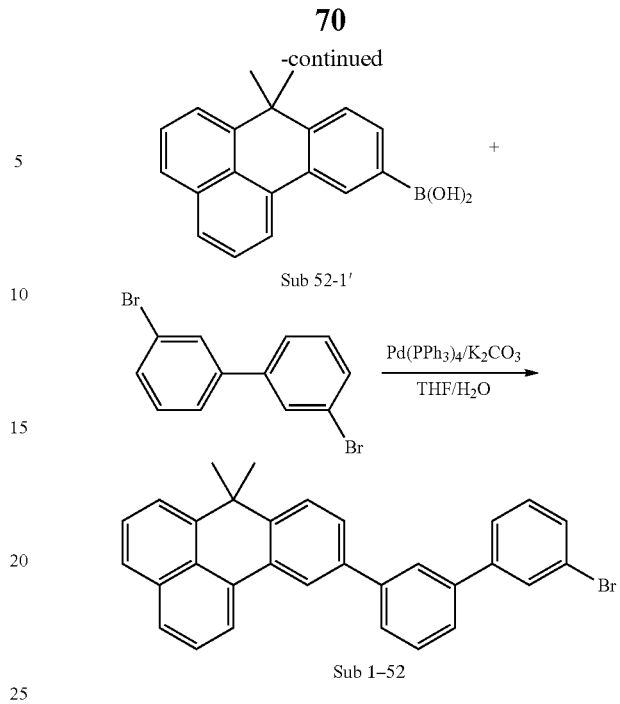

(1) Synthesis of Sub 52-1'

Product Sub 52-1' was obtained in the amount of 29 g (65%) where S-12 (50 g, 154.7 mmol), anhydrous ether 541 mL, n-BuLi (2.5M in hexane) (68.1 mL, 170.2 mmol) and triisopropyl borate (53.5 mL, 232 mmol) were used in the same manner as described above for the synthesis of compound Sub 1-2'.

(2) Synthesis of Sub 1-52

Product Sub 1-52 was obtained in the amount of 36.8 g (77%) where Sub 52-1' (29 g, 100.6 mmol), 3,3'-dibromo-1,1'-biphenyl (47.1 g, 151 mmol), Pd(PPh$_3$)$_4$ (5.82 g, 5.03 mmol), K$_2$CO$_3$ (41.7 g, 302 mmol), THF 442 mL and water 221 mL were used in the same manner as described above for the synthesis of compound Sub 1.

6. Synthesis of Sub 1-54

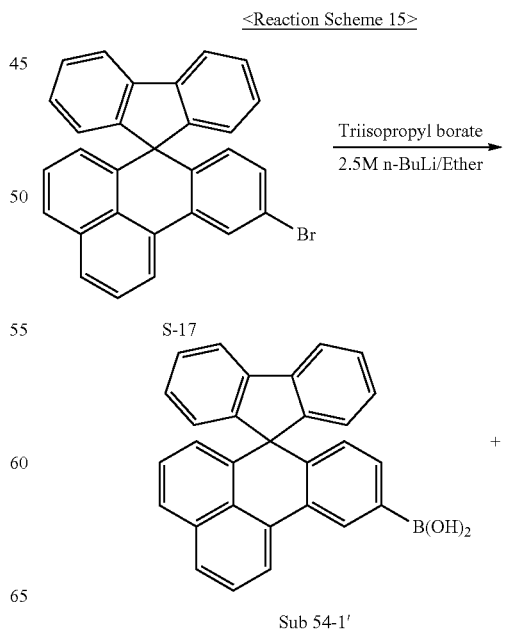

-continued

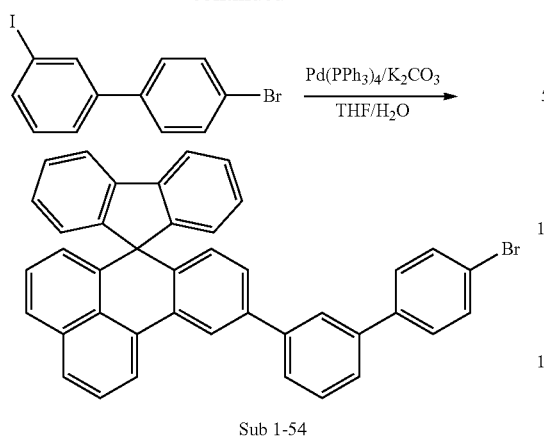

Sub 1-54

(1) Synthesis of Sub 54-1'

Product Sub 54-1' was obtained in the amount of 23.2 g (63%) where S-17 (40 g, 89.8 mmol), anhydrous ether 314 mL, n-BuLi (2.5M in hexane) (39.5 mL, 98.8 mmol) and triisopropyl borate (31.1 mL, 135 mmol) were used in the same manner as described above for the synthesis of compound Sub 1-2'.

(2) Synthesis of Sub 1-54

Product Sub 1-54 was obtained in the amount of 25 g (74%) where Sub 54-1' (23.2 g, 56.5 mmol), 4'-bromo-3-iodo-1,1'-biphenyl (30.5 g, 84.8 mmol), Pd(PPh$_3$)$_4$ (3.3 g, 2.83 mmol), K$_2$CO$_3$ (23.4 g, 169.6 mmol), THF 248 mL and water 124 mL were used in the same manner as described above for the synthesis of compound Sub 1.

Examples of Sub 1 compounds include, but are not limited to, the following compounds, and FD-MS (Field Desorption-Mass Spectrometry) data of the compounds is given in Table 2 below.

Sub 1-1

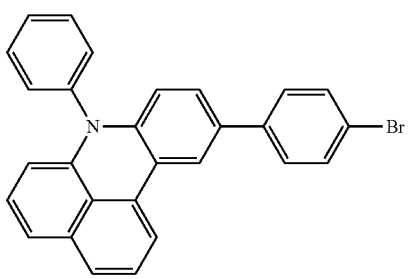

Sub 1-2

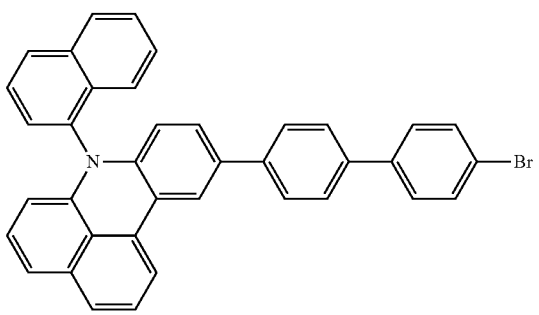

-continued

Sub 1-3

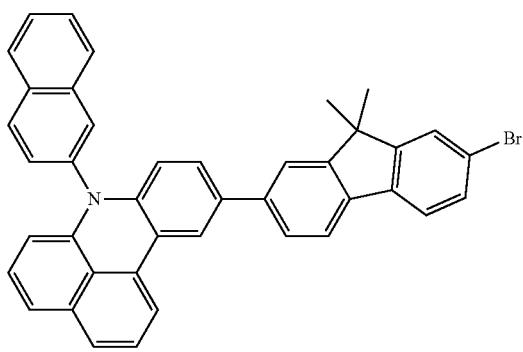

Sub 1-4

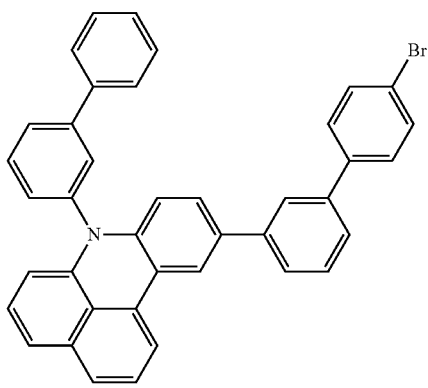

Sub 1-5

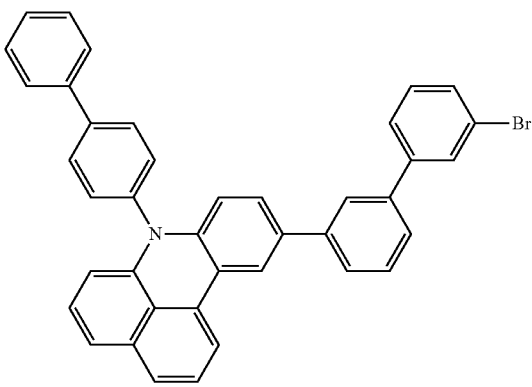

Sub 1-6

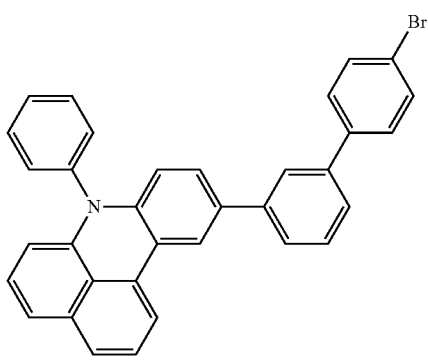

-continued
Sub 1-7
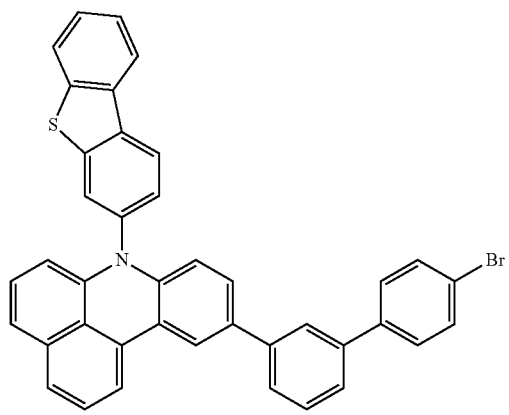
Sub 1-8
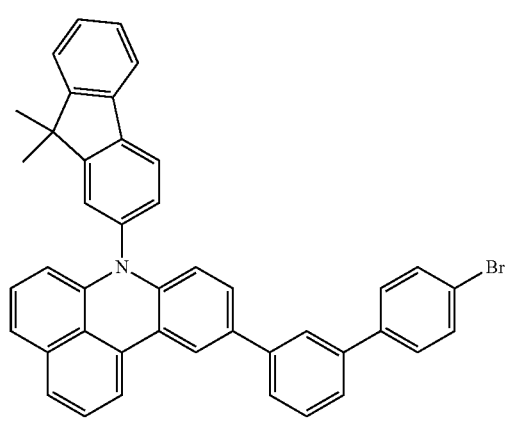
Sub 1-9
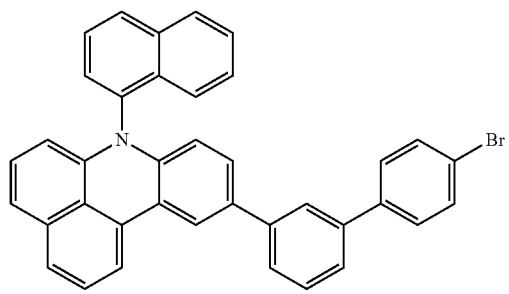
Sub 1-10
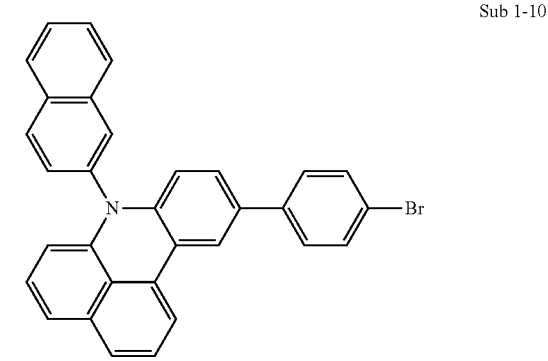
-continued
Sub 1-11
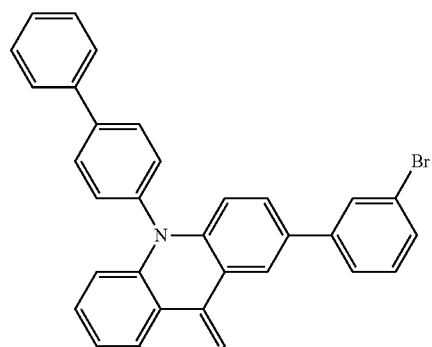
Sub 1-12
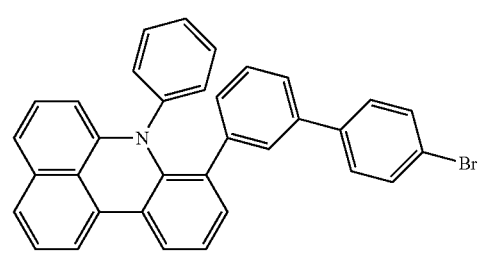
Sub 1-13
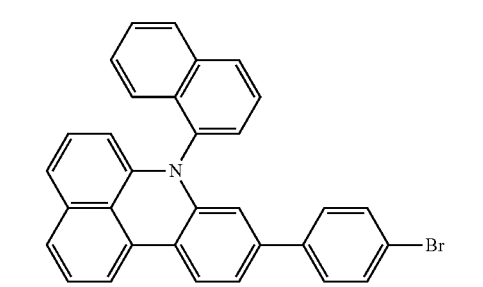
Sub 1-14
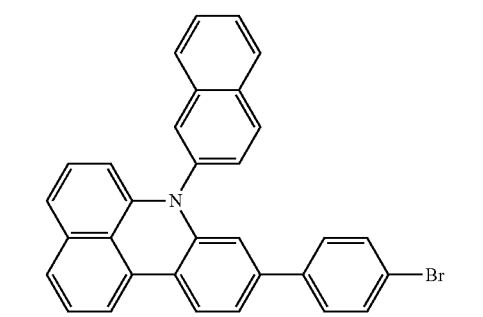
Sub 1-15
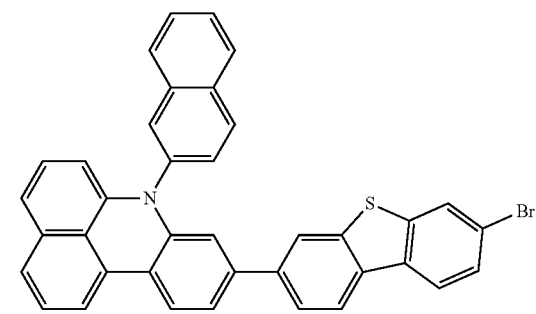

-continued
Sub 1-16
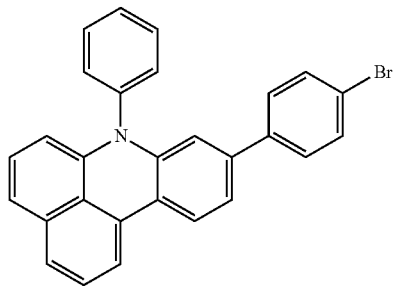
Sub 1-17
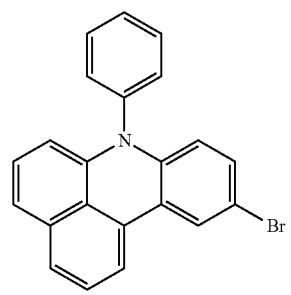
Sub 1-18
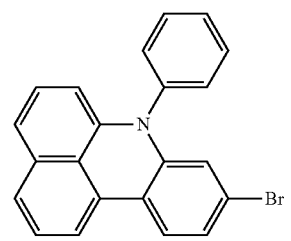
Sub 1-19
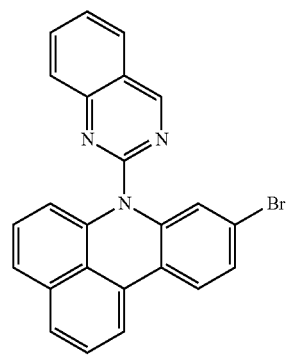
Sub 1-20
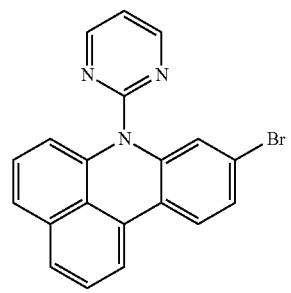
-continued
Sub 1-21
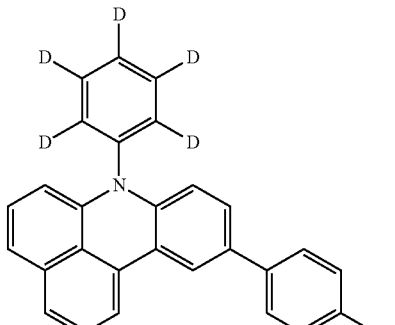
Sub 1-22
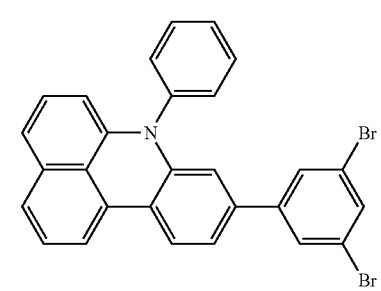
Sub 1-23
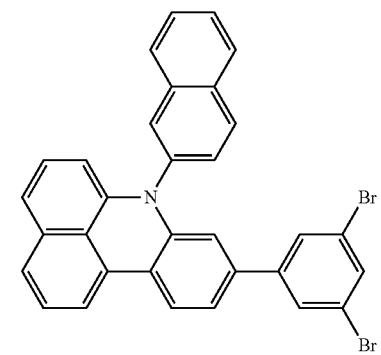
Sub 1-24
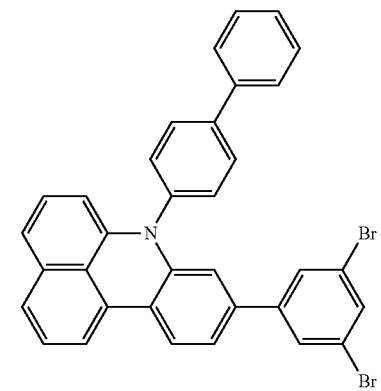

Sub 1-25
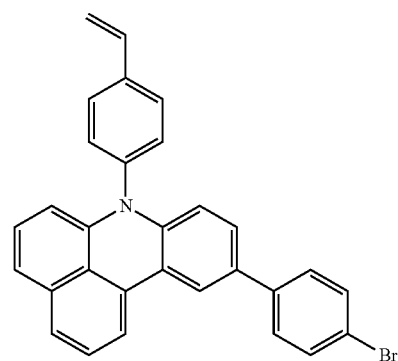
Sub 1-26
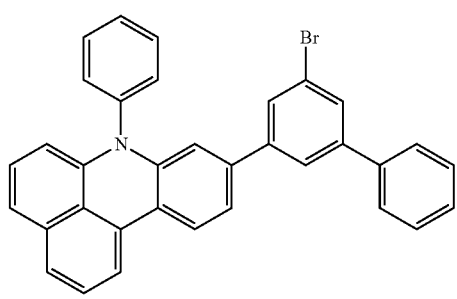
Sub 1-27
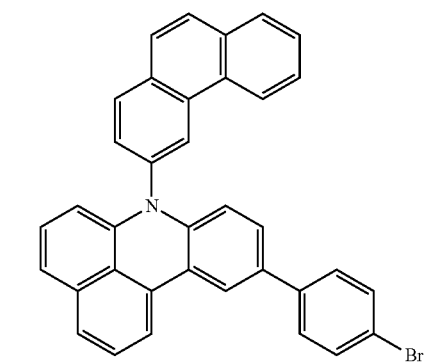
Sub 1-28
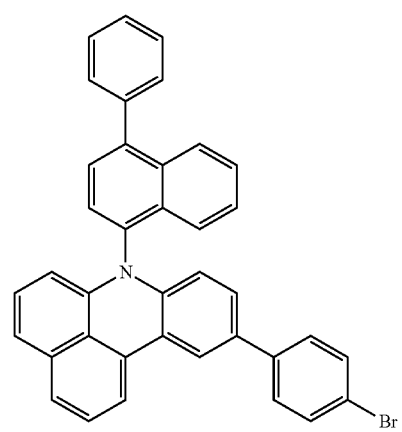
Sub 1-29
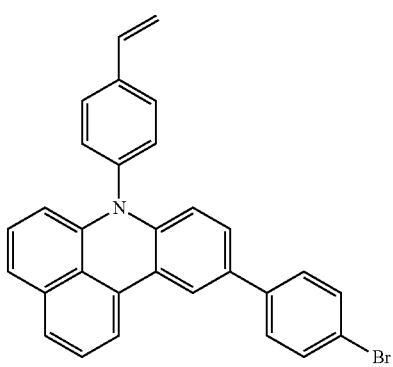
Sub 1-30
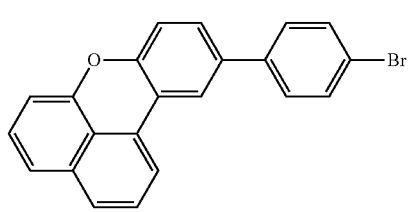
Sub 1-31
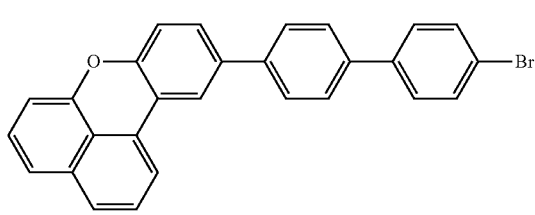
Sub 1-32
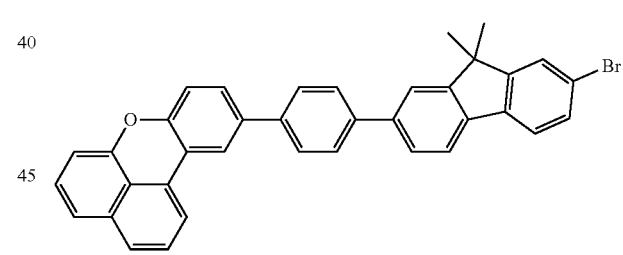
Sub 1-33
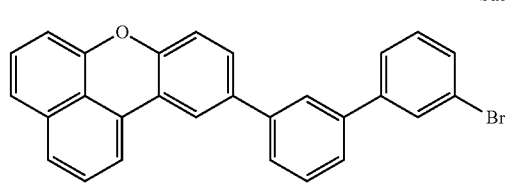
Sub 1-34
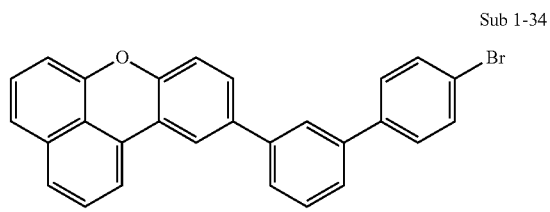

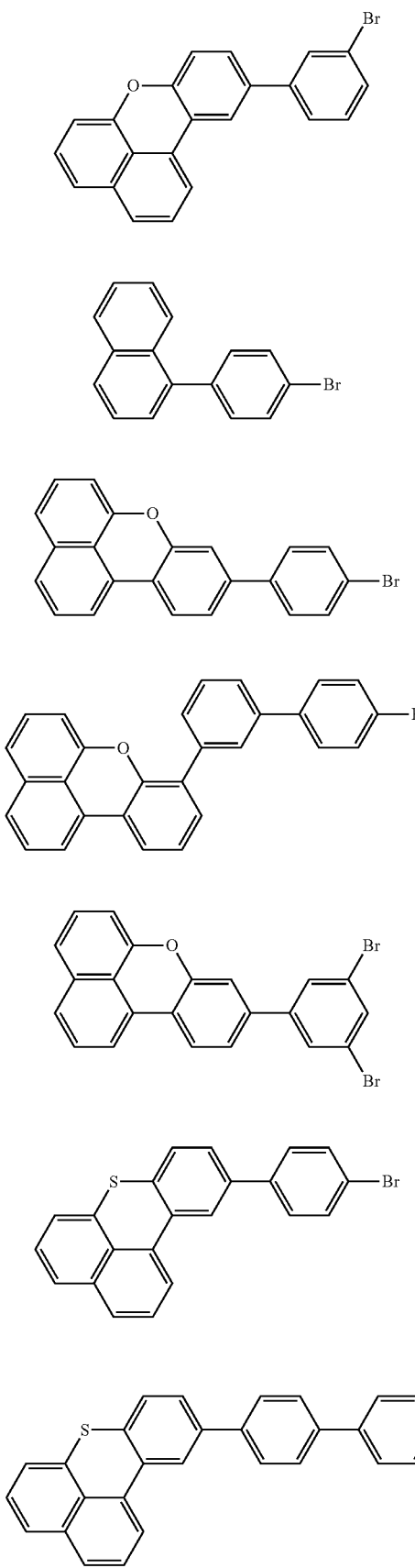
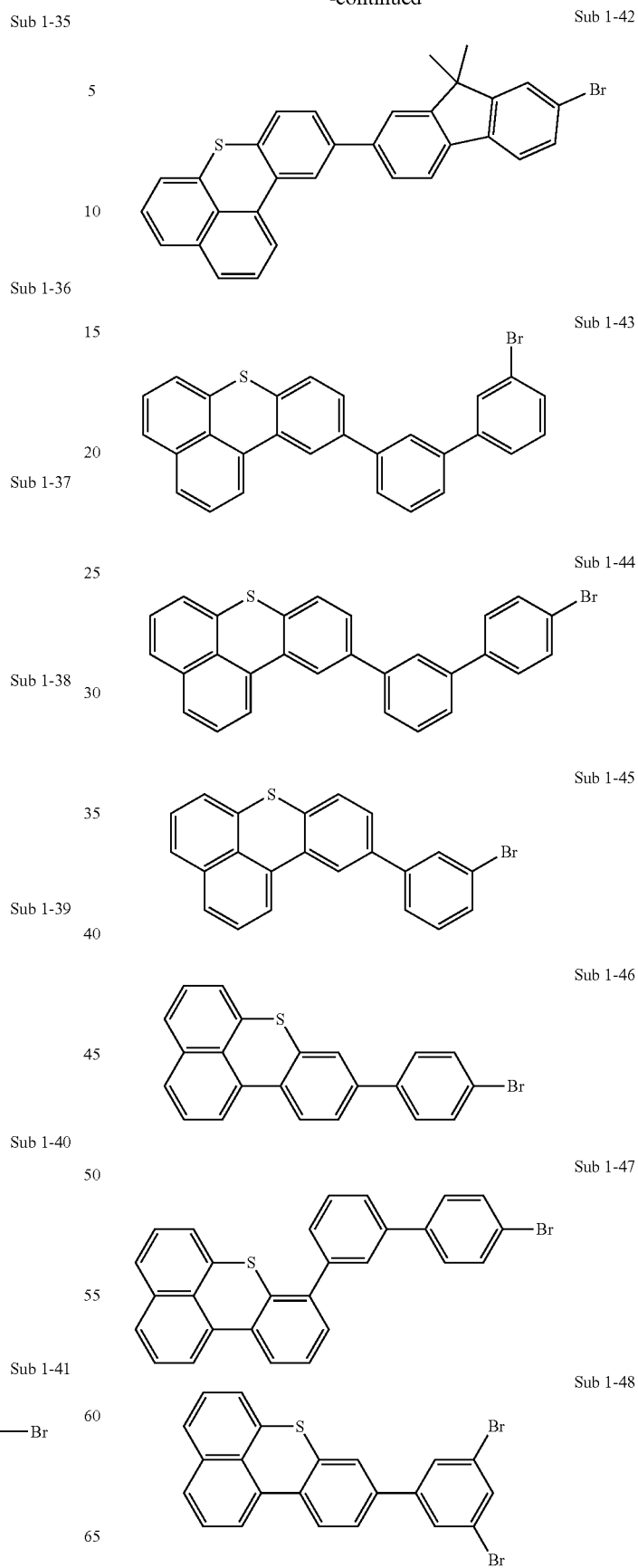

Sub 1-49
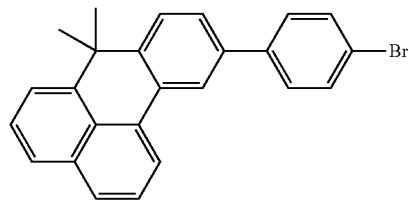
Sub 1-50
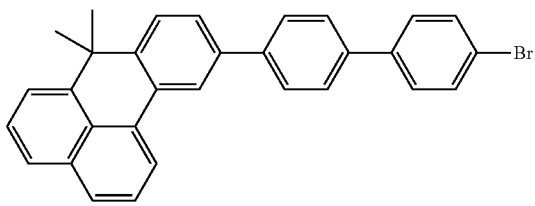
Sub 1-51
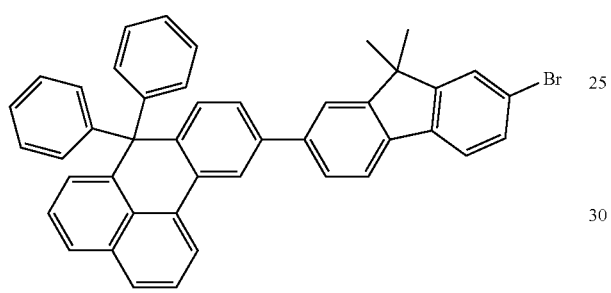
Sub 1-52
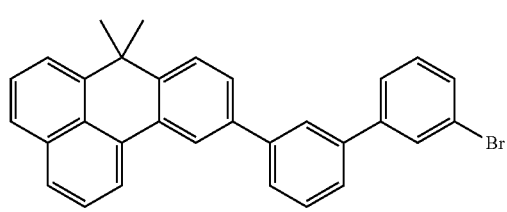
Sub 1-53
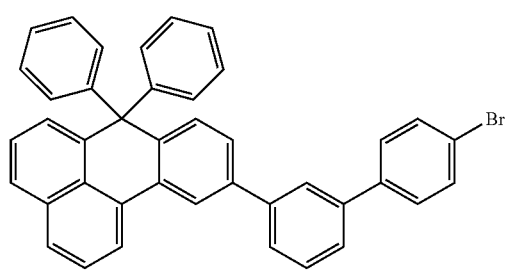
Sub 1-54
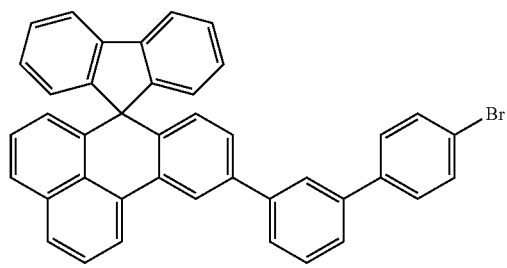
Sub 1-55
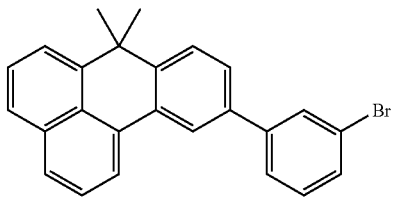
Sub 1-56
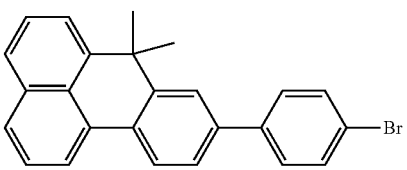
Sub 1-57
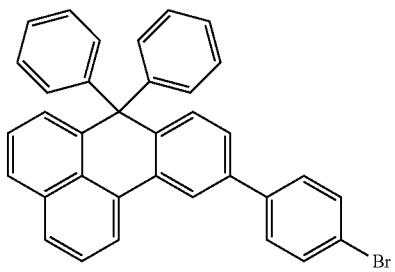
Sub 1-58
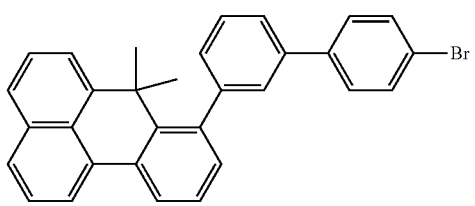
Sub 1-59
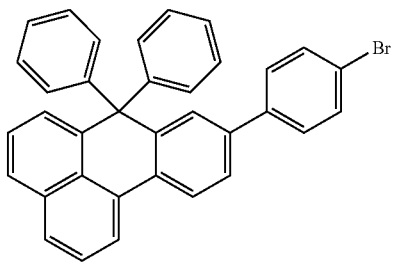
Sub 1-60
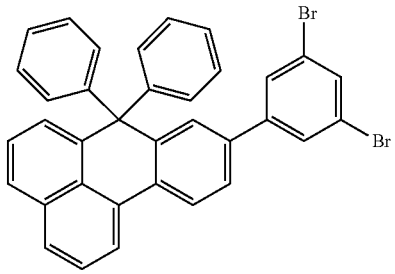

TABLE 2

| Compound | FD-MS | Compound | FD-MS |
|---|---|---|---|
| Sub 1-1 | m/z = 447.06($C_{28}H_{18}BrN$ = 448.35) | Sub 1-2 | m/z = 573.11($C_{31}H_{24}BrN$ = 574.51) |
| Sub 1-3 | m/z = 613.14($C_{41}H_{28}BrN$ = 614.57) | Sub 1-4 | m/z = 599.12($C_{40}H_{26}BrN$ = 600.55) |
| Sub 1-5 | m/z = 599.12($C_{40}H_{28}BrN$ = 600.55) | Sub 1-6 | m/z = 523.09($C_{34}H_{22}BrN$ = 524.45) |
| Sub 1-7 | m/z = 629.08($C_{40}H_{26}BrNS$ = 630.59) | Sub 1-8 | m/z = 639.16($C_{43}H_{20}BrN$ = 640.61) |
| Sub 1-9 | m/z = 573.11($C_{28}H_{14}BrN$ = 574.51) | Sub 1-10 | m/z = 497.08($C_{22}H_{20}BrN$ = 498.41) |
| Sub 1-11 | m/z = 523.09($C_{28}H_{22}BrN$ = 524.45) | Sub 1-12 | m/z = 523.09($C_{34}H_{22}BrN$ = 524.45) |
| Sub 1-13 | m/z = 497.08($C_{22}H_{20}BrN$ = 498.41) | Sub 1-14 | m/z = 497.08($C_{32}H_{20}BrN$ = 498.41) |
| Sub 1-15 | m/z = 603.07($C_{38}H_{10}BrNS$ = 604.56) | Sub 1-16 | m/z = 447.06($C_{28}H_{18}BrN$ = 448.35) |
| Sub 1-17 | m/z = 371.03($C_{22}H_{14}BrN$ = 372.26) | Sub 1-18 | m/z = 371.03($C_{22}H_{14}BrN$ = 372.26) |
| Sub 1-19 | m/z = 423.04($C_{24}H_{14}BrN_3$ = 424.29) | Sub 1-20 | m/z = 373.02($C_{20}H_{12}BrN_3$ = 374.23) |
| Sub 1-21 | m/z = 452.09($C_{18}H_{13}D_5BrN$ = 453.38) | Sub 1-22 | m/z = 524.97($C_{28}H_{17}Br_2N$ = 527.25) |
| Sub 1-23 | m/z = 574.99($C_{22}H_{19}Br_2N$ = 577.31) | Sub 1-24 | m/z = 601.00($C_{34}H_{21}Br_2N$ = 603.35) |
| Sub 1-25 | m/z = 473.08($C_{30}H_{20}BrN$ = 474.39) | Sub 1-26 | m/z = 523.09($C_{34}H_{22}BrN$ = 524.45) |
| Sub 1-27 | m/z = 547.09($C_{30}H_{22}BrN$ = 548.47) | Sub 1-28 | m/z = 573.11($C_{38}H_{24}BrN$ = 574.51) |
| Sub 1-29 | m/z = 473.08($C_{30}H_{28}BrN$ = 474.39) | Sub 1-30 | m/z = 372.01($C_{22}H_{13}BrN$ = 373.24) |
| Sub 1-31 | m/z = 448.05($C_{29}H_{27}BrO$ = 449.34) | Sub 1-32 | m/z = 488.08($C_{31}H_{21}BrO$ = 489.40) |
| Sub 1-33 | m/z = 448.05($C_{29}H_{17}BrO$ = 449.34) | Sub 1-34 | m/z = 448.05($C_{28}H_{17}BrO$ = 449.34) |
| Sub 1-35 | m/z = 372.01($C_{22}H_{13}BrO$ = 373.24) | Sub 1-36 | m/z = 282.00($C_{16}H_{11}Br$ = 283.16) |
| Sub 1-37 | m/z = 372.01($C_{22}H_{13}BrO$ = 373.24) | Sub 1-38 | m/z = 448.05($C_{28}H_{17}BrO$ = 449.34) |
| Sub 1-39 | m/z = 449.93($C_{22}H_{12}Br_2O$ = 452.14) | Sub 1-40 | m/z = 387.99($C_{22}H_{18}BrS$ = 389.31) |
| Sub 1-41 | m/z = 464.02($C_{29}H_{17}BrS$ = 465.40) | Sub 1-42 | m/z = 504.05($C_{31}H_{21}BrS$ = 505.47) |
| Sub 1-43 | m/z = 464.02($C_{29}H_{17}BrS$ = 465.40) | Sub 1-44 | m/z = 464.02($C_{28}H_{17}BrS$ = 465.40) |
| Sub 1-45 | m/z = 387.99($C_{22}H_{13}BrS$ = 389.31) | Sub 1-46 | m/z = 387.99($C_{22}H_{13}BrS$ = 389.31) |
| Sub 1-47 | m/z = 464.02($C_{29}H_{17}BrS$ = 465.40) | Sub 1-48 | m/z = 465.90($C_{22}H_{12}Br_2S$ = 468.20) |
| Sub 1-49 | m/z = 398.07($C_{29}H_{19}Br$ = 399.32) | Sub 1-50 | m/z = 474.10($C_{31}H_{21}Br$ = 475.42) |
| Sub 1-51 | m/z = 638.16($C_{244}H_{31}Br$ = 639.62) | Sub 1-52 | m/z = 474.10($C_{31}H_{23}Br$ = 475.42) |
| Sub 1-53 | m/z = 598.13($C_{41}H_{17}Br$ = 599.56) | Sub 1-54 | m/z = 596.11($C_{41}H_{21}Br$ = 597.54) |
| Sub 1-55 | m/z = 398.07($C_{29}H_{19}Br$ = 399.32) | Sub 1-56 | m/z = 398.07($C_{21}H_{19}Br$ = 399.32) |
| Sub 1-57 | m/z = 398.07($C_{29}H_{19}Br$ = 399.32) | Sub 1-58 | m/z = 474.10($C_{31}H_{23}Br$ = 475.42) |
| Sub 1-59 | m/z = 522.10($C_{35}H_{23}Br$ = 523.46) | Sub 1-60 | m/z = 600.01($C_{31}H_{22}Br_2$ = 602.36) |

III. Synthesis Example of Sub 2

<Reaction Scheme 16>

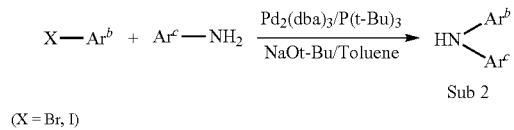

(X = Br, I)

1. Synthesis Example of Sub 2-1

<Reaction Scheme 17>

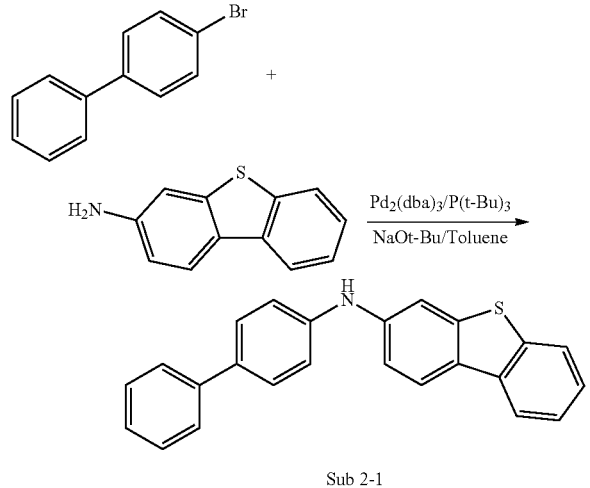

Sub 2-1

4-bromo-1,1'-biphenyl (32.2 g, 138 mmol), dibenzo[b,d]thiophen-3-amine (25 g, 125.5 mmol), $Pd_2(dba)_3$ (5.74 g, 6.3 mmol), $P(t-Bu)_3$ (2.54 g, 12.5 mmol), NaOt-Bu (36.2 g, 376.4 mmol) and toluene 1320 mL were loaded into a round bottom flask and then the reaction proceeded at 100° C. After the completion of the reaction, the reaction product was extracted with ether and water. The extracted organic layer was dried with $MgSO_4$ and concentrated. The concentrated product was separated by silica gel column chromatography, and was then recrystallized, whereby compound Sub 2-1 was obtained in the amount of 34 g (77%).

2. Synthesis Example of Sub 2-6

<Reaction Scheme 18>

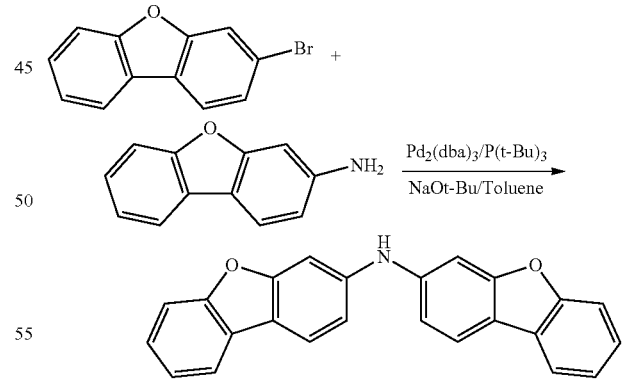

Sub 2-6

Product Sub 2-6 was obtained in the amount of 35.3 g (74%) where 3-bromodibenzo[b,d]furan (37.1 g, 150 mmol), dibenzo[b,d]furan-3-amine (25 g, 136.5 mmol), $Pd_2(dba)_3$ (6.25 g, 6.82 mmol), $P(t-Bu)_3$ (2.76 g, 13.65 mmol), NaOt-Bu (39.3 g, 409.4 mmol) and toluene 1430 mL were used in the same manner as described above for the synthesis of compound Sub 2-1.

3. Synthesis Example of Sub 2-10

<Reaction Scheme 19>

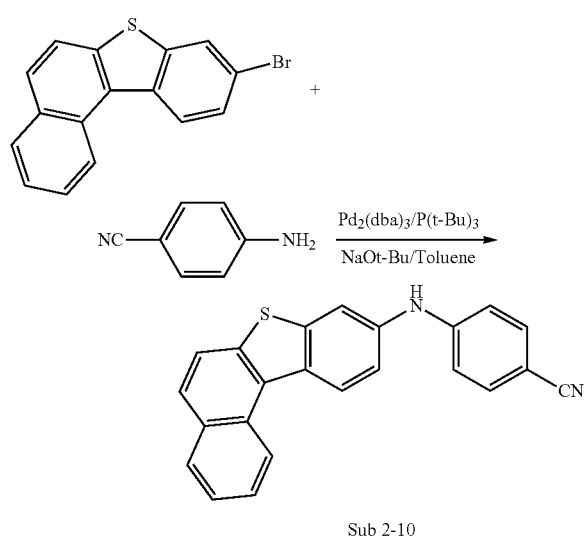

Sub 2-10

Product Sub 2-10 was obtained in the amount of 51.9 g (70%) where 9-bromobenzo[b]naphtho[1,2-d]thiophene (72.9 g, 233 mmol), 4-aminobenzonitrile (25 g, 211.6 mmol), $Pd_2(dba)_3$ (9.7 g, 10.6 mmol), $P(t-Bu)_3$ (4.28 g, 21.2 mmol), NaOt-Bu (61.01 g, 634.8 mmol) and toluene 2220 mL were used in the same manner as described above for the synthesis of compound Sub 2-1.

4. Synthesis Example of Sub 2-25

<Reaction Scheme 20>

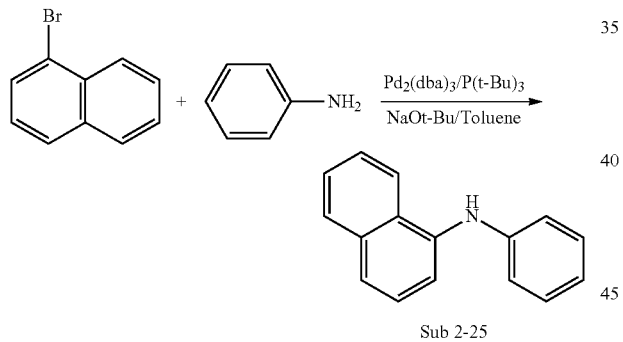

Sub 2-25

Product Sub 2-25 was obtained in the amount of 27.2 g (77%) where 1-bromonaphthalene (36.7 g, 177.2 mmol), aniline (15 g, 161.1 mmol), $Pd_2(dba)_3$ (7.37 g, 8.05 mmol), $P(t-Bu)_3$ (3.26 g, 16.1 mmol), NaOt-Bu (46.4 g, 483.2 mmol) and toluene 1690 mL were used in the same manner as described above for the synthesis of compound Sub 2-1.

5. Synthesis Example of Sub 2-43

<Reaction Scheme 21>

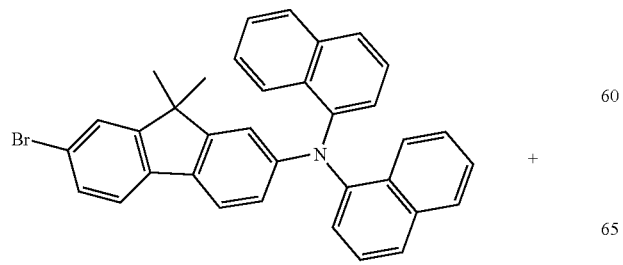

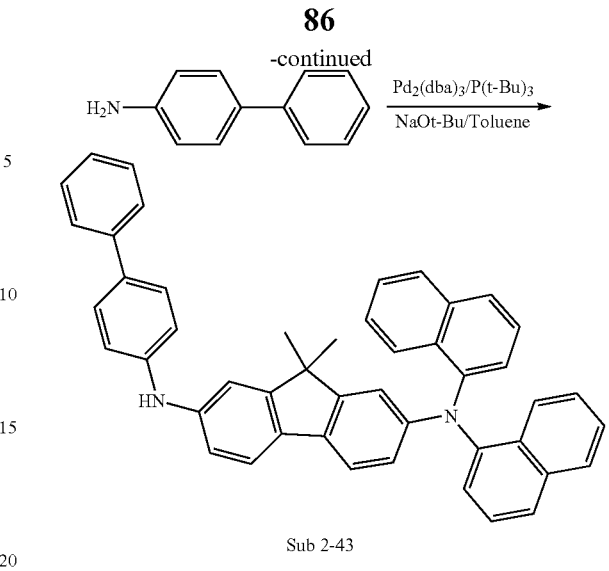

Sub 2-43

Product Sub 2-43 was obtained in the amount of 39.6 g (71%) where 7-bromo-9,9-dimethyl-N,N-di(naphthalen-1-yl)-9H-fluoren-2-amine (52.7 g, 97.5 mmol), [1,1'-biphenyl]-4-amine (15 g, 88.6 mmol), $Pd_2(dba)_3$ (4.1 g, 4.43 mmol), $P(t-Bu)_3$ (1.8 g, 8.9 mmol), NaOt-Bu (25.6 g, 266 mmol) and toluene 930 mL were used in the same manner as described above for the synthesis of compound Sub 2-1.

Examples of Sub 2 compounds include, but are not limited to, the following compounds, and FD-MS (Field Desorption-Mass Spectrometry) data of the compounds is given in Table 3 below.

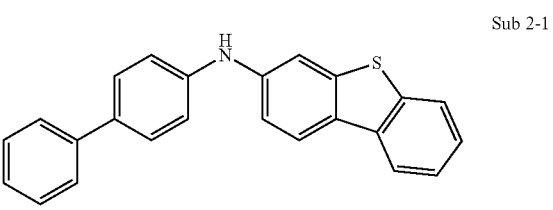

Sub 2-1

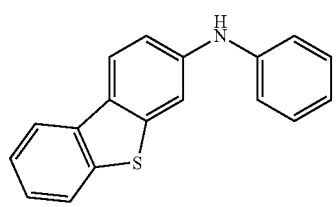

Sub 2-2

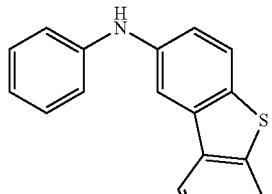

Sub 2-3

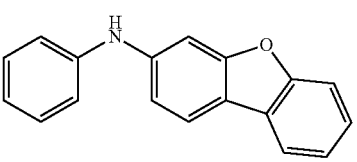

Sub 2-4

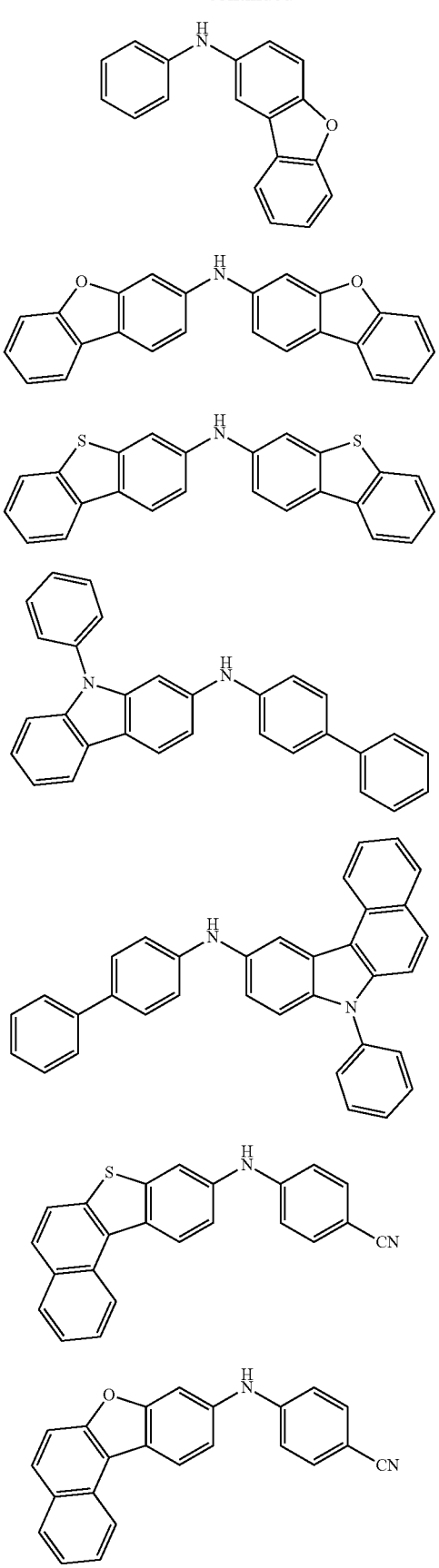
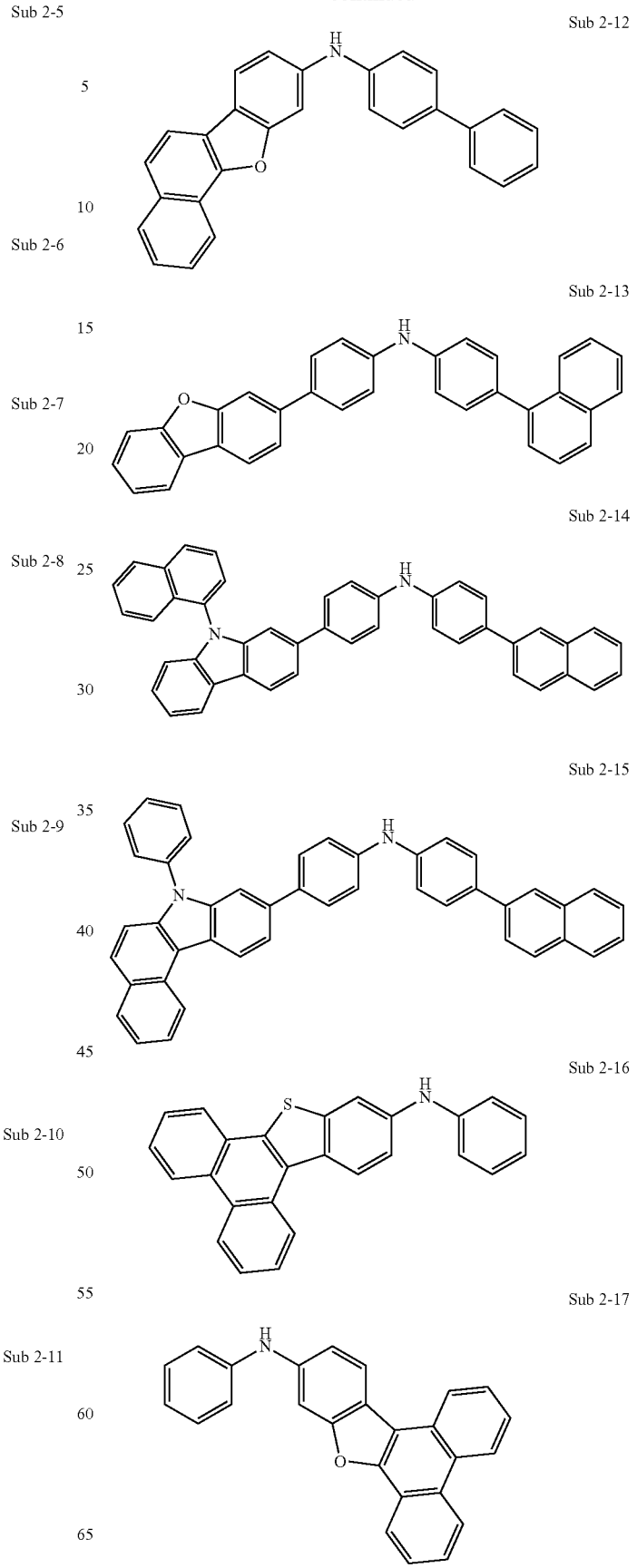

Sub 2-18
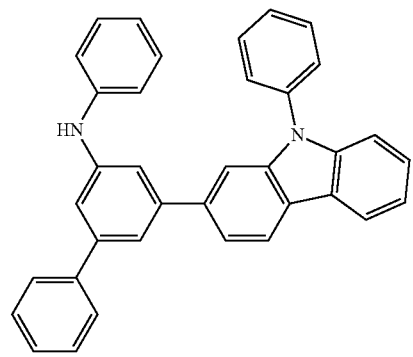
Sub 2-19
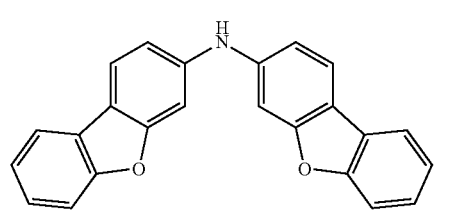
Sub 2-20
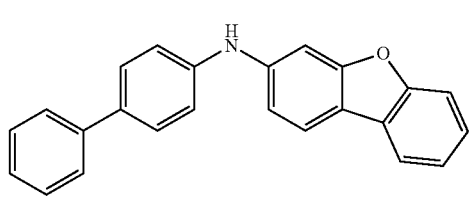
Sub 2-21
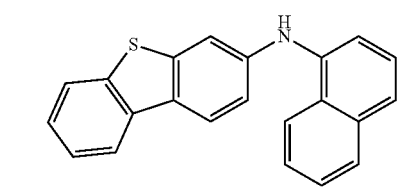
Sub 2-22
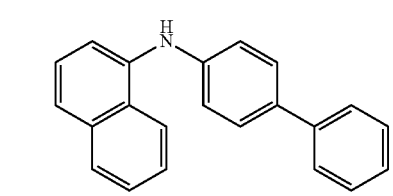
Sub 2-23
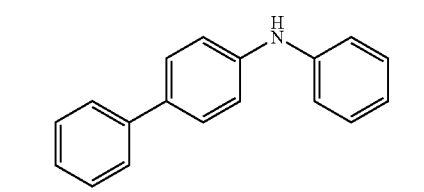
Sub 2-24
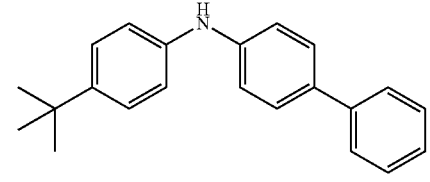
Sub 2-25
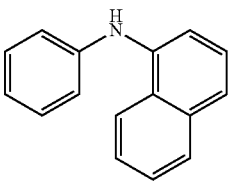
Sub 2-26
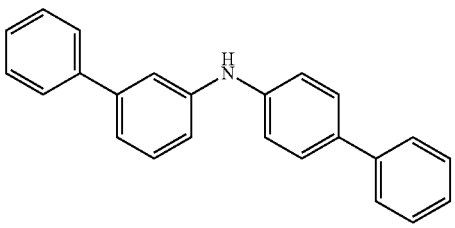
Sub 2-27
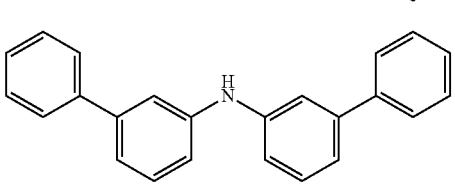
Sub 2-28
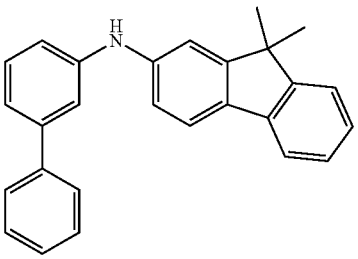
Sub 2-29
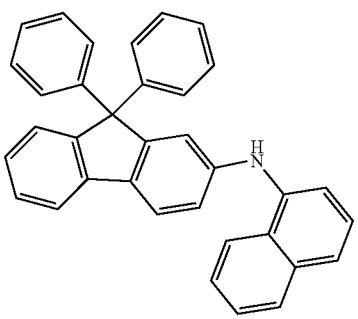
Sub 2-30
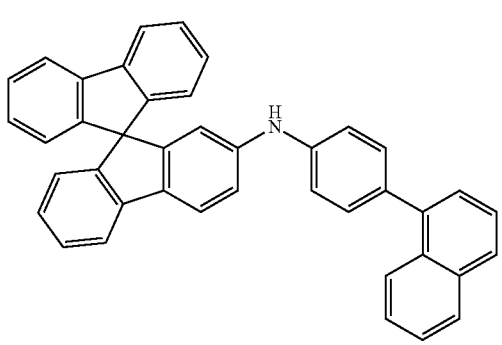

Sub 2-31
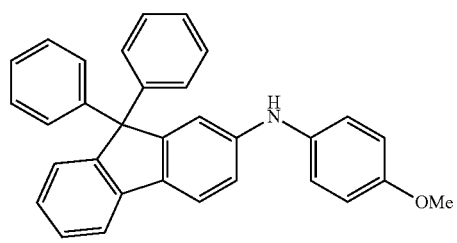
Sub 2-32
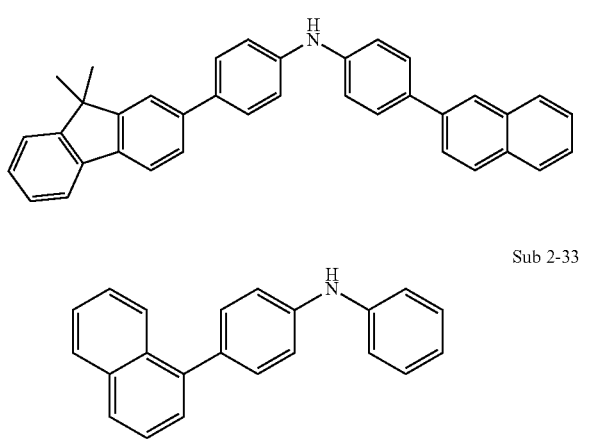
Sub 2-33
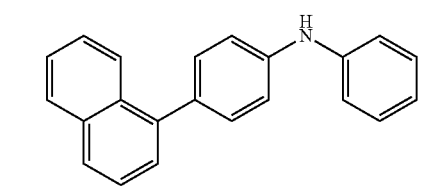
Sub 2-34
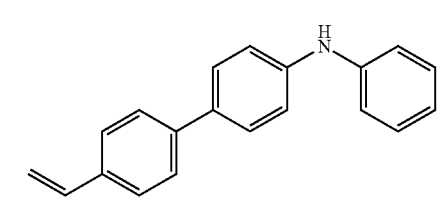
Sub 2-35
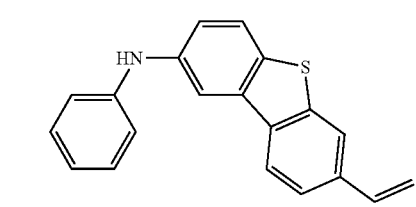
Sub 2-36
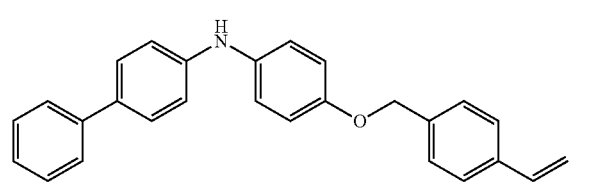
Sub 2-37
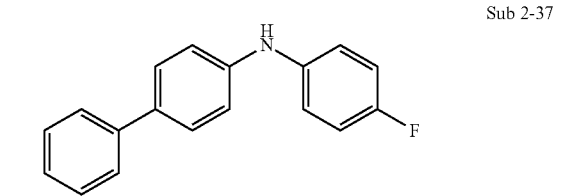
Sub 2-38
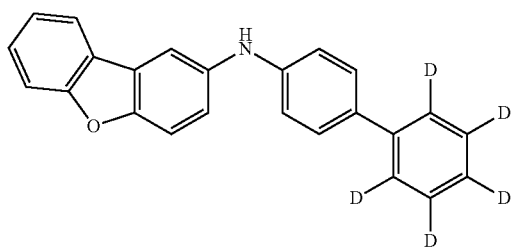
Sub 2-39
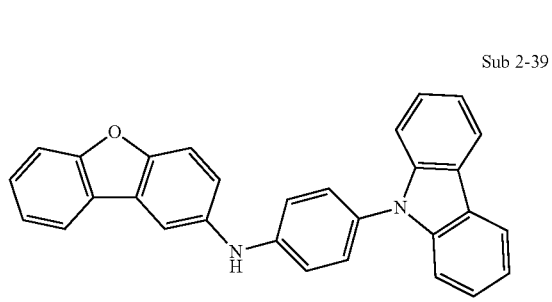
Sub 2-40
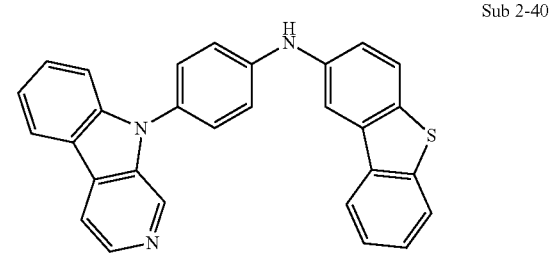
Sub 2-41
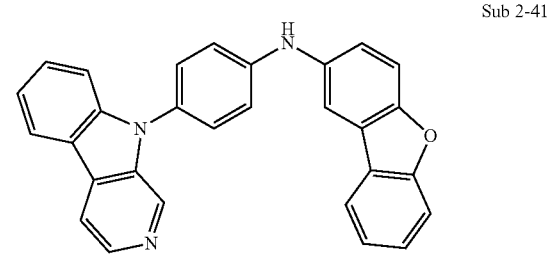
Sub 2-42
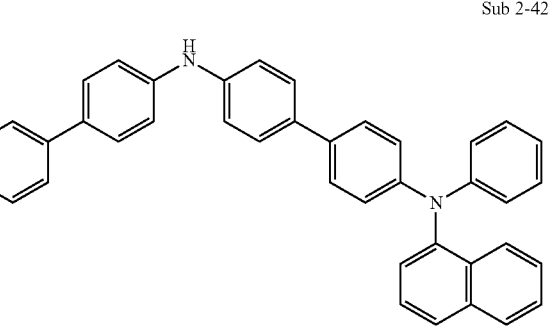

Sub 2-43
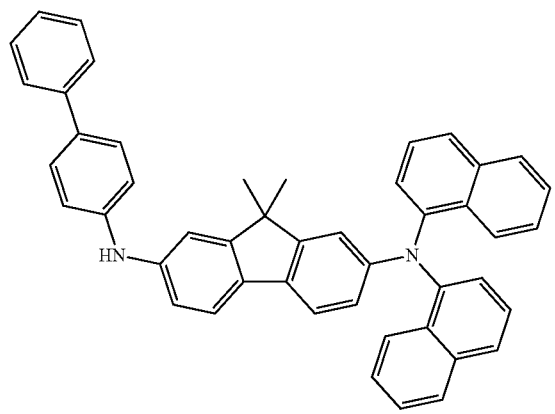
Sub 2-44
Sub 2-45
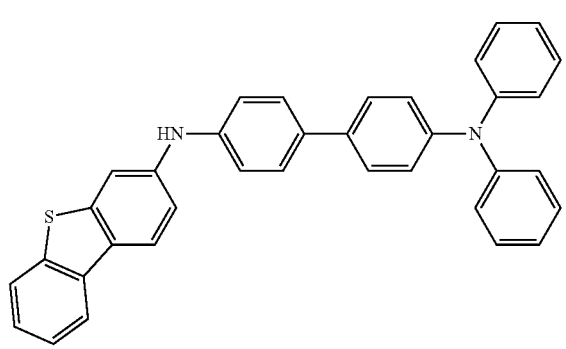
Sub 2-46
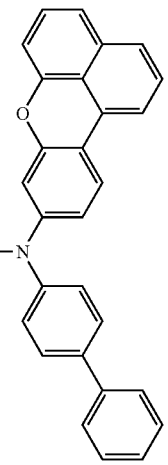
Sub 2-47
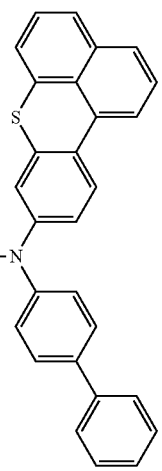
Sub 2-48
Sub 2-49
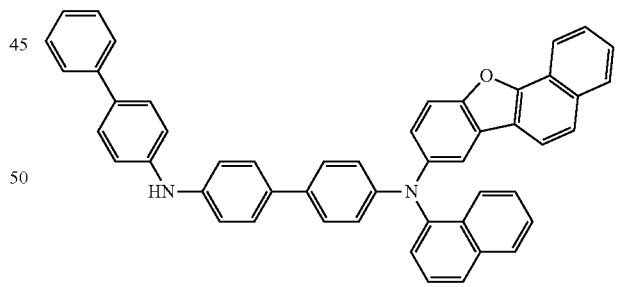
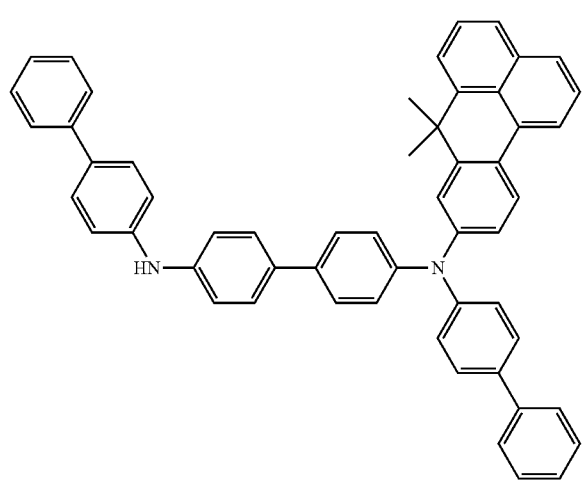

Sub 2-50

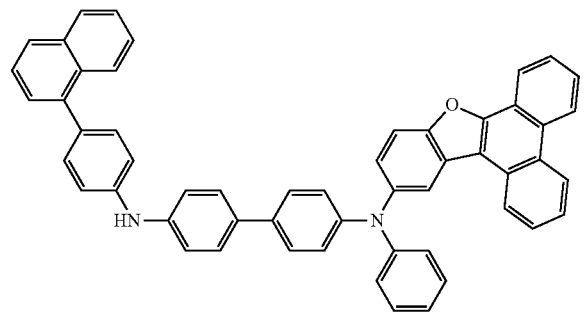

Sub 2-52

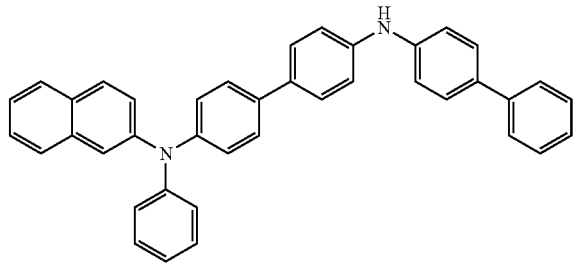

Sub 2-51

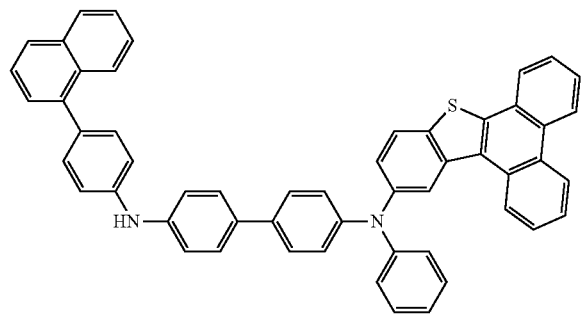

Sub 2-53

TABLE 3

| Compound | FD-MS | Compound | FD-MS |
|---|---|---|---|
| Sub 2-1 | m/z = 351.11($C_{24}H_{17}NS$ = 351.46) | Sub 2-2 | m/z = 275.08($C_{18}H_{13}NS$ = 275.37) |
| Sub 2-3 | m/z = 275.08($C_{18}H_{13}NS$ = 275.37) | Sub 2-4 | m/z = 259.10($C_{18}H_{13}NO$ = 259.30) |
| Sub 2-5 | m/z = 259.10($C_{18}H_{13}NO$ = 259.30) | Sub 2-6 | m/z = 349.11($C_{24}H_{13}NO_2$ = 349.38) |
| Sub 2-7 | m/z = 381.06($C_{24}H_{15}NS_2$ = 381.51) | Sub 2-8 | m/z = 410.18($C_{30}H_{22}N_2$ = 410.51) |
| Sub 2-9 | m/z = 460.19($C_{34}H_{24}N_2$ = 460.57) | Sub 2-10 | m/z = 350.09($C_{23}H_{14}N_2S$ = 350.44) |
| Sub 2-11 | m/z = 334.11($C_{23}H_{14}N_2O$ = 334.37) | Sub 2-12 | m/z = 385.15($C_{28}H_{19}NO$ = 385.46) |
| Sub 2-13 | m/z = 461.18($C_{34}H_{23}NO$ = 461.55) | Sub 2-14 | m/z = 586.24($C_{44}H_{30}N_2$ = 586.72) |
| Sub 2-15 | m/z = 586.24($C_{44}H_{30}N_2$ = 586.72) | Sub 2-16 | m/z = 375.11($C_{26}H_{17}NS$ = 375.48) |
| Sub 2-17 | m/z = 359.13($C_{26}H_{17}NO$ = 359.42) | Sub 2-18 | m/z = 486.21($C_{36}H_{26}N_2$ = 486.61) |
| Sub 2-19 | m/z = 349.11($C_{24}H_{13}NO_2$ = 349.38) | Sub 2-20 | m/z = 335.13($C_{24}H_{12}NO$ = 335.40) |
| Sub 2-21 | m/z = 325.09($C_{22}H_{15}NS$ = 325.43) | Sub 2-22 | m/z = 295.14($C_{22}H_{17}N$ = 295.38) |
| Sub 2-23 | m/z = 245.12($C_{18}H_{15}N$ = 245.32) | Sub 2-24 | m/z = 301.18($C_{22}H_{23}N$ = 301.42) |
| Sub 2-25 | m/z = 219.10($C_{18}H_{15}N$ = 219.28) | Sub 2-26 | m/z = 321.15($C_{24}H_{19}N$ = 321.41) |
| Sub 2-27 | m/z = 321.15($C_{24}H_{15}N$ = 321.41) | Sub 2-28 | m/z = 361.18($C_{27}H_{23}N$ = 361.48) |
| Sub 2-29 | m/z = 459.20($C_{35}H_{25}N$ = 459.58) | Sub 2-30 | m/z = 533.21($C_{41}H_{27}N$ = 533.66) |
| Sub 2-31 | m/z = 439.19($C_{32}H_{25}NO$ = 439.55) | Sub 2-32 | m/z = 487.23($C_{37}H_{29}N$ = 487.63) |
| Sub 2-33 | m/z = 295.14($C_{22}H_{17}N$ = 295.38) | Sub 2-34 | m/z = 271.14($C_{20}H_{17}N$ = 271.36) |
| Sub 2-35 | m/z = 301.09($C_{20}H_{15}NS$ = 301.40) | Sub 2-36 | m/z = 377.18($C_{27}H_{23}NO$ = 377.48) |
| Sub 2-37 | m/z = 263.11($C_{18}H_{14}FN$ = 263.31) | Sub 2-38 | m/z = 340.16($C_{24}H_{12}D_5NO$ = 340.43) |
| Sub 2-39 | m/z = 424.16($C_{30}H_{20}N_2O$ = 424.49) | Sub 2-40 | m/z = 441.13($C_{29}H_{19}N_3S$ = 441.55) |
| Sub 2-41 | m/z = 425.15($C_{29}H_{19}N_3O$ = 425.48) | Sub 2-42 | m/z = 538.24($C_{40}H_{30}N_2$ = 538.68) |
| Sub 2-43 | m/z = 628.29($C_{47}H_{23}N_2$ = 628.80) | Sub 2-44 | m/z = 518.18($C_{36}H_{26}N_2S$ = 518.67) |
| Sub 2-45 | m/z = 730.33($C_{36}H_{42}N_2$ = 730.94) | Sub 2-46 | m/z = 704.28($C_{32}H_{30}N_2O$ = 704.86) |
| Sub 2-47 | m/z = 720.26($C_{32}H_{38}N_2S$ = 720.92) | Sub 2-48 | m/z = 678.27($C_{30}H_{34}N_2O$ = 678.82) |
| Sub 2-49 | m/z = 694.24($C_{30}H_{34}N_2S$ = 694.88) | Sub 2-50 | m/z = 728.28($C_{34}H_{36}N_2O$ = 728.88) |
| Sub 2-51 | m/z = 744.26($C_{34}H_{35}N_2S$ = 744.94) | Sub 2-52 | m/z = 538.24($C_{40}H_{30}N_2$ = 538.68) |
| Sub 2-53 | m/z = 640.29($C_{48}H_{36}N_2$ = 640.81) | | |

IV. Synthesis Example of Final Products

1. Synthesis Example 1 of a Final Product: (in Case of One of Sub 2 being Bonded)

Sub 2 (1 eq.), Sub 1 (1.1 eq.), Pd$_2$(dba)$_3$ (0.05 eq.), P(t-Bu)$_3$ (0.1 eq.), NaOt-Bu (3 eq.) and toluene (10.5 mL/Sub 21 mmol) were loaded into a round bottom flask and stirred at 100° C. After the completion of the reaction, the reaction product was extracted with CH$_2$Cl$_2$ and water. The extracted organic layer was dried with MgSO$_4$ and concentrated. The concentrated product was separated by silica gel column chromatography, and was then recrystallized, whereby a final product was obtained.

2. Synthesis Example 2 of a Final Product: (in Case of the Same Two Sub 2 being Bonded)

Sub 2 (2.2 eq.), Sub 1 (1 eq.), Pd$_2$(dba)$_3$ (0.1 eq.), P(t-Bu)$_3$ (0.2 eq.), NaOt-Bu (6.6 eq.) and toluene (6 mL/Sub 21 mmol) were loaded into a round bottom flask and stirred at 100° C. After the completion of the reaction, the reaction product was extracted with CH$_2$Cl$_2$ and water. The extracted organic layer was dried with MgSO$_4$ and concentrated. The concentrated product was separated by silica gel column chromatography, and was then recrystallized, whereby a final product was obtained.

3. Synthesis Example 3 of a Final Product: (in Case of Different Two Sub 2 being Bonded)

Sub 2 (1 eq.), Sub 1 (1.1 eq.), Pd$_2$(dba)$_3$ (0.06 eq.), P(t-Bu)$_3$ (0.12 eq.), NaOt-Bu (3 eq.) and toluene (10.5 mL/Sub 21 mmol) were loaded into a round bottom flask and stirred at 100° C. After the completion of the reaction, the reaction product was extracted with CH$_2$Cl$_2$ and water. The extracted organic layer was dried and concentrated. The concentrated product was separated by silica gel column chromatography, was then recrystallized. The recrystallized product (1.1 eq.), Sub 2 (1 eq.) being different from the above Sub 2, Pd$_2$(dba)$_3$ (0.05 eq.), P(t-Bu)$_3$ (0.1 eq.), NaOt-Bu (3 eq.) and toluene (10.5 mL/Sub 2 mmol) were loaded into a round bottom flask and the reaction proceeded. Upon the completion of the reaction, a final product was obtained as described in the above synthesis example 2.

(1) Synthesis of P1-1

<Reaction Scheme 22>

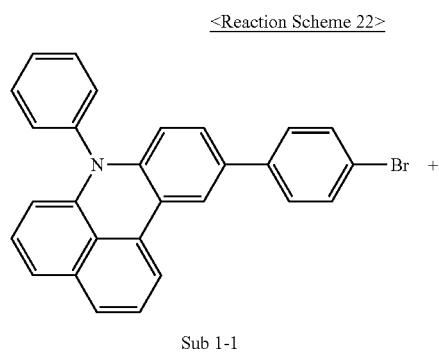

Sub 1-1

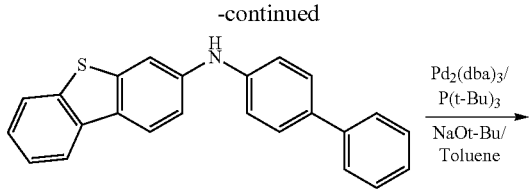

Sub 2-1

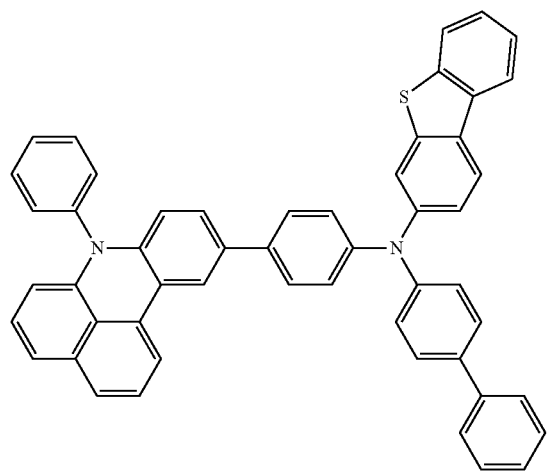

P1-1

The final product P1-1 was obtained in the amount of 22.1 g (72%) where Sub 2-1 (15 g, 42.7 mmol), Sub 1-1 (21 g, 46.9 mmol), Pd$_2$(dba)$_3$ (1.95 g, 2.13 mmol), P(t-Bu)$_3$ (0.86 g, 4.3 mmol), NaOt-Bu (12.3 g, 128 mmol) and toluene 448 mL were used in the same manner as described in the above synthesis example 1 of a final product.

(2) Synthesis of P1-7

<Reaction Scheme 23>

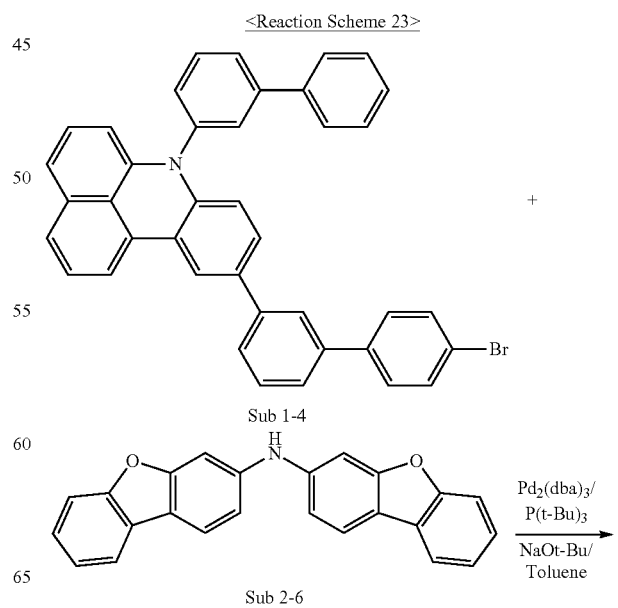

Sub 1-4

Sub 2-6

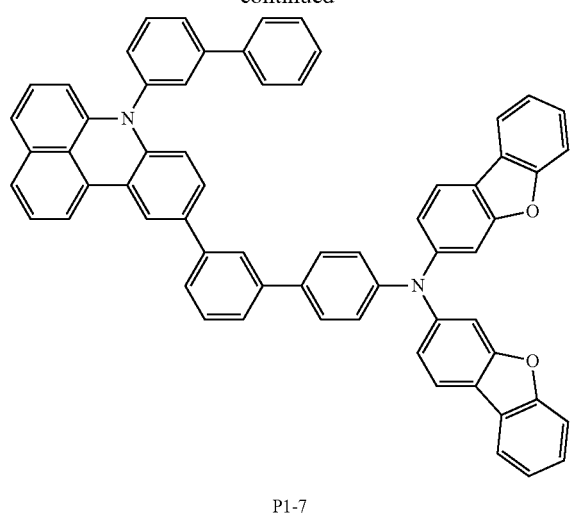

P1-7

The final product P1-7 was obtained in the amount of 26.1 g (70%) where Sub 2-6 (15 g, 42.9 mmol), Sub 1-4 (28.4 g, 47.2 mmol), Pd$_2$(dba)$_3$ (1.97 g, 2.15 mmol), P(t-Bu)$_3$ (0.87 g, 4.3 mmol), NaOt-Bu (12.4 g, 128.8 mmol) and toluene 450 mL were used in the same manner as described in the above synthesis example 1 of a final product.

(3) Synthesis of P1-17

<Reaction Scheme 24>

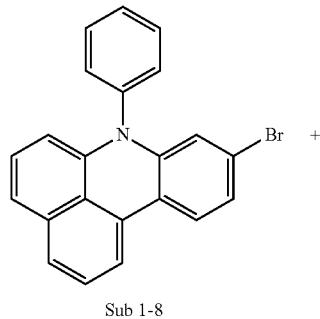

Sub 1-8

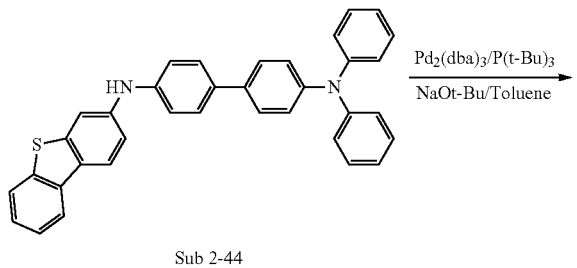

Sub 2-44

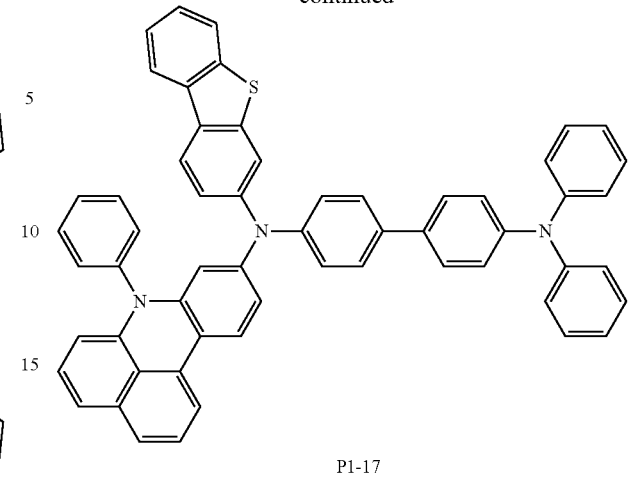

P1-17

The final product P1-17 was obtained in the amount of 17.1 g (73%) where Sub 2-44 (15 g, 28.9 mmol), Sub 1-18 (11.8 g, 31.8 mmol), Pd$_2$(dba)$_3$ (1.32 g, 1.45 mmol), P(t-Bu)$_3$ (0.59 g, 2.89 mmol), NaOt-Bu (8.34 g, 86.8 mmol) and toluene 304 mL were used in the same manner as described in the above synthesis example 1 of a final product.

(4) Synthesis of P2-5

<Reaction Scheme 25>

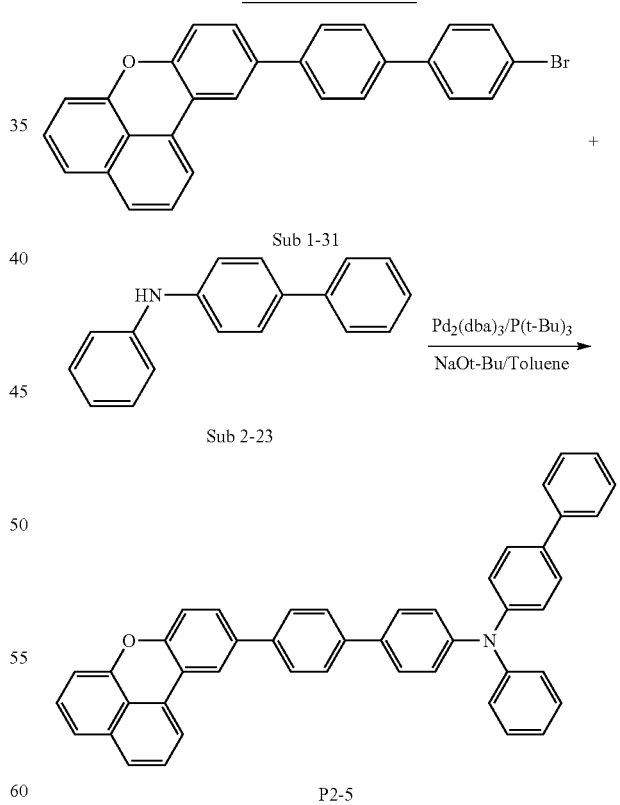

P2-5

The final product P2-5 was obtained in the amount of 28.5 g (76%) where Sub 2-23 (15 g, 61.1 mmol), Sub 1-31 (30.2 g, 67.3 mmol), Pd$_2$(dba)$_3$ (2.8 g, 3.06 mmol), P(t-Bu)$_3$ (1.24 g, 6.11 mmol), NaOt-Bu (17.63 g, 183.4 mmol) and toluene 642 mL were used in the same manner as described in the above synthesis example 1 of a final product.

(5) Synthesis of P2-17

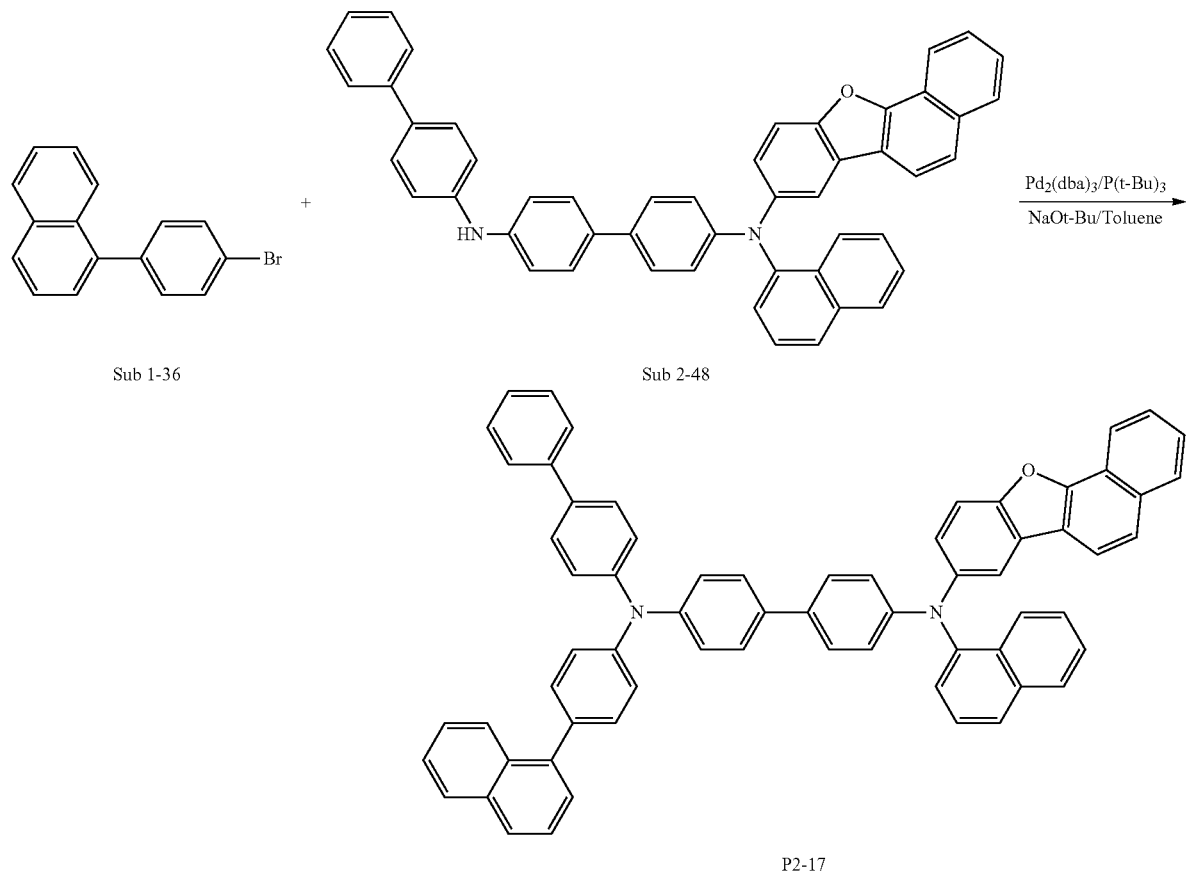

The final product P2-17 was obtained in the amount of 13.8 g (71%) where Sub 2-48 (15 g, 22.1 mmol), Sub 1-36 (6.88 g, 24.3 mmol), Pd$_2$(dba)$_3$ (1.01 g, 1.10 mmol), P(t-Bu)$_3$ (0.45 g, 2.21 mmol), NaOt-Bu (6.37 g, 66.3 mmol) and toluene 232 mL were used in the same manner as described in the above synthesis example 1 of a final product.

(6) Synthesis of P3-6

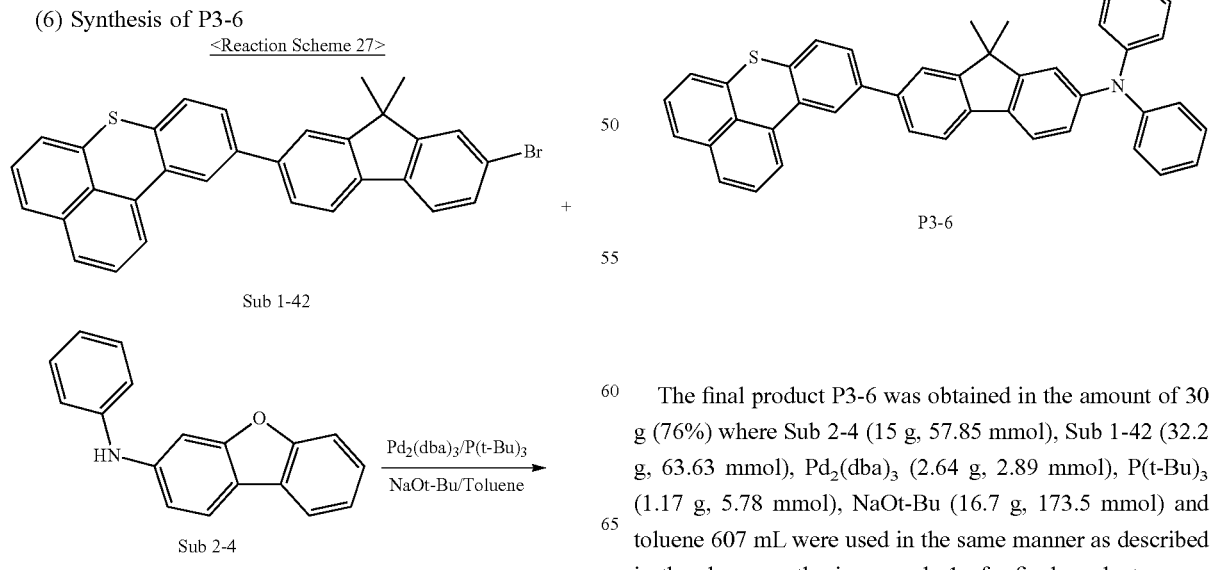

The final product P3-6 was obtained in the amount of 30 g (76%) where Sub 2-4 (15 g, 57.85 mmol), Sub 1-42 (32.2 g, 63.63 mmol), Pd$_2$(dba)$_3$ (2.64 g, 2.89 mmol), P(t-Bu)$_3$ (1.17 g, 5.78 mmol), NaOt-Bu (16.7 g, 173.5 mmol) and toluene 607 mL were used in the same manner as described in the above synthesis example 1 of a final product.

(7) Synthesis of P3-10

<Reaction Scheme 28>

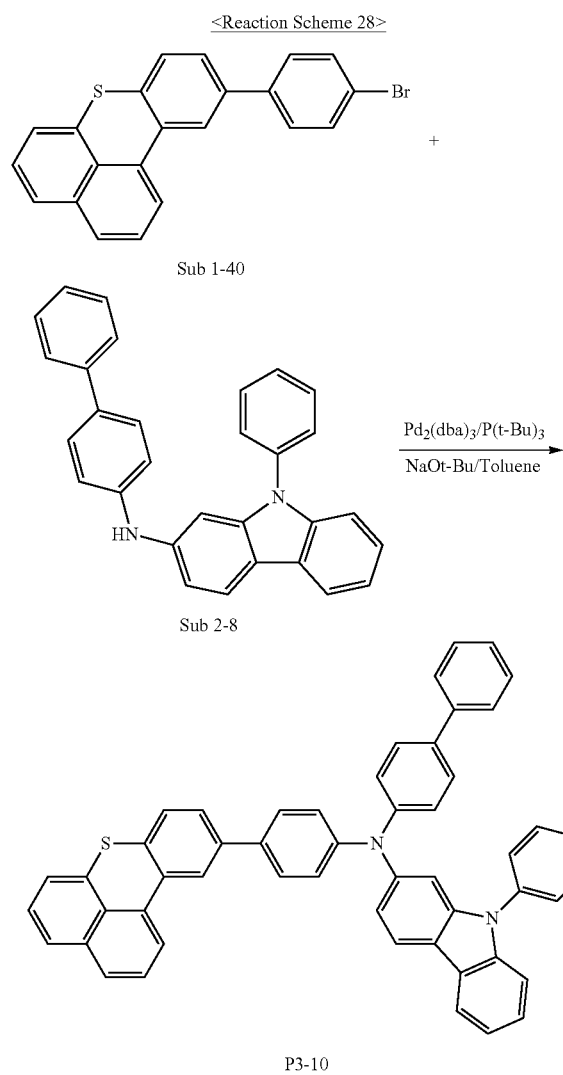

P3-10

The final product P3-10 was obtained in the amount of 20.2 g (77%) where Sub 2-8 (15 g, 36.5 mmol), Sub 1-40 (15.65 g, 40.2 mmol), Pd₂(dba)₃ (1.67 g, 1.83 mmol), P(t-Bu)₃ (0.74 g, 3.65 mmol), NaOt-Bu (10.5 g, 109.6 mmol) and toluene 383 mL were used in the same manner as described in the above synthesis example 1 of a final product.

(8) Synthesis of P3-25

<Reaction Scheme 29>

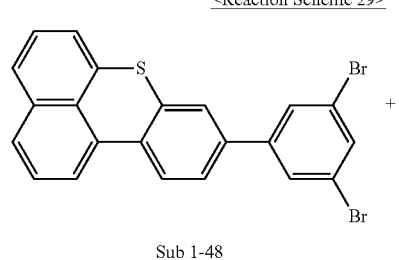

Sub 1-48

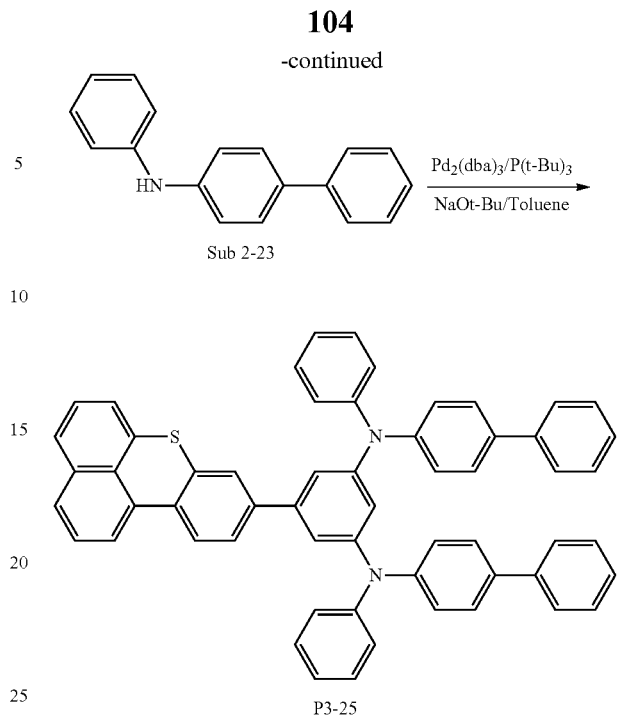

P3-25

The final product P3-25 was obtained in the amount of 37.8 g (74%) where Sub 2-23 (34.6 g, 141 mmol), Sub 1-48 (30 g, 64.08 mmol), Pd₂(dba)₃ (5.86 g, 6.41 mmol), P(t-Bu)₃ (2.6 g, 12.8 mmol), NaOt-Bu (40.6 g, 423 mmol) and toluene 845 mL were used in the same manner as described in the above synthesis example 2 of a final product.

(9) Synthesis of P4-9

<Reaction Scheme 30>

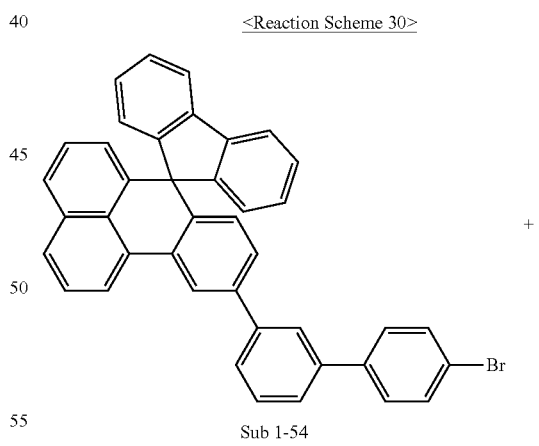

-continued

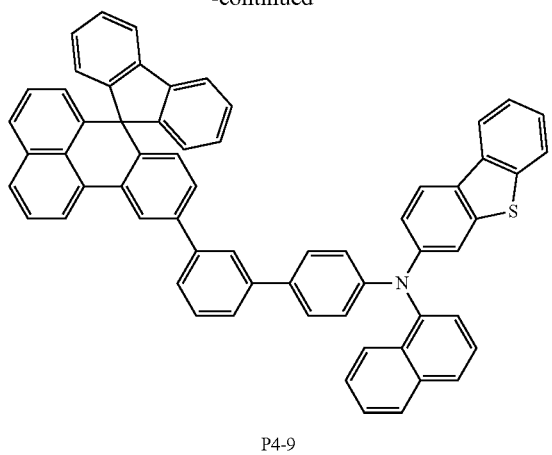

P4-9

The final product P4-9 was obtained in the amount of 26.4 g (68%) where Sub 2-21 (15 g, 46.1 mmol), Sub 1-54 (30.3 g, 50.7 mmol), Pd₂(dba)₃ (2.11 g, 2.3 mmol), P(t-Bu)₃ (0.93 g, 4.6 mmol), NaOt-Bu (13.3 g, 138.3 mmol) and toluene 484 mL were used in the same manner as described in the above synthesis example 1 of a final product.

(10) Synthesis of P4-23

<Reaction Scheme 31>

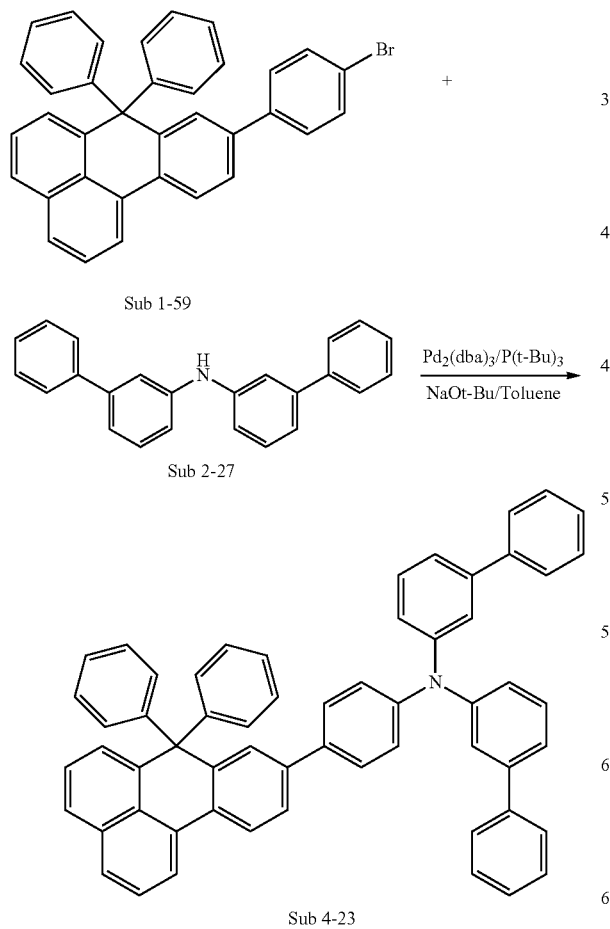

The final product P4-23 was obtained in the amount of 26.7 g (75%) where Sub 2-27 (15 g, 46.7 mmol), Sub 1-59 (26.9 g, 51.3 mmol), Pd₂(dba)₃ (2.14 g, 2.33 mmol), P(t-Bu)₃ (0.94 g, 4.67 mmol), NaOt-Bu (13.5 g, 140 mmol) and toluene 490 mL were used in the same manner as described in the above synthesis example 1 of a final product.

(11) Synthesis of P4-29

<Reaction Scheme 32>

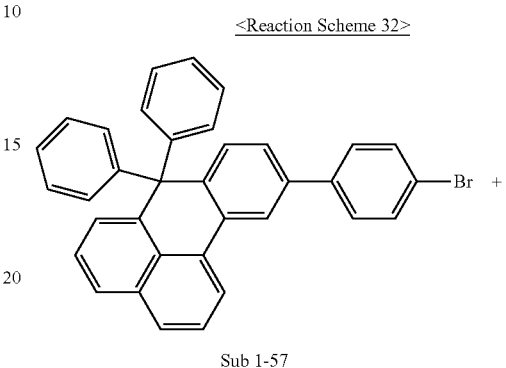

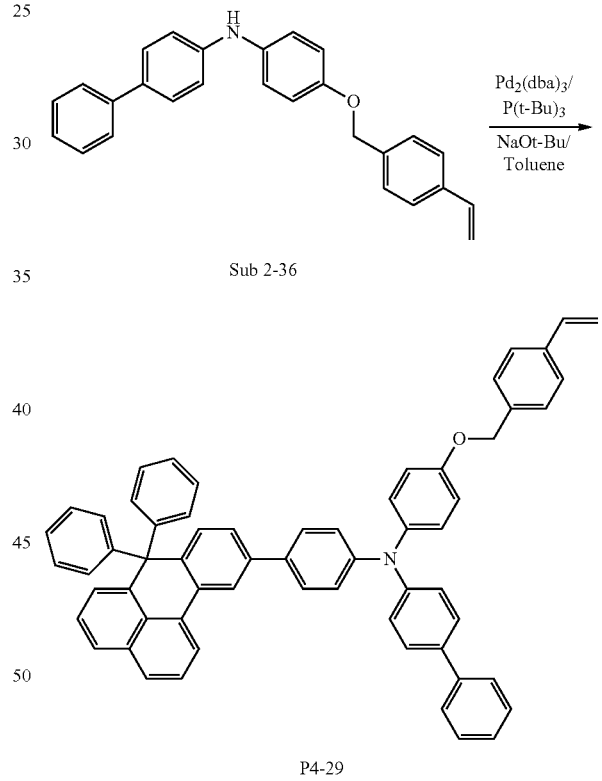

P4-29

The final product P4-29 was obtained in the amount of 23.1 g (71%) where Sub 2-36 (15 g, 39.7 mmol), Sub 1-57 (22.9 g, 43.7 mmol), Pd₂(dba)₃ (1.82 g, 1.99 mmol), P(t-Bu)₃ (0.80 g, 3.97 mmol), NaOt-Bu (11.5 g, 119.2 mmol) and toluene 417 mL were used in the same manner as described in the above synthesis example 1 of a final product.

FD-MS data of the final products P1-1 to P1-40, P2-1 to P2-30, P3-1 to P3-30 and P4-1 to P4-30 of the present invention synthesized by the above synthesises is given in Table 4 below.

TABLE 4

| Compound | FD-MS | Compound | FD-MS |
|---|---|---|---|
| P1-1 | m/z = 718.24($C_{52}H_{34}N_2S$ = 718.90) | P1-2 | m/z = 626.24($C_{46}H_{30}N_2O$ = 626.74) |
| P1-3 | m/z = 728.32($C_{55}H_{40}N_2$ = 728.92) | P1-4 | m/z = 662.27($C_{30}H_{34}N_2$ = 662.82) |
| P1-5 | m/z = 738.30($C_{50}H_{38}N_2$ = 738.91) | P1-6 | m/z = 808.29($C_{39}H_{40}N_2S$ = 809.03) |
| P1-7 | m/z = 868.31 ($C_{64}H_{40}N_2O_2$ = 869.01) | P1-8 | m/z = 900.26($C_{84}H_{40}N_2S_2$ = 901.15) |
| P1-9 | m/z = 688.29($C_{32}H_{38}N_2$ = 688.86) | P1-10 | m/z = 850.34($C_{82}H_{46}N_2S$ = 851.11) |
| P1-11 | m/z = 1018.43($C_{78}H_{54}N_2$ = 1019.28) | P1-12 | m/z = 1026.40($C_{79}H_{50}N_2$ = 1027.26) |
| P1-13 | m/z = 827.33($C_{62}H_{41}N_3$ = 828.01) | P1-14 | m/z = 903.36($C_{68}H_{41}N_3$ = 904.10) |
| P1-15 | m/z = 829.35($C_{62}H_{43}N_3$ = 830.02) | P1-16 | m/z = 919.39($C_{89}H_{49}N_3$ = 920.15) |
| P1-17 | m/z = 809.29($C_{58}H_{39}N_3S$ = 810.02) | P1-18 | m/z = 767.24($C_{35}H_{33}N_3S$ = 767.94) |
| P1-19 | m/z = 802.30($C_{60}H_{38}N_2O$ = 802.96) | P1-20 | m/z = 818.28($C_{60}H_{38}N_2S$ = 819.02) |
| P1-21 | m/z = 752.28($C_{55}H_{35}N_2O$ = 752.90) | P1-22 | m/z = 877.35($C_{55}H_{43}N_3$ = 878.07) |
| P1-23 | m/z = 877.35($C_{66}H_{43}N_3$ = 878.07) | P1-24 | m/z = 818.28($C_{60}H_{38}N_2S$ = 819.02) |
| P1-25 | m/z = 830.34($C_{61}H_{42}N_4$ = 831.01) | P1-26 | m/z = 614.25($C_{44}H_{30}N_4$ = 614.74) |
| P1-27 | m/z = 688.29($C_{32}H_{36}N_2$ = 688.86) | P1-28 | m/z = 718.24($C_{32}H_{34}N_2S$ = 718.90) |
| P1-29 | m/z = 859.30($C_{62}H_{41}N_3S$ = 860.07) | P1-30 | m/z = 905.38($C_{60}H_{47}N_3$ = 906.12) |
| P1-31 | m/z = 991.31($C_{70}H_{45}N_3S_2$ = 992.26) | P1-32 | m/z = 832.35($C_{62}H_{44}N_2O$ = 833.03) |
| P1-33 | m/z = 738.30($C_{56}H_{38}N_2$ = 738.91) | P1-34 | m/z = 794.28($C_{58}H_{38}N_2S$ = 795.00) |
| P1-35 | m/z = 744.31($C_{55}H_{40}N_2O$ = 744.92) | P1-36 | m/z = 630.25($C_{46}H_{31}FN_2$ = 630.75) |
| P1-37 | m/z = 707.30($C_{52}H_{29}D_5N_2O$ = 707.87) | P1-38 | m/z = 631.27($C_{46}H_{25}D_5N_2O$ = 631.77) |
| P1-39 | m/z = 796.33($C_{58}H_{32}D_5N_3O$ = 796.96) | P1-40 | m/z = 818.30($C_{39}H_{38}N_4O$ = 818.96) |
| P2-1 | m/z = 643.20($C_{46}H_{29}NOS$ = 643.79) | P2-2 | m/z = 551.19($C_{40}H_{25}NO_2$ = 551.63) |
| P2-3 | m/z = 653.27($C_{49}H_{39}NO$ = 653.81) | P2-4 | m/z = 587.22($C_{44}H_{29}NO$ = 587.71) |
| P2-5 | m/z = 613.24($C_{46}H_{31}NO$ = 613.74) | P2-6 | m/z = 683.23($C_{49}H_{33}NOS$ = 683.86) |
| P2-7 | m/z = 749.18($C_{52}H_{31}NOS_2$ = 749.94) | P2-8 | m/z = 613.24($C_{46}H_{31}NO$ = 613.74) |
| P2-9 | m/z = 827.32($C_{63}H_{41}NO$ = 828.01) | P2-10 | m/z = 702.27($C_{32}H_{34}N_2O$ = 702.84) |
| P2-11 | m/z = 752.28($C_{50}H_{30}N_2O$ = 752.90) | P2-12 | m/z = 754.30($C_{50}H_{38}N_2O$ = 754.91) |
| P2-13 | m/z = 754.30($C_{36}H_{38}N_2O$ = 754.91) | P2-14 | m/z = 844.35($C_{83}H_{44}N_2O$ = 845.04) |
| P2-15 | m/z = 946.39($C_{71}H_{50}N_2O$ = 947.17) | P2-16 | m/z = 734.24($C_{32}H_{34}N_2OS$ = 734.90) |
| P2-17 | m/z = 880.35($C_{66}H_{44}N_2O$ = 881.07) | P2-18 | m/z = 930.36($C_{79}H_{46}N_2O$ = 931.13) |
| P2-19 | m/z = 642.18($C_{45}H_{26}N_2OS$ = 642.77) | P2-20 | m/z = 677.24($C_{30}H_{33}NO_2$ = 677.79) |
| P2-21 | m/z = 802.30($C_{50}H_{38}N_2O$ = 802.96) | P2-22 | m/z = 743.23($C_{54}H_{33}NOS$ = 743.91) |
| P2-23 | m/z = 613.24($C_{46}H_{31}NO$ = 613.74) | P2-24 | m/z = 702.27($C_{52}H_{34}N_2O$ = 702.84) |
| P2-25 | m/z = 780.31($C_{58}H_{40}N_2O$ = 780.95) | P2-26 | m/z = 840.23($C_{38}H_{36}N_2OS_2$ = 841.05) |
| P2-27 | m/z = 731.28($C_{54}H_{37}NO_2$ = 731.88) | P2-28 | m/z = 563.22($C_{42}H_{29}NO$ = 563.69) |
| P2-29 | m/z = 669.27($C_{49}H_{35}NO_2$ = 669.81) | P2-30 | m/z = 733.22($C_{31}H_{31}N_3OS$ = 733.88) |
| P3-1 | m/z = 643.20($C_{46}H_{29}NOS$ = 643.79) | P3-2 | m/z = 567.17($C_{40}H_{25}NOS$ = 567.70) |
| P3-3 | m/z = 669.25($C_{49}H_{35}NS$ = 669.87) | P3-4 | m/z = 603.20($C_{44}H_{29}NS$ = 603.77) |
| P3-5 | m/z = 629.22($C_{49}H_{31}NS$ = 629.81) | P3-6 | m/z = 683.23($C_{49}H_{33}NOS$ = 683.86) |
| P3-7 | m/z = 733.21($C_{52}H_{31}NO_2S$ = 733.87) | P3-8 | m/z = 629.22($C_{46}H_{31}NS$ = 629.81) |
| P3-9 | m/z = 843.30($C_{63}H_{41}NS$ = 844.07) | P3-10 | m/z = 718.24($C_{52}H_{34}N_2S$ = 718.90) |
| P3-11 | m/z = 768.26($C_{63}H_{41}NS$ = 768.96) | P3-12 | m/z = 770.28($C_{56}H_{38}N_2S$ = 770.98) |
| P3-13 | m/z = 770.28($C_{56}H_{38}N_2S$ = 770.98) | P3-14 | m/z = 860.32($C_{53}H_{44}N_2S$ = 861.10) |
| P3-15 | m/z = 936.32($C_{68}H_{44}N_2OS$ = 937.15) | P3-16 | m/z = 952.29($C_{68}H_{44}N_2S_2$ = 953.22) |
| P3-17 | m/z = 896.32($C_{66}H_{44}N_2S$ = 897.13) | P3-18 | m/z = 946.34($C_{70}H_{46}N_2S$ = 947.19) |
| P3-19 | m/z = 642.18($C_{46}H_{26}N_2OS$ = 642.77) | P3-20 | m/z = 693.21($C_{50}H_{31}NOS$ = 693.85) |
| P3-21 | m/z = 818.28($C_{60}H_{38}N_2S$ = 819.02) | P3-22 | m/z = 743.23($C_{54}H_{33}NOS$ = 743.91) |
| P3-23 | m/z = 629.22($C_{46}H_{31}NS$ = 629.81) | P3-24 | m/z = 718.24($C_{52}H_{34}N_2S$ = 718.90) |
| P3-25 | m/z = 796.29($C_{58}H_{40}N_2S$ = 797.02) | P3-26 | m/z = 824.25($C_{58}H_{36}N_2O_2S$ = 824.98) |
| P3-27 | m/z = 747.26($C_{54}H_{37}NOS$ = 747.94) | P3-28 | m/z = 579.20($C_{42}H_{29}NS$ = 579.75) |
| P3-29 | m/z = 685.24($C_{49}H_{35}NOS$ = 685.87) | P3-30 | m/z = 749.20($C_{61}H_{31}N_3S_2$ = 749.94) |
| P4-1 | m/z = 653.27($C_{49}H_{35}NO$ = 653.81) | P4-2 | m/z = 593.22($C_{43}H_{31}NS$ = 593.78) |
| P4-3 | m/z = 679.32($C_{52}H_{41}N$ = 679.89) | P4-4 | m/z = 613.28($C_{47}H_{35}N$ = 613.79) |
| P4-5 | m/z = 639.29($C_{49}H_{47}N$ = 639.82) | P4-6 | m/z = 817.33($C_{62}H_{43}NO$ = 818.01) |
| P4-7 | m/z = 743.28($C_{55}H_{37}NO_2$ = 743.89) | P4-8 | m/z = 763.32($C_{59}H_{41}N$ = 763.96) |
| P4-9 | m/z = 841.28($C_{63}H_{39}NS$ = 842.06) | P4-10 | m/z = 728.32($C_{55}H_{40}N_2$ = 728.92) |
| P4-11 | m/z = 778.33($C_{59}H_{42}N_2$ = 778.98) | P4-12 | m/z = 780.35($C_{55}H_{44}N_2$ = 780.99) |
| P4-13 | m/z = 904.38($C_{69}H_{48}N_2$ = 905.13) | P4-14 | m/z = 904.38($C_{69}H_{48}N_2$ = 905.13) |
| P4-15 | m/z = 1006.43($C_{77}H_{54}N_2$ = 1007.27) | P4-16 | m/z = 994.43($C_{76}H_{54}N_2$ = 995.26) |
| P4-17 | m/z = 1070.42($C_{81}H_{14}N_2O$ = 1071.31) | P4-18 | m/z = 1086.40($C_{81}H_{54}N_2S$ = 1087.37) |
| P4-19 | m/z = 652.25($C_{48}H_{32}N_2O$ = 652.78) | P4-20 | m/z = 703.29($C_{53}H_{37}NO$ = 703.87) |
| P4-21 | m/z = 828.35($C_{63}H_{44}N_2$ = 829.04) | P4-22 | m/z = 753.30($C_{57}H_{39}NO$ = 753.93) |
| P4-23 | m/z = 763.32($C_{59}H_{41}N$ = 763.96) | P4-24 | m/z = 728.32($C_{55}H_{40}N_2$ = 728.92) |
| P4-25 | m/z = 930.40($C_{71}H_{50}N_2$ = 931.17) | P4-26 | m/z = 834.32($C_{61}H_{42}N_2O_2$ = 835.00) |
| P4-27 | m/z = 757.33($C_{57}H_{43}NO$ = 757.96) | P4-28 | m/z = 731.31($C_{55}H_{39}N$ = 713.90) |
| P4-29 | m/z = 819.35($C_{62}H_{45}NO$ = 820.03) | P4-30 | m/z = 883.30($C_{64}H_{41}N_3S$ = 884.10) |

Production and Evaluation of Organic Electronic Element

[Example 1] Green OLED (A Hole Transport Layer)

Organic light emitting diodes (OLEDs) were produced by a general process by using a compound of the present invention as a hole transport layer material.

First, an ITO layer (anode) was formed on a glass substrate, and a film of $N^1$-(naphthalen-2-yl)-$N^4$,$N^4$-bis(4-(naphthalen-2-yl(phenyl)amino)phenyl)-$N^1$-phenylbenzene-1,4-diamine (hereinafter, "2-TNATA") was vacuum-deposited on the ITO layer to form a hole injection layer with a thickness of 60 nm.

Next, the compound P1-1 of the present invention was vacuum-deposited with a thickness of 60 nm on the hole injection layer to form a hole transport layer.

Subsequently, a light emitting layer with a thickness of 30 nm was formed by vacuum-deposition on the hole transport layer by using 4,4'-N,N'-dicarbazole-biphenyl (hereinafter, "CBP") as a host material and tris(2-phenylpyridine)-iridium (hereinafter, "Ir(ppy)$_3$") as a dopant material in a weight ratio of 90:10.

Next, a film of ((1,1'-bisphenyl)-4-olato)bis(2-methyl-8-quinolinolato) aluminum (hereinafter, "BAlq") was vacuum-deposited with a thickness of 10 nm on the light emitting layer to form a hole blocking layer, and a film of tris(8-quinolinolato)aluminum (hereinafter, "Alq$_3$") was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example 2] to [Example 61] Green OLED (A Hole Transport Layer)

The OLEDs were each manufactured in the same manner as described in Example 1 except that any one of the compounds listed in Table 5 below was used as the hole transport layer material of the light emitting layer, instead of the inventive compound P1-1.

[Comparative Example 1] to [Comparative Example 5]

An OLED was manufactured in the same manner as described in Example 1, except that Comparative compound 1 in comparative example 1, Comparative Compound 2 in comparative example 2, Comparative Compound 3 in comparative example 3, Comparative Compound 4 in comparative example 4 and Comparative Compound 5 in comparative example 5 were each used as a hole transport layer material, instead of the inventive compound P1-1.

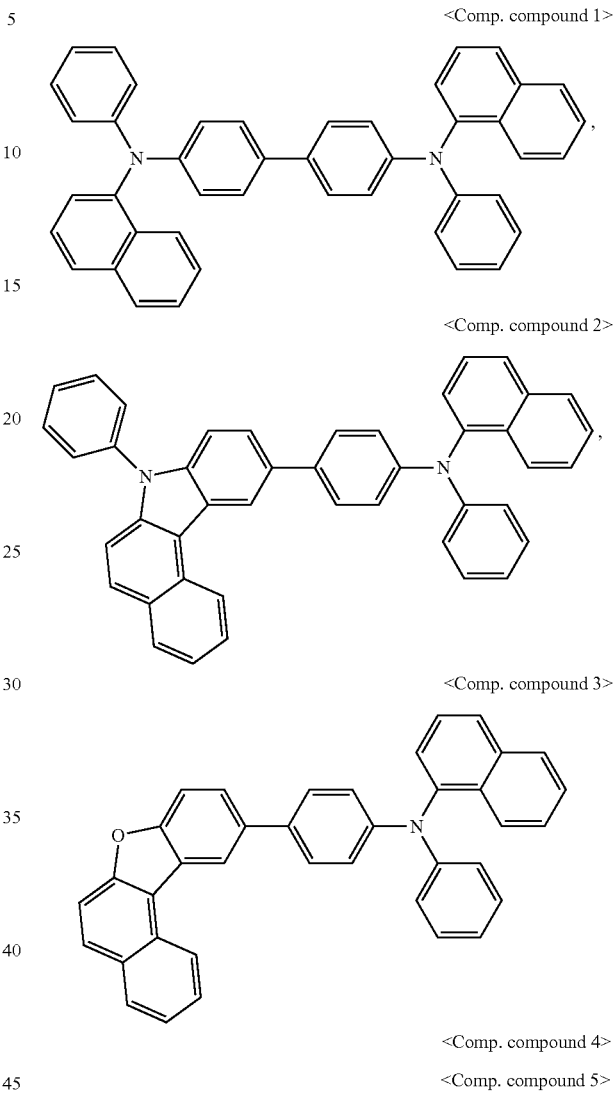

A forward bias DC voltage was applied to each of the OLEDs produced through the Examples 1 to 61 and the Comparative Examples 1 to 5, and electro-luminescence (EL) characteristics of the OLED were measured by PR-650 (Photoresearch). Also, T90 life span was measured by life span measuring equipment (Mcscience) at reference brightness of 5000 cd/m$^2$. Table 5 shows evaluation results of the OLEDs.

TABLE 5

| | Compound | Voltage (V) | Current Density (mA/cm') | Brightness (cd/m') | Efficiency (cd/A) | Lifetime T(90) | CIE x | CIE y |
|---|---|---|---|---|---|---|---|---|
| comp. Ex(1) | comp. Com(1) | 6 | 21.7 | 5000 | 23 | 56.3 | 0.33 | 0.61 |
| comp. Ex(2) | comp. Com(2) | 5.6 | 17.1 | 5000 | 29.2 | 105.6 | 0.33 | 0.62 |
| comp. Ex(3) | comp. Com(3) | 5.7 | 18 | 5000 | 27.8 | 72.4 | 0.33 | 0.62 |
| comp. Ex(4) | comp. Com(4) | 5.6 | 17.5 | 5000 | 28.6 | 74.6 | 0.33 | 0.62 |
| comp. Ex(5) | comp. Com(5) | 5.7 | 18.3 | 5000 | 27.3 | 71.8 | 0.33 | 0.62 |
| Ex. (1) | Com. P1-1 | 5.7 | 13.9 | 5000 | 36 | 116.9 | 0.33 | 0.62 |

TABLE 5-continued

| | Compound | Voltage (V) | Current Density (mA/cm') | Brightness (cd/m') | Efficiency (cd/A) | Lifetime T(90) | CIE x | CIE y |
|---|---|---|---|---|---|---|---|---|
| Ex. (2) | Com. P1-2 | 5.7 | 13.9 | 5000 | 35.9 | 117.3 | 0.33 | 0.61 |
| Ex. (3) | Com. P1-4 | 5.6 | 11.9 | 5000 | 42 | 127.3 | 0.33 | 0.61 |
| Ex. (4) | Com. P1-5 | 5.6 | 11.8 | 5000 | 42.4 | 119.5 | 0.33 | 0.62 |
| Ex. (5) | Com. P1-6 | 5.7 | 13.8 | 5000 | 36.2 | 116.9 | 0.33 | 0.62 |
| Ex. (6) | Com. P1-8 | 5.6 | 14.1 | 5000 | 35.6 | 129.7 | 0.33 | 0.61 |
| Ex. (7) | Com. P1-9 | 5.5 | 11.6 | 5000 | 43.2 | 125.5 | 0.33 | 0.61 |
| Ex. (8) | Com. P1-11 | 5.5 | 14 | 5000 | 35.7 | 124.2 | 0.33 | 0.62 |
| Ex. (9) | Com. P1-12 | 5.5 | 13.7 | 5000 | 36.6 | 126.3 | 0.33 | 0.61 |
| Ex. (10) | Com. P1-13 | 5.7 | 14.2 | 5000 | 35.3 | 129.4 | 0.33 | 0.61 |
| Ex. (11) | Com. P1-15 | 5.6 | 11.6 | 5000 | 43.1 | 129.6 | 0.33 | 0.62 |
| Ex. (12) | Com. P1-16 | 5.6 | 13.4 | 5000 | 37.4 | 115.1 | 0.33 | 0.61 |
| Ex. (13) | Com. P1-17 | 5.5 | 14.2 | 5000 | 35.2 | 129.9 | 0.33 | 0.61 |
| Ex. (14) | Com. P1-18 | 5.6 | 13.2 | 5000 | 37.8 | 126.9 | 0.33 | 0.61 |
| Ex. (15) | Com. P1-19 | 5.5 | 13.3 | 5000 | 37.5 | 128.3 | 0.33 | 0.61 |
| Ex. (16) | Com. P1-20 | 5.7 | 13.4 | 5000 | 37.2 | 119.4 | 0.33 | 0.61 |
| Ex. (17) | Com. P1-21 | 5.7 | 13.7 | 5000 | 36.5 | 125.8 | 0.33 | 0.62 |
| Ex. (18) | Com. P1-23 | 5.6 | 14.3 | 5000 | 35 | 119.1 | 0.33 | 0.61 |
| Ex. (19) | Com. P1-25 | 5.5 | 14.2 | 5000 | 35.1 | 123 | 0.33 | 0.61 |
| Ex. (20) | Com. P1-26 | 5.6 | 14 | 5000 | 35.7 | 120.3 | 0.33 | 0.62 |
| Ex. (21) | Com. P1-28 | 5.6 | 13.5 | 5000 | 37 | 115.5 | 0.33 | 0.62 |
| Ex. (22) | Com. P1-30 | 5.6 | 13.6 | 5000 | 36.7 | 118 | 0.33 | 0.62 |
| Ex. (23) | Com. P1-33 | 5.7 | 13.7 | 5000 | 36.6 | 117.7 | 0.33 | 0.62 |
| Ex. (24) | Com. P1-37 | 5.5 | 13.5 | 5000 | 36.9 | 117.9 | 0.33 | 0.62 |
| Ex. (25) | Com. P1-25 | 5.6 | 13.5 | 5000 | 37 | 117.6 | 0.33 | 0.62 |
| Ex. (26) | Com. P2-1 | 5.7 | 14.3 | 5000 | 34.9 | 111.4 | 0.33 | 0.62 |
| Ex. (27) | Com. P2-2 | 5.7 | 14.5 | 5000 | 34.6 | 117.6 | 0.33 | 0.62 |
| Ex. (28) | Com. P2-3 | 5.7 | 14.7 | 5000 | 34.1 | 115.2 | 0.33 | 0.61 |
| Ex. (29) | Com. P2-4 | 5.8 | 14.3 | 5000 | 34.9 | 111.7 | 0.33 | 0.62 |
| Ex. (30) | Com. P2-5 | 5.7 | 13.6 | 5000 | 36.9 | 110.4 | 0.33 | 0.61 |
| Ex. (31) | Com. P2-8 | 5.7 | 13.6 | 5000 | 36.7 | 110.2 | 0.33 | 0.62 |
| Ex. (32) | Com. P2-9 | 5.8 | 14 | 5000 | 35.8 | 122.4 | 0.33 | 0.61 |
| Ex. (33) | Com. P2-12 | 5.8 | 14.3 | 5000 | 35.1 | 110.3 | 0.33 | 0.62 |
| Ex. (34) | Com. P2-13 | 5.8 | 13.6 | 5000 | 36.8 | 118.1 | 0.33 | 0.62 |
| Ex. (35) | Com. P2-14 | 5.7 | 13.7 | 5000 | 36.5 | 114.9 | 0.33 | 0.62 |
| Ex. (36) | Com. P2-15 | 5.8 | 14.5 | 5000 | 34.6 | 110.2 | 0.33 | 0.62 |
| Ex. (37) | Com. P2-16 | 5.8 | 14.2 | 5000 | 35.3 | 124.4 | 0.33 | 0.61 |
| Ex. (38) | Com. P2-17 | 5.8 | 14.6 | 5000 | 34.3 | 119.9 | 0.33 | 0.61 |
| Ex. (39) | Com. P2-18 | 5.8 | 14.0 | 5000 | 35.8 | 121.4 | 0.33 | 0.61 |
| Ex. (40) | Com. P2-23 | 5.8 | 14.3 | 5000 | 35.1 | 111.1 | 0.33 | 0.61 |
| Ex. (41) | Com. P2-24 | 5.7 | 13.7 | 5000 | 36.6 | 123.6 | 0.33 | 0.62 |
| Ex. (42) | Com. P3-1 | 5.7 | 14.6 | 5000 | 34.2 | 102.7 | 0.33 | 0.62 |
| Ex. (43) | Com. P3-2 | 5.7 | 14.7 | 5000 | 34 | 103.4 | 0.33 | 0.61 |
| Ex. (44) | Com. P3-4 | 5.8 | 13.9 | 5000 | 36 | 91 | 0.33 | 0.61 |
| Ex. (45) | Com. P3-5 | 5.7 | 14.1 | 5000 | 35.4 | 126.8 | 0.33 | 0.61 |
| Ex. (46) | Com. P3-6 | 5.7 | 13.8 | 5000 | 36.2 | 129.6 | 0.33 | 0.61 |
| Ex. (47) | Com. P3-8 | 5.7 | 13.9 | 5000 | 36 | 94.8 | 0.33 | 0.62 |
| Ex. (48) | Com. P3-9 | 5.7 | 14.3 | 5000 | 34.9 | 124.3 | 0.33 | 0.62 |
| Ex. (49) | Com. P3-12 | 5.8 | 14 | 5000 | 35.6 | 117.8 | 0.33 | 0.61 |
| Ex. (50) | Com. P3-13 | 5.8 | 13.6 | 5000 | 36.9 | 98.4 | 0.33 | 0.61 |
| Ex. (51) | Com. P3-14 | 5.8 | 14.3 | 5000 | 35 | 120.9 | 0.33 | 0.61 |
| Ex. (52) | Com. P3-17 | 5.8 | 14.3 | 5000 | 34.9 | 115.9 | 0.33 | 0.61 |
| Ex. (53) | Com. P3-23 | 5.7 | 14.5 | 5001 | 34.6 | 126.2 | 0.33 | 0.62 |
| Ex. (54) | Com. P4-1 | 5.8 | 14.3 | 5002 | 34.9 | 97.1 | 0.33 | 0.62 |
| Ex. (55) | Com. P4-2 | 5.7 | 14.3 | 5003 | 35 | 126.9 | 0.33 | 0.62 |
| Ex. (56) | Com. P4-5 | 5.7 | 14 | 5004 | 35.7 | 92.8 | 0.33 | 0.61 |
| Ex. (57) | Com. P4-8 | 5.7 | 13.6 | 5005 | 36.9 | 90.9 | 0.33 | 0.62 |
| Ex. (58) | Com. P4-12 | 5.7 | 14.5 | 5006 | 34.6 | 107.4 | 0.33 | 0.61 |
| Ex. (59) | Com. P4-13 | 5.7 | 14.6 | 5007 | 34.4 | 116.8 | 0.33 | 0.61 |
| Ex. (60) | Com. P4-14 | 5.7 | 14.6 | 5008 | 34.4 | 129.1 | 0.33 | 0.61 |
| Ex. (61) | Com. P4-23 | 5.7 | 14.7 | 5009 | 34.1 | 110.8 | 0.33 | 0.62 |

It can be seen from the results in Table 5 above, that the OLEDs employing the inventive compounds as hole transport layer materials showed predominantly improved efficiency and lifespan, compared to the OLEDs employing comparative compounds.

In detail, it is confirmed that the OLEDs employing the inventive compounds as hole transport layer materials showed predominantly improved efficiency and lifespan, compared to the OLEDs employing a comparative compound 1 NPB or any one of comparative compounds 2 to 5.

NPB is generally used as a hole transport layer material. Each of comparative compounds 2 to 5 contains a five-membered ring having one less carbon number than the inventive compounds having a six-membered ring that comprise $X^1$.

This may be caused by the fact that the packing density of the inventive compounds having a six-membered ring including $X^1$ is higher than that of comparative compounds 2 to 5 having a five-membered ring thereby facilitating the hole mobility and securing the more space for the hole trapping, which improves charge balance in an light emitting layer, as a result, efficiency is increased. Further, it can be seen that a driving voltage and Joule's heat generated upon driving an OLED are decreased as a packing density increases resulting in high thermal stability of the OLED. Therefore, it is believed that the lifespan of the OLED employing the inventive compounds is more improved, compared to comparative compounds.

Furthermore, it is believed that in the case of $X^1$ not forming a ring (namely, in case of n being "0" in Formula 2 such as P2-17, P2-18 and P3-17), naphthyl group at the end makes the HOMO value lowered thereby trapping holes and increasing charge balance of the light emitting layer which may result in increasing efficiency and lifespan.

Although the exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed herein is intended to illustrate the scope of the technical idea of the present invention, and the scope of the present invention is not limited by the embodiments. The scope of the present invention shall be construed on the basis of the accompanying claims, and it shall be construed that all of the technical ideas included within the scope equivalent to the claims belong to the present invention.

The invention claimed is:
1. A compound of Formula 1:

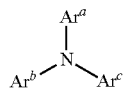

[Formula 1]

wherein:
$Ar^a$ is Formula 2 below,
$Ar^b$ is Formula 3 below, and
$Ar^c$ is selected from the group consisting of a $C_6$-$C_{60}$ aryl group; a fluorenyl group; and a $C_2$-$C_{60}$ heterocyclic group containing at least one heteroatom selected from the group consisting of O, N, S, Si, and P;

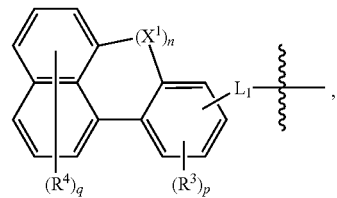

[Formula 2]

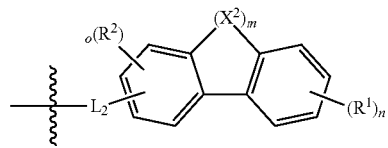

[Formula 3]

in Formulas 2 and 3,
m and n are each an integer of 0 or 1,
$X^1$ and $X^2$ are each independently N(R'), O, S or C(R')(R''), wherein R' and R'' are each independently selected from the group consisting of a $C_6$-$C_{60}$ aryl group; a fluorenyl group; a $C_2$-$C_{60}$ heterocyclic group containing at least one heteroatom selected from the group consisting of O, N, S, Si, and P; and a $C_1$-$C_{60}$ alkyl group,
$L_1$ and $L_2$ are each independently selected from the group consisting of a single bond; a $C_6$-$C_{60}$ arylene group; a fluorenylene group; a $C_2$-$C_{60}$ heterocyclic group containing at least one heteroatom selected from the group consisting of O, N, S, Si, and P; and fused ring formed by a $C_3$-$C_{60}$ aliphatic ring and a $C_6$-$C_{60}$ aromatic ring,
l is an integer of 0 to 4, o and p are each an integer of 0 to 3, and q is an integer of 0 to 6,
i) $R^1$ to $R^4$ are each independently selected from the group consisting of deuterium; tritium; halogen; a $C_6$-$C_{60}$ aryl group; a fluorenyl group; a $C_2$-$C_{60}$ heterocyclic group containing at least one heteroatom selected from the group consisting of O, N, S, Si, and P; a $C_1$-$C_{60}$ alkyl group; a $C_2$-$C_{20}$ alkenyl group; a $C_2$-$C_{20}$ alkynyl group; $C_3$-$C_{60}$ cycloalkyl group; $C_1$-$C_{30}$ alkoxy group; a $C_6$-$C_{30}$ aryloxy group; and -$L_3$-N($R^5$)($R^6$), or ii) any adjacent $R^1$ to $R^4$ groups may be linked together to form at least one ring and the group(s) of $R^1$ to $R^4$ not forming a ring are the same as defined in i) above,
$L_3$ is selected from the group consisting of a single bond; a $C_6$-$C_{60}$ arylene group; a fluorenylene group; a $C_2$-$C_{60}$ heterocyclic group containing at least one heteroatom selected from the group consisting of O, N, S, Si, and P; and fused ring formed by a $C_3$-$C_{60}$ aliphatic ring and a $C_6$-$C_{60}$ aromatic ring,
$R^5$ and $R^6$ are each independently selected from the group consisting of a $C_6$-$C_{60}$ aryl group; a fluorenyl group; a $C_2$-$C_{60}$ heterocyclic group containing at least one heteroatom selected from the group consisting of O, N, S, Si, and P; and a $C_1$-$C_{60}$ alkyl group,
$R^5$ and $R^6$, $L_3$ (except for single bond) and $R^5$, or $L_3$ (except for single bond) and $R^6$ may be linked to form a heterocyclic compound comprising N together with N attached to $L_3$, $R^5$ and $R^6$, and
each of the above aryl group, fluorenyl group, heterocyclic group, fused ring group, alkyl group, alkenyl group, alkynyl group, cycloalkyl group, alkoxy group, aryloxy group, arylene group and fluorenylene group may be substituted with one or more substituents selected from the group consisting of deuterium; halogen; a silane group; a siloxane group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si, and P; a $C_3$-$C_{20}$ cycloalkyl group; a $C_7$-$C_{20}$ arylalkyl group; a $C_8$-$C_{20}$ arylalkenyl group; and -$L_3$-N($R^5$)($R^6$), with the proviso that:

i) where m and n are each an integer of 0 and $Ar^c$ is an aryl group, the aryl group of $Ar^c$ is an unsubstituted $C_6$-$C_{12}$ aryl group or a $C_6$-$C_{60}$ aryl group substituted with -$L_3$-N($R^5$)($R^6$), wherein $R^5$ and $R^6$ do not form a heterocyclic compound comprising N together with the N attached to $L_3$, ii) where n is an integer of 1 and m is an integer of 0 or 1, $Ar^c$ is a $C_6$-$C_{60}$ aryl group substituted with -$L_3$-N($R^5$)($R^6$), and iii) where n is an integer of 0 and m is an integer of 1, $Ar^c$ is selected from the group consisting of a $C_6$-$C_{12}$ aryl group unsubstituted or substituted with -$L_3$-N($R^5$)($R^6$); a fluorenyl group substituted with -$L_3$-N($R^5$)($R^6$); and a $C_2$-$C_{60}$ heterocyclic group substituted with -$L_3$-N($R^5$)($R^6$) and containing at least one heteroatom selected from the group consisting of O, N, S, Si, and P, and in the case where $Ar^c$ is selected as the aryl group, an arylene group of $L_1$ in Formula 2 is not substituted with -$L_3$-N($R^5$)($R^6$).

2. The compound of claim 1, wherein Formula 2 is represented by one of Formulas below:

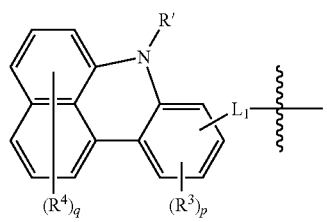

[Formula 4]

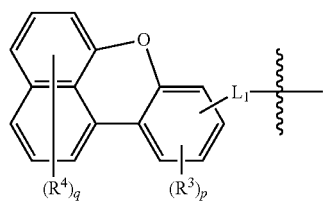

[Formula 5]

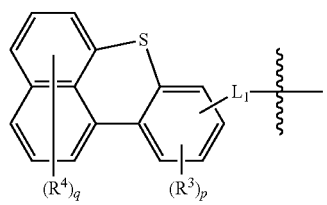

[Formula 6]

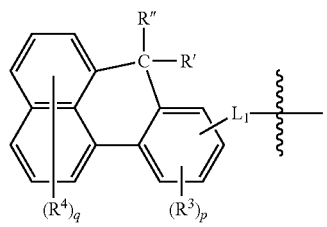

[Formula 7]

wherein, R', R", $R^3$, $R^4$, $L_1$, p and q are the same as defined in claim 1.

3. The compound of claim 1, wherein Formula 3 is represented by one of Formulas below:

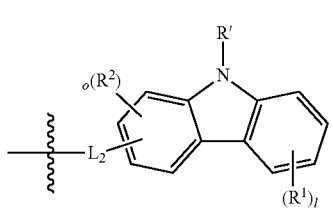

[Formula 8]

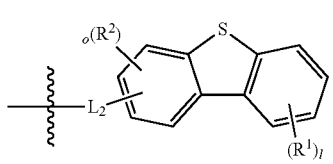

[Formula 9]

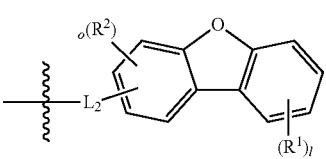

[Formula 10]

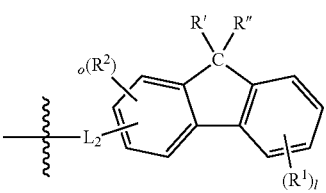

[Formula 11]

wherein, R', R", $R^1$, $R^2$, $L_2$, l and o are the same as defined in claim 1.

4. The compound of claim 1, wherein at least one of o, p, q and l is not 0 and at least one of $R^1$ to $R^4$ comprises deuterium.

5. An organic electric element comprising a first electrode, a second electrode, and an organic material layer disposed between the first electrode and the second electrode, wherein the organic material layer comprises the compound of claim 1.

6. The organic electric element of claim 5, wherein the organic material layer comprises at least one of a hole injection layer, a hole transport layer, an emission-auxiliary layer and an light emitting layer, and at least one of the layers comprises the compound in the same kind or two or more different kinds.

7. The organic electric element of claim 5, wherein the organic material layer is formed by any one of the processes of spin coating, nozzle printing, inkjet printing, slot coating, dip coating and roll-to-roll.

8. An electronic device comprising a display device, which comprises the organic electric element of claim 5, and a control unit for driving the display device.

9. The electronic device of claim 8, wherein the organic electric element comprises at least one of an organic light emitting diode, an organic solar cell, an organic photo conductor, an organic transistor, and an element for monochromatic or white illumination.

10. A compound selected from the group consisting of the compounds below:

P1-1
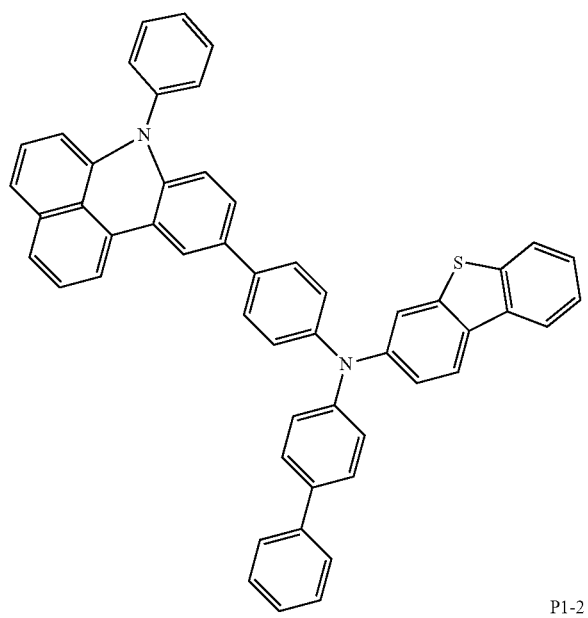
P1-2
P1-3
P1-4
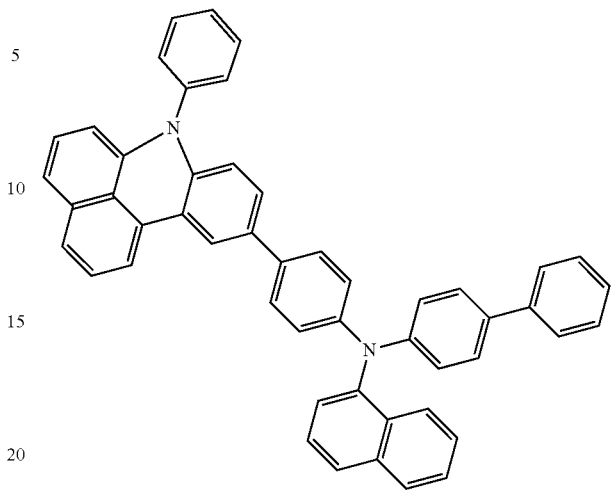
P1-5
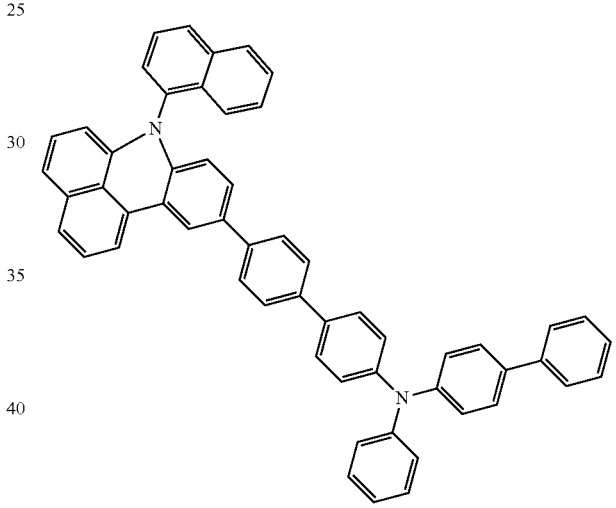
P1-6
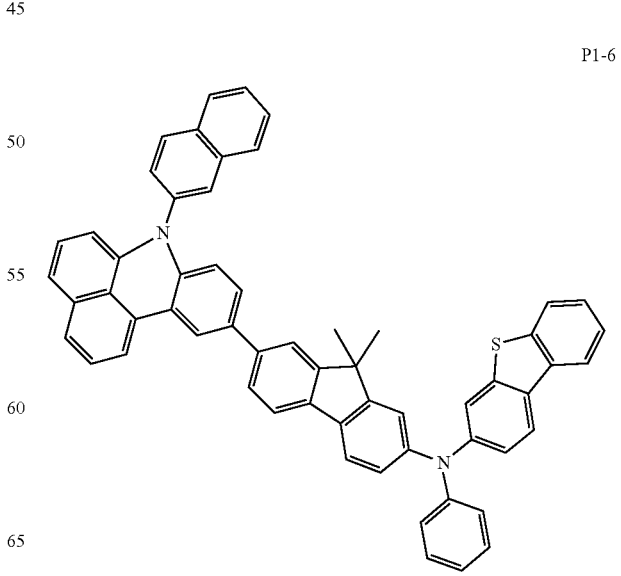

-continued
P1-7
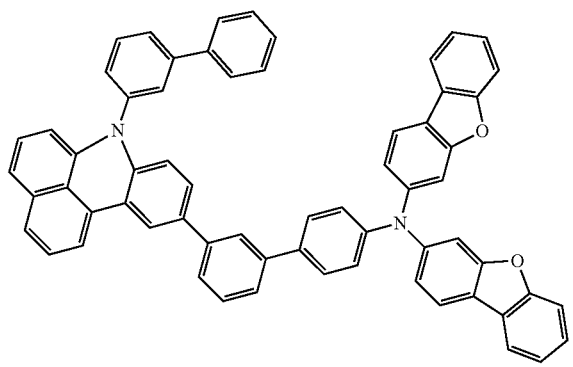
P1-8
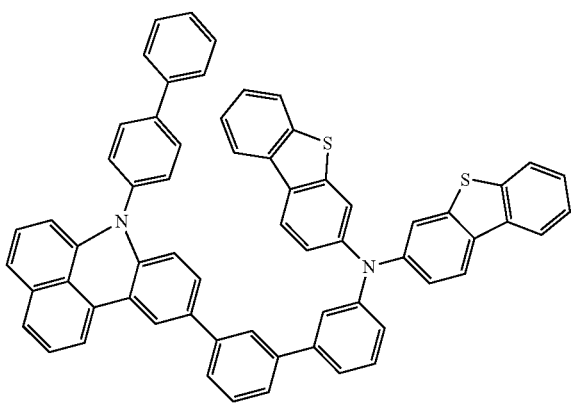
P1-9
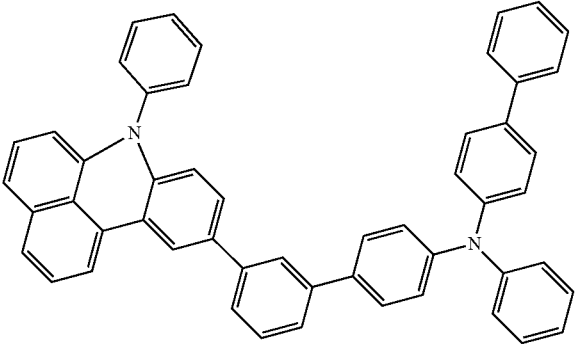
-continued
P1-10
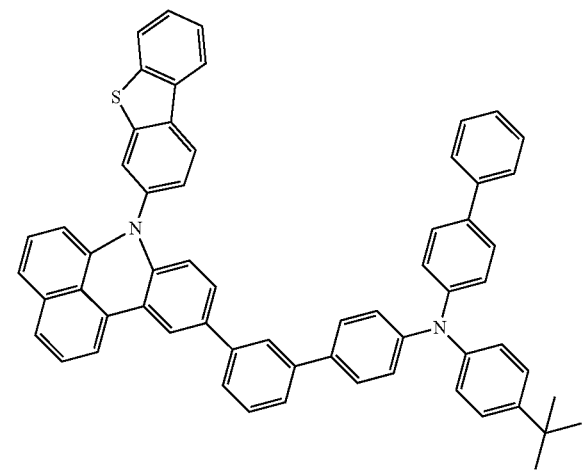
P1-11
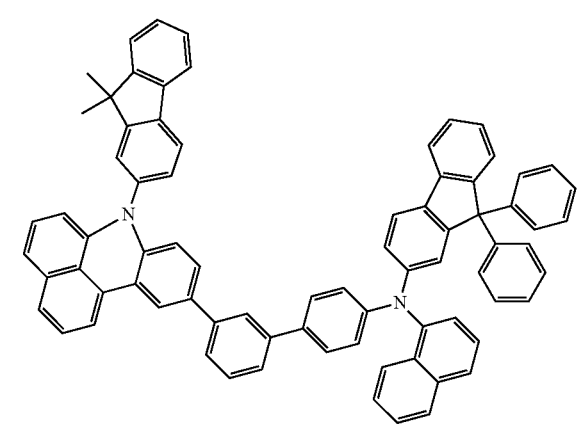
P1-12
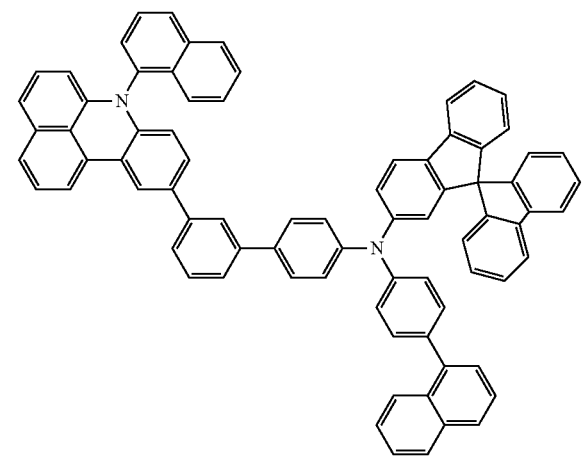

-continued
P1-13
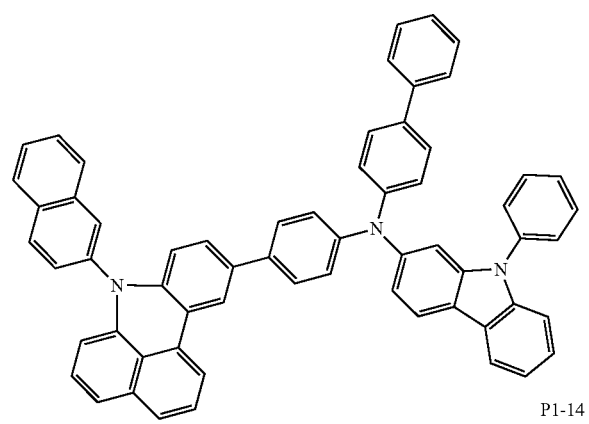
P1-14
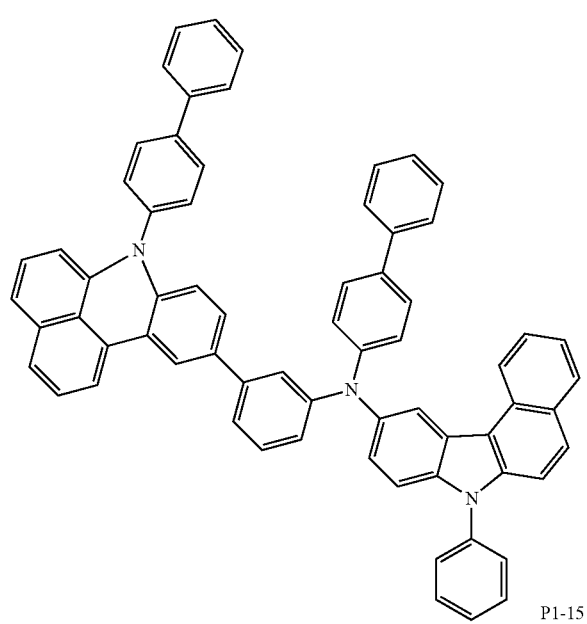
P1-15
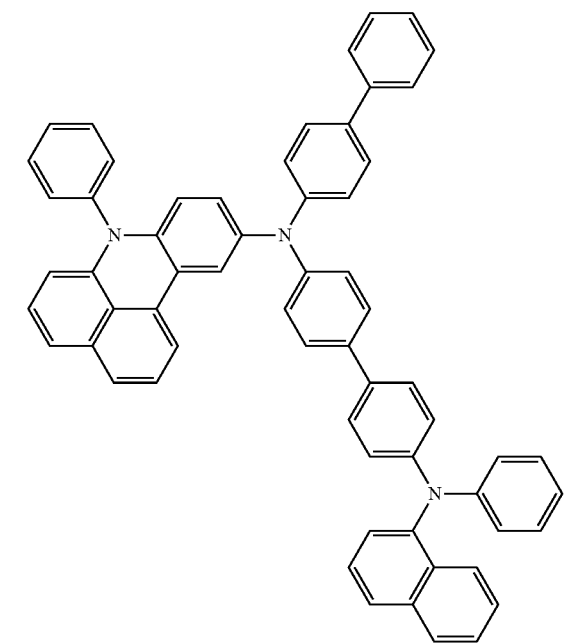
-continued
P1-16
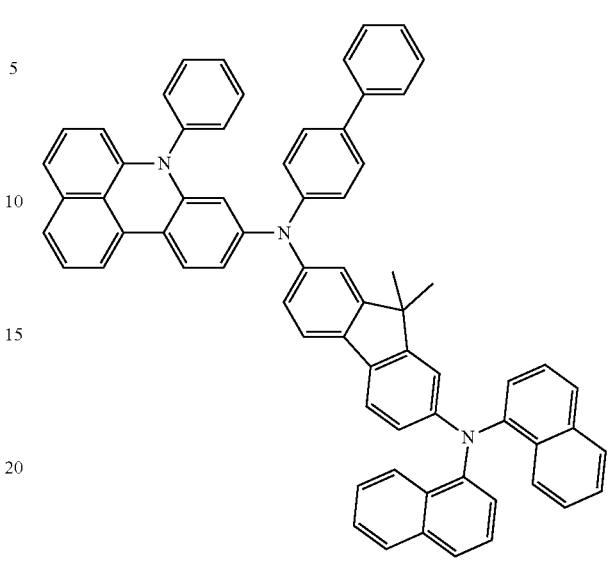
P1-17
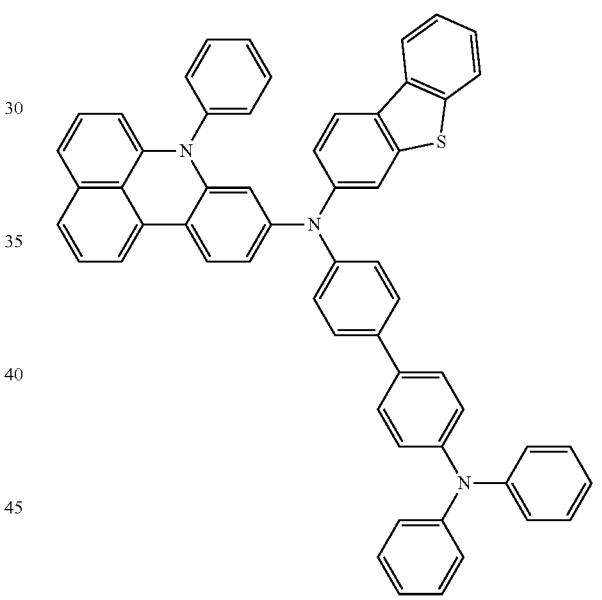
P1-18
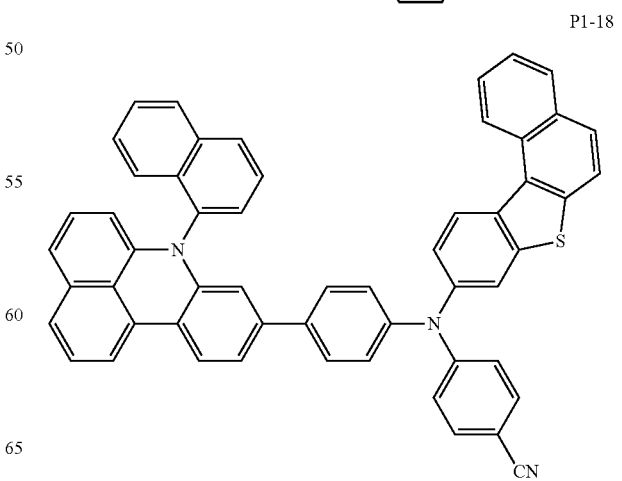

P1-19
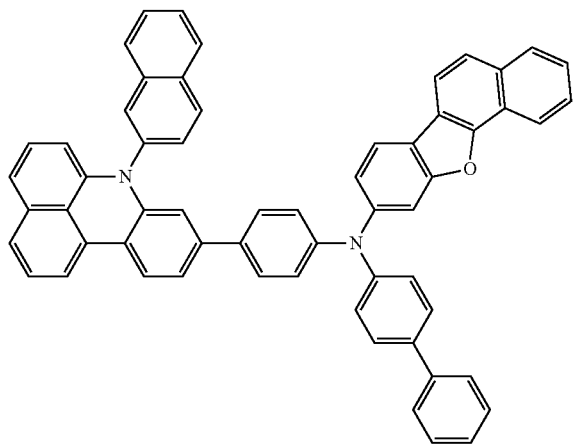
P1-20
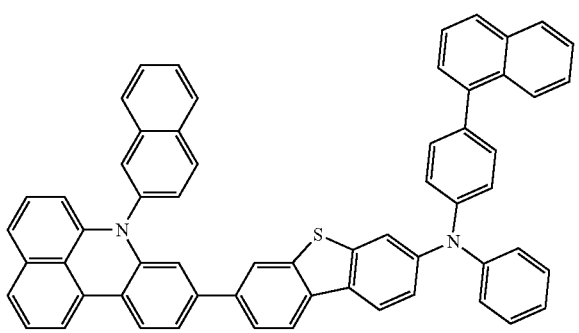
P1-21
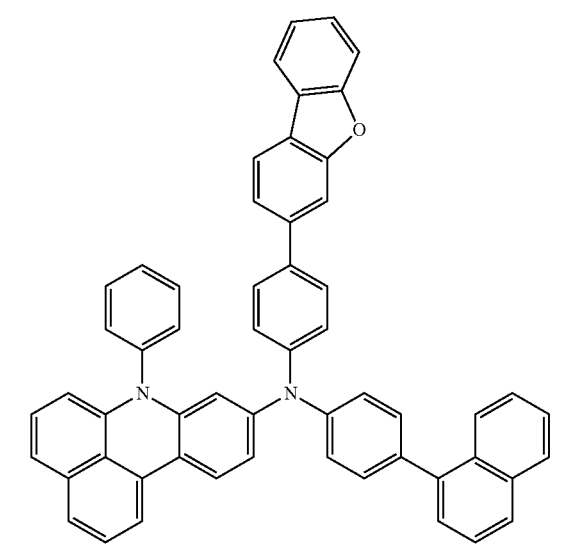
P1-22
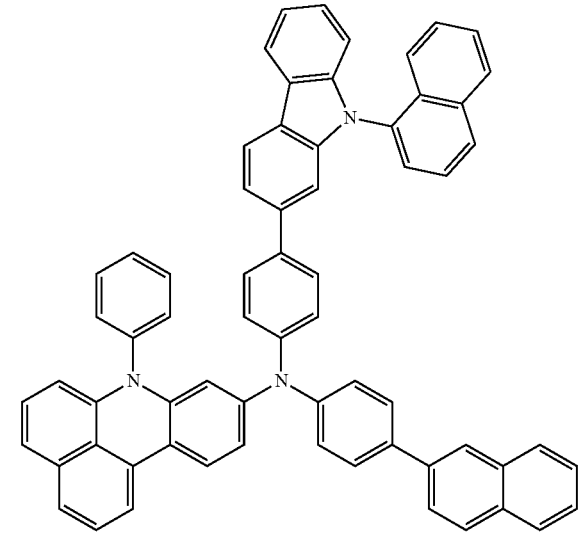
P1-23
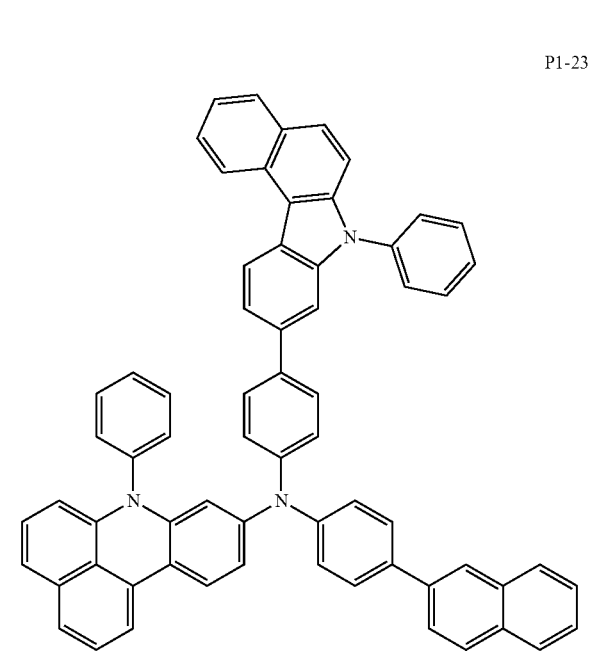
P1-24
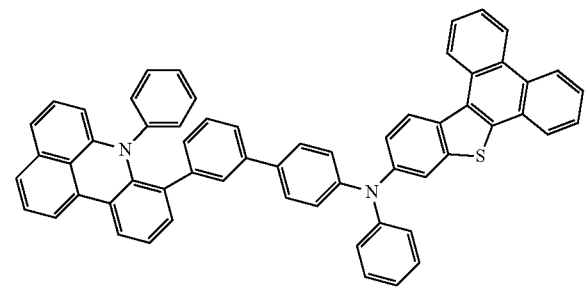

P1-25
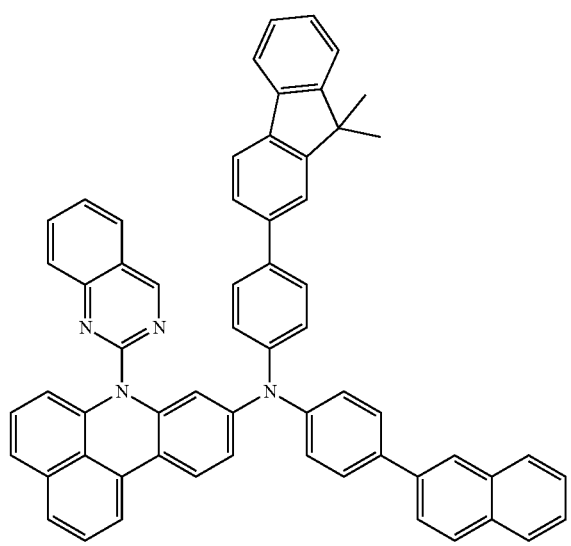
P1-28
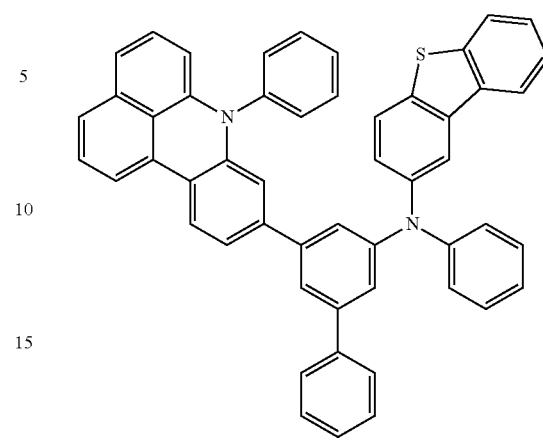
P1-26
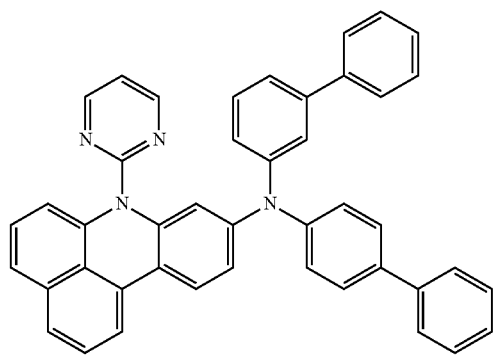
P1-29
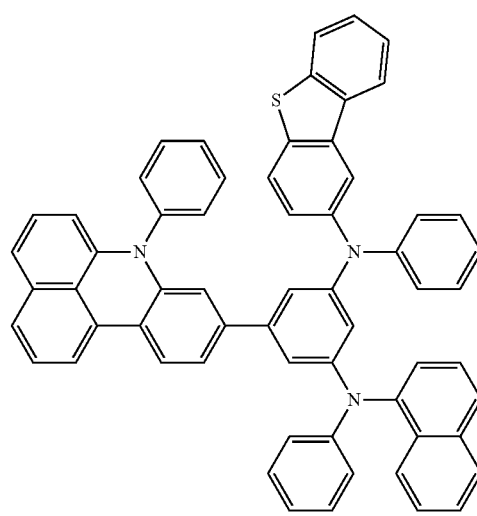
P1-27
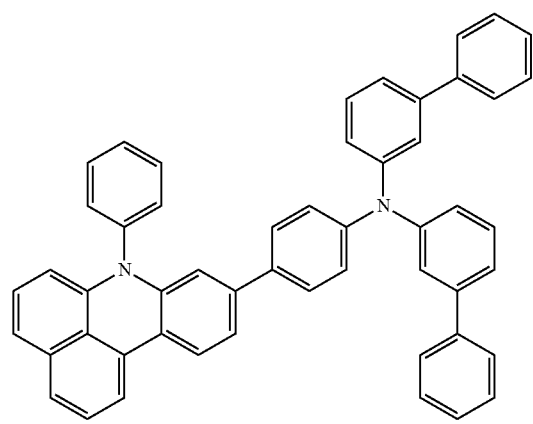
P1-30
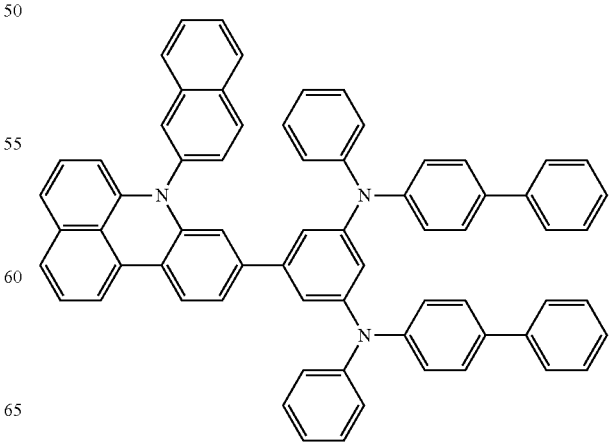

P1-31
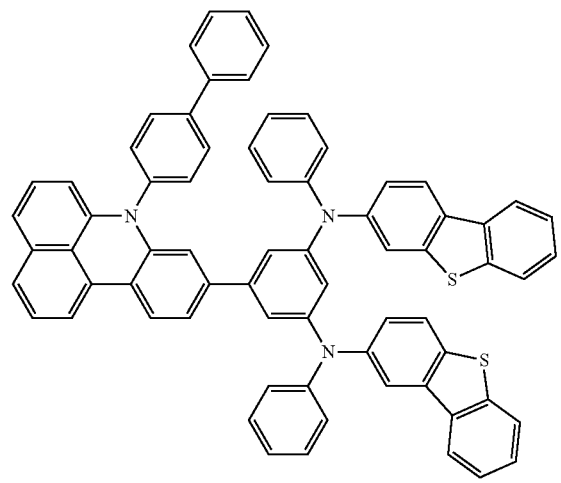
P1-32
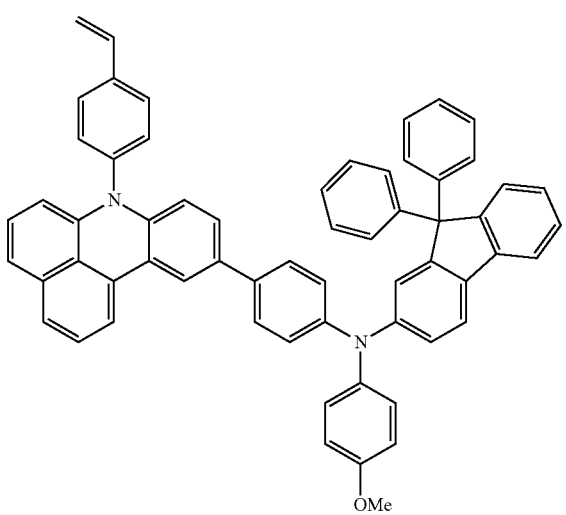
P1-33
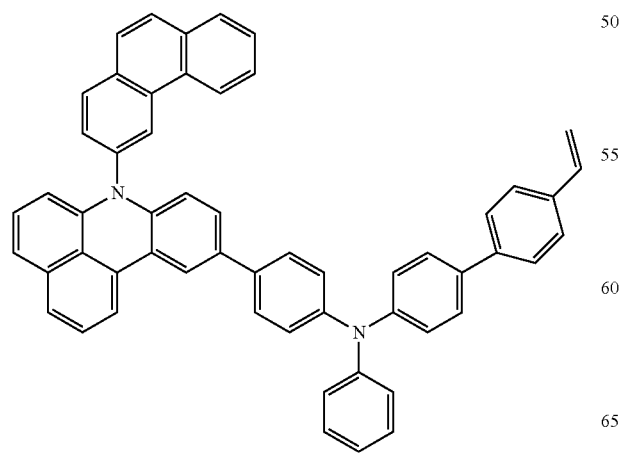
P1-34
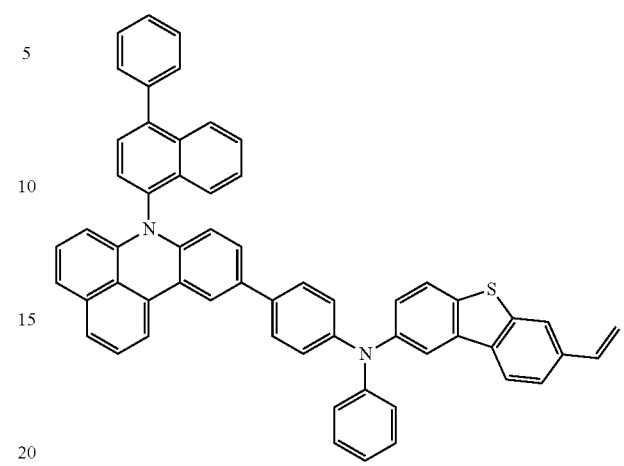
P1-35
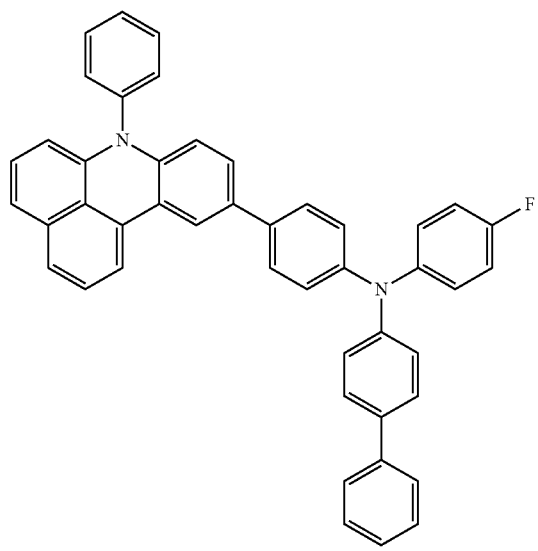
P1-36

P1-37
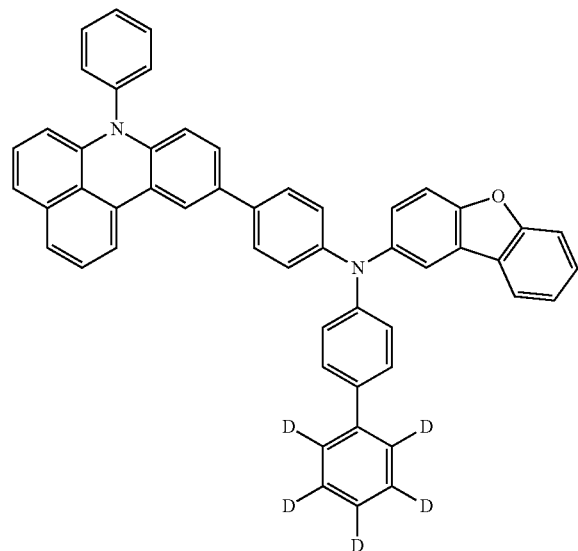
P1-38
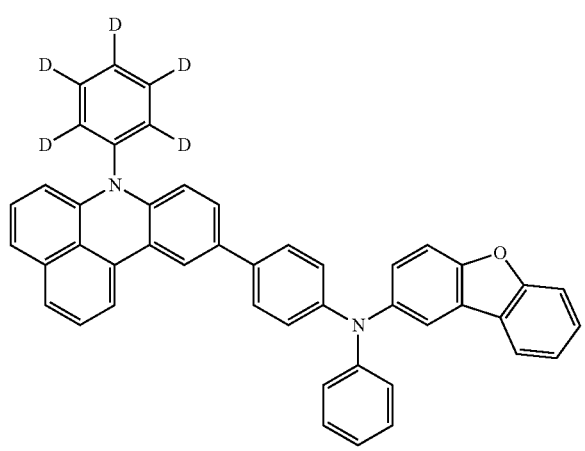
P1-39
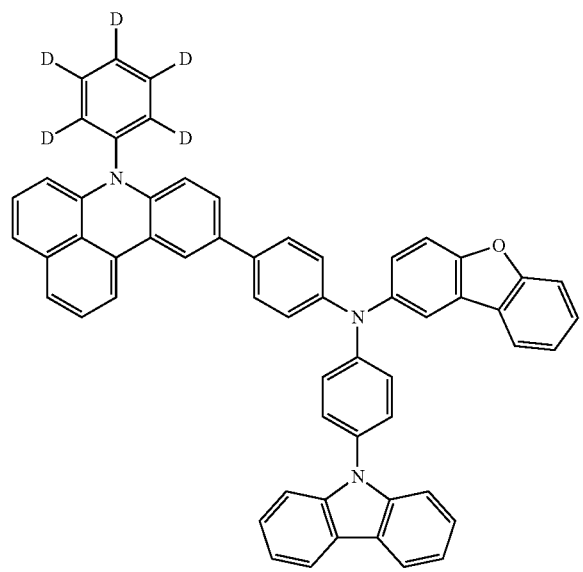
P1-40
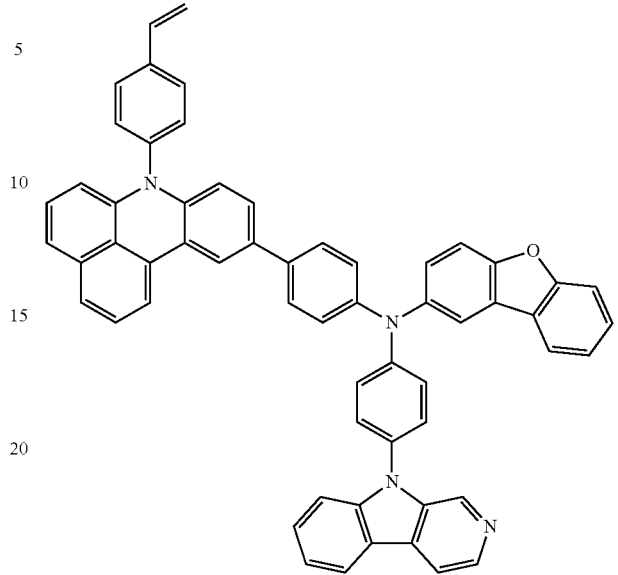
P2-1
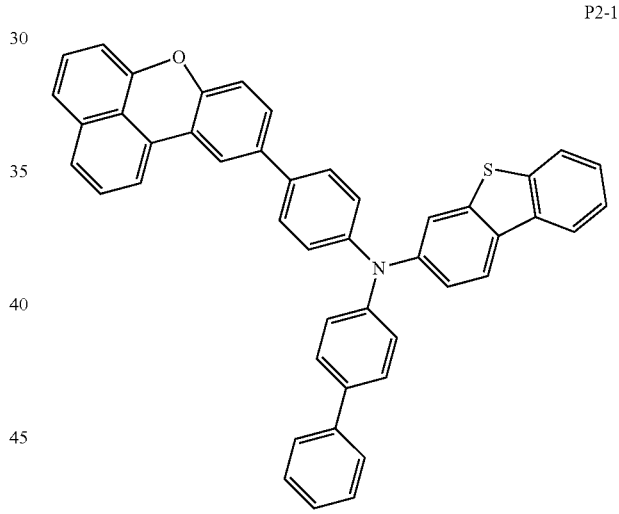
P2-2
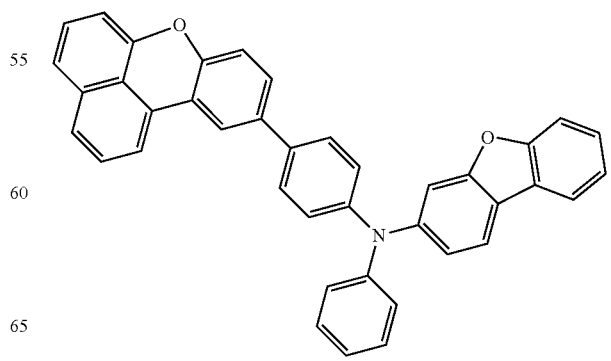

-continued
P2-3
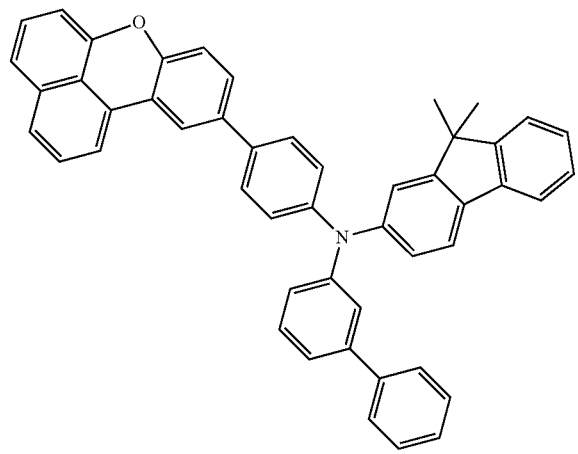
P2-4
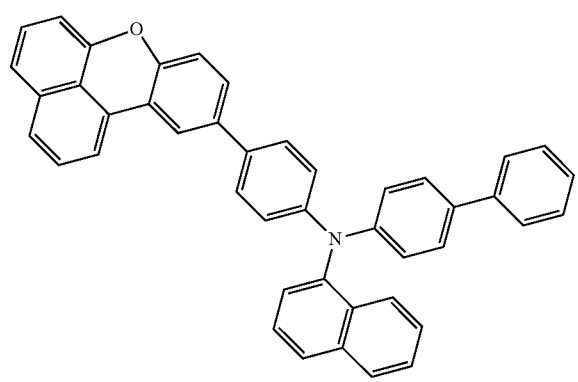
P2-5
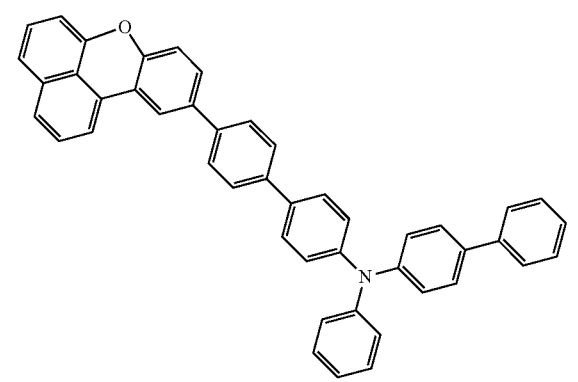
P2-6
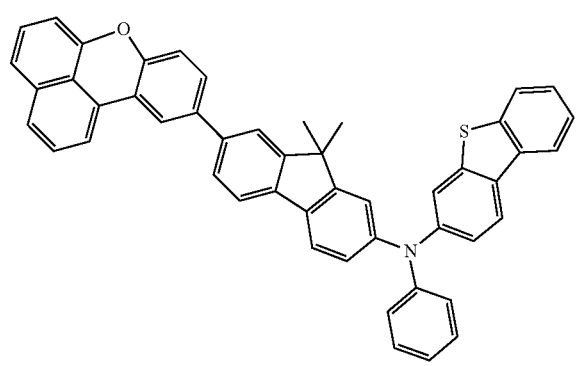
-continued
P2-7
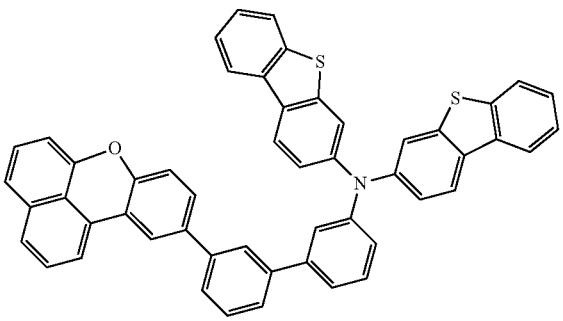
P2-8
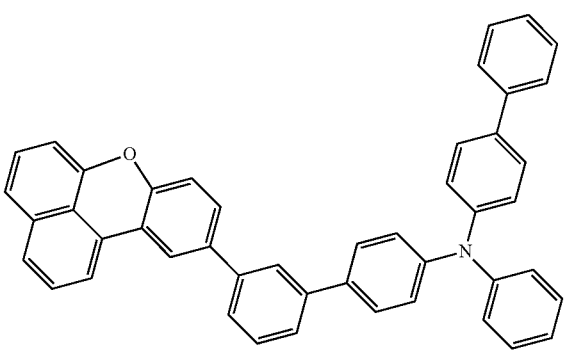
P2-9
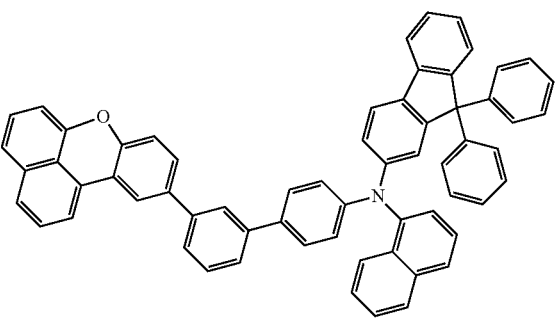
P2-10
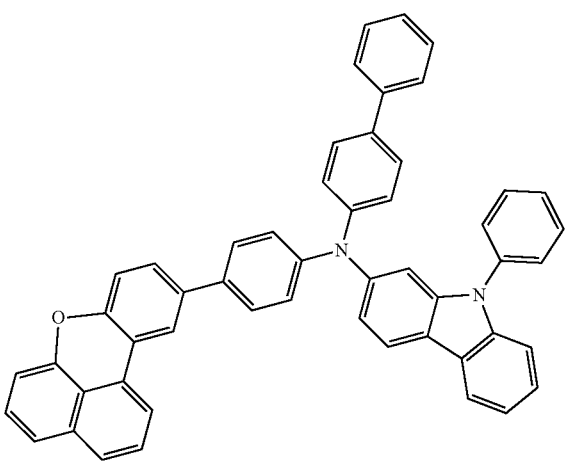

P2-11
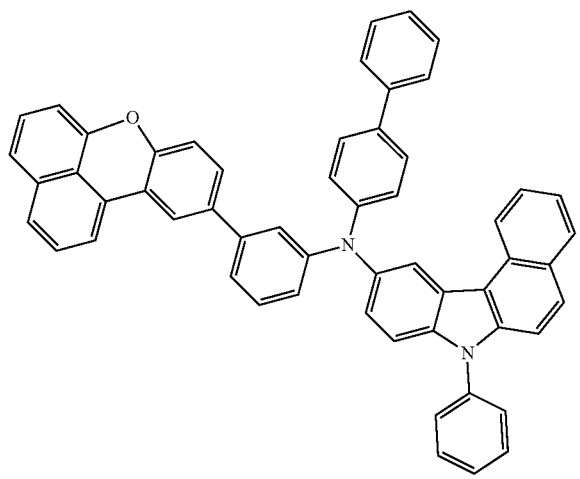
P2-14
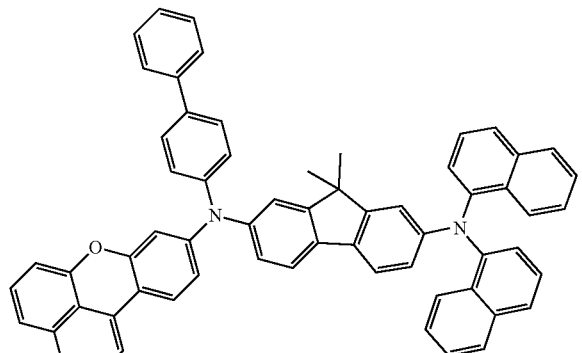
P2-12
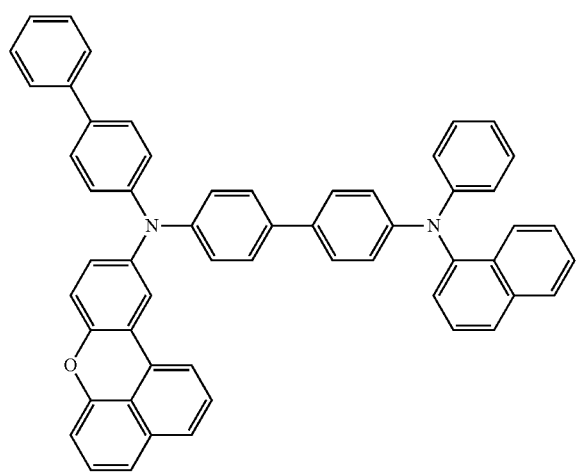
P2-15
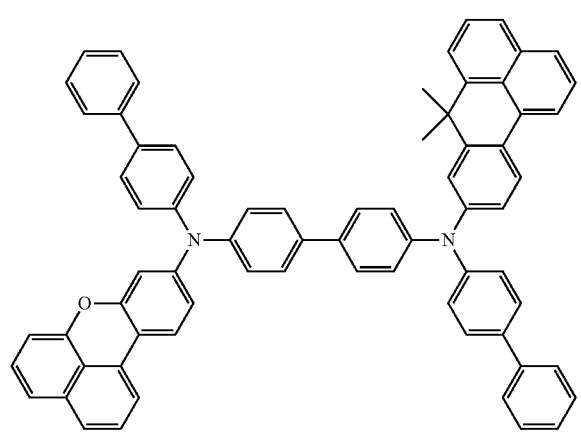
P2-13
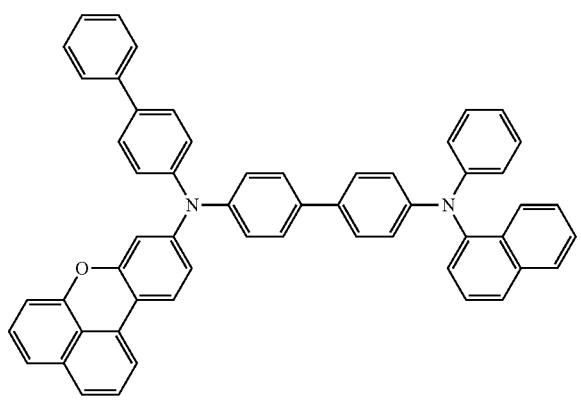
P2-16
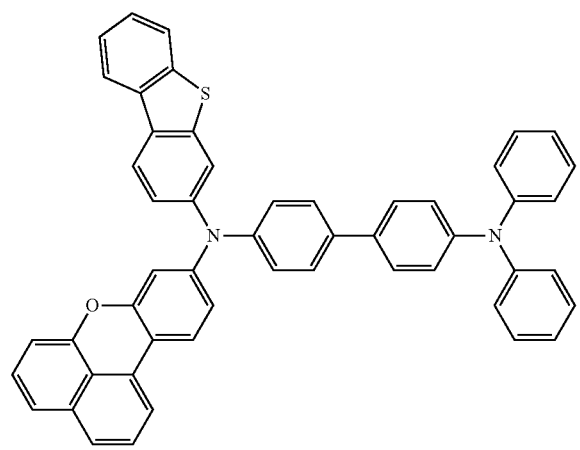

P2-17
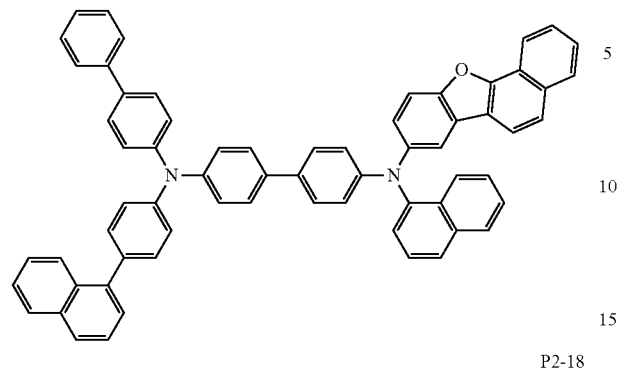
P2-18
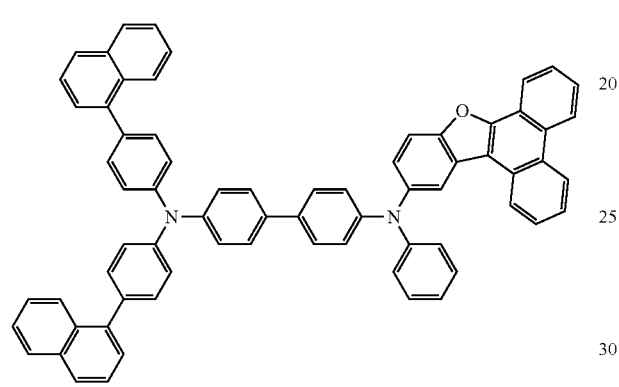
P2-19
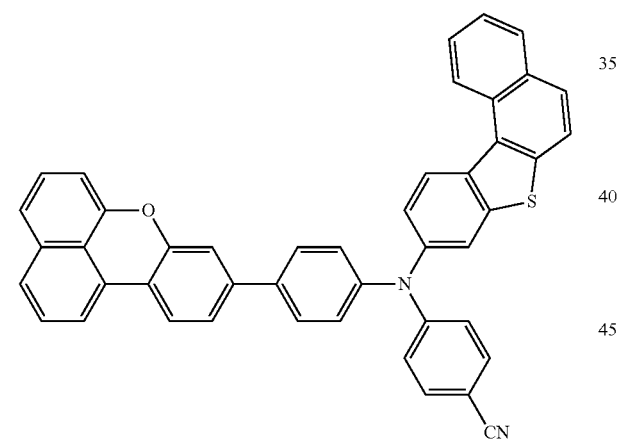
P2-20
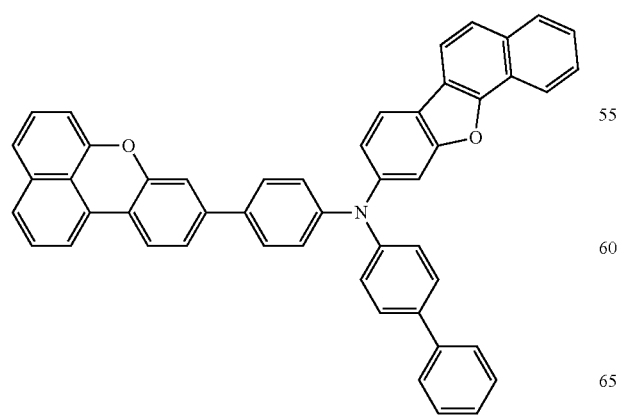
P2-21
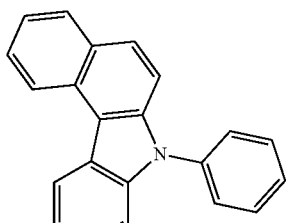
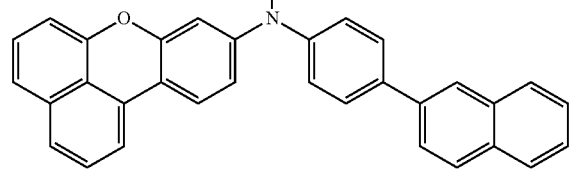
P2-22
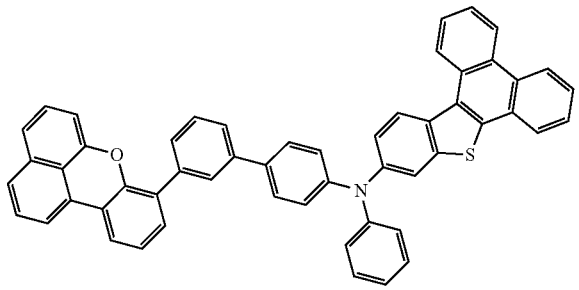
P2-23
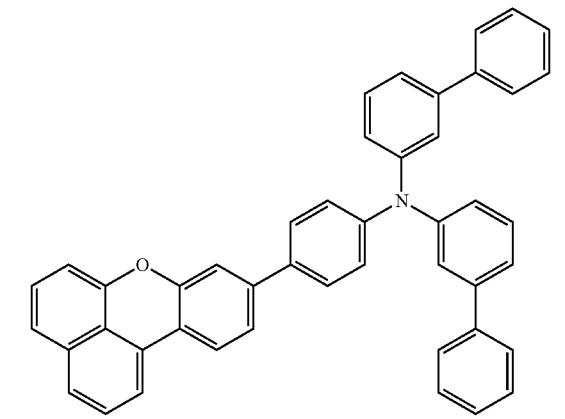

P2-24
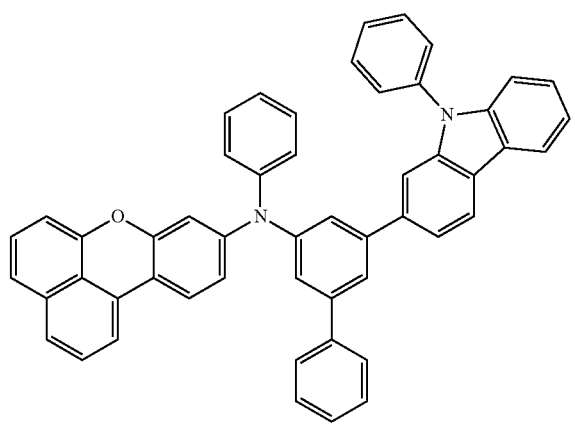
P2-25
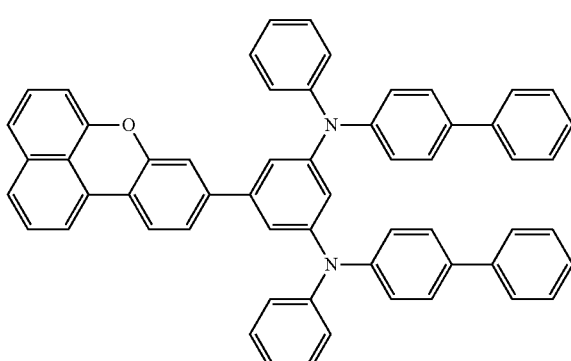
P2-26
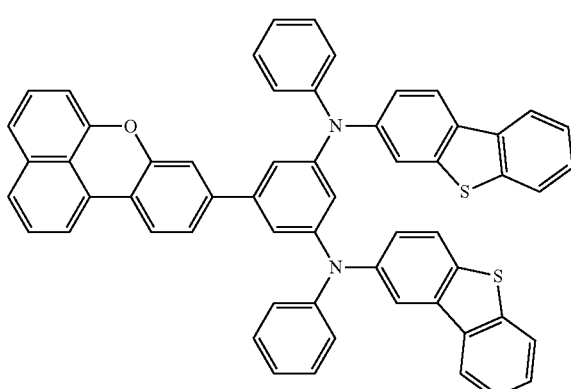
P2-27
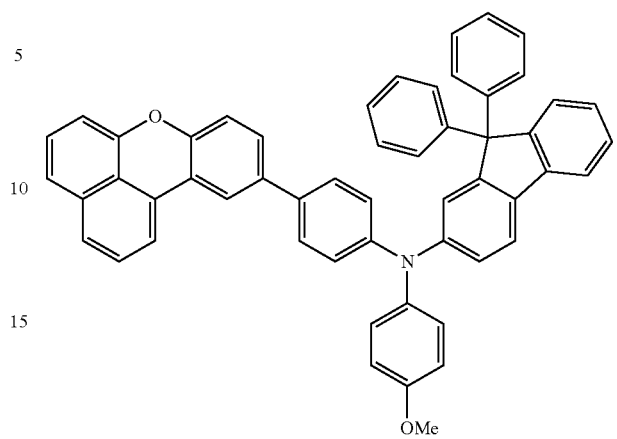
P2-28
P2-29
P2-30
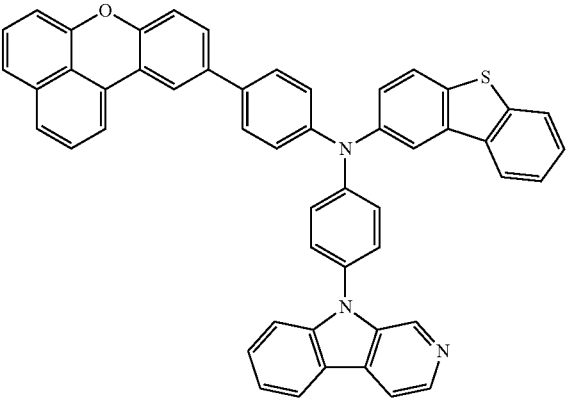

P3-1
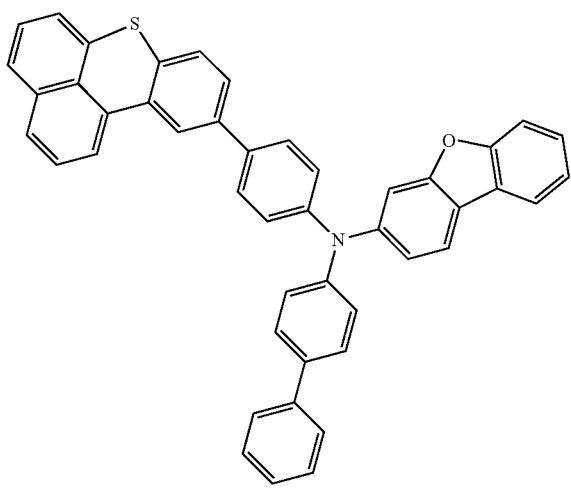
P3-2
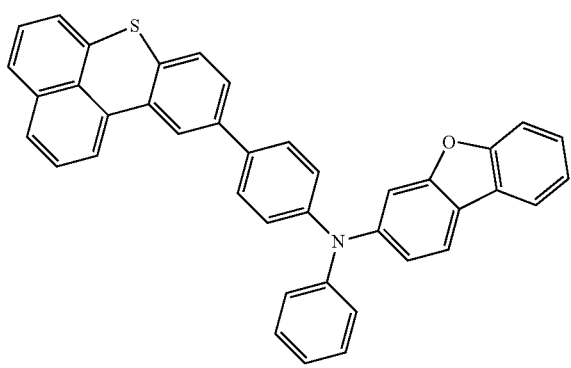
P3-3
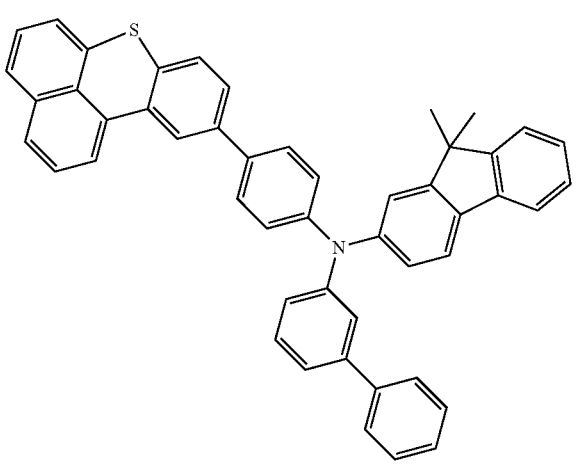
P3-4
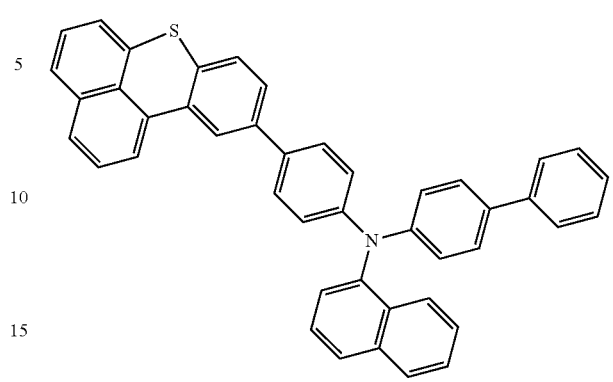
P3-5
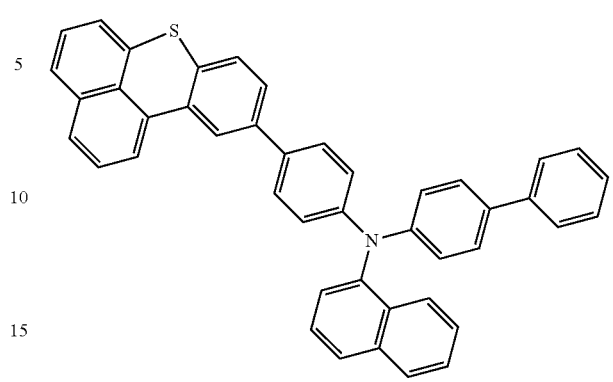
P3-6
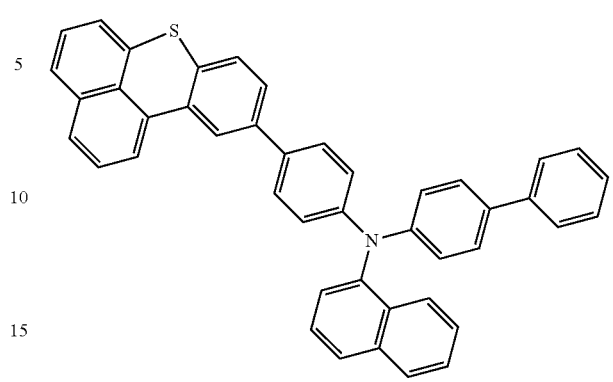
P3-7
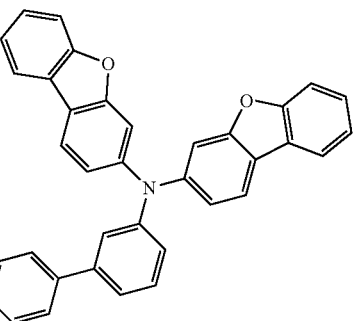

-continued
P3-8
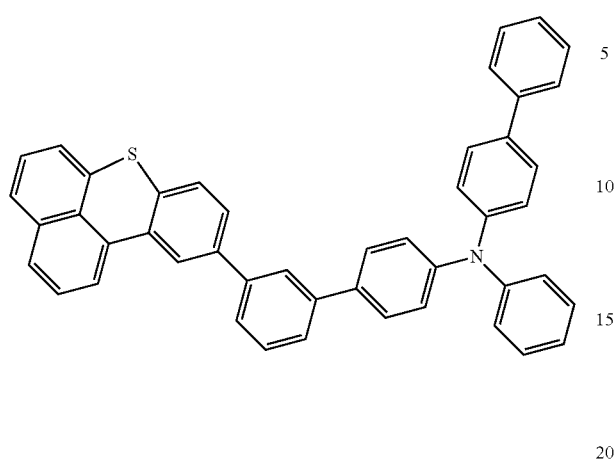
P3-11
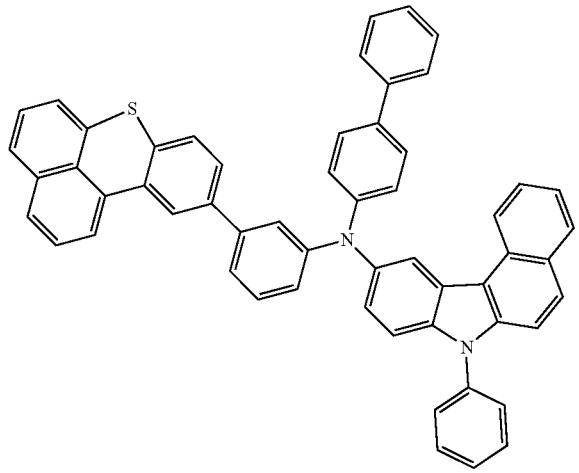
P3-9
P3-12
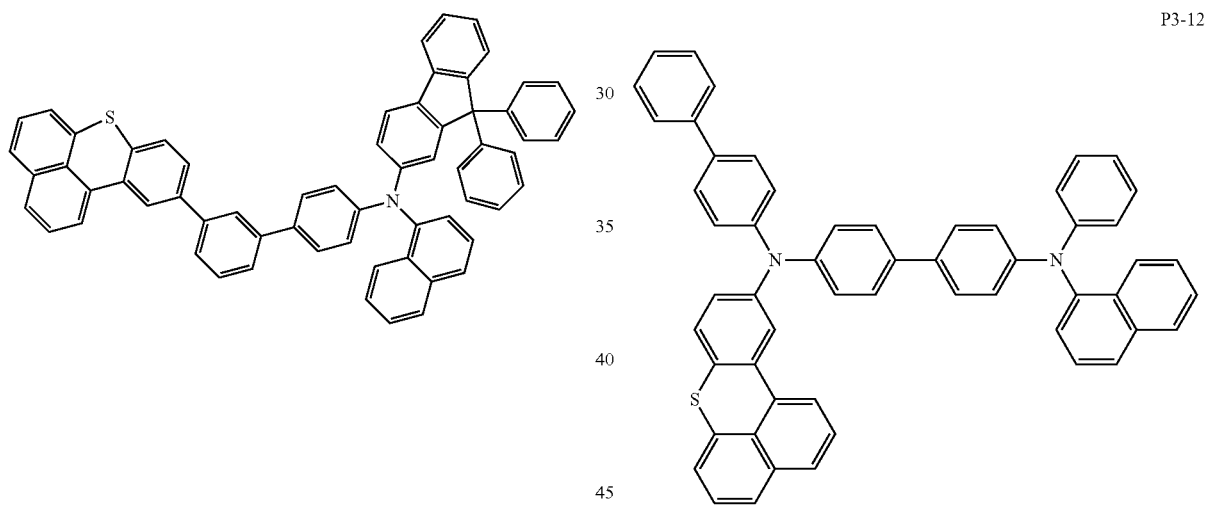
P3-10
P3-13
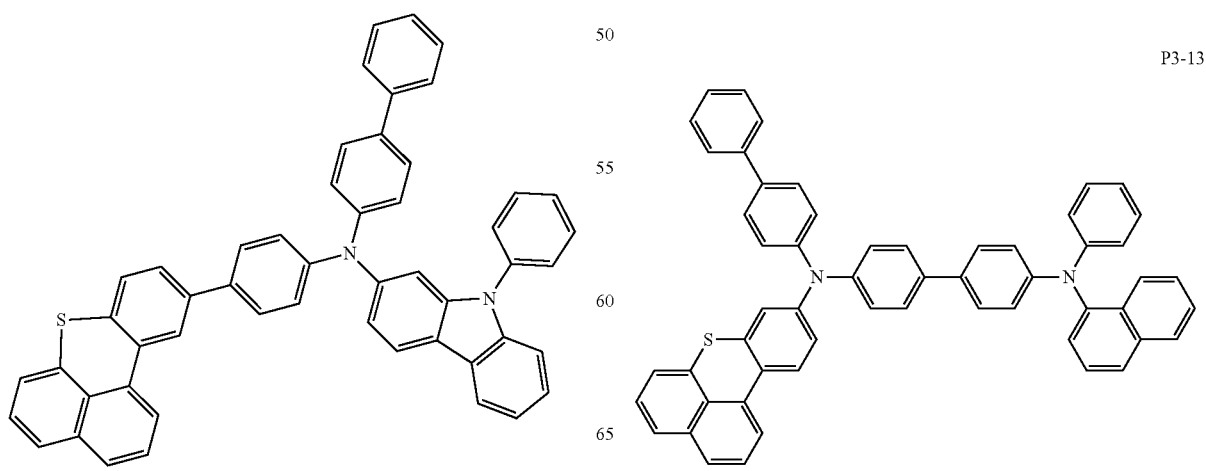

P3-14
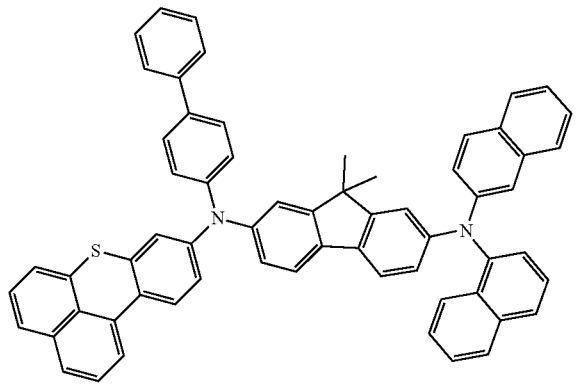
P3-18
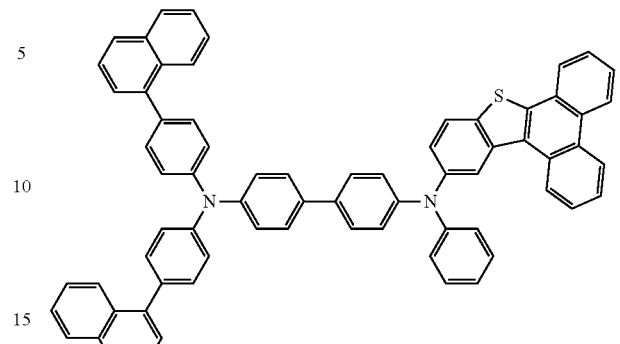
P3-15
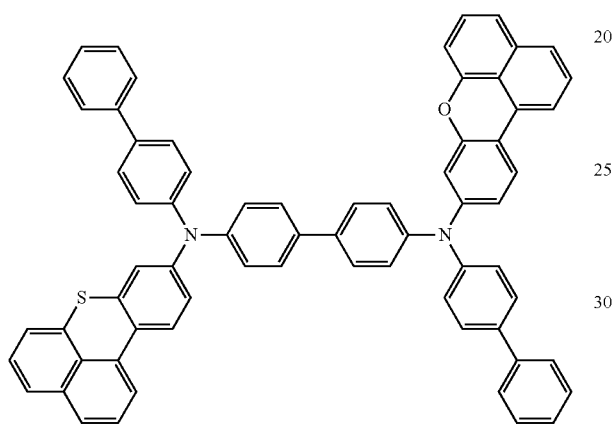
P3-16
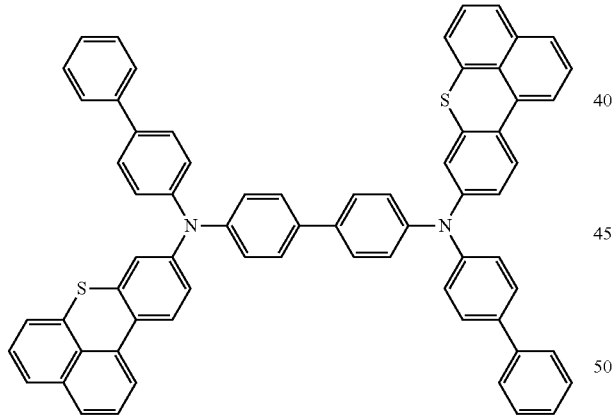
P3-19
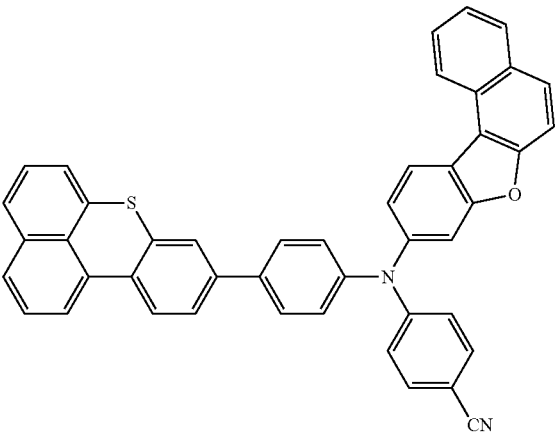
P3-17
P3-20
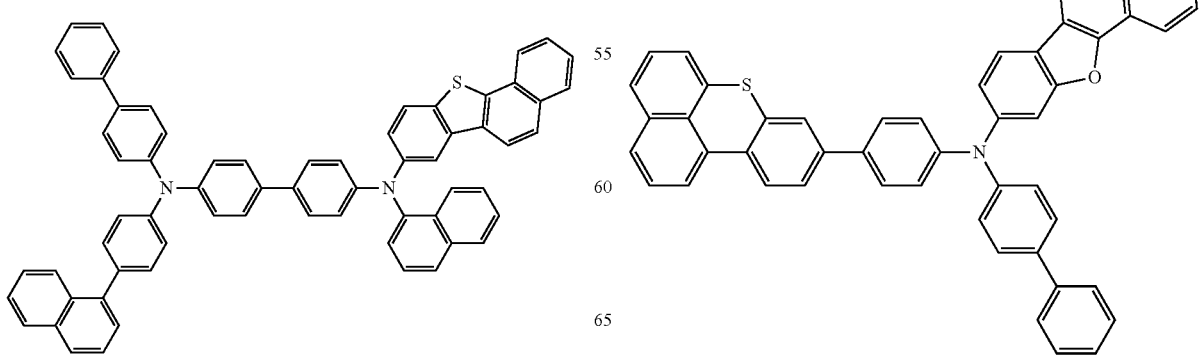

P3-21
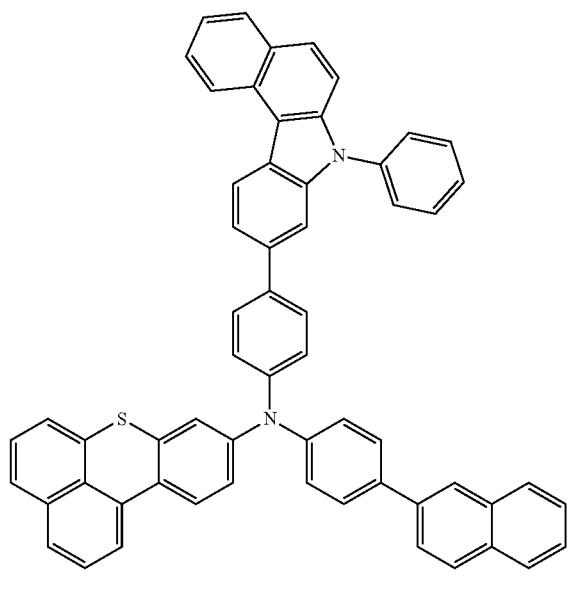
P3-24
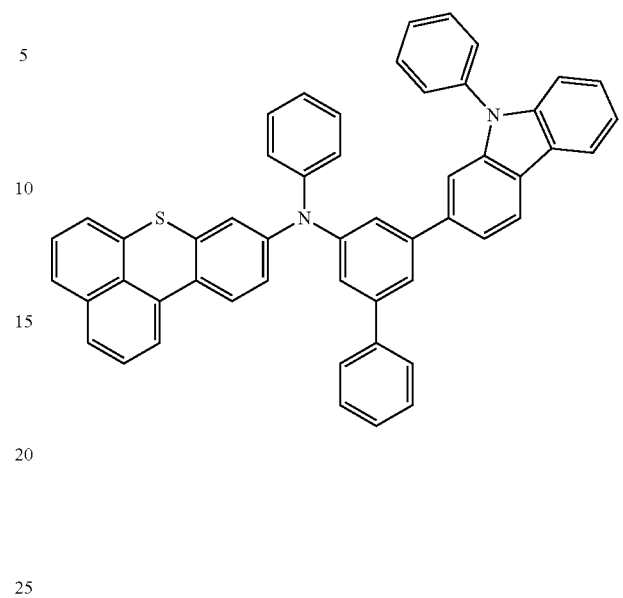
P3-22
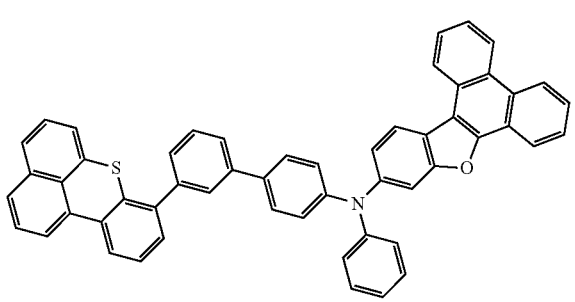
P3-25
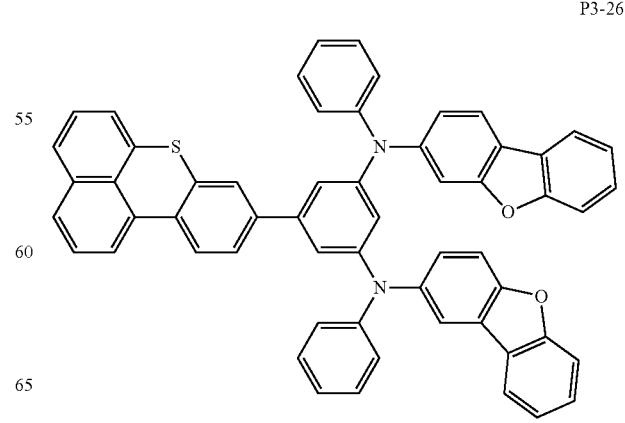
P3-23
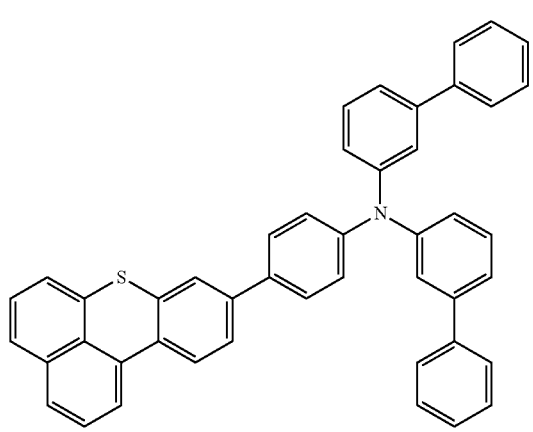
P3-26

-continued
P3-27
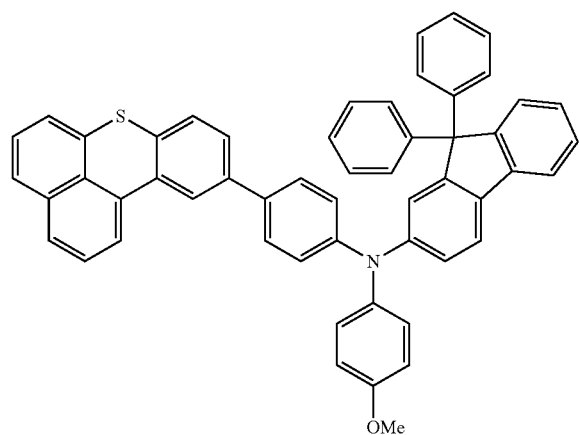
P3-28
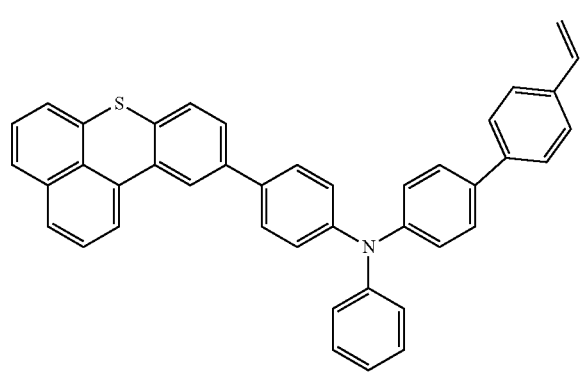
P3-29
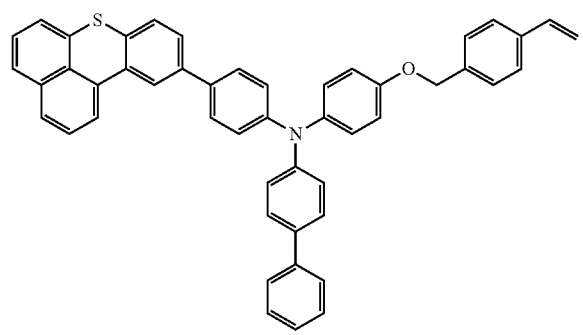
P3-30
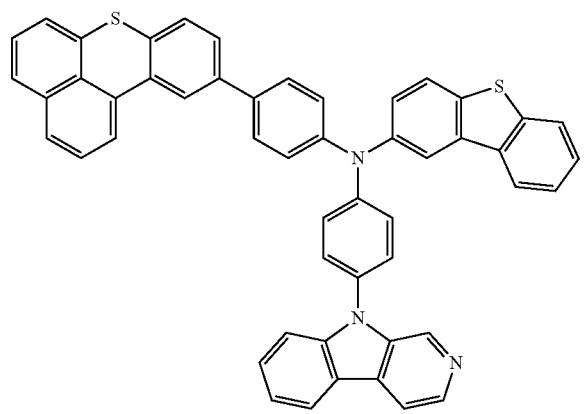
-continued
P4-1
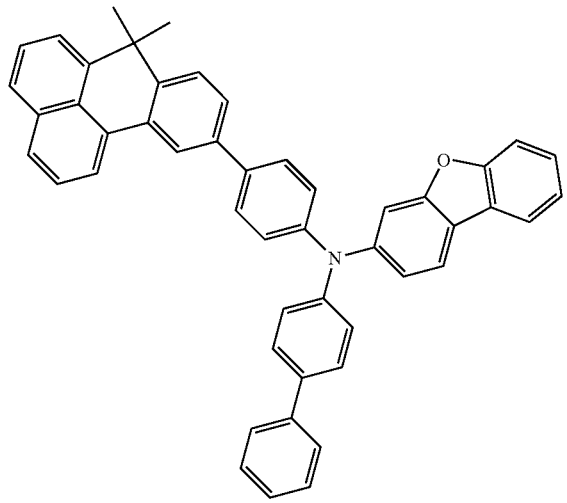
P4-2
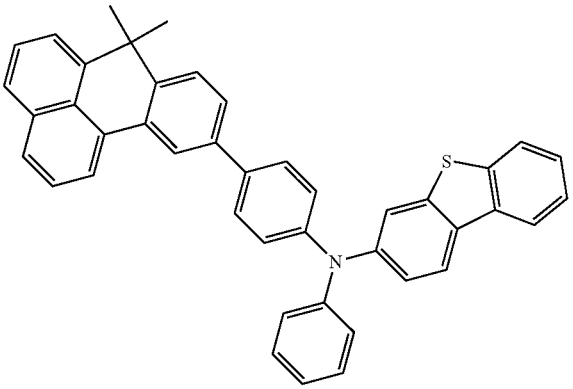
P4-3
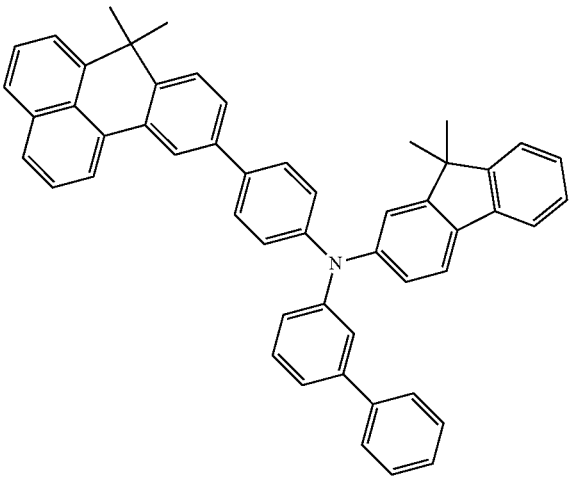

-continued
P4-4
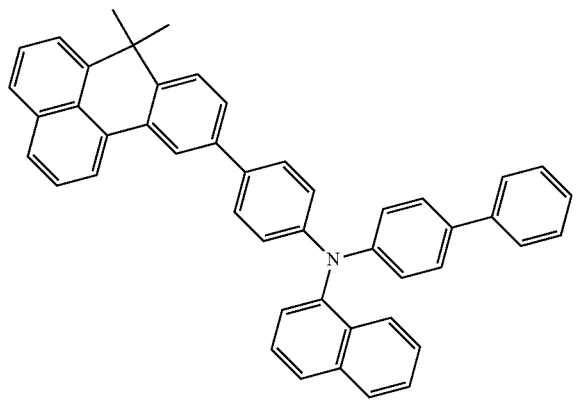
P4-5
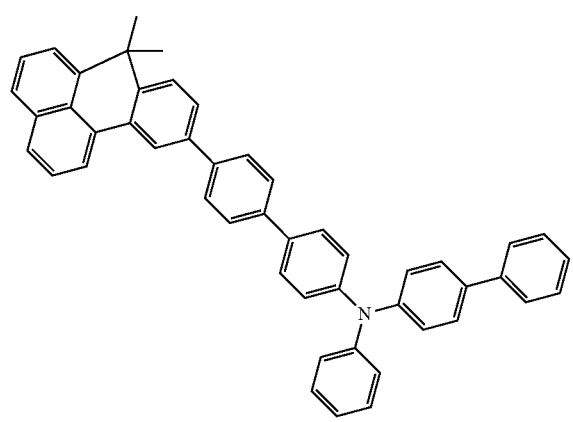
P4-6
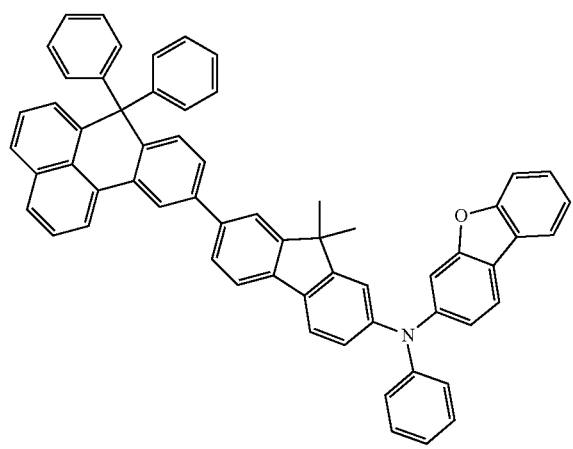
-continued
P4-7
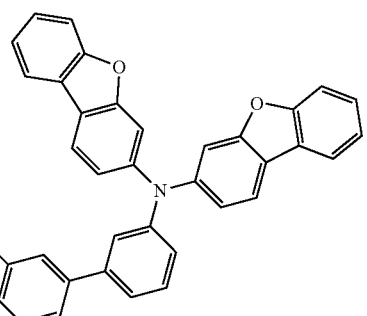
P4-8
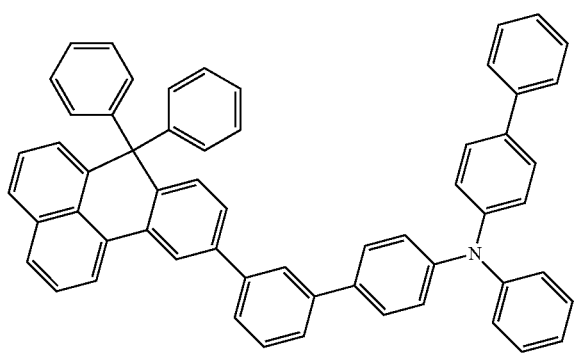
P4-9
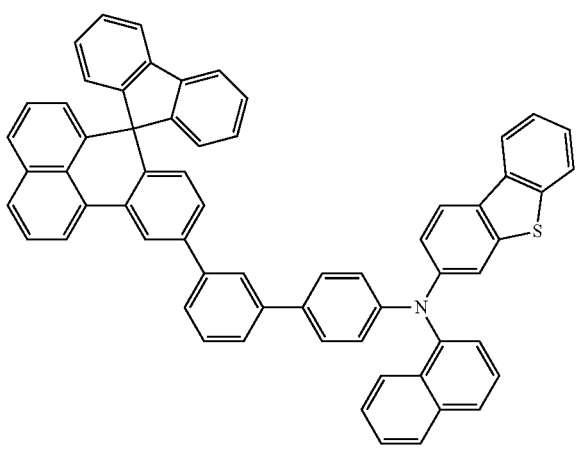

P4-10
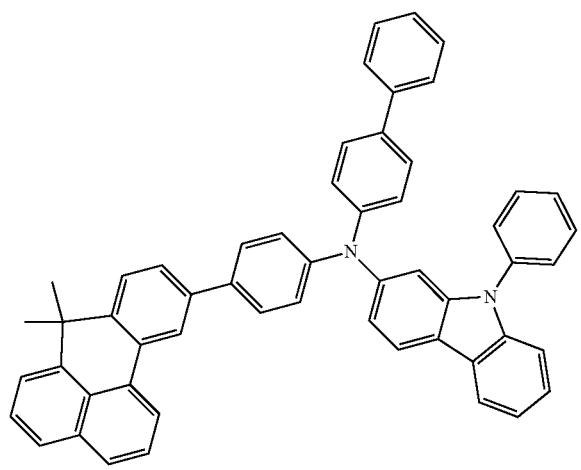
P4-13
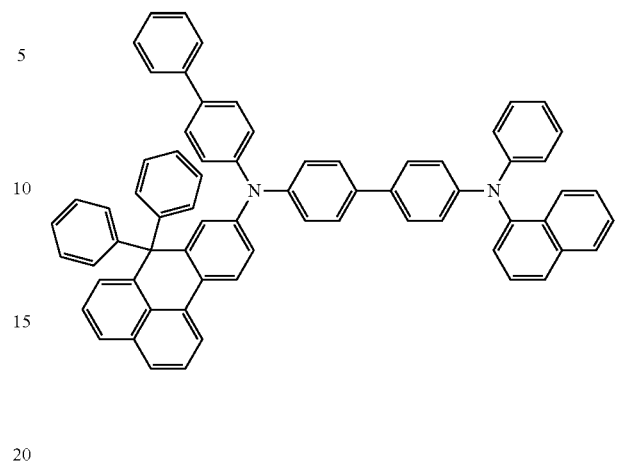
P4-11
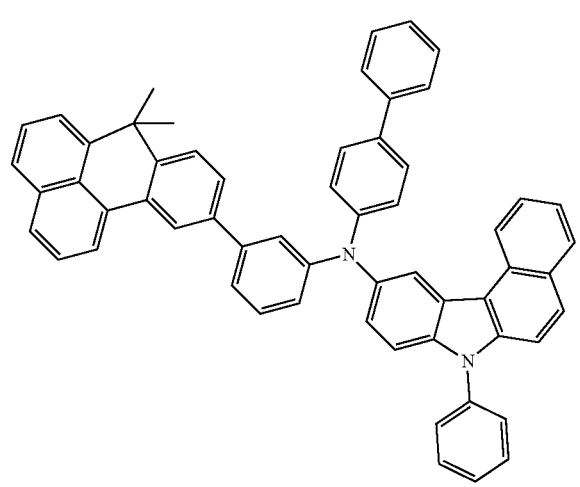
P4-14
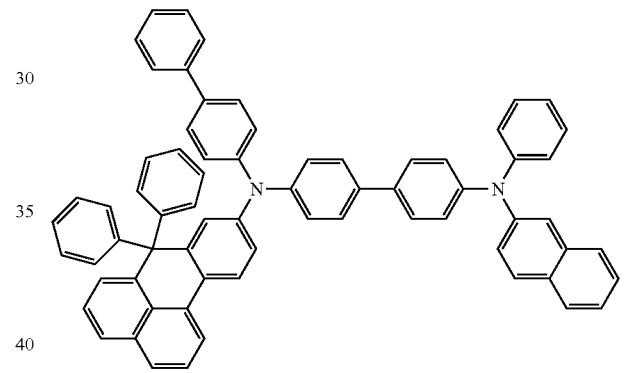
P4-12
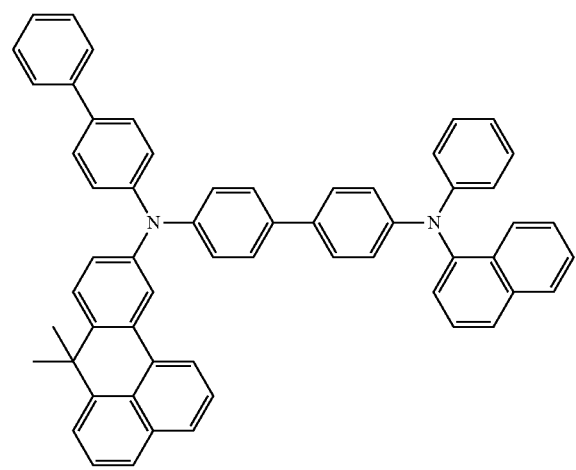
P4-15
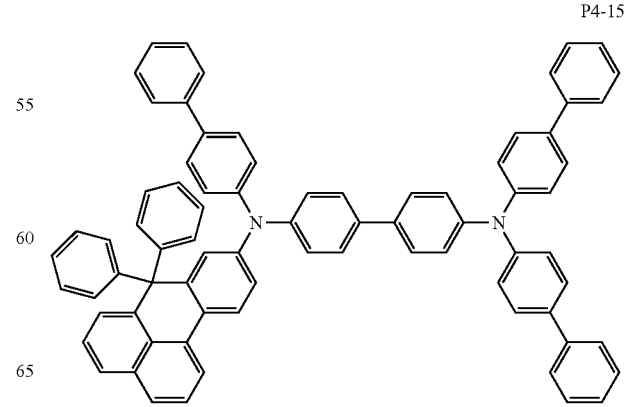

P4-16
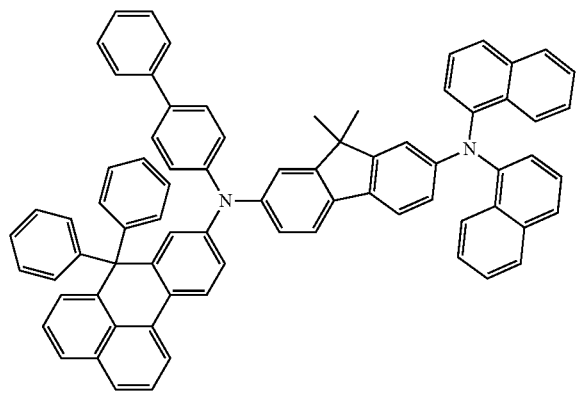
P4-19
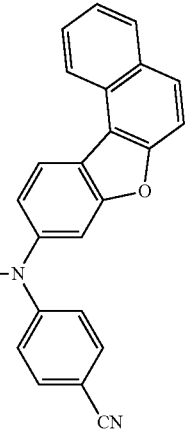
P4-17
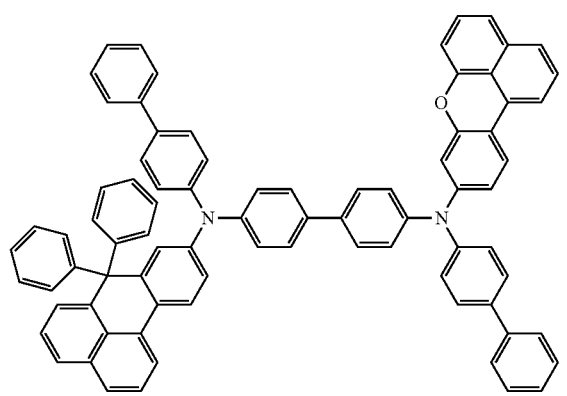
P4-20
P4-18
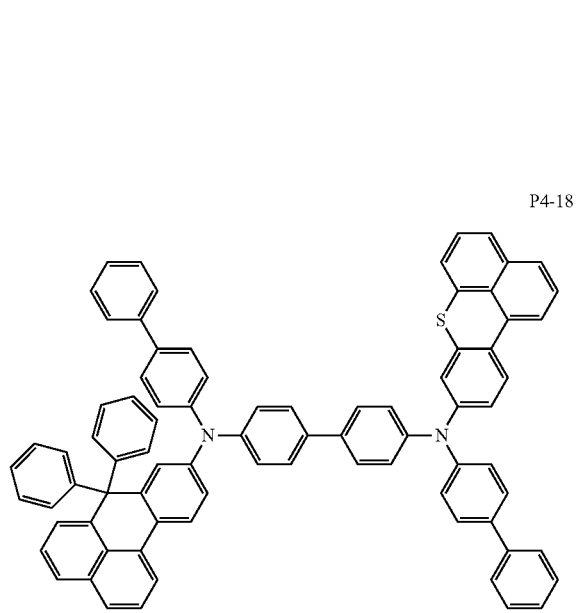
P4-21
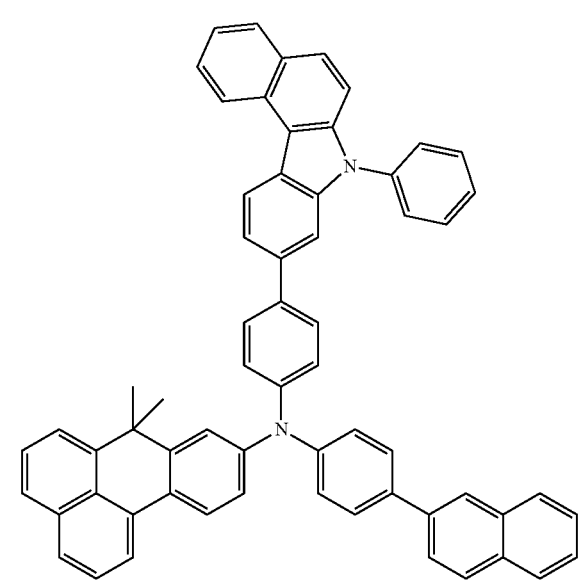

P4-22
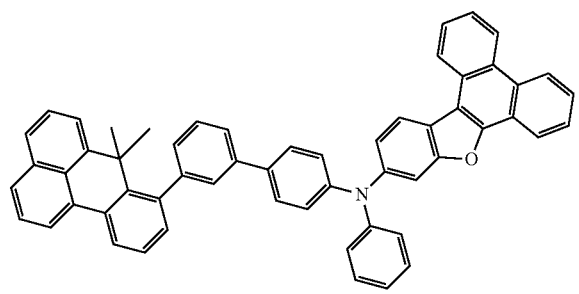
P4-25
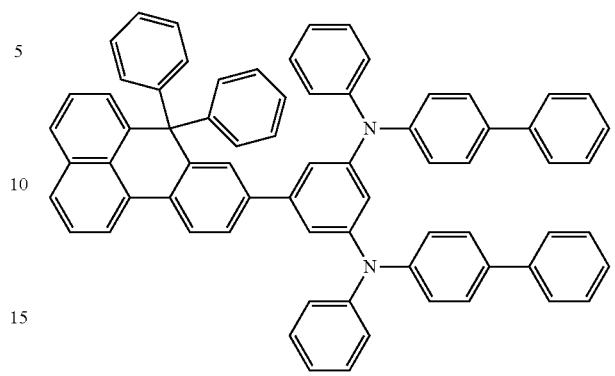
P4-23
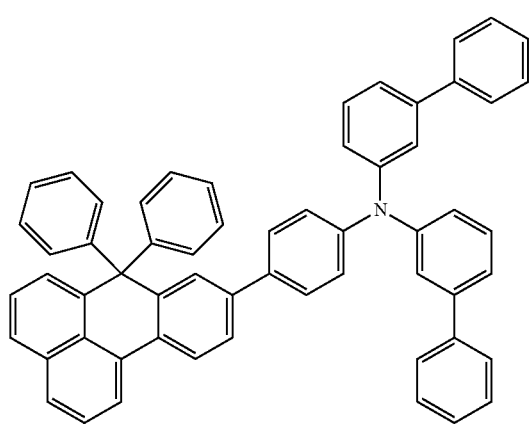
P4-26
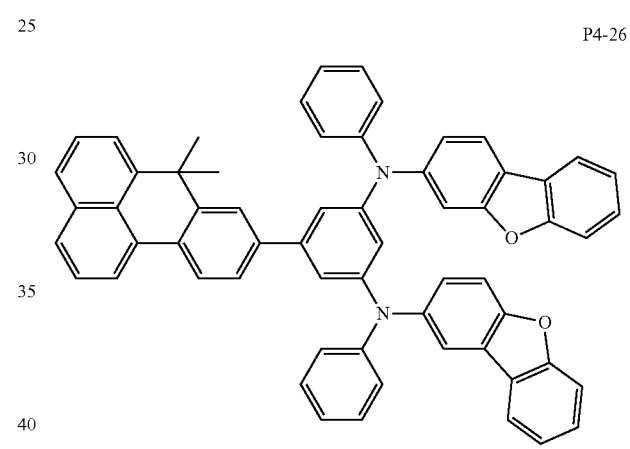
P4-24
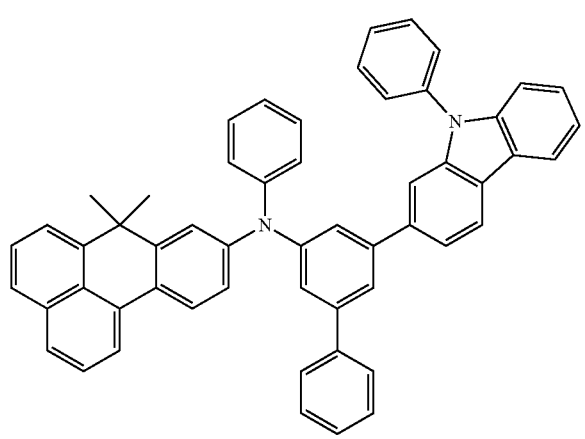
P4-27
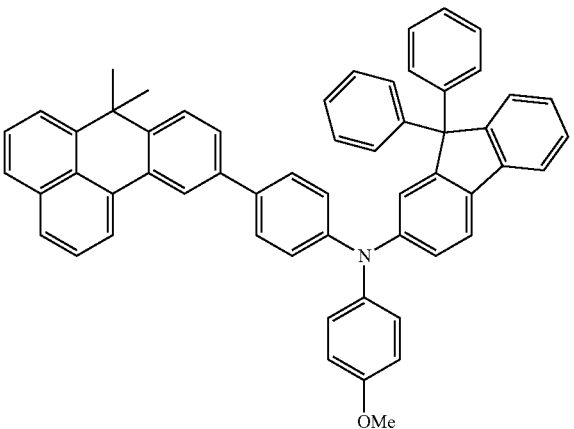

-continued

P4-28

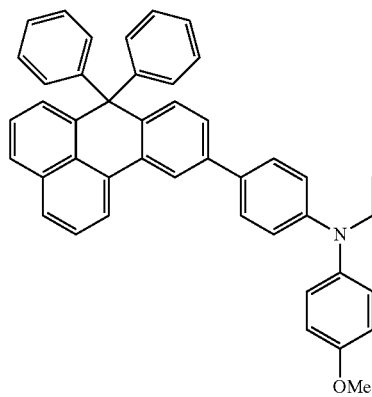

P4-29

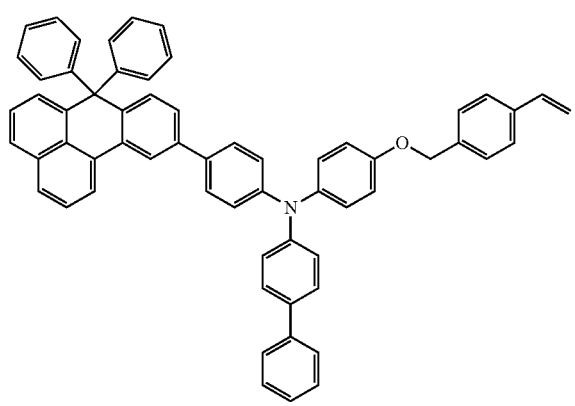

-continued

P4-30

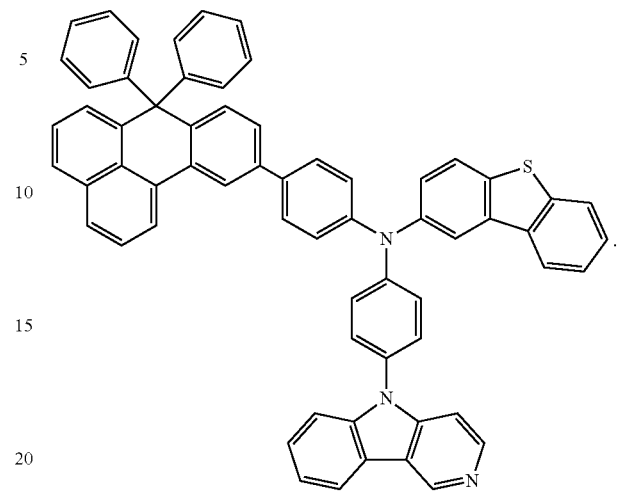

11. An organic electric element comprising a first electrode, a second electrode, and an organic material layer disposed between the first electrode and the second electrode, wherein the organic material layer comprises the compound of claim 10.

12. An electronic device comprising a display device, which comprises the organic electric element of claim 11, and a control unit for driving the display device.

* * * * *

(12) EX PARTE REEXAMINATION CERTIFICATE (12046th)
United States Patent
Mun et al.

(10) Number: US 10,600,969 C1
(45) Certificate Issued: *May 5, 2022

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Soung Yun Mun, Yongin-si (KR); Bum Sung Lee, Cheonan-si (KR); Jung Cheol Park, Suwon-si (KR); Hee Sun Ji, Cheonan-si (KR); Sun-Hee Lee, Hwaseong-si (KR); Jae-Taek Kwon, Jeonju-si (KR)

(73) Assignee: DUK SAN NEOLUX CO., LTD., Cheonan-si (KR)

Reexamination Request:
No. 90/014,855, Sep. 10, 2021

Reexamination Certificate for:
Patent No.: 10,600,969
Issued: Mar. 24, 2020
Appl. No.: 15/312,444
PCT Filed: Apr. 9, 2015
PCT No.: PCT/KR2015/003560
§ 371 (c)(1),
(2) Date: Nov. 18, 2016
PCT Pub. No.: WO2015/178585
PCT Pub. Date: Nov. 26, 2015

(*) Notice: This patent is subject to a terminal disclaimer.

(30) Foreign Application Priority Data

May 22, 2014 (KR) .................. 10-2014-0061622
Dec. 2, 2014 (KR) .................. 10-2014-0170768

(51) Int. Cl.
| | | |
|---|---|---|
| H01L 51/00 | (2006.01) |
| C07C 211/54 | (2006.01) |
| C07C 211/58 | (2006.01) |
| C07C 211/61 | (2006.01) |
| C07C 217/92 | (2006.01) |
| C07D 221/18 | (2006.01) |
| C07D 307/77 | (2006.01) |
| C07D 307/91 | (2006.01) |
| C07D 311/78 | (2006.01) |
| C07D 333/76 | (2006.01) |
| C07D 335/04 | (2006.01) |
| C07D 401/04 | (2006.01) |
| C07D 405/14 | (2006.01) |
| C07D 409/12 | (2006.01) |
| C07D 413/14 | (2006.01) |
| C07D 471/04 | (2006.01) |
| H01L 51/50 | (2006.01) |

(52) U.S. Cl.
CPC ........ *H01L 51/0061* (2013.01); *C07C 211/54* (2013.01); *C07C 211/58* (2013.01); *C07C 211/61* (2013.01); *C07C 217/92* (2013.01); *C07D 221/18* (2013.01); *C07D 307/77* (2013.01); *C07D 307/91* (2013.01); *C07D 311/78* (2013.01); *C07D 333/76* (2013.01); *C07D 335/04* (2013.01); *C07D 401/04* (2013.01); *C07D 405/14* (2013.01); *C07D 409/12* (2013.01); *C07D 413/14* (2013.01); *C07D 471/04* (2013.01); *H01L 51/006* (2013.01); *C07C 2603/18* (2017.05); *C07C 2603/42* (2017.05); *H01L 51/0003* (2013.01); *H01L 51/0005* (2013.01); *H01L 51/0052* (2013.01); *H01L 51/0054* (2013.01); *H01L 51/0056* (2013.01); *H01L 51/0058* (2013.01); *H01L 51/0072* (2013.01); *H01L 51/0073* (2013.01); *H01L 51/0074* (2013.01); *H01L 51/5056* (2013.01); *Y02E 10/549* (2013.01)

(58) Field of Classification Search
None
See application file for complete search history.

(56) References Cited

To view the complete listing of prior art documents cited during the proceeding for Reexamination Control Number 90/014,855, please refer to the USPTO's public Patent Application Information Retrieval (PAIR) system under the Display References tab.

*Primary Examiner* — Alan D Diamond

(57) ABSTRACT

Provided are a compound of Formula 1 and an organic electric element including a first electrode, a second electrode, and an organic material layer between the first electrode and the second electrode and comprising the compound, the element showing improved luminous efficiency, stability, and life span.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 3 and 4 are cancelled.
Claim 5 is determined to be patentable as amended.
Claims 6 and 8, dependent on an amended claim, are determined to be patentable.
New claim 13 is added and determined to be patentable.
Claims 2, 7 and 9-12 were not reexamined.

5. An organic electric element comprising a first electrode, a second electrode, and an organic material layer disposed between the first electrode and the second electrode, wherein the organic material layer comprises the compound of claim [1] *13*.

*13. A compound of Formula 1:*

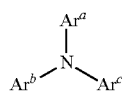

[Formula 1]

wherein:
$Ar^a$ is Formula 2, below,
$Ar^b$ is Formula 3 below, and
$Ar^c$ is selected from the group consisting of a $C_6$-$C_{60}$ aryl group; a fluorenyl group; and a $C_2$-$C_{60}$ heterocyclic group containing at least one heteroatom selected from the group consisting of O, N, S, Si, and P:

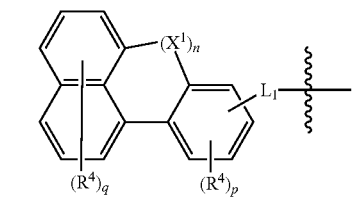

[Formula 2]

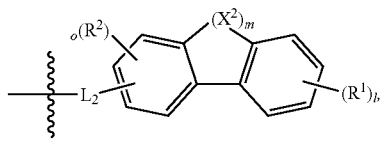

[Formula 3]

in Formulas 2 and 3,
m and n are each an integer of 0 or 1,
$X^1$ is $N(R')$, O, S or $C(R')(R'')$ and $X^2$ is $C(R')(R'')$, wherein R' and R" are each independently selected from the group consisting of a $C_6$-$C_{60}$ aryl group; a fluorenyl group; a $C_2$-$C_{60}$ heterocyclic group containing at least one heteroatom selected from the group consisting of O, N, S, Si, and P; and a $C_1$-$C_{60}$ alkyl group,
$L_1$ and $L_2$ are each independently selected from the group consisting of a single bond; a $C_6$-$C_{60}$ arylene group; a fluorenylene group; and a fused ring formed by a $C_3$-$C_{60}$ aliphatic ring and a $C_6$-$C_{60}$ aromatic ring, l is an integer of 0 to 4, o and p are each an integer of 0 to 3, and q is an integer of 1 to 6,
i) $R^1$ to $R^4$ are each independently selected from the group consisting of deuterium; tritium; halogen; a $C_6$-$C_{60}$ aryl group; a fluorenyl group; a $C_2$-$C_{60}$ heterocyclic group containing at least one heteroatom selected from the group consisting of O, N, S, Si, and P; a $C_1$-$C_{60}$ alkyl group; a $C_2$-$C_{20}$ alkenyl group; a $C_2$-$C_{20}$ alkynyl group; a $C_3$-$C_{60}$ cycloalkyl group; a $C_1$-$C_{30}$ alkoxy group; a $C_6$-$C_{30}$ aryloxy group; and —$L_3$-$N(R^5)(R^6)$, or
ii) any adjacent $R^1$ to $R^4$ groups may be linked together to form at least one ring and the group(s) of $R^1$ to $R^4$ not forming a ring are the same as defined in (i) above,
with the proviso that: $R^4$ is an unsubstituted $C_6$ aryl group or an unsubstituted $C_6$ aromatic ring formed by adjacent $R^4$ groups, and where m and n are both an integer of 0, $R^4$ is an unsubstituted $C_6$ aromatic ring formed by adjacent $R^4$ groups,
$L_3$ is selected from the group consisting of a single bond; a $C_6$-$C_{60}$ arylene group; a fluorenylene group; a $C_2$-$C_{60}$ heterocyclic group containing at least one heteroatom selected from the group consisting of O, N, S, Si, and P; and a fused ring formed by a $C_3$-$C_{60}$ aliphatic ring and a $C_6$-$C_{60}$ aromatic ring,
$R^5$ and $R^6$ are each independently selected from the group consisting of a $C_6$-$C_{60}$ aryl group; a fluorenyl group; a $C_2$-$C_{60}$ heterocyclic group containing at least one heteroatom selected from the group consisting of O, N, S, Si, and P; and a $C_1$-$C_{60}$ alkyl group,
$R^5$ and $R^6$, $L_3$ (except for the single bond) and $R^5$, or $L_3$ (except for the single bond) and $R^6$ may be linked to form a heterocyclic compound comprising N together with N attached to $L_3$, $R^5$ and $R^6$, and
each of the above aryl group, fluorenyl group, heterocyclic group, fused ring group, alkyl group, alkenyl group, alkynyl group, cycloalkyl group, alkoxy group, aryloxy group, arylene group and fluorenylene group may be substituted with one or more substituents selected from the group consisting of deuterium; halogen; a silane group; a siloxane group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si, and P; a $C_3$-$C_{20}$ cycloalkyl group; a $C_7$-$C_{20}$ arylalkyl group; a $C_8$-$C_{20}$ arylalkenyl group; and —$L_3$-$N(R^5)(R^6)$,
with the proviso that:
i) where m and n are each an integer of 0 and $Ar^c$ is an aryl group, the aryl group of $Ar^c$ is an unsubstituted $C_6$-$C_{12}$ aryl group or a $C_6$-$C_{60}$ aryl group substituted with —$L_3$-$N(R^5)(R^6)$, wherein $R^5$ and $R^6$ do not form a heterocyclic compound comprising N together with the N attached to $L_3$,
ii) where n is an integer of 1 and m is an integer of 0 or 1, $Ar^c$ is a $C_6$-$C_{60}$ aryl group substituted with —$L_3$-$N(R^5)(R^6)$,
iii) where n is an integer of 0 and m is an integer of 1, $Ar^c$ is selected from the group consisting of a $C_6$-$C_{12}$ aryl group unsubstituted or substituted with —$L_3$-$N(R^5)(R^6)$; a fluorenyl group substituted with —$L_3$-$N(R^5)(R^6)$; and a $C_2$-$C_{60}$ heterocyclic group substituted with —$L_3$-$N(R^5)(R^6)$ and containing at least one heteroatom selected from the group consisting of O, N, S, Si, and P, and in the case where $Ar^c$ is selected as the aryl group, an arylene group of $L_1$ in Formula 2 is not substituted with $-L_3-N(R^5)(R^6)$, and
iv) where m is an integer of 1, Formula 3 is
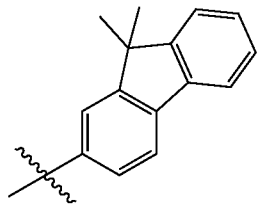
or
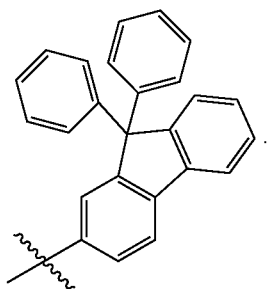
\* \* \* \* \*